(12) United States Patent
Sin et al.

(10) Patent No.: US 8,163,921 B2
(45) Date of Patent: *Apr. 24, 2012

(54) HEPATITIS C VIRUS INHIBITORS

(75) Inventors: Ny Sin, East Hampton, CT (US); Brian Lee Venables, Durham, CT (US); Paul Michael Scola, Glastonbury, CT (US); Alan Xiangdong Wang, Guilford, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 373 days.

This patent is subject to a terminal disclaimer.

(21) Appl. No.: 12/418,677

(22) Filed: Apr. 6, 2009

(65) Prior Publication Data

US 2009/0274652 A1    Nov. 5, 2009

Related U.S. Application Data

(60) Provisional application No. 61/045,434, filed on Apr. 16, 2008.

(51) Int. Cl.
*C07D 217/22* (2006.01)
*C07D 217/00* (2006.01)
*C07D 471/02* (2006.01)
*A61K 38/00* (2006.01)
*A61K 31/47* (2006.01)

(52) U.S. Cl. ........ 546/141; 546/139; 546/148; 546/149; 546/146; 546/113; 530/331; 514/307; 514/309

(58) Field of Classification Search .................. None
See application file for complete search history.

(56) References Cited

U.S. PATENT DOCUMENTS

| | | | |
|---|---|---|---|
| 5,223,432 A | 6/1993 | Wirz et al. | |
| 7,449,479 B2 | 11/2008 | Wang et al. | |
| 2005/0153877 A1 | 7/2005 | Miao et al. | |
| 2005/0209135 A1 | 9/2005 | Busacca et al. | |
| 2006/0199773 A1 | 9/2006 | Sausker et al. | |
| 2006/0257980 A1 | 11/2006 | Li | |
| 2007/0078081 A1 | 4/2007 | Casarez et al. | |
| 2008/0032936 A1 | 2/2008 | Gai et al. | |
| 2008/0039375 A1 | 2/2008 | Moore et al. | |
| 2008/0039470 A1 | 2/2008 | Niu et al. | |
| 2008/0181868 A1 | 7/2008 | Sun et al. | |
| 2008/0279821 A1 | 11/2008 | Niu et al. | |

FOREIGN PATENT DOCUMENTS

| WO | WO 98/17679 | 4/1998 |
|---|---|---|
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |

(Continued)

OTHER PUBLICATIONS

U.S. Appl. No. 12/202,603, filed Sep. 2, 2008, Wang et al.
U.S. Appl. No. 12/329,969, filed Dec. 8, 2008, Perrone et al.
U.S. Appl. No. 12/464,954, filed May 13, 2009, Sun et al.
U.S. Appl. No. 12/465,142, filed May 13, 2009, Sin et al.
U.S. Appl. No. 12/473,188, filed May 27, 2009, Wang et al.
U.S. Appl. No. 12/473,741, filed May 28, 2009, Wang et al.
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

(Continued)

*Primary Examiner* — Kamal Saeed
*Assistant Examiner* — Nyeemah A Grazier
(74) *Attorney, Agent, or Firm* — Pamela A. Mingo

(57) ABSTRACT

Hepatitis C virus inhibitors having the general formula

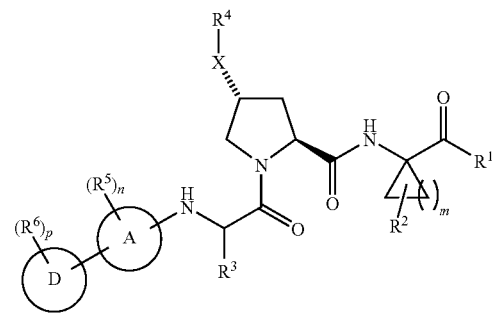

are disclosed. Compositions comprising the compounds and methods for using the compounds to inhibit HCV are also disclosed.

16 Claims, No Drawings

FOREIGN PATENT DOCUMENTS

| | | |
|---|---|---|
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/010804 | 1/2009 |
| WO | WO 2009/014730 | 1/2009 |

OTHER PUBLICATIONS

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalic Acid", Synthesis, pp. 365-366 (1992).

HEPATITIS C VIRUS INHIBITORS

CROSS-REFERENCE TO RELATED APPLICATIONS

This application claims the benefit of U.S. Provisional Application Ser. No. 61/045,434 filed Apr. 16, 2008.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with one or two additional compounds having anti-HCV activity.

In a first aspect the present disclosure provides a compound of Formula (I)

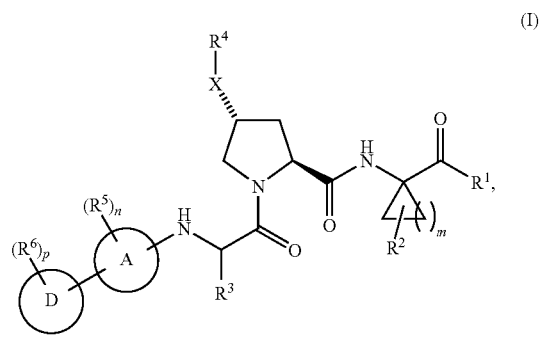

or a pharmaceutically acceptable salt thereof, wherein
m is 1, 2, or 3;
n is 0, 1, 2, 3, or 4;
p is 0, 1, 2, 3, 4, or 5;
A is a five- or six-membered saturated or unsaturated ring optionally containing one, two, three, or four heteroatoms selected from nitrogen, oxygen, and sulfur;
D is a five- to eight-membered saturated or unsaturated ring optionally containing one, two, three, or four heteroatoms selected from nitrogen, oxygen, and sulfur; wherein the five- to eight-membered ring is optionally fused to a second five- to eight-membered saturated or unsaturated ring optionally containing one, two, three, or four heteroatoms selected from nitrogen, oxygen, and sulfur;
X is O, S, SO, $SO_2$, $OCH_2$, $CH_2O$ or NH;
$R^1$ is selected from hydroxy and —$NHSO_2R^7$; wherein $R^7$ is selected from alkyl, aryl, cycloalkyl, (cycloalkyl)alkyl, heterocyclyl, and —$NR^aR^b$, wherein the alkyl the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^eR^f$)carbonyl;
$R^2$ is selected from hydrogen, alkenyl, alkyl, and cycloalkyl, wherein the alkenyl, alkyl, and cycloalkyl are optionally substituted with halo;
$R^3$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxy, haloalkyl, (heterocyclyl)alkyl, hydroxyalkyl, ($NR^cR^d$)alkyl, and ($NR^eR^f$)carbonylalkyl;
$R^4$ is selected from aryl, arylalkyl, and heterocyclyl;
each $R^5$ is independently selected from alkoxy, alkoxycarbonyl, alkyl, alkylcarbonyl, alkylsulfanyl, aryl, carboxy, cyano, cycloalkyl, cycloalkyloxy, halo, haloalkyl, haloalkoxy, heterocyclyl, hydroxy, —$NR^cR^d$, ($NR^eR^f$)carbonyl, ($NR^eR^f$)sulfonyl, and oxo; provided that when A is a six-membered substituted ring all $R^5$ groups on the ring other than those where $R^5$ is fluoro must be in the meta and/or para positions relative to the ring's point of attachment to the parent molecular moiety;

each $R^6$ is independently selected from alkoxy, alkoxycarbonyl, alkyl, alkylcarbonyl, alkylsulfanyl, alkylsulfonyl, aryl, aryloxy, arylsulfonyl, carboxy, cyano, cycloalkyl, cycloalkyloxy, halo, haloalkoxy, haloalkyl, heterocyclyl, hydroxy, —$NR^cR^d$, ($NR^eR^f$)carbonyl, ($NR^eR^f$)sulfonyl, and oxo;

$R^a$ and $R^b$ are independently selected from hydrogen, alkoxy, alkyl, aryl, arylalkyl, cycloalkyl, (cycloalkyl)alkyl, haloalkoxy, haloalkyl, heterocyclyl, and heterocyclylalkyl; or $R^a$ and $R^b$ together with the nitrogen atom to which they are attached form a four to seven-membered monocyclic heterocyclic ring;

$R^c$ and $R^d$ are independently selected from hydrogen, alkoxyalkyl, alkoxycarbonyl, alkyl, alkylcarbonyl, arylalkyl, arylcarbonyl, haloalkoxyalkyl, haloalkoxycarbonyl, haloalkyl, and ($NR^eR^f$)carbonyl; and $R^e$ and $R^f$ are independently selected from hydrogen, alkyl, aryl, arylalkyl, and heterocyclyl; wherein the aryl, the aryl part of the arylalkyl, and the heterocyclyl are optionally substituted with one, two, three, four, or five substituents independently selected from alkoxy, alkyl, and halo.

In a first embodiment of the first aspect the present disclosure provides a compound of Formula (I), or a pharmaceutically acceptable salt thereof, wherein m is 1.

In a second embodiment of the first aspect the present disclosure provides a compound of Formula (I), or a pharmaceutically acceptable salt thereof, wherein $R^1$ is —$NHSO_2R^7$. In a third embodiment of the first aspect $R^7$ is cycloalkyl.

In a fourth embodiment of the first aspect the present disclosure provides a compound of Formula (I), or a pharmaceutically acceptable salt thereof, wherein X is O.

In a fifth embodiment of the first aspect the present disclosure provides a compound of Formula (I), or a pharmaceutically acceptable salt thereof, wherein $R^4$ is heterocyclyl. In a sixth embodiment of the first aspect the heterocyclyl is isoquinolinyl.

In a seventh embodiment of the first aspect the present disclosure provides a compound of Formula (I), or a pharmaceutically acceptable salt thereof, wherein
m is 1;
$R^1$ is —$NHSO_2R^7$;
$R^7$ is cycloalkyl;
X is O; and
$R^4$ is heterocyclyl.
In an eighth embodiment of the first aspect the heterocyclyl is isoquinolinyl.

In a ninth embodiment of the first aspect the present disclosure provides a compound of Formula (I), or a pharmaceutically acceptable salt thereof, wherein
m is 1;
$R^1$ is —$NHSO_2R^7$;
$R^7$ is cycloalkyl;
X is O; and
$R^4$ is heterocyclyl, wherein the heterocyclyl is selected from optionally substituted isoquinolinyl and quinolinyl.

In a tenth embodiment of the first aspect the present disclosure provides a compound of Formula (I), or a pharmaceutically acceptable salt thereof, wherein
m is 1, 2, or 3;
n is 0, 1, 2, 3, or 4;
p is 1, 2, 3, 4, or 5;
A is a five- or six-membered saturated or unsaturated ring optionally containing one, two, three, or four heteroatoms selected from nitrogen, oxygen, and sulfur;

D is a five- to eight-membered saturated or unsaturated ring optionally containing one, two, three, or four heteroatoms selected from nitrogen, oxygen, and sulfur; wherein the five- to eight-membered ring is optionally fused to a second five- to eight-membered saturated or unsaturated ring optionally containing one, two, three, or four heteroatoms selected from nitrogen, oxygen, and sulfur;

X is O, S, SO, $SO_2$, $OCH_2$, $CH_2O$ or NH;

$R^1$ is selected from hydroxy and —$NHSO_2R^7$; wherein $R^7$ is selected from alkyl, aryl, cycloalkyl, (cycloalkyl)alkyl, heterocyclyl, and —$NR^aR^b$, wherein the alkyl, the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^eR^f$)carbonyl;

$R^2$ is selected from hydrogen, alkenyl, alkyl, and cycloalkyl, wherein the alkenyl, alkyl, and cycloalkyl are optionally substituted with halo;

$R^3$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxy, haloalkyl, (heterocyclyl)alkyl, hydroxyalkyl, ($NR^cR^d$)alkyl, and ($NR^eR^f$)carbonyl alkyl;

$R^4$ is selected from aryl, arylalkyl, and heterocyclyl;

each $R^5$ is independently selected from alkoxy, alkoxycarbonyl, alkyl, alkylcarbonyl, alkylsulfanyl, aryl, carboxy, cyano, cycloalkyl, cycloalkyloxy, halo, haloalkyl, haloalkoxy, heterocyclyl, hydroxy, —$NR^cR^d$, ($NR^eR^f$)carbonyl, ($NR^eR^f$)sulfonyl, and oxo; provided that when A is a six-membered substituted ring all $R^5$ groups on the ring other than those where $R^5$ is fluoro must be in the meta and/or para positions relative to the ring's point of attachment to the parent molecular moiety;

one $R^6$ is aryl or heterocyclyl and, when present, the others are independently selected from alkoxy, alkoxycarbonyl, alkyl, alkylcarbonyl, alkylsulfanyl, alkylsulfonyl, aryl, aryloxy, arylsulfonyl, carboxy, cyano, cycloalkyl, cycloalkyloxy, halo, haloalkoxy, haloalkyl, heterocyclyl, hydroxy, —$NR^cR^d$, ($NR^eR^f$)carbonyl, ($NR^eR^f$)sulfonyl, and oxo;

$R^a$ and $R^b$ are independently selected from hydrogen, alkoxy, alkyl, aryl, arylalkyl, cycloalkyl, (cycloalkyl)alkyl, haloalkoxy, haloalkyl, heterocyclyl, and heterocyclylalkyl; or $R^a$ and $R^b$ together with the nitrogen atom to which they are attached form a four to seven-membered monocyclic heterocyclic ring;

$R^c$ and $R^d$ are independently selected from hydrogen, alkoxyalkyl, alkoxycarbonyl, alkyl, alkylcarbonyl, arylalkyl, arylcarbonyl, haloalkoxyalkyl, haloalkoxycarbonyl, haloalkyl, and ($NR^eR^f$)carbonyl; and $R^e$ and $R^f$ are independently selected from hydrogen, alkyl, aryl, arylalkyl, and heterocyclyl; wherein the aryl, the aryl part of the arylalkyl, and the heterocyclyl are optionally substituted with one, two, three, four, or five substituents independently selected from alkoxy, alkyl, and halo.

In an eleventh embodiment of the first aspect the present disclosure provides a compound of Formula (I), or a pharmaceutically acceptable salt thereof, wherein
m is 1, 2, or 3;
n is 0, 1, 2, 3, or 4;
p is 0, 1, 2, 3, 4, or 5;
A is a five- or six-membered saturated or unsaturated ring optionally containing one, two, three, or four heteroatoms selected from nitrogen, oxygen, and sulfur;
D is a five- to eight-membered saturated or unsaturated ring optionally containing one, two, three, or four heteroatoms selected from nitrogen, oxygen, and sulfur; wherein the five- to eight-membered ring is optionally fused to a second five- to eight-membered saturated or unsaturated ring optionally containing one, two, three, or four heteroatoms selected from nitrogen, oxygen, and sulfur;

X is O, S, SO, $SO_2$, $OCH_2$, $CH_2O$ or NH;

$R^1$ is selected from hydroxy and —$NHSO_2R^7$; wherein $R^7$ is selected from alkyl, aryl, cycloalkyl, (cycloalkyl)alkyl, heterocyclyl, and —$NR^aR^b$, wherein the alkyl, the cycloalkyl and the cycloalkyl part of the (cycloalkyl)alkyl are optionally substituted with one, two, or three substituents selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^eR^f$)carbonyl, $R^2$ is alkyl substituted with halo;

$R^3$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxy, haloalkyl, (heterocyclyl)alkyl, hydroxyalkyl, ($NR^cR^d$)alkyl, and ($NR^eR^f$)carbonylalkyl;

$R^4$ is selected from aryl, arylalkyl, and heterocyclyl;

each $R^5$ is independently selected from alkoxy, alkoxycarbonyl, alkyl, alkylcarbonyl, alkylsulfanyl, aryl, carboxy, cyano, cycloalkyl, cycloalkyloxy, halo, haloalkyl, haloalkoxy, heterocyclyl, hydroxy, —$NR^cR^d$, ($NR^eR^f$)carbonyl, ($NR^eR^f$)sulfonyl, and oxo; provided that when A is a six-membered substituted ring all $R^5$ groups on the ring other than those where $R^5$ is fluoro must be in the meta and/or para positions relative to the ring's point of attachment to the parent molecular moiety;

each $R^6$ is independently selected from alkoxy, alkoxycarbonyl, alkyl, alkylcarbonyl, alkylsulfanyl, alkylsulfonyl, aryl, aryloxy, arylsulfonyl, carboxy, cyano, cycloalkyl, cycloalkyloxy, halo, haloalkoxy, haloalkyl, heterocyclyl, hydroxy, —$NR^cR^d$, ($NR^eR^f$)carbonyl, ($NR^eR^f$)sulfonyl, and oxo;

$R^a$ and $R^b$ are independently selected from hydrogen, alkoxy, alkyl, aryl, arylalkyl, cycloalkyl, (cycloalkyl)alkyl, haloalkoxy, haloalkyl, heterocyclyl, and heterocyclylalkyl; or $R^a$ and $R^b$ together with the nitrogen atom to which they are attached form a four to seven-membered monocyclic heterocyclic ring;

$R^c$ and $R^d$ are independently selected from hydrogen, alkoxyalkyl, alkoxycarbonyl, alkyl, alkylcarbonyl, arylalkyl, arylcarbonyl, haloalkoxyalkyl, haloalkoxycarbonyl, haloalkyl, and ($NR^eR^f$)carbonyl; and $R^e$ and $R^f$ are independently selected from hydrogen, alkyl, aryl, arylalkyl, and heterocyclyl; wherein the aryl, the aryl part of the arylalkyl, and the heterocyclyl are optionally substituted with one, two, three, four, or five substituents independently selected from alkoxy, alkyl, and halo.

In a second aspect the present disclosure provides a compound of formula (II)

(II)

or a pharmaceutically acceptable salt thereof, wherein
n is 0, 1, 2, 3, or 4;
p is 0, 1, 2, 3, 4, or 5;

A is a five- or six-membered partially or fully unsaturated ring optionally containing one, two, three, or four heteroatoms selected from nitrogen, oxygen, and sulfur;

D is a five- to eight-membered partially or fully unsaturated ring optionally containing one, two, three, or four heteroatoms selected from nitrogen, oxygen, and sulfur; wherein the five- to eight-membered ring is optionally fused to a second five- to eight-membered partially or fully unsaturated ring optionally containing one, two, three, or four heteroatoms selected from nitrogen, oxygen, and sulfur;

$R^2$ is selected from hydrogen, alkenyl, alkyl, and cycloalkyl, wherein the alkenyl, alkyl, and cycloalkyl are optionally substituted with halo;

$R^3$ is alkyl;

$R^4$ is heterocyclyl;

each $R^5$ is independently selected from alkoxy, alkoxycarbonyl, alkyl, alkylcarbonyl, alkylsulfanyl, aryl, carboxy, cyano, cycloalkyl, cycloalkyloxy, halo, haloalkyl, haloalkoxy, heterocyclyl, hydroxy, —$NR^cR^d$, ($NR^eR^f$)carbonyl, ($NR^eR^f$)sulfonyl, and oxo; provided that when A is a six-membered substituted ring all $R^5$ groups on the ring other than those where $R^5$ is fluoro must be in the meta and/or para positions relative to the ring's point of attachment to the parent molecular moiety;

each $R^6$ is independently selected from alkoxy, alkoxycarbonyl, alkyl, alkylcarbonyl, alkylsulfanyl, alkylsulfonyl, aryl, aryloxy, carboxy, cyano, cycloalkyl, cycloalkyloxy, halo, haloalkoxy, haloalkyl, heterocyclyl, hydroxy, —$NR^cR^d$, ($NR^eR^f$)carbonyl, ($NR^eR^f$)sulfonyl, and oxo; alkylcarbonyl, alkylsulfanyl, $R^7$ is cycloalkyl;

$R^a$ and $R^b$ are independently selected from hydrogen, alkoxy, alkyl, aryl, arylalkyl, cycloalkyl, (cycloalkyl)alkyl, haloalkoxy, haloalkyl, heterocyclyl, and heterocyclylalkyl; or $R^a$ and $R^b$ together with the nitrogen atom to which they are attached form a four to seven-membered monocyclic heterocyclic ring;

$R^c$ and $R^d$ are independently selected from hydrogen, alkoxyalkyl, alkoxycarbonyl, alkyl, alkylcarbonyl, arylalkyl, haloalkoxyalkyl, haloalkoxycarbonyl, haloalkyl, and ($NR^eR^f$)carbonyl; and $R^e$ and $R^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a first embodiment of the second aspect the present disclosure provides a compound of Formula (II), or a pharmaceutically acceptable salt thereof, wherein
n is 0 or 1;
p is 0, 1, 2, 3, 4, or 5;

A is a five- or six-membered partially or fully unsaturated ring optionally containing one, two, three, or four heteroatoms selected from nitrogen, oxygen, and sulfur;

D is a five- to eight-membered partially or fully unsaturated ring optionally containing one, two, three, or four heteroatoms selected from nitrogen, oxygen, and sulfur; wherein the five- to eight-membered ring is optionally fused to a second five- to eight-membered partially or fully unsaturated ring optionally containing one, two, three, or four heteroatoms selected from nitrogen, oxygen, and sulfur;

$R^2$ is alkenyl;

$R^3$ is alkyl;

$R^4$ is heterocyclyl;

each $R^5$ is independently selected from alkoxy, alkyl and aryl; provided that when A is a six-membered substituted ring all R⁵ groups on the ring other must be in the meta and/or para positions relative to the ring's point of attachment to the parent molecular moiety;

each R⁶ is independently selected from alkoxy, alkyl, alkylsulfonyl, aryloxy, carboxy, cyano, halo, haloalkoxy, haloalkyl, heterocyclyl, hydroxy, and —NR^c R^d;

R⁷ is cycloalkyl; and

R^c and R^d are each alkyl.

In a third embodiment of the second aspect R⁴ is heterocyclyl wherein the heterocyclyl is isoquinolinyl.

In a fourth embodiment of the second aspect the present disclosure provides a compound of formula (II)

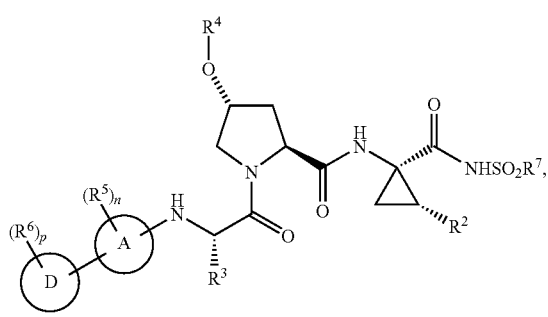

(II)

or a pharmaceutically acceptable salt thereof, wherein n is 0, 1, 2, 3, or 4;

p is 0, 1, 2, 3, 4, or 5;

A is a five- or six-membered partially or fully unsaturated ring optionally containing one, two, three, or four heteroatoms selected from nitrogen, oxygen, and sulfur;

D is a five- to eight-membered partially or fully unsaturated ring optionally containing one, two, three, or four heteroatoms selected from nitrogen, oxygen, and sulfur; wherein the five- to eight-membered ring is optionally fused to a second five- to eight-membered partially or fully unsaturated ring optionally containing one, two, three, or four heteroatoms selected from nitrogen, oxygen, and sulfur;

R² is selected from hydrogen, alkenyl, alkyl, and cycloalkyl, wherein the alkenyl, alkyl, and cycloalkyl are optionally substituted with halo;

R³ is alkyl;

R⁴ is heterocyclyl;

each R⁵ is independently selected from alkoxy, alkoxycarbonyl, alkyl, alkylcarbonyl, alkylsulfanyl, aryl, carboxy, cyano, cycloalkyl, cycloalkyloxy, halo, haloalkyl, haloalkoxy, heterocyclyl, hydroxy, —NR^c R^d, (NR^e R^f)carbonyl, (NR^e R^f)sulfonyl, and oxo; provided that when A is a six-membered substituted ring all R⁵ groups on the ring other than those where R⁵ is fluoro must be in the meta and/or para positions relative to the ring's point of attachment to the parent molecular moiety;

each R⁶ is independently selected from alkoxy, alkoxycarbonyl, alkyl, alkylcarbonyl, alkylsulfanyl, alkylsulfonyl, aryl, aryloxy, carboxy, cyano, cycloalkyl, cycloalkyloxy, halo, haloalkoxy, haloalkyl, heterocyclyl, hydroxy, —NR^c R^d, (NR^e R^f)carbonyl, (NR^e R^f)sulfonyl, and oxo; alkylcarbonyl, alkylsulfanyl, R⁷ is cycloalkyl;

R^a and R^b are independently selected from hydrogen, alkoxy, alkyl, aryl, arylalkyl, cycloalkyl, (cycloalkyl)alkyl, haloalkoxy, haloalkyl, heterocyclyl, and heterocyclylalkyl; or R^a and R^b together with the nitrogen atom to which they are attached form a four to seven-membered monocyclic heterocyclic ring;

R^c and R^d are independently selected from hydrogen, alkoxyalkyl, alkoxycarbonyl, alkyl, alkylcarbonyl, arylalkyl, haloalkoxyalkyl, haloalkoxycarbonyl, haloalkyl, and (NR^e R^f)carbonyl; and R^e and R^f are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a third aspect the present disclosure provides a composition comprising the compound of Formula (I), or a pharmaceutically acceptable salt thereof, and a pharmaceutically acceptable carrier. In a first embodiment of the third aspect the composition further comprises at least one additional compound having anti-HCV activity. In a second embodiment of the third aspect at least one of the additional compounds is an interferon or a ribavirin. In a third embodiment of the third aspect the interferon is selected from interferon alpha 2B, pegylated interferon alpha, consensus interferon, interferon alpha 2A, and lymphoblastiod interferon tau.

In a fourth embodiment of the third aspect the present disclosure provides a composition comprising the compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a composition comprising the compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a composition comprising a compound of Formula (I), or a pharmaceutically acceptable salt thereof, one, two, three, four, or five additional compounds having anti-HCV activity, and a pharmaceutically acceptable carrier. In a first embodiment of the fourth aspect the compsition comprises three or four additional compounds having anti-HCV activity. In a second embodiment of the fourth aspect the composition comprises one or two additional compounds having anti-HCV activity.

In a fifth aspect the present disclosure provides a method of treating an HCV infection in a patient, comprising administering to the patient a therapeutically effective amount of Formula (I), or a pharmaceutically acceptable salt thereof. In a first embodiment of the fifth aspect the method further comprises administering at least one additional compound having anti-HCV activity prior to, after, or simultaneously with the compound of Formula (I), or a pharmaceutically acceptable salt thereof. In a second embodiment of the fifth aspect at least one of the additional compounds is an interferon or a ribavirin. In a third embodiment of the fifth aspect the interferon is selected from interferon alpha 2B, pegylated interferon alpha, consensus interferon, interferon alpha 2A, and lymphoblastiod interferon tau.

In a fourth embodiment of the fifth aspect the present disclosure provides a method of treating an HCV infection in a patient, comprising administering to the patient a therapeutically effective amount of Formula (I), or a pharmaceutically acceptable salt thereof, and at least one additional compound having anti-HCV activity prior to, after, or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fifth aspect the present disclosure provides a method of treating an HCV infection in a patient, comprising administering to the patient a therapeutically effective amount of Formula (I), or a pharmaceutically acceptable salt thereof, and at least one additional compound having anti-HCV activity prior to, after, or simultaneously with the compound of Formula (I), or a pharmaceutically acceptable salt thereof wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a sixth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the sixth aspect the method comprises administering three or four additional compounds having anti-HCV activity. In a second embodiment of the sixth aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^5$ groups may be the same or different.

In the present disclosure, $R^2$ is selected from hydrogen, alkenyl, alkyl, and cycloalkyl, wherein the alkenyl, alkyl, and cycloalkyl are optionally substituted with halo. It should be understood that when the alkenyl, alkyl, or cycloalkyl are substituted, they are substituted with from one to the maximum number of allowable halogen substituents. In one embodiment the alkenyl, alkyl, and cycloalkyl are optionally substituted with one, two, or three halo groups. In another embodiment the alkenyl, alkyl, and cycloalkyl are optionally substituted with one or two halo groups.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxycarbonyl, alkyl, alkylcarbonyl, a second aryl group, carboxy, cycloalkyl, cycloalkyloxy, cyano, halo, haloalkoxy, haloalkyl, heterocyclyl, hydroxy, nitro, —$NR^cR^d$, ($NR^cR^d$)carbonyl, and oxo; wherein the second aryl group and the heterocyclyl are further optionally substituted with one, two, three, four, or five substituents independently selected from alkoxy, alkyl, halo, haloalkoxy, haloalkyl, and nitro.

The term "arylalkyl," as used herein, refers to an alkyl group substituted with one, two, or three aryl groups.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "arylsulfonyl," as used herein, refers to an aryl group attached to the parent molecular moiety through a sulfonyl group.

The term "carbonyl," as used herein, refers to —C(O)—.

The term "carboxy," as used herein, refers to —$CO_2H$.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic or bicyclic hydrocarbon ring system having three to ten carbon atoms and zero heteroatoms. Representative examples of cycloalkyl groups include, but are not limited to, cyclopropyl, cyclobutyl, and cyclopentyl.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, quinazolinyl, quinolinyl, thiazolyl, thienyl, and thiomorpholinyl. The heterocyclyl groups of the present disclosure are optionally substituted with one, two, three, four, or five substituents independently selected from alkoxy, alkoxycarbonyl, alkyl, alkylcarbonyl, aryl, carboxy, cycloalkyl, cycloalkyloxy, cyano, halo, haloalkoxy, haloalkyl, a second heterocyclyl group, hydroxy, nitro, —$NR^cR^d$, ($NR^cR^d$)carbonyl, and oxo; wherein the aryl and the second heterocyclyl group are further optionally substituted with one, two, three, four, or five substituents independently selected from alkoxy, alkyl, halo, haloalkoxy, haloalkyl, and nitro.

The term "heterocyclylalkyl," as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "nitro," as used herein, refers to —$NO_2$.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkoxy, alkyl, aryl, arylalkyl, cycloalkyl, (cycloalkyl)alkyl, heterocyclyl, and heterocyclylalkyl; or $R^a$ and $R^b$ together with the nitrogen atom to which they are attached form a five or six-membered monocyclic heterocyclic ring.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkoxycarbonyl, alkyl, and alkylcarbonyl.

The term "($NR^cR^d$)alkoxy," as used herein, refers to an ($NR^cR^d$)alkyl group attached to the parent molecular moiety through an oxygen atom.

The term "($NR^cR^d$)alkyl," as used herein, refers to an alkyl group substituted with one, two, or three —$NR^cR^d$ groups.

The term ($NR^cR^d$)carbonyl," as used herein, refers to an —$NR^cR^d$ group attached to the parent molecular moiety through a carbonyl group.

The term "—$NR^eR^f$," as used herein, refers to two groups, $R^e$ and $R^f$, which are attached to the parent molecular moiety through a nitrogen atom. $R^e$ and $R^f$ are independently selected from hydrogen, alkyl, aryl, and arylalkyl.

The term "($NR^eR^f$)carbonyl," as used herein, refers to an —$NR^eR^f$ group attached to the parent molecular moiety through a carbonyl group.

The term "($NR^eR^f$)carbonylalkyl," as used herein, refers to an ($NR^eR^f$)carbonyl group attached to the parent molecular moiety through an alkyl group.

The term "($NR^eR^f$)sulfonyl," as used herein, refers to an —$NR^eR^f$ group attached to the parent molecular moiety through a sulfonyl group.

The term "oxo," as used herein, refers to =O.

The term "sulfonyl," as used herein, refers to —$SO_2$—.

The term "prodrug," as used herein, represents compounds which are rapidly transformed in vivo to the parent compounds by hydrolysis in blood. Prodrugs of the present disclosure include esters of hydroxy groups on the parent molecule, esters of carboxy groups on the parent molecule, and amides of the amines on the parent molecule.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

The following figure shows the designations for the compounds of the present disclosure.

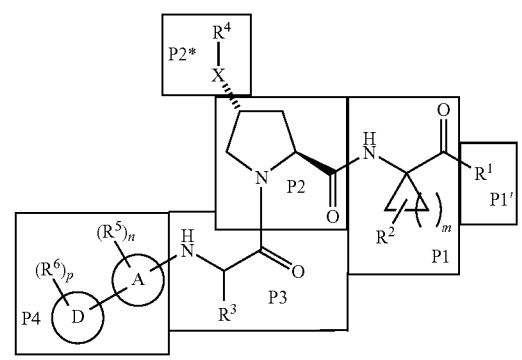

Asymmetric centers exist in the compounds of the present disclosure. For example, the compounds may include P1 cyclopropyl element of formula

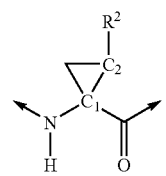

P1 wherein $C_1$ and $C_2$ each represent an asymmetric carbon atom at positions 1 and 2 of the cyclopropyl ring.

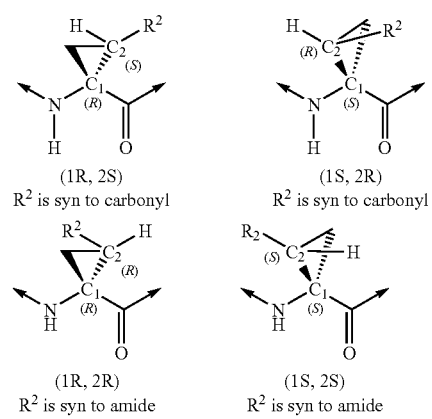

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an alginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Pharmaceuticals Inc., New York, NY |

TABLE 1-continued

| Brand Name | Physiological Class | Type of Inhibitor or Target | Source Company |
|---|---|---|---|
| Summetrel | Antiviral | antiviral | Endo Pharmaceuticals Holdings Inc., Chadds Ford, PA |
| GS-9132 (ACH-806) | Antiviral | HCV Inhibitor | Achillion/ Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/ Viropharma |
| NM-283 | Antiviral | NS5B Replicase Inhibitor | Idenix/ Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |

TABLE 1-continued

| Brand Name | Physiological Class | Type of Inhibitor or Target | Source Company |
|---|---|---|---|
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |

TABLE 1-continued

| Brand Name | Physiological Class | Type of Inhibitor or Target | Source Company |
| --- | --- | --- | --- |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| TMC-435350 | Antiviral | serine protease inhibitor | Tibotec/Medivir |
| MK-7009 | Antiviral | serine protease inhibitor | Merck |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: THF for tetrahydrofuran; DBU for 1,8-diazabicyclo[5.4.0]undec-7-ene; CDI for 1,1'-carbonyldiimidazole; Boc or BOC for tert-butoxycarbonyl; TFA for trifluoroacetic acid; HATU for O-(7-azabenzotriazol-1-yl)-N,N,N',N'-tetramethyluronium phosphate; PyBOP for benzotriazol-1-yl-oxy-tris-pyrrolidino-phosphoniumhexafluorophosphate; MeI for methyl iodide; MOtBu for potassium, sodium, or lithium tert-butoxide; TBME or MTBE for tert-butyl methyl ether; DMF for N,N-dimethylformamide; DMSO for dimethylsulfoxide; DEAD for diethylazodicarboxylate; Ph for phenyl; POPd for [(t-Bu)$_2$POH]$_2$ PdCl$_2$; NaOBu for sodium tert-butoxide; OAc for acetate; MeOH for methanol; DCM for dichloromethane; t-BuOK for potassium tert-butoxide; PyBrop for bromo-tris-pyrrolidino phosphoniumhexafluorophosphate; NMO for N-methylmorpholine-N-oxide; NMM for N-methylmorpholine; HBTU for O-benzotriazole-N,N,N',N'-tetramethyl-uroniumhexafluorophosphate; DIEA, DIPEA, or iPr$_2$EtN for diisopropylethylamine; HOBt or HOBT for N-hydroxybenzotriazole; n-BuLi for n-butyllithium; t-BuLi or tBuLi for tert-butyllithium; DCM for dichloromethane; 4-DMAP or DMAP for 4-N,N-dimethylaminopyridine; DCE for 1,2-dichloroethane; HOAt for 1-hydroxy-7-azabenzotriazole; Fmoc for 9-fluorenylmethyloxycarbonyl; PVP for polyvinylpyridine; NBS for N-bromosuccinimide; (i-PrO)$_3$B for triisopropoxyborane; TMSCHN$_2$ for trimethylsilyldiazomethane; RT or rt for room temperature or retention time (context will dictate); MeCN for acetonitrile; and EtOAc for ethyl acetate.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Scheme I shows the general process wherein compounds of Formula (I) are constructed by the coupling of tripeptide carboxylic acid intermediate (1) with a P1' sulfonamide. Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or methylene chloride in the presence of a base such as DBU.

Scheme I

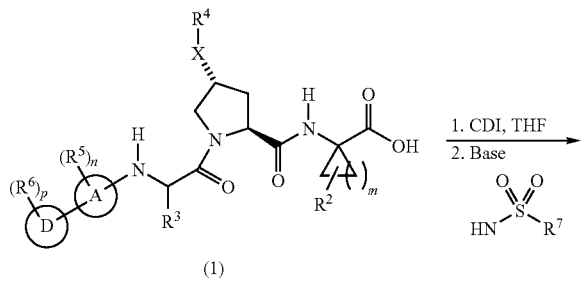

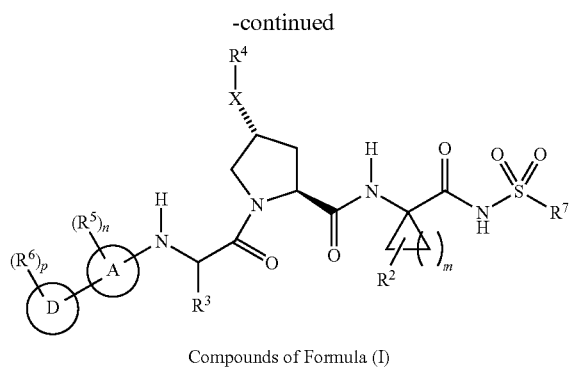

Compounds of Formula (I)

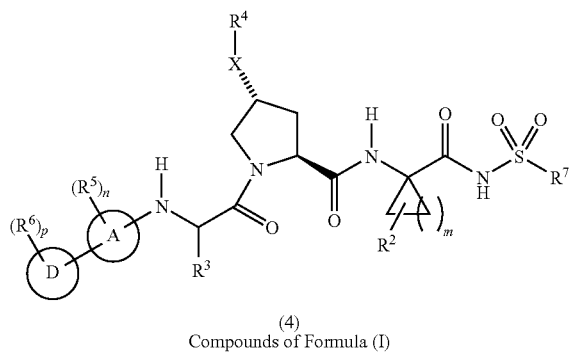

(4)
Compounds of Formula (I)

An alternative process for the construction of compounds of Formula (I) is shown in Scheme II. Therein the P1' sulfonamide element is coupled to the P1 element using the process employed in Scheme I. The resulting P1-P1' moiety can then be deprotected at its amino terminus. In this general example a Boc protecting group is employed but one skilled in the art would recognize that a number of suitable amino protecting groups could be employed in this process. The Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme II. The coupling of said HCl amine salt (3) with the carboxyl terminus of a P4-P3-P2 intermediate can be achieved using coupling reagents, such as HATU, in solvents such as dichloromethane to provide compounds of Formula (I) (4).

An alternative process for the construction of compounds of Formula (I) is shown in Scheme III. Here the hydrochloride salt of the P1-P1' terminal amine (1) is coupled to the free carboxyl group of the P2 element using coupling agents such as PyBOP, in the presence of a base such as diisopropylamine, and in a solvent such as methylene chloride. The resulting P2-P1-P1' intermediate can be converted to compounds of Formula (I) in a two step process wherein the first step is deprotection of the P2 amine terminus using an acid such as TFA in a solvent such as methylene chloride. The resulting trifluoroacetic acid salt can be coupled with the carboxyl terminus of the P4-P3 element using standard coupling agents such as PyBop in the presence of base such as diisopropyl amine, and using solvents such methylene chloride to provide compounds of Formula (I) (4).

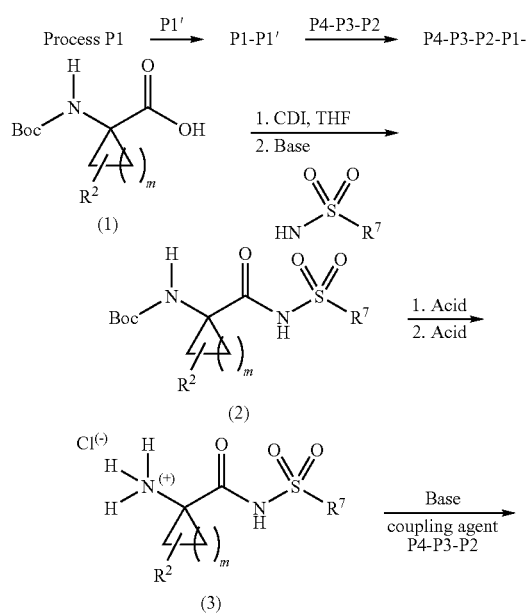

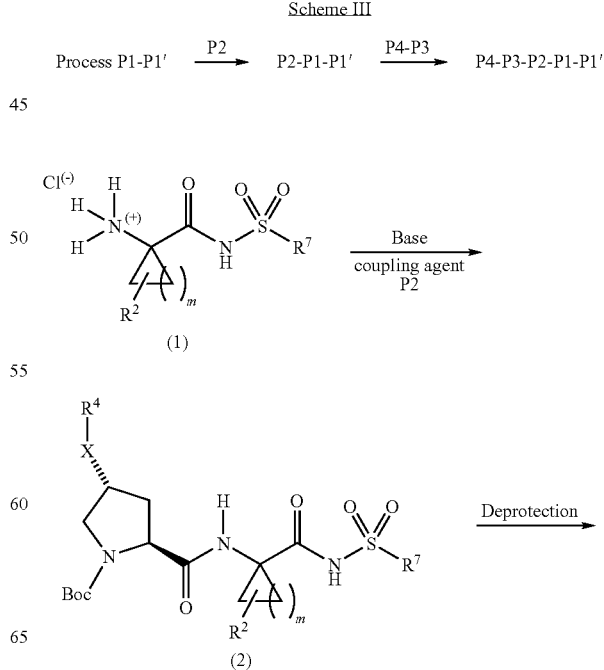

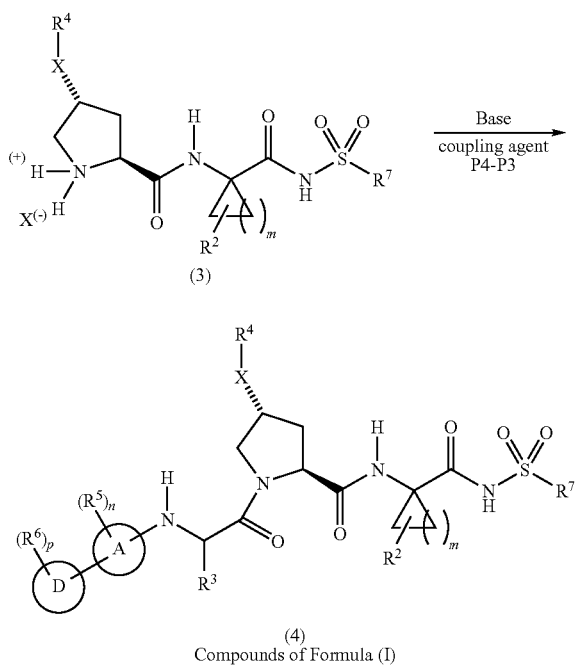

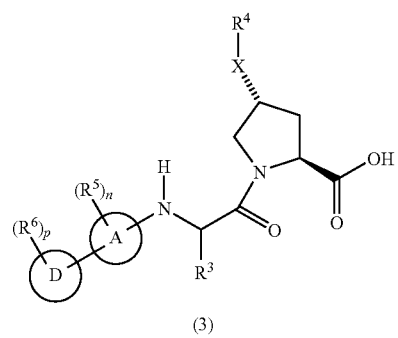

The P4-P3-P2 intermediate utilized in the above schemes can be constructed as previously described with a further description of this process shown in general Scheme IV. The free carboxyl terminus of the P4-P3 intermediate (1), can be coupled to the amino terminus of the P2 element to provide the P4-P3-P2 dipeptide (2). The carboxyl terminus of the P4-P3-P2 intermediate can be deprotected by saponification of the ester group to provide P4-P3-P2 as the free carboxylic acid (3). Intermediates like (3) can be converted to compounds of Formula (I) using the methods described herein.

In the construction of compounds of Formula (I), the P1' terminus is incorporated into the molecules using one of the general processes outlined above and described in more detail below. In some examples the P1' elements, that is the cycloalkyl or alkyl sulfonamides, are commercially available or can be prepared from the corresponding alkyl or cycloalkylsulfonyl chloride by treating the sulfonyl chloride with ammonia. Alternatively, these sulfonamides can be synthesized using the general process outline in Scheme V. Commercially available 3-chloropropylsulfonyl chloride (1) is converted to a suitably protected sulfonamide, for example, by treatment with tert-butyl amine. The sulfonamide obtained (2) is then converted to the corresponding cycloalkylsulfonamide by treatment with two equivalents of a base such as butyllithium in a solvent such as THF at low temperature. The resulting cycloalkylsulfonamide can be deprotected by treatment with an acid to provide the desired unprotected cycloalkylsulfoamide.

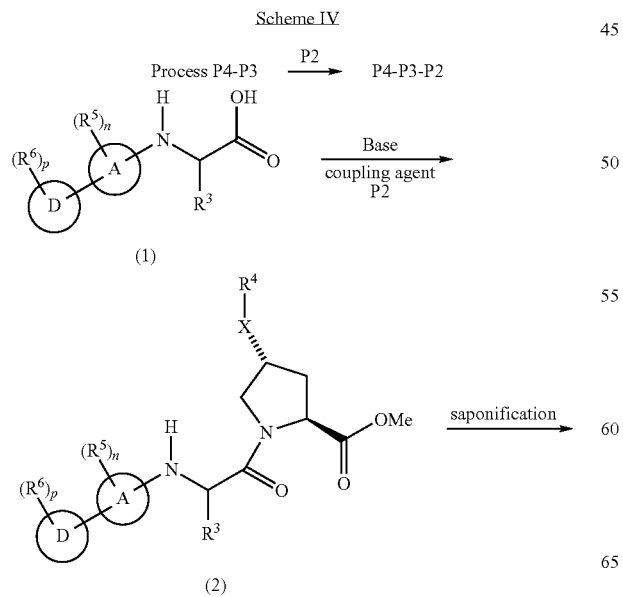

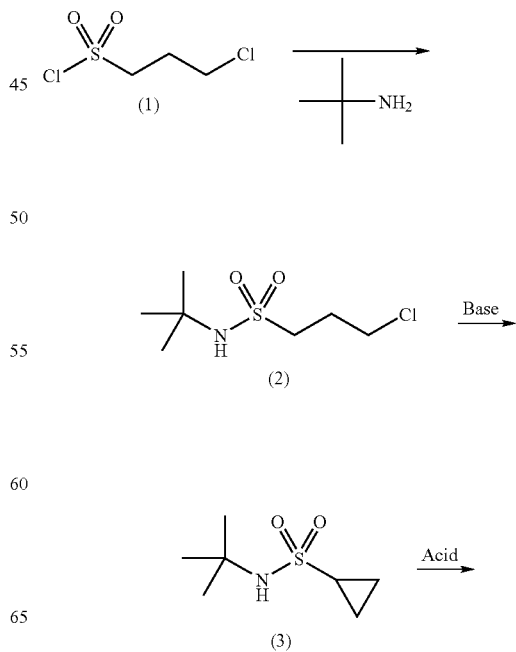

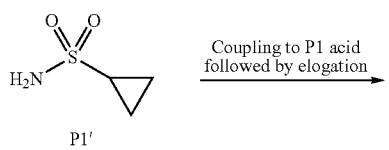

Substituted cycloalkysulfonamides can also be incorporated into compounds of Formula (I) using a modification of the above said procedure. For example, intermediate 2 of Scheme VI can be treated with two equivalents of base such as butyllithium and the resulting reaction mixture can be treated with an electrophile such as methyl iodide to provide a substituted cycloalkylsulfonamide (3). This intermediate (3) can be deprotected at the N-terminus and the resulting compound (4) utilized as an intermediate in the preparation of compounds of Formula (I).

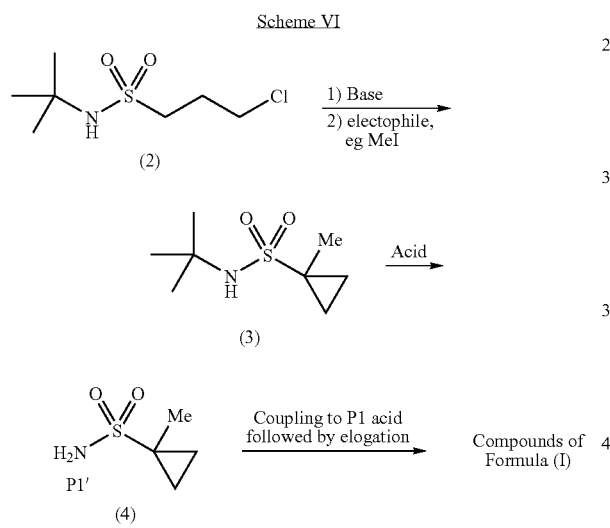

The P1' intermediates employed in generating compounds of Formula (I) are in some cases derived from sulfamide derivatives. In such cases the sulfamide intermediates are available by several synthetic routes as, for example, by the pathway outlined in Scheme VII.

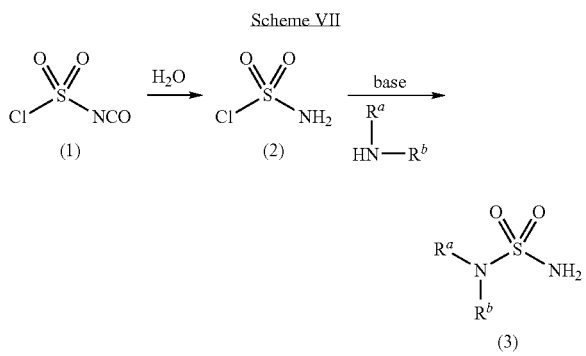

Sulfamoyl chloride (2) can be prepared in situ by the addition of water (e.g., 1 equivalent) to chlorosulfonyl isocyanate 1 (e.g., 1 equivalent) in a solvent such as THF while maintained at a low temperature such as −20° C. The resulting solution is then allowed to warm to 0° C. To this solution a base, such as anhydrous triethylamine (eg., 1 equivalent), is added followed by an amine (eg., 1 equivalent). The reaction mixture is then warmed to room temperature, filtered, and the filtrate concentrated to provide the desired sulfamides (3).

The sulfamides can be incorporated into compounds of Formula (I) by several processes as, for example, by following the synthetic pathway defined in Scheme VIII. A carboxylic acid P1 element (1) is treated with an activating agent such as CDI. In a separate flask, a strong base is added to a solution of the above described sulfamide and the resulting reaction mixture is stirred for several hours after which this reaction mixture is added to the flask containing the activated carboxylic acid, to provide acylsulfamide derivatives (2). Intermediates like 2 can be converted to compounds of Formula (I) as described herein.

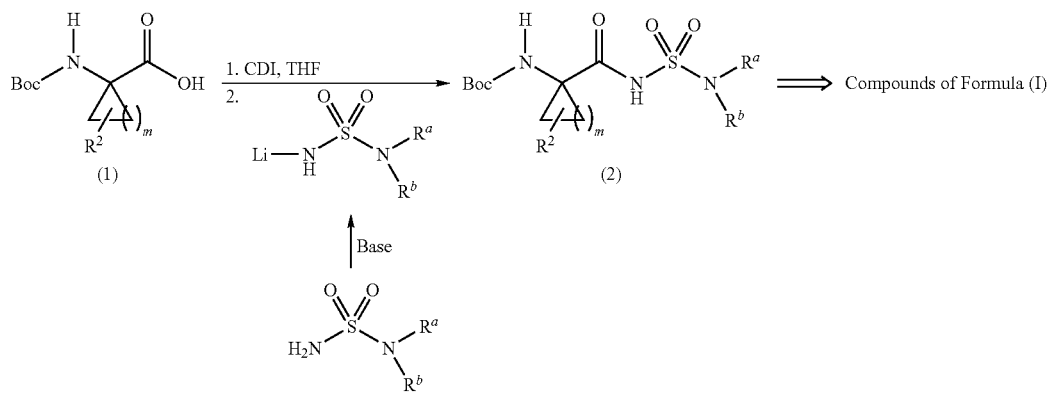

The P1 elements utilized in generating compounds of Formula (I) are in some cases commercially available, but are otherwise synthesized using the methods described herein and are subsequently incorporated into compounds of Formula (I) using the methods described herein. The substituted P1 cyclopropylamino acids can be synthesized following the general process outline in Scheme IX.

Treatment of commercially available or easily synthesized imine (1) with 1,4-dihalobutene (2) in presence of a base provides the resulting imine (3). Acid hydrolysis of 3 then provides 4, which has an allyl substituent syn to the carboxyl group, as a major product. The amine moiety of 4 can protected using a Boc group to provide the fully protected amino acid 5. This intermediate is a racemate which can be resolved by an enzymatic process wherein the ester moiety of 5 is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, the more preferred stereoisomer for integration into compounds of Formula (I) is 5a which houses the (1R,2S) stereochemistry. In the presence of the enzyme, this enantiomer does not undergo ester cleavage and thereby this enantiomer, 5a, is recovered from the reaction mixture. However, the less preferred enantiomer, 5b, which houses the (1S,2R) stereochemistry, undergoes ester cleavage, i.e., hydrolysis, to provide the free acid 6. Upon completion of this reaction, the ester 5a can be separated from the acid product 6 by routine methods such as, for example, aqueous extraction methods or chromatography.

Procedures for making P2 intermediates and compounds of Formula (I) are shown in the schemes below. It should be noted that in many cases reactions are depicted for only one position of an intermediate. However, it is to be understood that such reactions could be used to impart modifications to other positions within this intermediate. Moreover, said intermediates, reaction conditions, and methods given in the specific examples are broadly applicable to compounds with other substitution patterns. Both general and specific examples are non-limiting.

$R^z$ is hydrogen or a substituent as listed in the definition of the term "heterocyclyl." Each $R^z$ is independent, meaning that its identity in one position is independent from its identity in any other position.

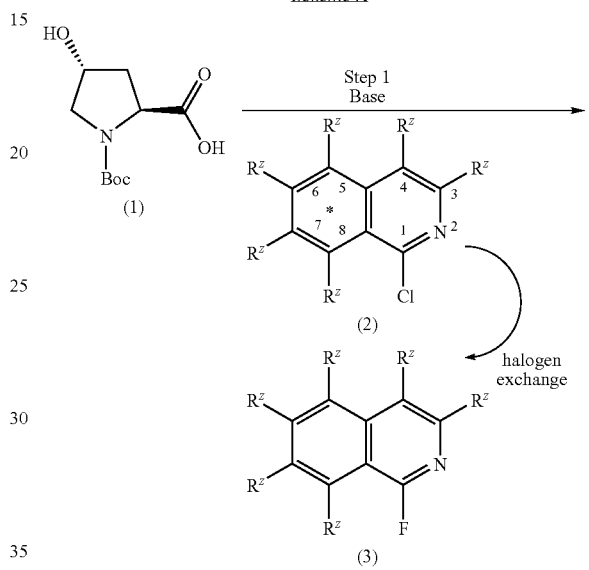

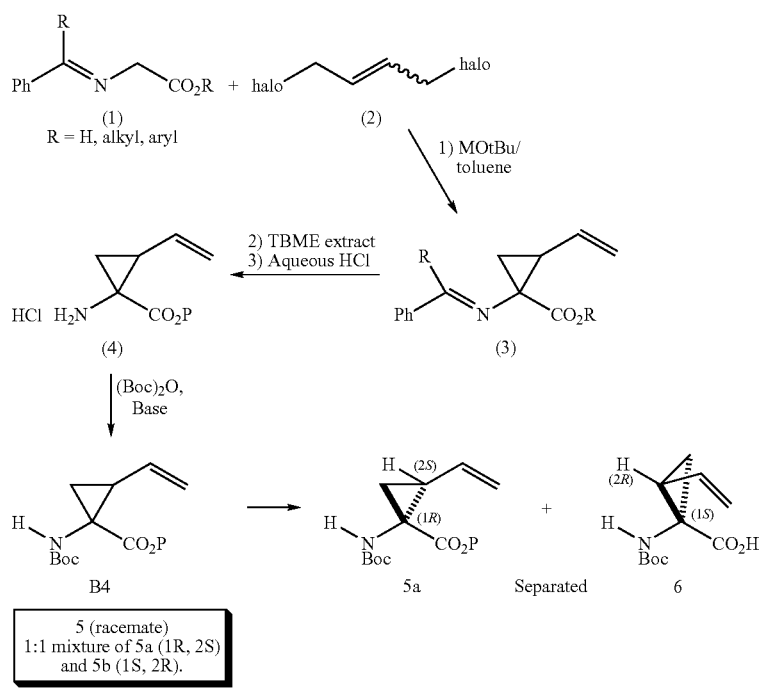

-continued

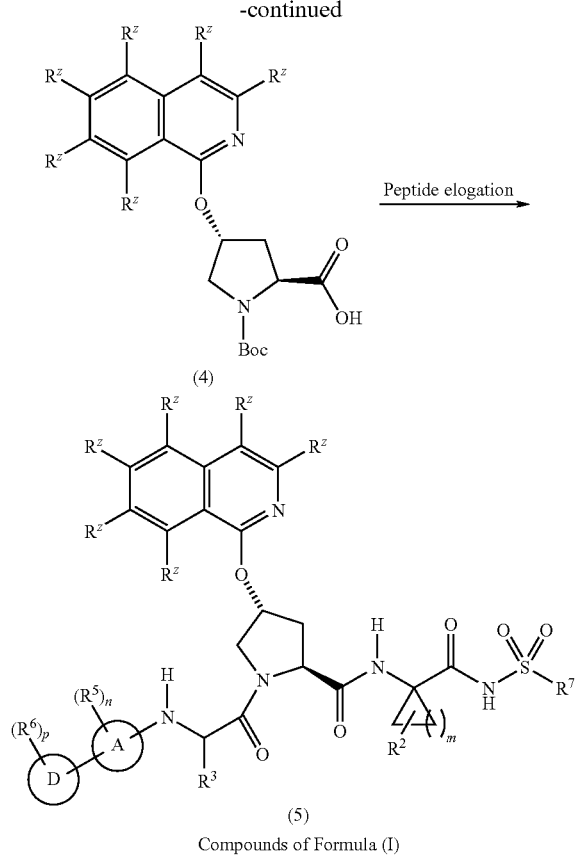

(4)

(5)

Compounds of Formula (I)

Scheme X shows the coupling of an N-protected C4-hydroxyproline moiety with a heterocycle to form intermediate (4) and the subsequent modification of said intermediate (4) to a compound of Formula (I) by the process of peptide elongation as described herein. It should be noted that in the first step, that is the coupling of the C4-hydroxy proline group with the heteroaryl element, a base is employed. One skilled in the art would recognized that this coupling can be done using bases such as potassium tert-butoxide, or sodium hydride, in a solvent such as DMF or DMSO or THF. This coupling to the isoquinoline ring system occurs at the C1 position (numbering for isoquinoline ring system shown in intermediate 2 of Scheme XI) and is directed by the chloro group which is displaced in this process. It should be noted that alternative leaving groups can be utilized at this position (e.g., fluoro) as shown in the scheme. Said fluoro intermediates (3) are available from the corresponding chloro compound using literature procedures described herein.

An alternative to the method described above for the coupling of the C4-hydroxyproline to the isoquinoline nucleus is provided in the Mitsunobu reaction as depicted in step 1 of Scheme XI. In this general reaction scheme a C4-hydroxy proline derivative is coupled to an isoquinoline ring system. This reaction makes use of reagents such as triphenylphosphine and DEAD (diethylazodicarboxylate) in aprotic solvents such as THF or dioxane and can be used for the formation of heteroaryl ethers. Note that in the course of this coupling reaction the stereochemistry of the C4 chiral center in the C4-hydroxyproline derivative is inverted and thereby it is necessary to use the C4-hydroxyproline derivative housing the (S) stereochemistry at the C4 position as starting material (as shown in Scheme XI). It should be noted that numerous modifications and improvements of the Mitsunobu reaction have been described in the literature, the teachings of which are incorporated herein.

Scheme XI

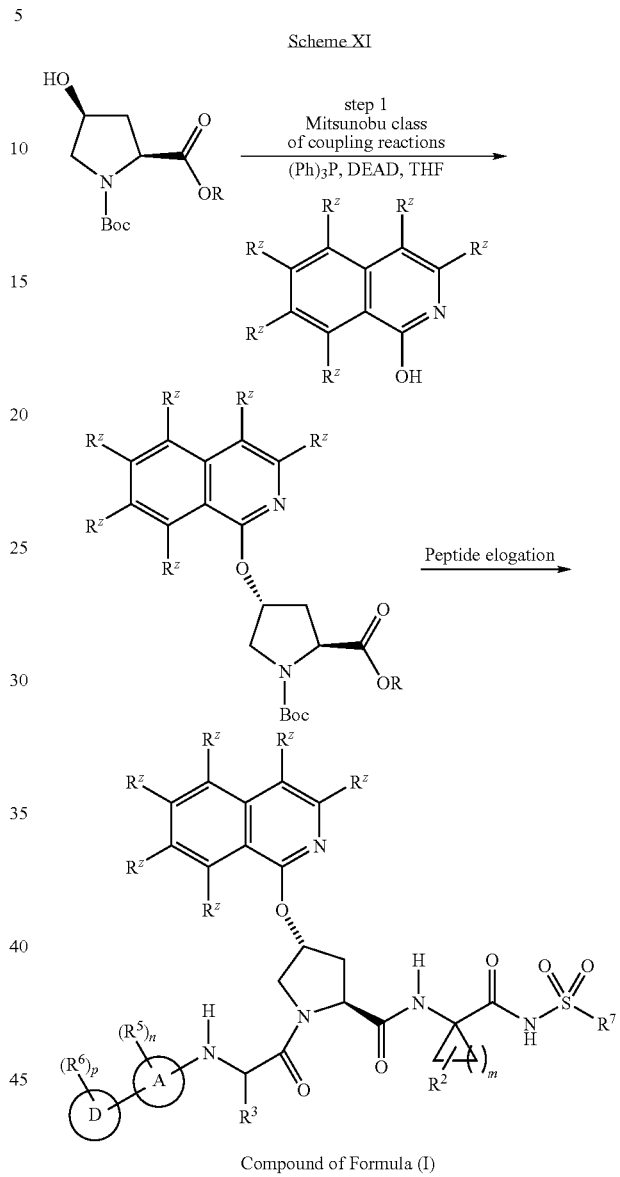

Compound of Formula (I)

In examples herein, isoquinolines are incorporated into the final compounds and specifically into the P2 region of said compounds. One skilled in the art would recognize that a number of general methods are available for the synthesis of isoquinolines. Moreover, the isoquinolines generated by these methods can be readily incorporated into final compounds of Formula (I) using the processes described herein. One general methodology for the synthesis of isoquinolines is shown in Scheme XII, wherein cinnamic acid derivatives, shown in general form as structure (2), are converted to 1-chloroisoquinolines in a four step process. The chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is coverted to the corresponding isoquinolone (4) while heating to a temperature of approximately 190° C. in a high boiling solvent such a diphenylmethane. This reaction is general and provides moderate to good yields of substituted isoquinolone from the corresponding cinnamic acid derivatives. It should noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) of Scheme XII can be converted to the corresponding 1-chloroisoquinoline by treatment with phosphorous oxychloride. This reaction is general and can be applied to the isoquinolones shown herein.

An alternative method for the synthesis of the isoquinoline ring system is the Pomeranz-Fritsh procedure. This general method is outlined in Scheme XIII. The process begins with the conversion of a benzaldehyde derivative (1) to a functionalized imine (2). The imine is then converted to the isoquinoline ring system by treatment with acid at elevated temperature. This isoquinoline synthesis of Scheme XIII is general, and it should be noted that this process is particularly useful in procuring isoquinoline intermediates that are substituted at the C8 position. The intermediate isoquinolines (3) can be converted to the corresponding 1-chloroquinolines (5) in a two step process as shown. The first step in this sequence is the formation of the isoquinoline N-oxide (4) by treatment of isoquinoline (3) with meta-chloroperbenzoic acid in an aprotic solvent such as dichloromethane. Intermediate (4) can be converted to the corresponding 1-chloroquinoline by treatment with phosphorous oxychloride in refluxing chloroform. Note that this two step process is general for the formation of chloroisoquinolines from isoquinolones.

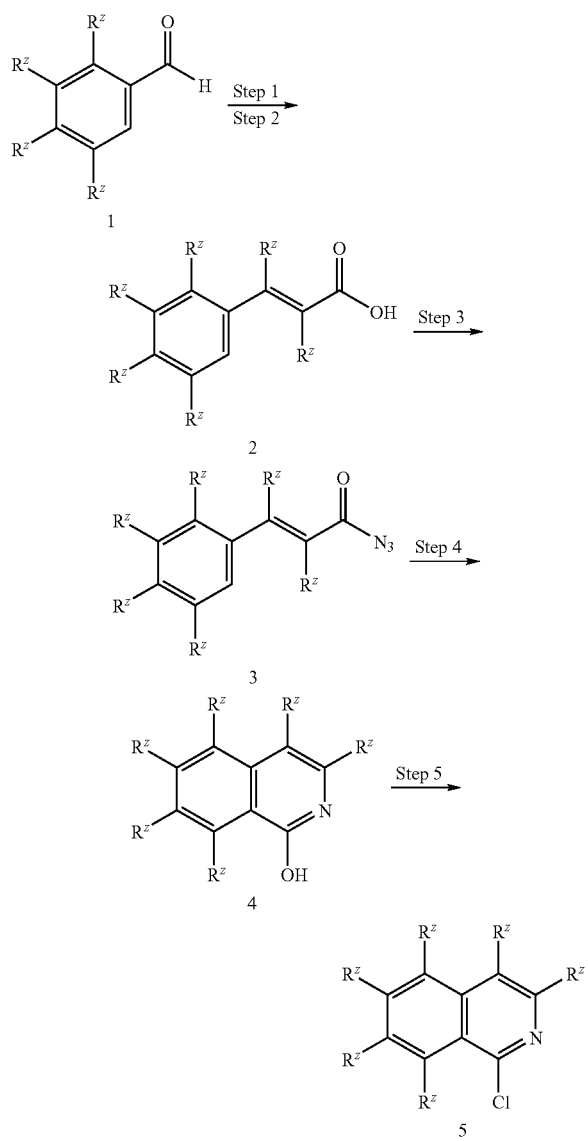

Reference: N. Briet at al, Tetrahedron, 2002, 5761

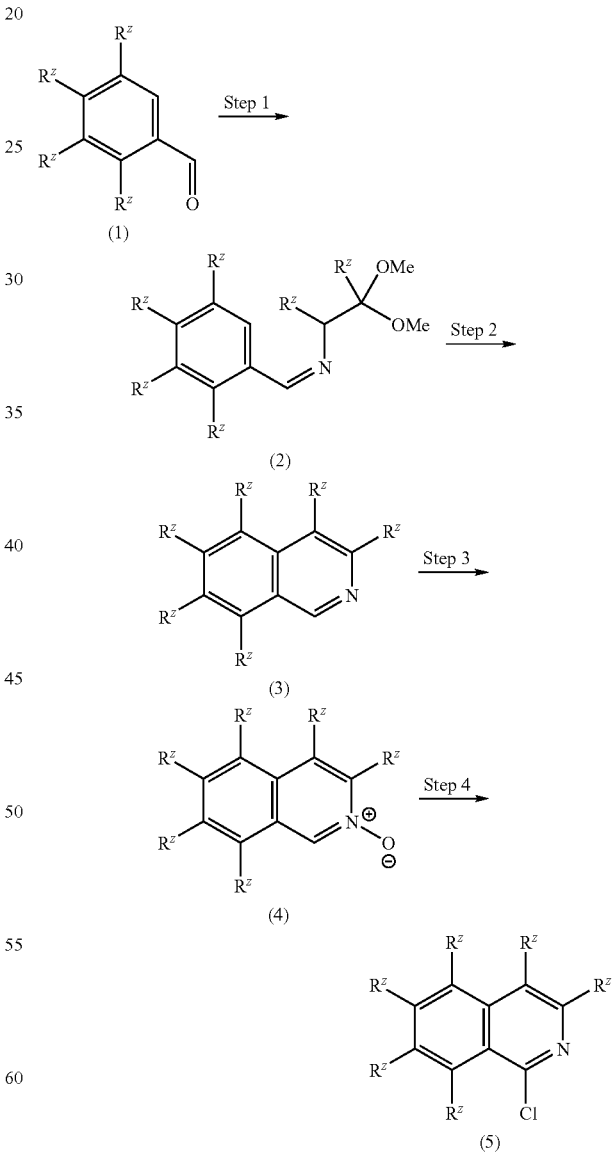

Pomeranz-Fritsch Synthesis
K. Hirao, R. Tsuchiya, Y. Yano, H. Tsue, Heterocycles 42(1) 1996, 415-422

Another method for the synthesis of the isoquinoline ring system is shown in Scheme XIV. In this process an ortho-alkylbenzamide derivative (1) is treated with a strong base such as tert-butyllithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of Scheme XIV can be converted to the corresponding 1-chloroquinoline by the methods described herein.

Scheme XIV

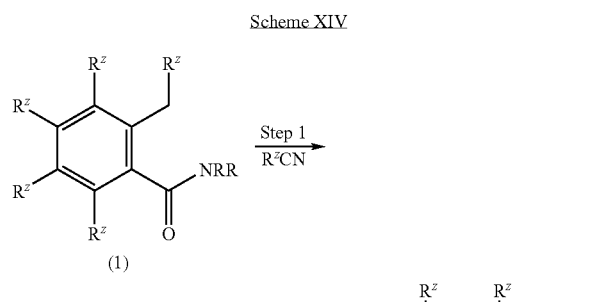

An additional method for the synthesis of isoquinolines is shown in Scheme XV. The deprotonation of intermediate (1) using tert-butyllithium is described above. In the present method however, the intermediate anion is trapped by an ester, resulting in the formation of intermediate (2) as shown below. In a subsequent reaction, ketone (2) is condensed with ammoniumn acetate at elevated temperature providing for the formation of quinolone (3). This reaction is general and can be applied to the construction of substituted isoquinolones which can then be converted to the corresponding 1-chloroisoquinolines as described herein.

Scheme XV

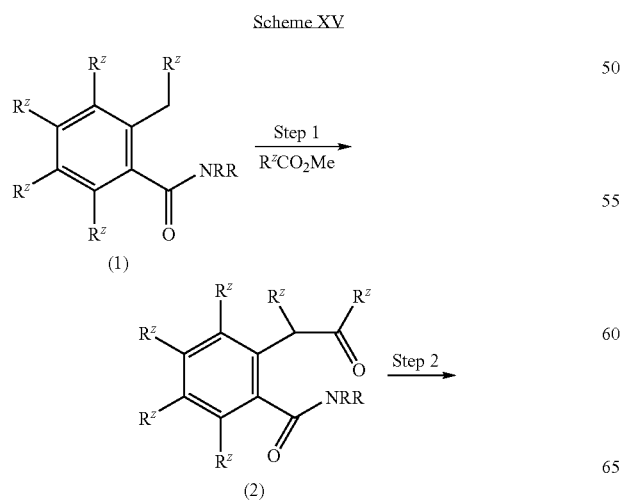

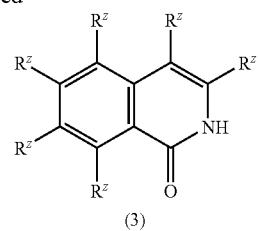

Another method for the construction of isoquinolines is found in Scheme XVI. In the first step of this process an ortho-alkylarylimine derivatives such as (1) are subjected to deprotonation conditions (sec-butyl lithium, THF) and the resulting anion is quenched by the addition of an activated carboxylic acid derivative such as a Weinreb amide. The resulting ketoimine (2) can be converted to the corresponding isoquinoline by condensation with ammonium acetate at elevated temperatures. This method is general and can be used for the synthesis of substituted isoquinolines. The isoquinolines can be converted to the corresponding 1-chloroquinoline by the methods described herein.

Scheme XVI

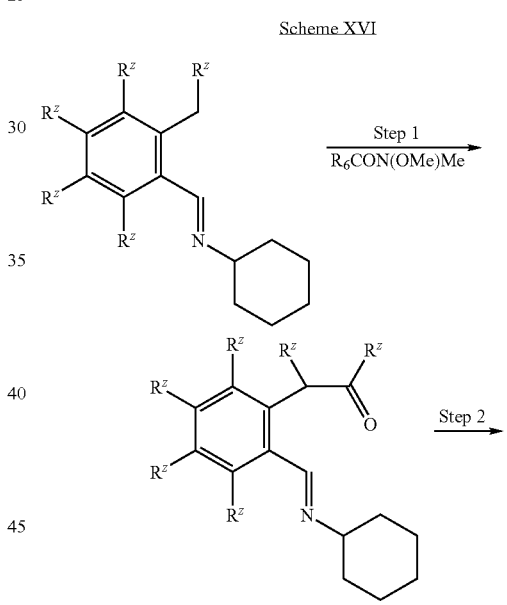

L. Flippin, J. Muchowski, JOC, 1993, 2631-2632

The isoquinolines described herein, and which are incorporated into the compounds of Formula (I), can be further functionalized. It is obvious to one skilled in the art that additional functionalization of said heterocycles can be done either before or after incorporation of these functionalities into compounds of Formula (I). The following schemes illustrate this point. For example Scheme XVII shows the conversion of a 1-chloro-6-fluoro-isoquinoline to the corresponding 1-chloro-6-alkoxy-isoquinoline species, by treatment of (1) with a sodium or potassium alkoxide species in the alcohol solvent from which the alkoxide is derived at room tempera- Scheme XVII

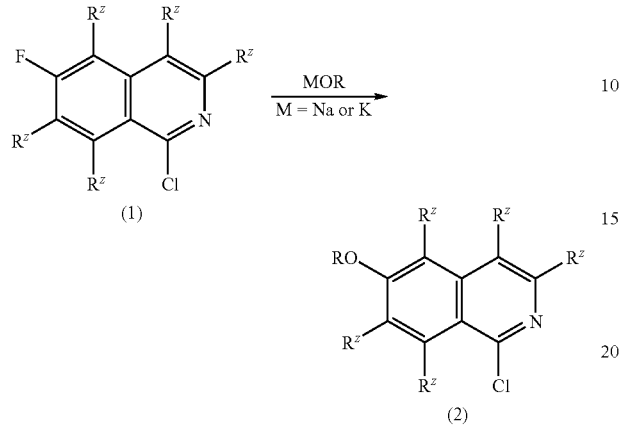

Scheme XVIII provides a general example for the modification of isoquinolines as defined herein by employing palladium mediated coupling reactions. The couplings can be employed to functionalize a heterocycle at each position of the ring system provided the ring is suitably activated or functionalized, as for example with a chloride as shown in the scheme. This sequence begins with 1-chloroisoquinoline (1) which upon treatment with metachloroperbenzoic acid can be converted to the corresponding N-oxide (2). Intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the scheme. Intermediate (5) can undergo a Suzuki coupling with an aryl boronic acid, in the presence of a palladium reagent and base, and in a solvent such as THF or toluene or DMF to provide the C3-arylisoquinoline intermediate (6). Heteroarylboronic acids can also be employed in this palladium-mediated coupling process to provide C3-heteroarylisoquinolines. Intermediate (6) can be converted into final compounds of Formula (I) by the methods described herein.

Scheme XVIII

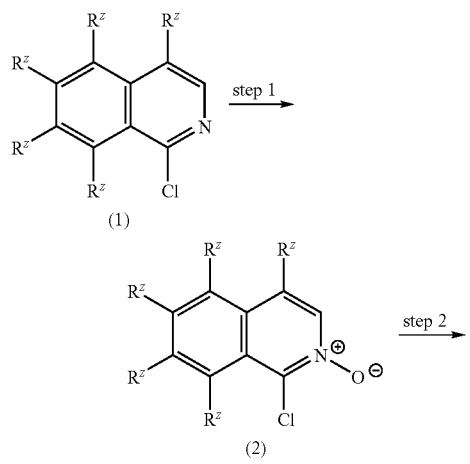

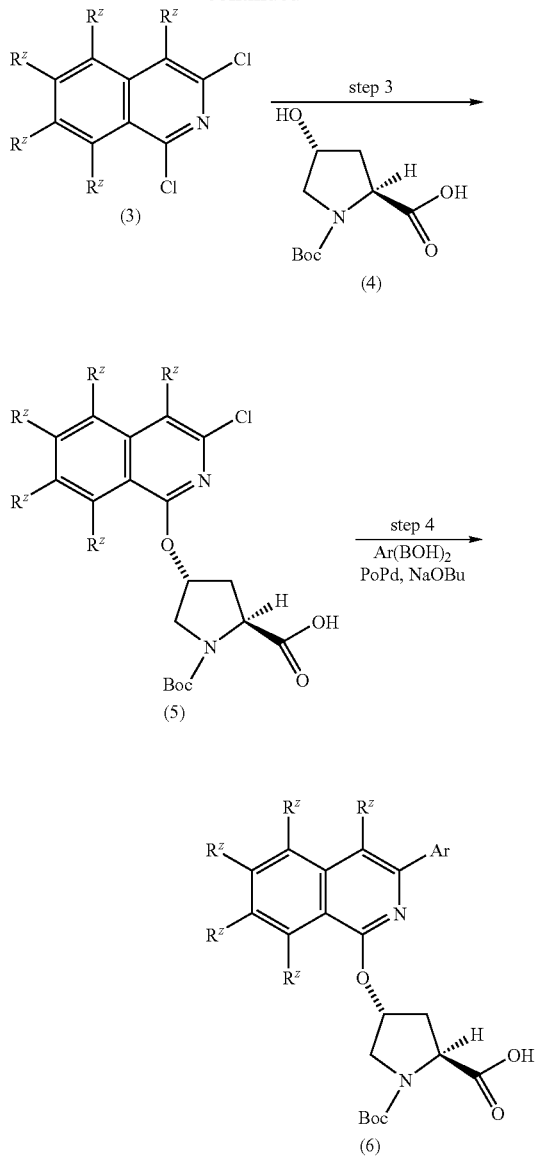

Palladium mediated couplings of isoquinoline systems with aryl or heteroaryl elements can also be employed at a later synthetic stage in the construction of compounds of Formula (I) as shown in Scheme XIX. Tripeptide acylsulfonamide intermediate (1) is coupled to a 1-chloro-3-bromoisoquinoline (2) using the previously described process to provide intermediate (3) The coupling of (1) and (2) is most efficient in the presence of a catalyst such as lanthanum chloride as described herein. The isoquinoline ring system of intermediate (3) can be further functionalized by employing either Suzuki couplings (Process 1: subjecting (3) to heteroaryl or aryl boronic acids in the presence of a palladium catalyst such as palladium tetrakistriphenylphosphine and a base such as cesium carbonate in solvents such as DMF) or Stille couplings (Process 2: subjecting (3) to heteraryl or aryl tin derivatives in the presence of a palladium catalyst such as palladium tetrakistriphenylphosphine in solvents such as toluene).

Scheme XIX

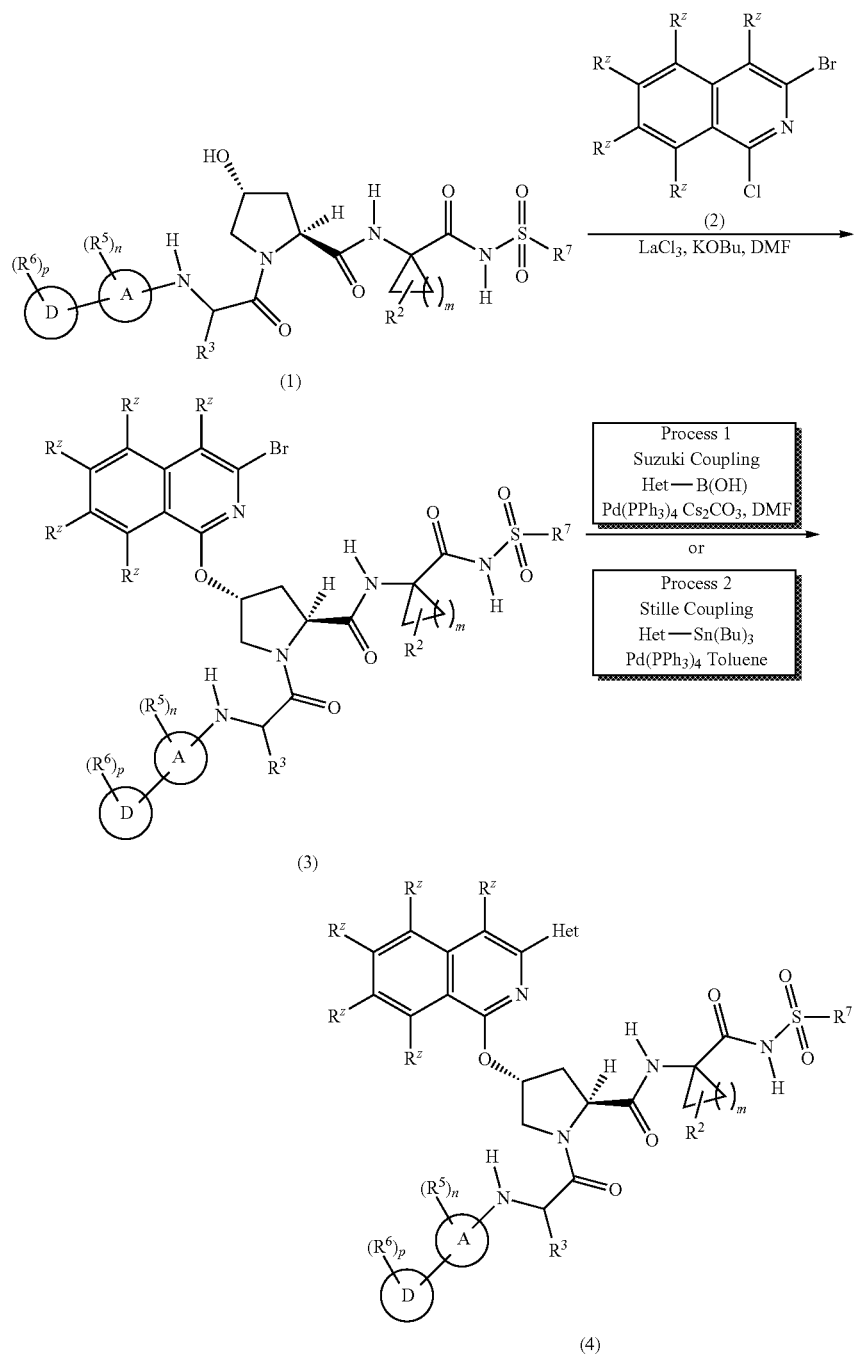

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (*J. Org. Chem.* 1978, 43, 2923).

Preparation of racemic
(1R,2S)/(1S,2R)-1-amino-2-vinylcyclopropane
carboxylic acid ethyl ester

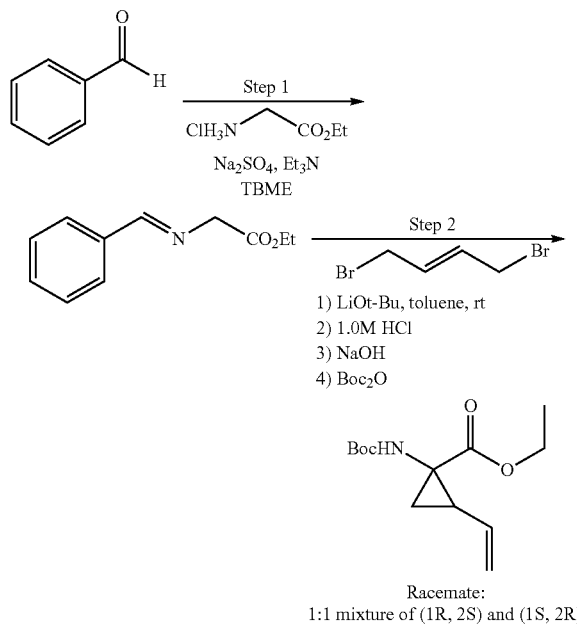

Racemate:
1:1 mixture of (1R, 2S) and (1S, 2R)

Step 1:

Glycine ethyl ester hydrochloride (304 g, 2.16 mole) was suspended in tert-butylmethyl ether (1.6 L). Benzaldehyde (231 g, 2.16 mole) and anhydrous sodium sulfate (155 g, 1.09 mole) were added, and the mixture was cooled to 0° C. using an ice-water bath. Triethylamine (455 mL, 3.26 mole) was added dropwise over 30 minutes and the mixture was stirred for 48 hours at room temperature. The reaction was then quenched by addition of ice-cold water (1 L) and the organic layer was separated. The aqueous phase was extracted with tert-butylmethyl ether (0.5 L) and the organic phases were combined and washed with a mixture of saturated aqueous $NaHCO_3$ (1 L) and brine (1 L). The organic layer was dried over $MgSO_4$, filtered, and concentrated in vacuo to provide 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Step 2:

To a suspension of lithium tert-butoxide (84.1 g, 1.05 mol) in dry toluene (1.2 L), was added dropwise a mixture of the N-benzyl imine of glycine ethyl ester (100 g, 0.526 mol) and trans-1,4-dibromo-2-butene (107 g, 0.500 mol) in dry toluene (0.6 L) over 60 minutes. Upon completion of the addition, the deep red mixture was quenched by addition of water (1 L) and tert-butylmethyl ether (TBME, 1 L). The aqueous phase was separated and extracted a second time with TBME (1 L). The organic phases were combined, 1.0M HCl (1 L) was added and the mixture stirred at room temperature for 2 hours. The organic phase was separated and extracted with water (0.8 L). The aqueous phases were then combined, saturated with salt (700 g), and TBME (1 L) was added and the mixture cooled to 0° C. The stirred mixture was then made basic to pH=14 by the dropwise addition of 10.0M NaOH, the organic layer was separated, and the aqueous phase was extracted with TBME (2×500 mL). The organic extracts were combined, dried over $MgSO_4$, filtered and concentrated to a volume of 1 L. To this solution of free amine was added $Boc_2O$ or di-tert-butyldicarbonate (131 g, 0.600 mol) and the mixture stirred for 4 days at room temperature. Additional di-tert-butyldicarbonate (50 g, 0.23 mol) was added to the reaction and the mixture was refluxed for 3 hours and was then allowed cool to room temperature overnight. The reaction mixture was dried over $MgSO_4$, filtered, and concentrated in vacuo to provide 80 g of crude material. This residue was purified by flash chromatography (2.5 kg of $SiO_2$, eluted with 1% to 2% $CH_3OH/CH_2Cl_2$) to provide 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR ($CDCl_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M-1).

Resolution of
N-Boc-(1R,2S)/(1S,2R)-1-amino-2-vinylcyclopropane
carboxylic acid ethyl ester

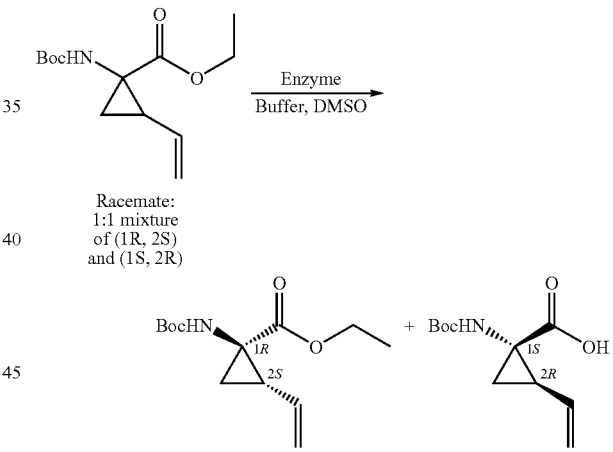

Resolution A:

To an aqueous solution of sodium phosphate buffer (0.1 M, 4.25 liter ("L"), pH 8) housed in a 12 liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 minutes. The reaction temperature was then maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and concentrated in vacuo to give the enantiomerically pure N-Boc-(1R,2S)/-1-amino-2-vinylcyclopropane carboxylic acid ethyl ester as light yellow solid (42.55 g; purity: 97% @210 nm, containing no acid; 100% enantiomeric excess ("ee").

The aqueous layer from the extraction process was then acidified to pH 2 with 50% H$_2$SO$_4$ and extracted with MTBE (2×2 L). The MTBE extract was washed with water (3×100 mL) and concentrated to give the acid as light yellow solid (42.74 g; purity: 99% @210 nm, containing no ester).

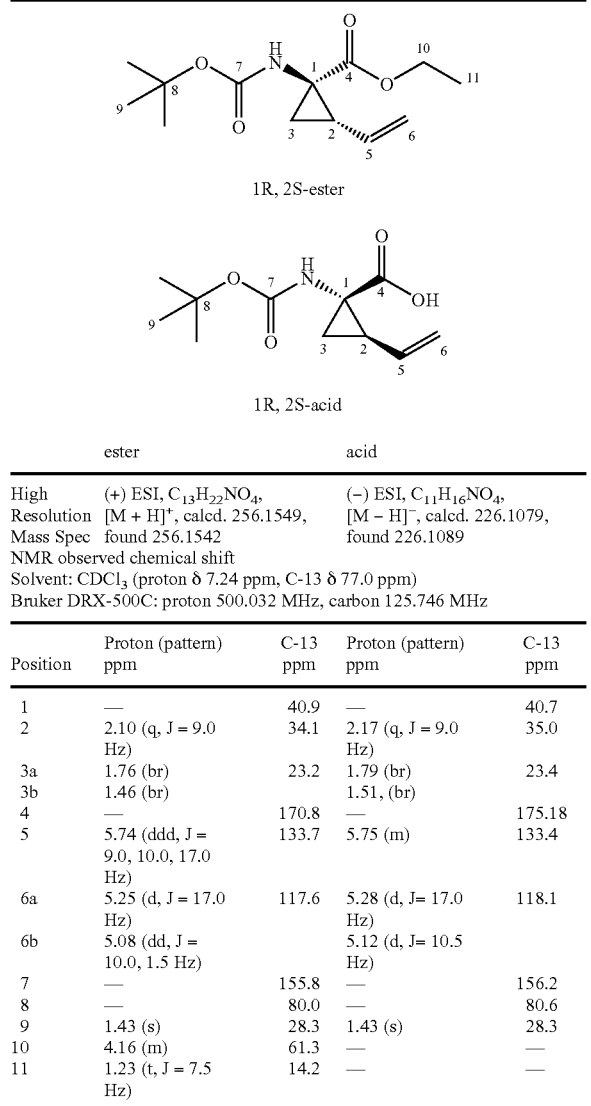

1R, 2S-ester 1R, 2S-acid

| | ester | acid |
|---|---|---|
| High Resolution Mass Spec | (+) ESI, C$_{13}$H$_{22}$NO$_4$, [M + H]$^+$, calcd. 256.1549, found 256.1542 | (−) ESI, C$_{11}$H$_{16}$NO$_4$, [M − H]$^-$, calcd. 226.1079, found 226.1089 |

NMR observed chemical shift
Solvent: CDCl$_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51, (br) | |
| 4 | — | 170.8 | — | 175.18 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B:

To 0.5 mL 100 mM Heps.Na buffer (pH 8.5) in a well of a 24 well plate (capacity: 10 mL/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% as following: 0.1 mL of the reaction mixture was removed and mixed well with 1 mL ethanol; after centrifugation, 10 microliter ("µL") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µL of the supernatant was analyzed with the chiral HPLC and enantio-excess of the ester was determined to be 100%.

Resolution C:

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after centrifugation, 10 µL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 µL of the supernatant was analyzed with the chiral HPLC and enantio-excess of the ester was determined to be 100%.

Samples analysis was carried out in the following manner:
1) Sample preparation: About 0.5 mL of the reaction mixture was mixed well with 10 volumes of ethanol. After centrifugation, 10 µL of the supernatant was injected onto HPLC column.
2) Conversion determination:
Column: YMC ODS A, 4.6×50 mm, S-5 µm
Solvent: A, 1 mM HCl in water; B, CH$_3$CN
Gradient: 30% B for 1 min; 30% to 45% B over 0.5 min; 45% B for 1.5 min; 45% to 30% B over 0.5 minutes.
Flow rate: 2 mL/min
UV Detection: 210 nm
Retention time: acid, 1.2 min; ester, 2.8 minutes.
3) Enantio-excess determination for the ester:
Column: CHIRACEL OD-RH, 4.6×150 mm, S-5 µm
Mobile phase: CH$_3$CN/50 mM HClO$_4$ in water (67/33)
Flow rate: 0.75 mL/min.
UV Detection: 210 nm.
Retention time:
(1S,c2R)-1-amino-2-vinylcyclopropane carboxylic acid 5.2 min;
Racemate (1R,2S)/(1S,2R)-1-amino-2-vinylcyclopropane carboxylic acid ethyl ester 18.5 minutes and 20.0 min;
(1R,2S)-1-amino-2-vinylcyclopropane carboxylic acid ethyl ester 18.5 minutes.
Resolution D:

5 L of 0.3 M sodium phosphate buffer (pH 8) was maintained at 38° C. in a 20 liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funnel. The reaction temperature was then adjusted to 48° C. After 21 hours, enantio-excess of the ester reached 99.3%. Heating was stopped at 24 hours and the reaction was slowly cooled down to room temperature (about 25° C.) and stirred overnight. The pH of the reaction mixture was adjusted to 8.5 with 10 N NaOH and the mixture was extracted with MTBE (2×4 L). The combined MTBE extract was washed with 5% NaHCO$_3$ (3×400 mL) and water (3×400 mL), and concentrated to give enantiomerically pure N-Boc-(1R,2S)/-1-amino-2-vinylcyclopropane carboxylic acid ethyl ester as light yellow crystal (259 g; purity: 96.9% @210 nm, containing no acid; 100% ee).

Resolution E:

10 L of 0.1 M sodium phosphate buffer (pH 8) was maintained at 40° C. in a 20 liter jacked reactor, stirred at 360 rpm. 1.5 liters of Alcalase 2.4 L (Novozymes North America Inc.) was added to the reactor. When the temperature of the mixture closed to 38° C., the pH was adjusted to 8.0 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, the pH was adjusted to 8.0 with 10 N NaOH. After 21 hours, the reaction was cooled down to 25° C., the pH of the reaction mixture was adjusted to 8.5 with 10 N NaOH and the mixture was extracted with MTBE (2×5 L). The combined MTBE extract was washed with 5% NaHCO$_3$ (3×500 mL) and water (3×200 mL), and concentrated to give 110 g of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% @210 nm, containing no acid; 100% ee).

The crystal structure enantiomerically pure N-Boc-(1R,2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester:

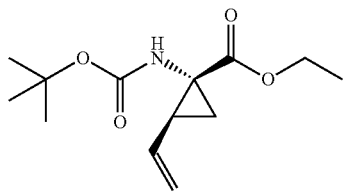

Crystal Data:
Chemical formula: C$_{13}$H$_{21}$N$_1$O$_4$
Crystal system: Orthorhombic
Space Group: P2$_1$2$_1$2$_1$
a = 5.2902(1) Å α = 90°
b = 13.8946(2) Å β = 90°
c = 19.9768(3) Å γ = 90°
V = 1468.40(4) Å$^3$
Z = 4   d$_x$ = 1.155 g cm$^{-3}$
No. of reflections for lattice parameters: 6817
θrange for lattice parameters (°): 2.2-65.2
Absorption coefficient (mm$^{-1}$): 0.700

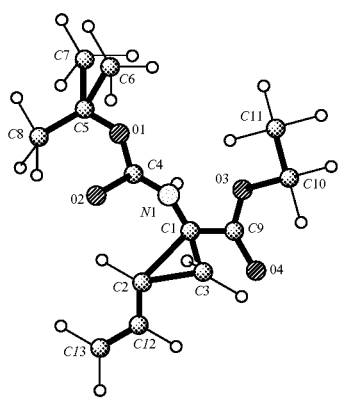

Experimental:
Crystallization
Crystal source: MTBE
Crystal description: Colorless rod
Crystal size (mm): 0.12 × 0.26 × 0.30
Data Collection
Temperature (K): 293
θ$_{max}$ (°): 65.2 (Cu Kα)
No. of reflections measured: 7518
No. of independent reflections: 2390
(R$_{int}$ = 0.0776)
No. of observed reflections (I ≥ 2σ: 2284
Absorption correction (T$_{min}$-T$_{max}$): 0.688-1.000

Resolution F:

5 L of 0.2 M sodium borate buffer (pH 9) was maintained at 45° C. in a 20 liter jacked reactor, and stirred at 400 rpm. Three liter of DI water and four liters of Savinase 16 L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 minutes, via an addition funnel. The reaction temperature was then adjusted to 48° C. After 2 hours, pH was adjusted to pH 9.0 with 10 N NaOH. At 18 hour, enantio-excess of the ester reached 72%, ph was adjusted to 9.0 with 10 N NaOH. At 24 hours, temperature was lowered to 35° C. At 42 hours, the temperature was raised to 48° C. and the pH was adjusted to 9.0 with 10 N NaOH. Heating was stopped at 48 hours and the reaction was slowly cooled down to room temperature (about 25° C.) and stirred overnight. At 66 hours, pH of the reaction mixture was 8.6. The mixture was extracted with MTBE (2×4 L). The combined MTBE extract was washed with 5% NaHCO$_3$ (6×300 mL) and water (3×300 mL), and concentrated to give enantiomerically pure N-Boc-(1R,2S)/-1-amino-2-vinylcyclopropane carboxylic acid ethyl ester as light yellow crystal (101 A g; purity: 95.9% @210 nm, containing no acid; 98.6% ee).

Preparation of chiral (1R,2S)-1-amino-2-vinylcyclopropane carboxylic acid ethyl ester hydrochloride

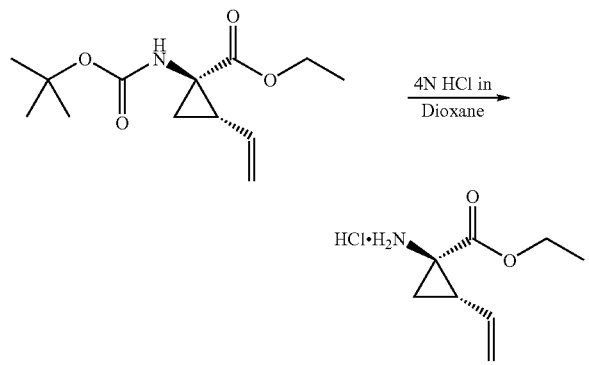

(1R,2S) N-Boc-1-amino-2-vinylcyclopropanecarboxylic acid ethyl ester (8.5 g, 33.3 mmol) was stirred under a nitrogen atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M$^+$+1).

Preparation of N-Boc-(1R,2S)-1-amino-2-cyclopropylcyclopropane carboxylic acid ethyl ester

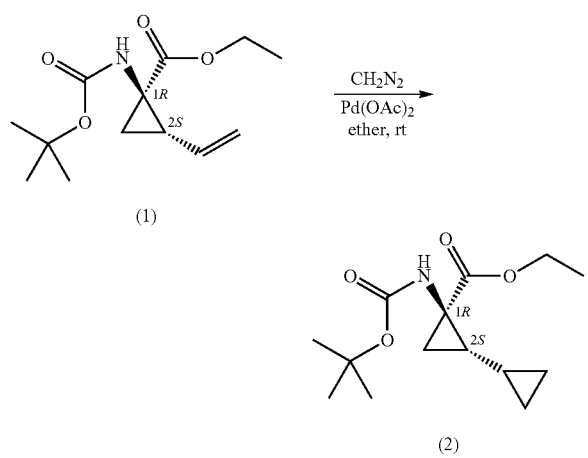

A solution of N-Boc-(1R,2S)-1-amino-2-vinylcyclopropane carboxylic acid (255 mg, 1.0 mmol) in diethyl ether (10 mL) was treated with palladium acetate (5 mg, 0.022 mmol). The orange/red solution was placed under a nitrogen atmosphere. An excess of diazomethane in diethyl ether was added dropwise over the course of 1 hour. The resulting solution was stirred at room temperature for 18 hours. The excess diazomethane was removed using a stream of nitrogen and the resulting solution was concentrated by rotary evaporation to give the crude product. Flash chromatography (10% ethyl acetate/hexane) provided 210 mg (78%) of (1R,2S)—N-Boc-1-amino-2-cyclopropylcyclopropane carboxylic acid ethyl ester as a colorless oil. MS m/z 270 (M$^+$+H).

Preparation of P1'-P1 Intermediates:
Preparation of P1P1':

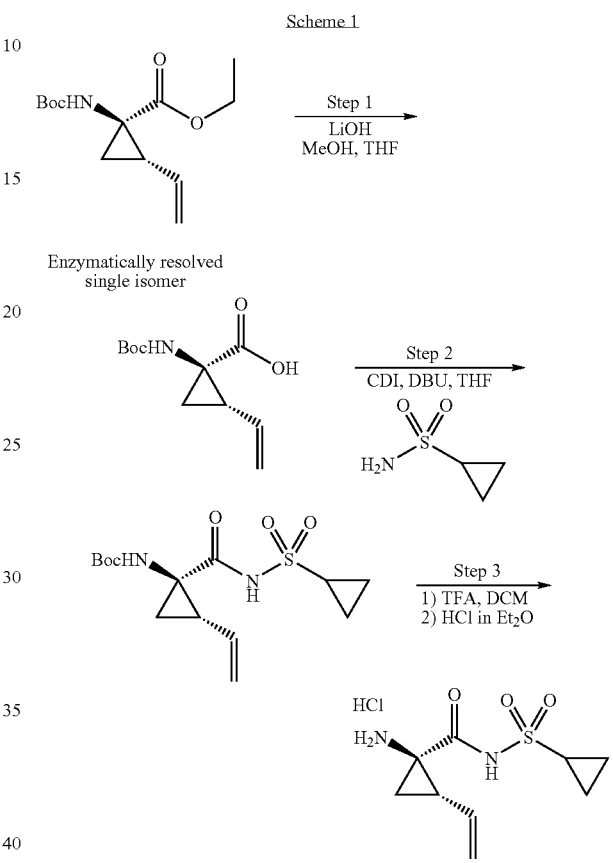

Scheme 1

Step 1

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature. To the mixture was added 1.0M NaOH (15 mL), water (20 mL) and ethyl acetate (20 mL). The mixture was shaken, the phases were separated, and the organic phase was again extracted with 20 mL 0.5M NaOH. The combined aqueous phases were acidified with 1.0M HCl until pH=4 and extracted with ethyl acetate (3×40 mL). The combined organic extracts were washed with brine, dried (MgSO$_4$), and filtered to provide the desired product as a white solid (2.62 g, 87%). $^1$H NMR: (DMSO-d$_6$) δ1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); LC-MS MS m/z 228 (M$^+$+H).

Step 2:

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1.0M HCl to pH=1, and THF was evaporated in vacuo. The suspension was extracted with ethyl acetate (2×50 mL) and the organic extracts were combined and dried (Na$_2$SO$_4$). Filtration, concentration, and purification by recrystallization from hexanes-ethyl acetate (1:1) provided the desired product (2.4 g) as a white solid. The mother liquor was purified by flash column chromatography (SiO$_2$, eluted 9% acetone in dichloromethane) to give a second batch of the desired product (1.1 g). Both batches were combined (total yield 92%). $^1$H NMR: (DMSO-d$_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers)); LC-MS, MS m/z 331 (M$^+$+H).

Step 3:

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1.0M HCl in diethyl ether (20 mL) and concentrated in vacuo. This procedure was repeated once. The resulting mixture was triturated with pentane and filtered to give the title compound as a hygroscopic, off-white solid (2.60 g, 92%). $^1$H NMR (DMSO-d$_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); LC-MS, MS m/z 231 (M$^+$+H).

Preparation of P1-P1' sulfamide derivative:

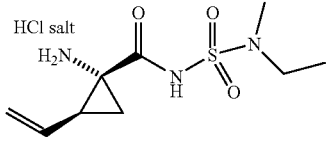

To a solution of (1R,2S) 1-tert-butoxycarbonylamino-2-vinyl-cyclopropanecarboxylic acid (217 mg, 1.194 mmol) in THF (5 mL), was added CDI (290 mg, 1.791 mmol) and the reaction mixture was heated to reflux for 45 minutes. In another round-bottomed flask, LiHMDS (1.0M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. The two reaction mixtures were combined and stirred at room temperature for 2 hours. Water was added to quench the reaction and the reaction solution was extracted with ethyl acetate. The organic layer was separated and dried over MgSO$_4$. Filtration and concentration gave crude product which was purified by preparative HPLC to provide the desired N-Boc protected N-acylsulfamide. The Boc protecting group was then removed as the compound was dissolved in 4N HCl solution in dioxane (2 mL) and stirred at room temperature for 4 hours. Concentration provided a brownish oil as the HCl salt. (112 mg, 33% yield). $^1$H NMR (400 Mz, CD$_3$OD) δ 1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS, MS m/z 270 (M+Na$^+$).

Preparation of Compound 1, Example 1

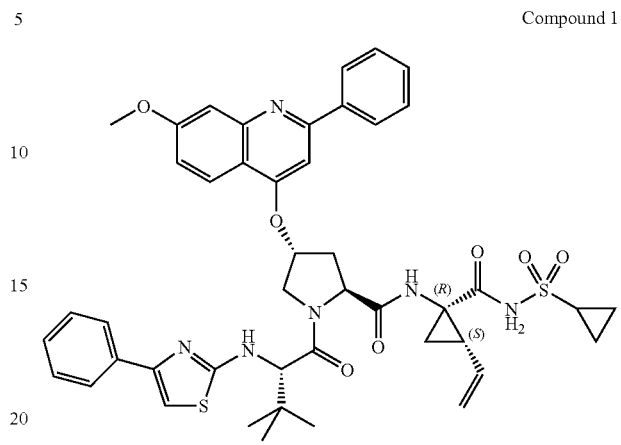

Compound 1

Scheme 1 of Example 1

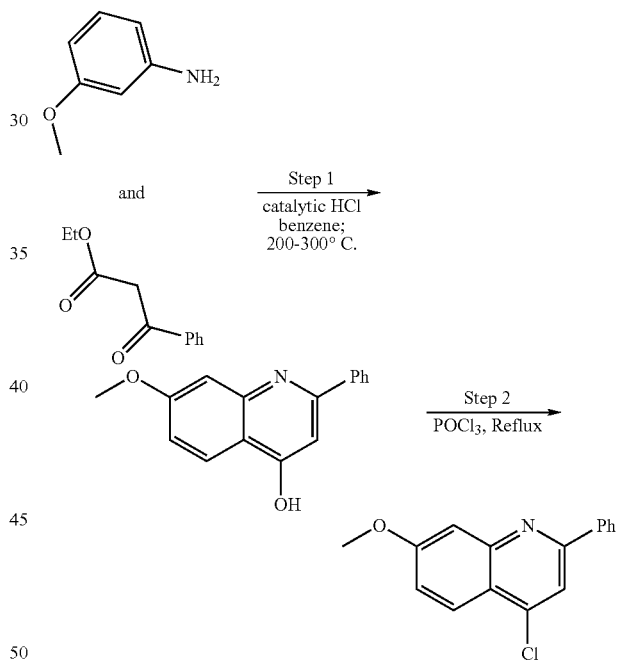

Step 1:

To a solution of m-anisidine (300 g, 2.44 mol) and ethyl benzoylacetate (234.2 g, 1.22 mol) in toluene (2.0 L) was added HCl (4.0N in dioxane, 12.2 mL, 48.8 mmol). The resulting solution was refluxed for 6.5 hours using a Dean-Stark apparatus (about 56 mL of aqueous solution was collected). The mixture was cooled to room temperature, partitioned multiple times with aqueous HCl (10%, 3×500 mL), aqueous NaOH (1.0N, 2×200 mL), water (3×200 mL), and the organic layer dried (MgSO$_4$), filtered, and concentrated in vacuo to supply an oily residue (329.5 g). The crude product was heated in an oil bath (280° C.) for 80 minutes using a Dean-Stark apparatus (about 85 mL liquid was collected). The reaction mixture was cooled down to room temperature, the solid residue triturated with CH$_2$Cl$_2$ (400 mL), the resulting suspension filtered, and the filter cake washed with more $CH_2Cl_2$ (2×150 mL). The resulting solid was dried in vacuo (50° C.; 1 torr; 1 day) affording analytically pure product as a light brown solid (60.7 g, 20% overall). $^1H$ NMR (DMSO-$d_6$) δ 3.86 (s, 3H), 6.26 (s, 1H), 6.94 (dd, J=9.0, 2.4 Hz, 1H), 7.21 (d, J=2.4 Hz, 1H), 7.55-7.62 (m, 3H), 7.80-7.84 (m, 2H), 8.00 (d, J=9.0 Hz, 1H), 11.54 (s, 1H); $^{13}C$ NMR (DMSO-$d_6$) δ 55.38, 99.69, 107.07, 113.18, 119.22, 126.52, 127.17, 128.97, 130.34, 134.17, 142.27, 149.53, 161.92, 176.48. LC-MS (MS m/z 252 (M$^+$+1).

Step 2;

The product of Step 1 (21.7 g, 86.4 mmol) was suspended in $POCl_3$ (240 mL). The suspension was refluxed for 2 hours. After removal of the $POCl_3$ in vacuo, the residue was partitioned between ethyl acetate (1 L), and cold aqueous NaOH (generated from 1.0N 200 mL NaOH and 20 mL 10.0N NaOH) and stirred for 15 minutes. The organic layer was washed with water (2×200 mL), brine (200 mL), dried ($MgSO_4$), filtered, and concentrated in vacuo to supply the desired product (21.0 g, 90%) as a light brown solid. $^1H$ NMR (DMSO-$d_6$) δ 3.97 (s, 3H), 7.36 (dd, J=9.2, 2.6 Hz, 1H), 7.49-7.59 (m, 4H), 8.08 (d, J=9.2 Hz, 1H), 8.19 (s, 1H), 8.26-8.30 (m, 2H); $^{13}C$ NMR (DMSO-$d_6$) δ 55.72, 108.00, 116.51, 119.52, 120.48, 124.74, 127.26, 128.81, 130.00, 137.58, 141.98, 150.20, 156.65, 161.30. LC-MS (MS m/z 270 (M$^+$+1).

Scheme 2 of Example 1

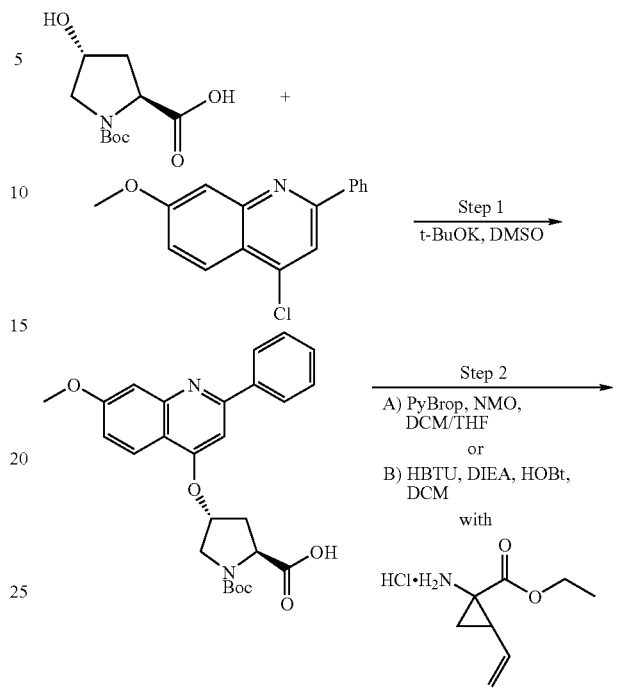

Step 1:

The racemix mixture of (1R,2S) and (1S,2R) of 1-(tert-butoxycarbonylamino)-2-vinylcyclopropanecarboxyate (9.39 g, 36.8 mmol) was dissolved in 4N HCl/dioxane (90 mL, 360 mmol) and was stirred for 2 hours at room temperature. The reaction mixture was concentrated to supply the desired product in quantitative yield (7 g, 100%). $^1H$ NMR (CD$_3$OD) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26-4.34 (m, 2H), 5.24 (dd, 10.3, 1.3 Hz, 1H) 5.40 (d, J=17.2, 1H), 5.69-5.81 (m, 1H).

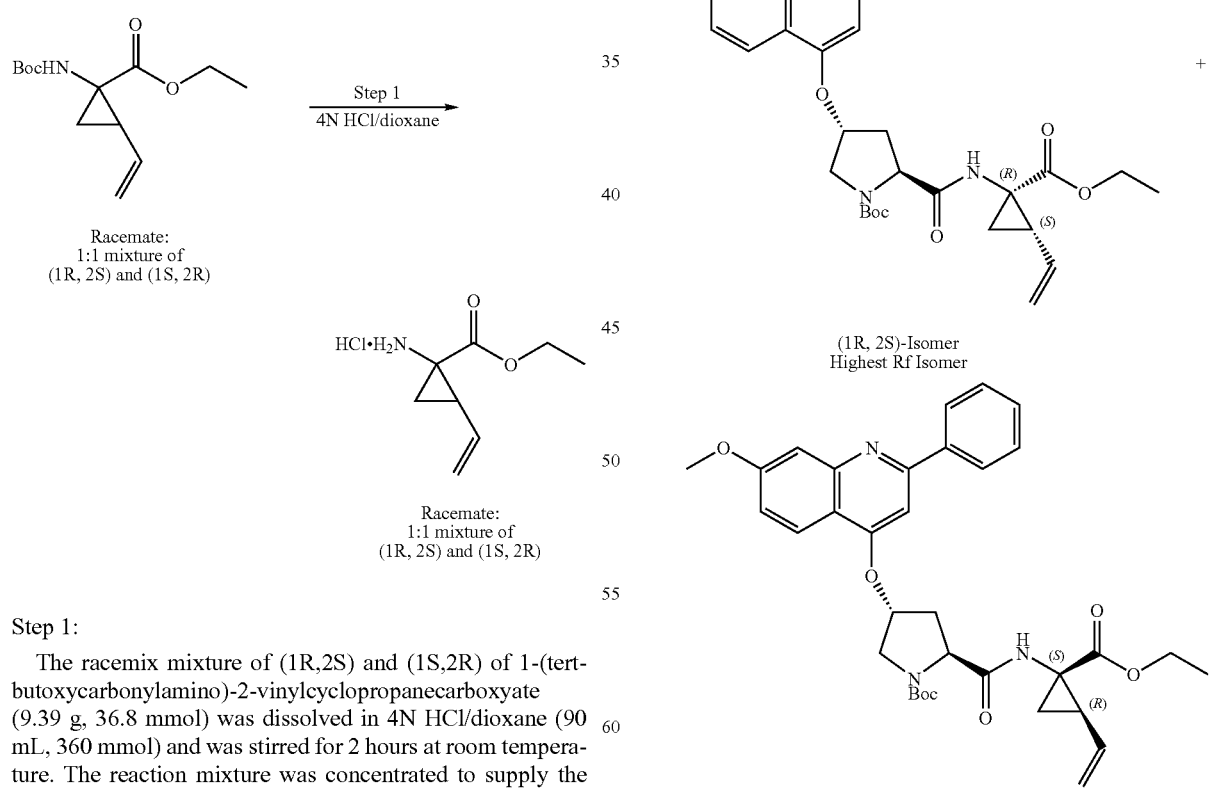

Step 1:

To a suspension of Boc-4R-hydroxyproline (16.44 g, 71.1 mmol) in DMSO (250 mL) was added t-BuOK (19.93 g, 177.6 mmol) at 0° C. The generated mixture was stirred for 1.5 hours and then the product of Step 2, Scheme 1 (21.02 g, 77.9 mmol) was added in three portions over 1 hour. The reaction was stirred for one day, poured into cold water (15 L) and washed with diethyl ether (4×200 mL). The aqueous solution was acidified to pH 4.6, filtered to obtain a white solid, and dried in vacuo to supply the product (32.5 g, 98%). $^1$H NMR (DMSO-$d_6$) δ 1.32, 1.35 (two s (rotamers) 9H), 2.30-2.42 (m, 1H), 2.62-2.73 (m, 1H), 3.76 (m, 2H), 3.91 (s, 3H), 4.33-4.40 (m, 1H), 5.55 (m, 1H), 7.15 (dd, J=9.2, 2.6 Hz, 1H), 7.37 (d, J=2.6 Hz, 1H), 7.42-7.56 (m, 4H), 7.94-7.99 (m, 1H), 8.25, 8.28 (2s, 2H), 12.53 (brs, 1H); LC-MS, MS m/z 465 (M$^+$+1).

Step 2A:

To a solution of the product of Step 1 (11.0 g, 23.7 mmol), the product of Step 1, Scheme 2 (5.40 g, 28.2 mmol), and NMM (20.8 mL; 18.9 mmol) in 500 mL of 50% $CH_2Cl_2$/THF was added the coupling reagent bromotrispyrrolidinophosphonium hexafluorophosphate (Pybrop) (16.0 g, 34.3 mmol) in three portions in 10 minutes at 0° C. The solution was stirred at room temperature for one day and then was washed with pH 4.0 buffer (4×50 mL). The organic layer was washed with saturated aqueous $NaHCO_3$ (100 mL), the aqueous wash extracted with ethyl acetate (150 mL), and the organic layer backwashed with pH 4.0 buffer (50 mL) and saturated aqueous $NaHCO_3$ (50 mL). The organic solution was dried ($MgSO_4$), filtered, concentrated, and purified by flash column chromatography ($SiO_2$, eluted with 50% ethyl acetate/hexanes) to provide over 7.5 g of a 1:1 mixture of (1R,2S) and (1S,2R) P1 isomers of the desired product (50% overall) or, alternatively, eluted slow with 15% to 60% ethyl acetate in hexanes gradient to supply 3.54 g (25%) of the high Rf eluted (1R,2S) P1 isomer, and 3.54 g (25%) of the low Rf eluted (1S,2R) P1 isomer.

Data for (1R,2S) P1 isomer: $^1$H NMR (CDCl$_3$) δ 1.21 (t, J=7 Hz, 3H), 1.43 (s, 9H), 1.47-1.57 (m, 1H), 1.88 (m, 1H), 2.05-2.19 (m, 1H), 2.39 (m, 1H), 2.88 (m, 1H), 3.71-3.98 (m, 2H), 3.93 (s, 3H), 4.04-4.24 (m, 2H), 4.55 (m, 1H), 5.13 (d, J=10 Hz, 1H), 5.22-5.40 (m, 1H), 5.29 (d, J=17 Hz, 1H), 5.69-5.81 (m, 1H), 7.02 (brs, 1H), 7.09 (dd, J=9, 2 Hz, 1H), 7.41-7.52 (m, 4H), 7.95 (d, J=9 Hz, 1H), 8.03, 8.05 (2s, 2H); $^{13}$C NMR (CDCl$_3$) δ: 14.22; 22.83, 28.25, 33.14, 33.58, 39.92, 51.84, 55.47, 58.32, 61.30, 75.86, 81.27, 98.14, 107.42, 115.00, 117.84, 118.27, 122.63, 123.03, 127.50, 128.72, 129.26, 133.39, 140.06, 151.23, 159.16, 160.34, 161.35, 169.78, 171.68. LC-MS (MS m/z 602 (M$^+$+1).

Data for the (1S,2R) P1 isomer: $^1$H NMR δ 1.25 (t, J=7 Hz, 3H), 1.44 (s, 9H), 1.46-1.52 (m, 1H), 1.84 (m, 1H), 2.12-2.21 (m, 1H), 2.39 (m, 1H), 2.94 (m, 1H), 3.82 (m, 2H), 3.97 (s, 3H), 4.05-4.17 (m, 2H), 4.58 (m, 1H), 5.15 (d, J=10.8 Hz, 1H), 5.33 (d, J=17 Hz, 1H), 5.30-5.43 (m, 1H), 5.72-5.85 (m, 1H), 7.05 (s, 1H), 7.13 (dd, J=9, 2 Hz, 1H), 7.46-7.60 (m, 4H), 7.98 (d, J=9, 1H), 8.06-8.10 (m, 2H). LC-MS MS m/z 602 (M$^+$+1).

Step 2B:

The product of Step 1, Scheme 2 (7.5 g, 39.1 mmol) was combined with diisopropylethylamine (32.5 mL, 186 mmol) in dichloromethane (150 mL). To the resulting mixture was added HOBT hydrate (6.85 g, 44.7 mmol) and the product from Step 1 (17.3 g, 37.3 mmol), followed by HBTU (16.96 g, 44.7 mmol). A slight exotherm occurred immediately, and the mixture was stirred at room temperature overnight. The mixture was then concentrated in vacuo and redissolved in ethyl acetate (600 mL). The solution was washed with water (2×200 mL), then with 10% aqueous sodium bicarbonate (2×200 mL), then with water (150 mL) and finally with brine (150 mL). The organic was dried over anhydrous magnesium sulfate and filtered, and the filtrate was concentrated in vacuo to a beige glassy solid. Purification was performed in multiple batches (7 g each) by flash chromatography ($SiO_2$, eluted with 66% hexanes/ethyl acetate) to provide the (1R,2S) P1 isomer as the initial eluted isomer (9.86 g total, 44.0% yield), followed by elution of the (1S,2R) P1 isomer as the second eluted isomer (10.43 g total, 46.5% yield). A total of 1.97 g of mixed fractions were recovered to give an overall conversion of 99.3% to the two diastereomers.

Data for (1R,2S) P1 isomer: $^1$H NMR (methanol-$d_4$) δ 1.23 (t, J=7.2 Hz, 3H), 1.4 (s, 4H), 1.45 (s, 6H), 1.73 (dd, J=7.9, 1.5 Hz, 0.4H), 1.79 (dd, J=7.8, 2.4 Hz, 0.6H), 2.21 (q, J=8.2 Hz, 1H), 2.44-2.49 (m, 1H), 2.66-2.72 (m, 0.4H), 2.73-2.78 (m, 0.6H), 3.93-3.95 (m, 2H), 3.96 (s, 3H), 4.10-4.17 (m, 2H), 4.44 (q, J=7.8 Hz, 1H), 5.13 (d, J=10.7 Hz, 1H), 5.31 (d, J=17.7 Hz, 0.4H), 5.32 (d, J=17.4 Hz, 0.6H), 5.49 (bs, 1H), 5.66-5.82 (m, 1H), 7.16 (dd, J=9.2, 2.5 Hz, 1H), 7.26 (s, 1H), 7.42 (d, J=2.4 Hz, 1H), 7.48-7.55 (m, 3H), 8.02-8.05 (m, 3H); LC-MS (MS m/z 602 (M$^+$+1).

Data for (1S,2R) P1 isomer: $^1$H NMR (methanol-$d_4$) δ 1.23 (t, J=7.2 Hz, 3H), 1.40 (s, 3.5H), 1.43 (s, 6.5H), 1.8 (dd, J=7.2, 5.3 Hz, 0.4H), 1.87 (dd, J=7.8, 5.7 Hz, 0.6H), 2.16 (q, J=8.9 Hz, 0.6H), 2.23 (q, J=8.85 Hz, 0.4H), 2.42-2.50 (m, 1H), 2.67-2.82 (m, 1H), 3.87-3.95 (m, 2H), 3.96 (s, 3H), 4.07-4.19 (m, 3H), 4.41-4.47 (m, 1H), 5.09-5.13 (m, 1H), 5.30 (dd, J=17.09, 0.92 Hz, 1H), 5.48 (s, 1H), 5.70-5.77 (m, 1H), 7.15 (dd, J=9.16, 2.44 Hz, 1H), 7.25 (s, 1H), 7.41 (d, J=2.14 Hz, 1H), 7.48-7.55 (m, 3H), 8.02-8.05 (m, 3H); LC-MS (MS m/z 602 (M$^+$+1).

Scheme 4 of Example 1

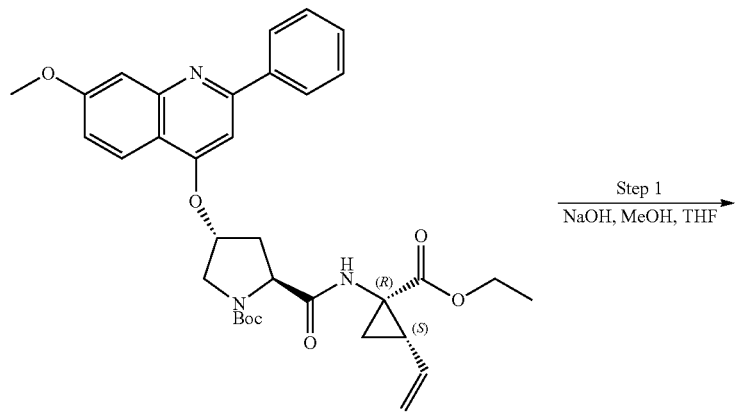

(1R, 2S)-Isomer
Highest Rf Isomer

-continued
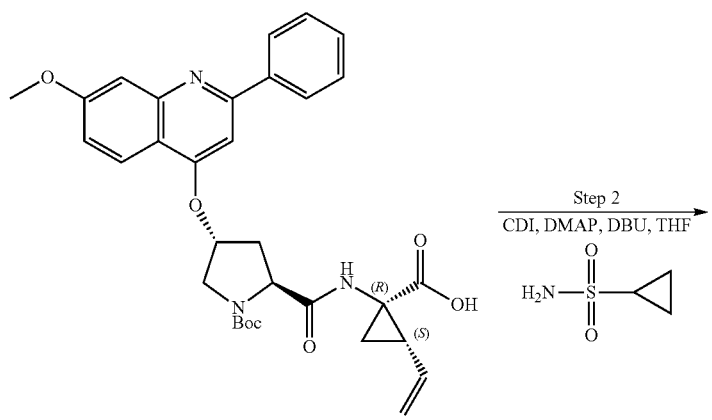
Step 2
CDI, DMAP, DBU, THF
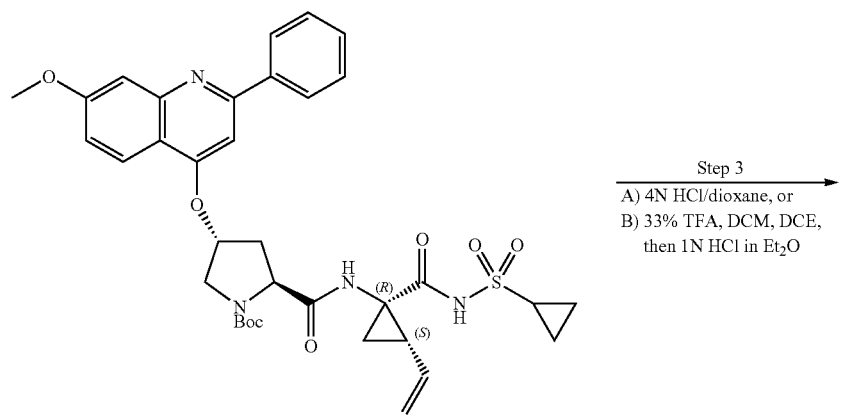
Step 3
A) 4N HCl/dioxane, or
B) 33% TFA, DCM, DCE,
then 1N HCl in Et₂O
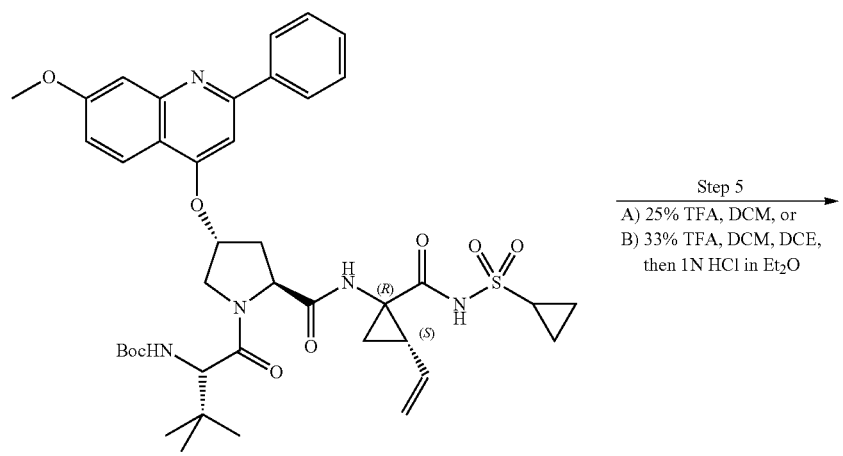
Step 5
A) 25% TFA, DCM, or
B) 33% TFA, DCM, DCE,
then 1N HCl in Et₂O

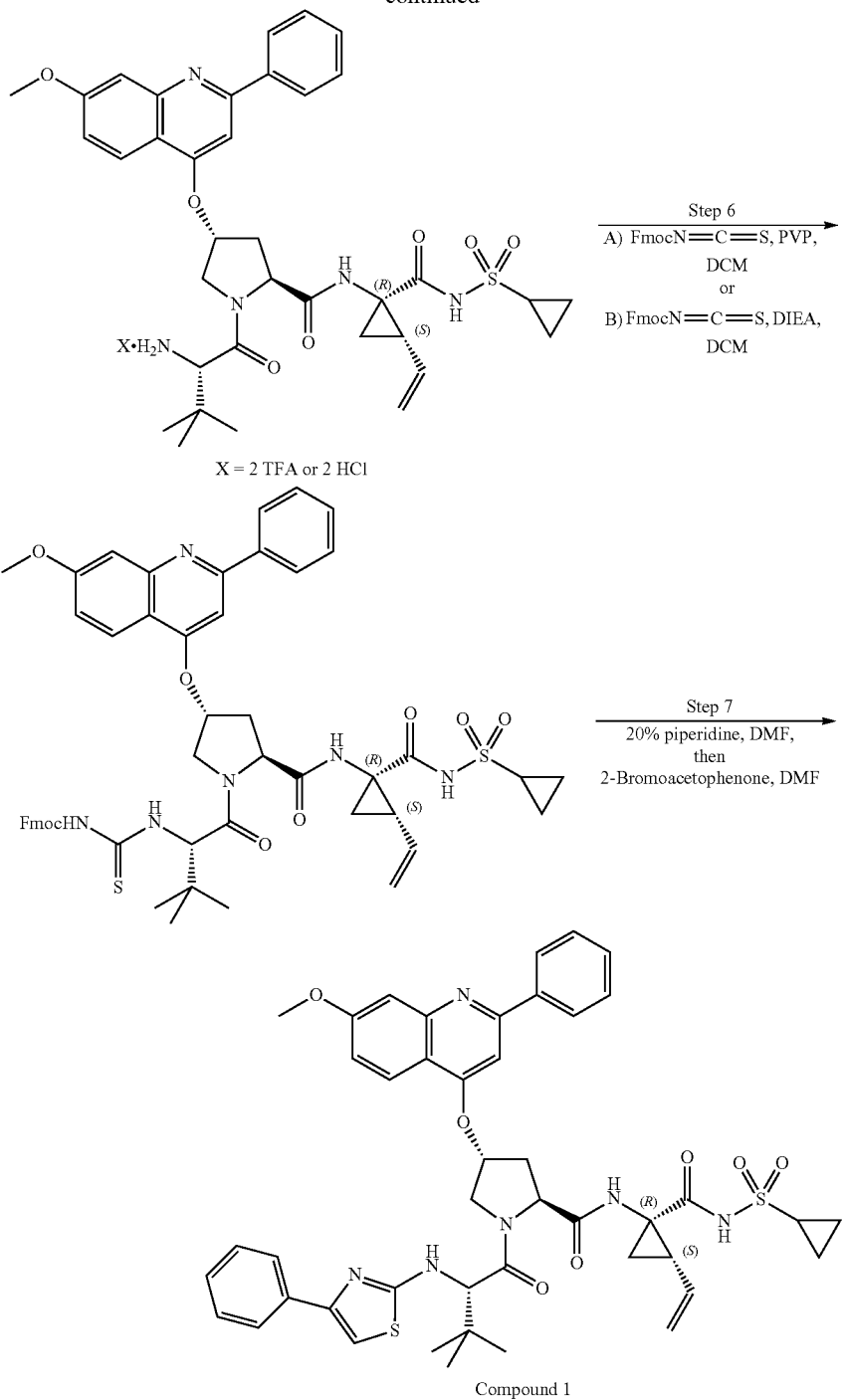

Compound 1

Step 1:

The (1R,2S) P1 isomer of Step 2, scheme 3 (9.86 g, 16.4 mmol) was treated with 1N NaOH (50 mL, 50 mmol) in a mixture of THF (150 mL) and methanol (80 mL) for 12 hours. The mixture was concentrated in vacuo until only the aqueous phase remained. Water (100 mL) was added and 1N HCl was added slowly until pH 3 was achieved. The mixture was then extracted with ethyl acetate (3×200 mL), and the combined organic extracts were washed with brine, dried over anhydrous sodium sulfate, and filtered. The filtrate was concentrated in vacuo to give the desired product as a white powder (9.2 g, 98% yield). $^1$H NMR (CD$_3$OD) δ 1.41 (s, 2H), 1.45 (s, 9H), 1.77 (dd, J=7.9, 5.5 Hz, 1H), 2.16-2.21 (m, 1H), 2.44-2.51 (m, 1H), 2.74-2.79 (m, 1H), 3.93-3.96 (m, 2H), 3.98 (s, 3H), 4.44 (t, J=7.9 Hz, 1H), 5.11 (dd J=9.5 Hz, 1H), 5.30 (d, J=17.1 Hz, 1H), 5.52 (s, 1H), 5.79-5.86 (m, 1H), 7.22 (dd, J=9.16, 2.14 Hz, 1H), 7.32 (s, 1H), 7.43 (d, J=2.14 Hz, 1H), 7.54-7.60 (m, 3H), 8.04 (dd, J=7.8, 1.4 Hz, 2H), 8.08 (d, J=9.1 Hz, 1H); LC-MS (MS m/z 574 (M$^+$+1).

Step 2:

The product of Step 1 (7.54 g, 13.14 mmol) was combined with CDI (3.19 g, 19.7 mmol) and DMAP (2.41 g, 19.7 mmol)

in anhydrous THF, and the resulting mixture was heated to reflux for 45 minutes. The slightly opaque mixture was allowed to cool to room temperature, and to it was added cyclopropylsulfonamide (1.91 g, 15.8 g). Upon addition of DBU (5.9 mL, 39.4 mmol), the mixture became clear. The brown solution was stirred overnight. The mixture was then concentrated in vacuo to an oil and was redissolved in ethyl acetate (500 mL). The solution was washed with pH 4 buffer (3×200 mL), and the combined buffer washes were back-extracted with ethyl acetate (200 mL). The combined organics were washed with brine (150 mL) and dried over anhydrous sodium sulfate and filtered. Concentration of the filtrate in vacuo gave a beige solid. The crude product was purified by flash chromatography (SiO$_2$, eluted with 25% hexanes/ethyl acetate) to give the desired product (5.85 g, 66% yield). $^1$H NMR (CD$_3$OD) δ 1.03-1.09 (m, 2H), 1.15-1.28 (m, 2H), 1.40-1.44 (m, 2H), 1.46 (s, 9H), 1.87 (dd, J=8.1, 5.6 Hz, 1H), 2.21-2.27 (m, 1H), 2.36-2.42 (m, 1H), 2.65 (dd, J=13.7, 6.7 Hz, 1H), 2.93-2.97 (m, 1H), 3.90-3.96 (m, 2H), 4.00 (s, 3H), 4.40 (dd, J=9.5, 7.0 Hz, 1H), 5.12 (d, J=10.4 Hz, 1H), 5.31 (d, J=17.4 Hz, 1H), 5.64 (s, 1H), 5.73-5.80 (m, 1H), 7.30 (dd, J=9.2, 2.1 Hz, 1H), 7.40 (s, 1H), 7.47 (s, 1H), 7.61-7.63 (m, 3H), 8.04-8.05 (m, 2H), 8.15 (d, J=9.5 Hz, 1H); LC-MS (MS m/z 677 (M$^+$+1).

Step 3A.

The product of Step 2 (5.78 g, 8.54 mmol) was treated with 4.0M HCl in 1,4-dioxane (50 mL, 200 mmol) overnight. The reaction mixture was concentrated in vacuo and placed in a vacuum oven at 50° C. for several days. The desired product was obtained as a beige powder (5.85 g, quantitative). $^1$H NMR (methanol-d$_4$) δ 1.03-1.18 (m, 3H), 1.26-1.30 (m, 1H), 1.36-1.40 (m, 2H), 1.95 (dd, J=8.2, 5.8 Hz, 1H), 2.37 (q, J=8.9 Hz, 1H), 2.51-2.57 (m, 1H), 2.94-2.98 (m, 1H), 3.09 (dd, J=14.6, 7.3 Hz, 1H), 3.98 (d, J=3.7 Hz, 1H), 3.99 (s, 1H), 4.08 (s, 3H), 4.80 (dd, J=10.7, 7.6 Hz, 1H), 5.15 (dd, J=10.2, 1.4 Hz, 1H), 5.32 (dd, J=17.1, 1.2 Hz, 1H), 5.61-5.69 (m, 1H), 5.99 (t, J=3.7 Hz, 1H), 7.51 (dd, J=9.3, 2.3 Hz, 1H), 7.59 (d, J=2.4 Hz, 1H), 7.65 (s, 1H), 7.72-7.79 (m, 3H), 8.09 (dd, J=7.0, 1.5 Hz, 2H), 8.53 (d, J=9.2 Hz, 1H); LC-MS (MS m/z 577 (M$^+$+1).

Step 3B:

To a solution of (2S,4R)-tert-butyl 2-((1R,2S)-1-(cyclopropylsulfonylcarbamoyl)-2-vinylcyclopropylcarbamoyl)-4-(7-(ethoxy-2-phenylquinolin-4-yloxy)pyrrolidine-1-carboxylate, the product of step 2 (3.0 g, 4.43 mmol) in 1:1 DCM (25 mL)/DCE (25.00 mL) was added trifluoroacetic acid (25 mL, 324 mmol). After stirring at 25° C. for 0.5 h, the resulting brown reaction mixture was concentrated to brown vicous oil which was redissolved in DCE (50 mL) and reconcentrated. The residue was dissolved in DCM (10 mL) and was added dropwise to a solution of 1N HCl in Et$_2$O (50 mL, 50.0 mmol). The resulting light brown precipitate was filtered, washed with a solution of 1N HCl in Et$_2$O (40 mL) and dried in a 50° C. vacuum oven for 1 h to afford (2S,4R)—N-((1R,2S)-1-(cyclopropylsulfonylcarbamoyl)-2-vinylcyclopropyl)-4-(7-methoxy-2-phenylquinolin-4-yloxy)pyrrolidine-2-carboxamide, 2 HCl salt (2.8 g, 4.31 mmol, 97% yield) as a light brown solid. $^1$H-NMR showed the product contained about 0.75 equivalents of tetramethyl urea byproduct (signal at 2.83 ppm as a siglet), but this material was used without further purification in the next step. $^1$H NMR (500 MHz, MeOD) δ ppm 1.0-1.2 (m, 3H), 1.2-1.3 (m, 1H), 1.4 (dd, J=9.5, 5.5 Hz, 2H), 1.9 (dd, J=7.9, 5.8 Hz, 2H), 2.4 (q, J=8.7 Hz, 1H), 2.5-2.6 (m, 1H), 2.9-2.9 (m, 1H), (dd, J=14.6, 7.3 Hz, 1H), 4.0-4.0 (m, 2H), 4.1 (s, 3H), 4.8-4.9 (m, 1H), 5.1 (dd, J=10.4, 1.5 Hz, 1H), 5.3 (dd, J=17.2, 1.4 Hz, 1H), 5.6-5.7 (m, 1H), 6.0 (s, 1H), 7.5 (dd, J=9.3, 2.3 Hz, 1H), 7.6 (d, J=2.4 Hz, 1H), 7.7 (s, 1H), 7.7-7.8 (m, 3H), 8.1 (d, J=6.7 Hz, 2H), 8.6 (d, J=9.2 Hz, 1H). LC-MS, MS m/z 577.2 (M$^+$+H).

Step 4A:

To a solution of the product from step 3A (0.671 mmol) in DCM (10 mL) was added DIEA (542 μL, 3.36 mmol), HATU (354 mg, 1.01 mmol), HOAt (127 mg, 1.01 mmol), and Boc-L-Tle-OH (173 mg, 0.805 mmol). After stirring at rt for 16 h, the solvent was concentrated and the resulting brown viscous oil was purified by flash column chromatography (SiO$_2$, eluted with 95% MeOH in DCM) to give a slightly yellow foam (527 mg, 99% yield). LC-MS (MS m/z 790 (M$^+$+1)).

Step 4B:

To a solution of (2S,4R)—N-((1R,2S)-1-(cyclopropylsulfonylcarbamoyl)-2-vinylcyclopropyl)-4-(7-methoxy-2-phenylquinolin-4-yloxy)pyrrolidine-2-carboxamide, 2 HCl salt, the product of step 3B (1.2 g, 1.847 mmol), N,N-diisopropylethylamine (1.126 mL, 6.47 mmol) and Boc-L-Tle-OH (0.513 g, 2.217 mmol) in DCM (15 mL) was added HATU (1.054 g, 2.77 mmol). The resulting light brown reaction mixture was stirred at rt for 13 h, the reaction mixture was concentrated and re-dissolved in EtOAc (50 mL) and washed with 1N aqueous HCl (25 mL). The acidic aqueous layer was extracted with EtOAc (50 mL). The organic layers were combined and washed with 10% aqueous Na$_2$CO$_3$ (20 mL), brine, dried over MgSO$_4$, filtered, and concentrated. The resulting vicous brown oil was purified by flash column chromatography (SiO$_2$, eluted with 95:5 DCM:MeOH) to give tert-butyl (S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3,3-dimethyl-1-oxobutan-2-ylcarbamate a a light brown foam which was of sufficient purity for use in the next step. However, for the analytical sample for characterization by NMR, 85 mg of this product was further purified by reverse phase HPLC using solvent sytem and conditions as the following: solvent A=H$_2$O, solvent B=MeOH, both containing 0.1% TFA; 50% B to 100% B 20 mins, hold at 100% B 4 mins. The combined HPLC fractions was neutralized with 1N aqueous NaOH and concentrated until mostly water remained. The resulting white creamy mixture was extracted with EtOAc (2×25 mL). The organic layers were combined, washed with brine, dried over MgSO$_4$, filtered, concentrated and dried in vacuo to afford analytically pure white powder product. $^1$H NMR (500 MHz, MeOD) δ ppm 0.9-1.0 (m, 2H), 1.0 (s, 9H), 1.1-1.2 (m, 1H), 1.2-1.2 (m, 3H), 1.3 (s, 9H), 1.4-1.4 (m, 1H), 1.9 (dd, J=7.9, 5.5 Hz, 1H), 2.2 (q, J=8.7 Hz, 1H), 2.3-2.3 (m, 1H), 2.6 (dd, J=13.9, 6.9 Hz, 1H), 2.9-3.0 (m, 1H), 3.9 (s, 3H), 4.0-4.1 (m, 1H), 4.2 (d, J=9.5 Hz, 1H), 4.5-4.5 (m, 2H), 5.1 (d, J=11.0 Hz, 1H), 5.3 (d, J=17.1 Hz, 1H), 5.5 (s, 1H), 5.7-5.8 (m, 1H), 6.6 (d, J=9.5 Hz, 1H), 7.1 (dd, J=9.0, 1.7 Hz, 1H), 7.2 (s, 1H), 7.4 (d, J=1.8 Hz, 1H), 7.5-7.5 (m, 3H), 8.0 (t, J=7.3 Hz, 3H). $^{13}$C NMR (126 MHz, MeOD) δ ppm 5.6, 5.8, 17.6, 22.6, 26.1, 27.6, 31.2, 34.7, 35.0, 35.2, 41.7, 42.8, 54.4, 55.1, 59.5, 59.9, 77.2, 79.5, 99.2, 106.4, 115.5, 117.6, 117.9, 118.4, 123.3, 128.0, 128.8, 129.7, 133.3, 140.1, 151.0, 151.1, 157.1, 160.2, 161.0, 162.3, 169.8, 172.5, 174.0. LC-MS, MS, m/z 790.30 (M$^+$+H).

Step 5A:

A solution of the product from step 4A (950 mg, 1.20 mmol) in DCM (75 mL) was treated with TFA (25 mL) slowly to control CO$_2$ gas from vigorously bubbling. After stirring at rt for 1.5 hr, the solvent was concentrated to give a light brown slurry and Et$_2$O was added to effect a precipitation. The light brown product (1.10 g, 99% yield) bis TFA salt was obtained by a vacuum filtration and used without further purification. LC-MS (MS m/z 690 (M$^+$+1)).

Step 5B:

To a solution of tert-butyl(S)-1-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidin-1-yl)-3,3-dimethyl-1-oxobutan-2-ylcarbamate, the product of step 4B (1.00 g, 1.266 mmol) in 1:1 DCM (5 mL) and DCE (5.00 mL) was added trifluoroacetic acid (5 mL, 64.9 mmol). After stirring at 25° C. for 15 mins, the reaction mixture was concentrated. The resulting viscous brown oil was redissolved in DCM (3 mL) and was added dropwise to a vigorously stirred solution of 1N HCl (50 mL) in Et$_2$O. The resulting light brown precipitate was filtered, washed with Et$_2$O (25 mL) and dried in a 50° C. vacuum oven for 2 h to afford (2S,4R)-1-((S)-2-amino-3,3-dimethylbutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide, 2 HCl salt (0.907 g, 1.189 mmol, 94% yield) as a light brown solid which was of sufficient purity for use in the next step. However, for the analytical sample for characterization by NMR, 80 mg of product was further purified by reverse phase HPLC using solvent sytem and conditions as the following: solvent A=H$_2$O, solvent B=MeOH, both containing 0.1% TFA; 15% B to 100% B 20 mins, hold at 100% B 4 mins. The combined HPLC fractions was treated with 1N aqueous HCl (3 mL), concentrated to dryness and dried in vacuo to afford the bis-HCl salt product as white powder. $^1$H NMR (500 MHz, MeOD) δ ppm 1.0-1.1 (m, 4H), 1.2 (s, 9H), 1.2-1.3 (m, 2H), 1.4 (s, 1H), 1.9 (s, 1H), 2.3 (d, J=5.8 Hz, 1H), 2.4 (s, 1H), 2.8-2.9 (m, 1H), 2.9-3.0 (m, 1H), 4.1 (s, 3H), 4.2 (s, 2H), 4.6 (d, J=8.2 Hz, 1H), 4.8 (s, 1H), 5.1 (d, J=10.4 Hz, 1H), 5.3 (d, J=17.1 Hz, 1H), 5.6-5.7 (m, 1H), 5.9 (s, 1H), 7.5 (d, J=8.2 Hz, 1H), 7.6-7.7 (m, 2H), 7.7-7.8 (m, 3H), 8.1 (d, J=4.0 Hz, 2H), 8.5 (d, J=8.5 Hz, 1N). $^{13}$C NMR (MeOD) δ ppm 5.0 (s), 5.8, 5.8, 22.4, 25.9, 31.3, 34.6, 34.9, 35.0, 41.8, 42.8, 54.7, 56.1, 59.5, 60.5, 80.4, 99.8, 101.5, 115.1, 117.9, 120.9, 125.8, 129.2, 129.8, 132.3, 132.9, 133.1, 142.7, 157.2, 165.6, 166.8, 168.2, 169.4, 173.2. LC-MS, MS m/z 690.2 (M++H).

Step 6A:

To a solution of product of step 5A (0.132 g, 0.143 mmol) in DCM (2 mL) was added polyvinylpyridine (PVP) (0.046 g, 0.429 mmol) and Fmoc-isothiocyanate (0.042 g, 0.150 mmol). The resulting brown solution was stirred at rt. After 16 hr, solvent was removed and residue was purified by flash column chromatography (SiO$_2$, eluted with 95:5 DCM:MeOH) to give a light brown solid product (0.126 mg, 91% yield).

Step 6B:

To a solution of (2S,4R)-1-((S)-2-amino-3,3-dimethylbutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide, 2 HCl, the product of step 5B (0.500 g, 0.656 mmol) and N,N-diisopropylethylamine (0.343 mL, 1.967 mmol) in DCM (8 mL) was added Fmoc-isothiocyanate (0.240 g, 0.852 mmol). The resulting brown reaction mixture was stirred at 25° C. for 16 h. The reaction mixture was concentrated, the residue was taken up with EtOAc (50 mL) and washed with 0.1N aqueous HCl (10 mL). The aqueous layer was extracted with EtOAc (25 mL). The organic layers were combined, washed with brine, dried over MgSO$_4$, filtered, and concentrated to a yellow solid crude product which was purified by flash column chromatography (SiO$_2$, eluted with 95:5 DCM:MeOH) to afford (2S,4R)-1-((S)-2-(3-(((9H-fluoren-9-yl)methoxy)carbonyl)thioureido)-3,3-dimethylbutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide (615.4 mg, 0.634 mmol, 97% yield) as a light yellow solid which was of sufficient purity for use in the next step. However, 45 mg of product was further purified by reverse phase HPLC using solvent sytem and conditions as the following: solvent A=H2O, solvent B=MeOH, both containing 0.1% TFA; 50% B to 100% B 20 mins, hold at 100% B 4 mins. Note: a half mL of DMF and 1 mL of MeOH were used to dissolve the HPLC sample in order to prevent sample precipitation on the HPLC column. After concentration of the combined HPLC fractions until mostly water remained, 1N aqueous NaOH was added to neutralize the white creamy mixture and it was then extracted with EtOAc (2×25 mL). The organic layers were combined, dried over MgSO$_4$, filtered, and concentrated to afford the analytically pure sample as a white powder which was used for LC/MS and NMR analysis. $^1$H NMR (500 MHz, MeOD) δ ppm 1.0-1.0 (m, 2H), 1.1 (s, 9H), 1.2-1.2 (m, 2H), 1.2 (t, J=7.2 Hz, 1H), 1.3 (s, 1H), 1.4 (dd, J=9.3, 5.3 Hz, 1H), 1.9 (dd, J=8.1, 5.6 Hz, 1H), 2.0 (s, 1H), 2.2 (q, J=8.7 Hz, 1H), 2.4-2.4 (m, 1H), 2.7 (dd, J=14.2, 6.9 Hz, 1H), 2.9-2.9 (m, 1H), 4.0 (s, 3H), 4.1-4.1 (m, 1H), 4.2 (t, J=6.9 Hz, 1H), 4.4-4.5 (m, 2H), 4.6 (dd, J=10.7, 7.0 Hz, 1H), 4.8 (d, J=7.3 Hz, 1H), 5.0 (d, J=12.2 Hz, 1H), 5.1 (dd, J=10.4, 1.2 Hz, 1H), 5.3 (dd, J=17.2, 1.1 Hz, 1H), 5.6-5.7 (m, 1H), 5.8 (s, 1H), 7.3-7.3 (m, 3H), 7.4 (t, J=7.5 Hz, 2H), 7.4 (d, J=2.1 Hz, 1H), 7.5 (s, 1H), 7.6 (d, J=7.0 Hz, 2H), 7.6-7.7 (m, 3H), 7.8 (d, J=7.6 Hz, 2H), 8.0 (dd, J=7.6, 1.8 Hz, 2H), 8.2 (d, J=9.2 Hz, 1H), 10.3 (d, J=7.3 Hz, 1H). $^{13}$C NMR (MeOD) δ ppm 5.6, 5.6, 13.5, 22.0, 26.3, 31.2, 34.7, 34.8, 35.4, 42.0, 42.8, 47.0, 54.2, 55.8, 60.0, 60.5, 64.3, 64.4, 68.1, 79.8, 100.9, 101.3, 115.3, 117.7, 120.0, 120.2, 125.1, 125.2, 127.3, 128.0, 128.7, 129.6, 132.1, 133.2, 141.6, 143.6, 143.8, 144.7, 154.1, 157.9, 164.8, 165.5, 169.4, 170.6, 172.0, 174.1, 180.8, 180.9, 188.0. LC-MS, MS m/z 971.18 (M++H).

Step 7:

To a solution of product of step 6 (0.342 mg, 0.352 mmol) in DMF (4 mL) was added piperidine (0.805 mL). The resulting brown solution mixture was stirred at rt overnight. Solvent and excess piperidine were removed using a roto-evaporator under reduced pressure to give the desired product and also an equivalent of 1-((9H-fluoren-9-yl)methyl)piperidine byproduct. The resulting crude product mixture was used in the next step without further purification. LC-MS, MS m/z 749 (M$^+$+H). To a solution of the residue from above (15.2 mg, 0.015 mmol) in DMF (2 mL) was added 2-bromoacetophenone (6.0 mg, 0.30 mmol). After stirring at rt for 24 hr, the reaction mixture was concentrated and product was purified by column chromatography to give a mono-TFA salt of compound 1 (1.7 mg, 12% yield in the second step) as a light green solid. $^1$H NMR (500 MHz, MeOH) δ ppm 1.1 (dd, J=8.5, 4.6 Hz, 2H), 1.2 (s, 9H), 1.2-1.3 (m, 2H), 1.4 (dd, J=9.5, 5.5 Hz, 1H), 1.9 (dd, J=8.2, 5.5 Hz, 1H), 2.2 (q, J=8.9 Hz, 1H), 2.4-2.4 (m, 1H), 2.6 (dd, J=14.0, 7.0 Hz, 1H), 2.9-3.0 (m, 1H), 4.0 (s, 3H), 4.3 (dd, J=12.2, 2.7 Hz, 1H), 4.6 (dd, J=10.4, 7.0 Hz, 1H), 4.9 (d, J=13.7 Hz, 2H), 5.1 (d, J=11.9 Hz, 1H), 5.1-5.2 (m, 1H), 5.3 (d, J=17.1 Hz, 1H), 5.7-5.8 (m, 1H), 6.0 (s, 1H), 6.8 (t, J=7.3 Hz, 1H), 6.9 (t, J=7.5 Hz, 2H), 7.1 (dd, J=9.3, 2.3 Hz, 1H), 7.3 (d, J=2.1 Hz, 1H), 7.5 (d, J=7.3 Hz, 1H), 7.6 (s, 1H), 7.6 (d, J=9.2 Hz, 1H), 7.7 (t, J=7.5 Hz, 2H), 7.8 (q, J=7.3 Hz, 1H), 8.0 (d, J=7.0 Hz, 1H); LC-MS, MS m/z 849 (M$^+$+H).

Preparation of Compound 2, Example 2

Compound 2

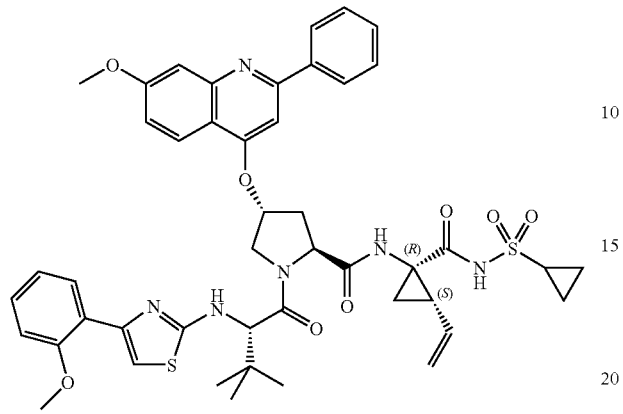

Compound 2 was prepared in 15% yield following the same procedure as described for the preparation of compound 1, except 2-methoxyphenacyl bromide was used instead of 2-bromo-acetophenone in step 7. $^1$H NMR (500 MHz, MeOH) δ ppm 1.0-1.1 (m, 3H), 1.2 (s, 9H), 1.3 (dd, J=7.0, 4.3 Hz, 2H), 1.4 (dd, J=9.5, 5.5 Hz, 1H), 1.9 (dd, J=8.2, 5.5 Hz, 1H), 2.2 (q, J=8.9 Hz, 1H), 2.4-2.4 (m, 1H), 2.6 (q, J=6.7 Hz, 1H), 2.9-3.0 (m, 1H), 3.8 (s, 3H), 4.0 (s, 3H), 4.2 (dd, J=11.9, 3.1 Hz, 1H), 4.6 (dd, J=10.4, 7.0 Hz, 1H), 5.0 (d, J=11.9 Hz, 1H), 5.1 (dd, J=10.5, 1.4 Hz, 1H), 5.3 (dd, J=17.2, 1.4 Hz, 1H), 5.7-5.8 (m, 1H), 6.0 (s, 1H), 6.6 (t, J=7.5 Hz, 1H), 6.7 (d, J=8.5 Hz, 1H), 6.9 (t, J=7.6 Hz, 1H), 7.1 (dd, J=9.2, 2.1 Hz, 1H), 7.3 (d, J=2.4 Hz, 1H), 7.6 (s, 1H), 7.6 (d, J=9.2 Hz, 1H), 7.7-7.7 (m, 2H) 7.8 (d, J=7.3 Hz, 1H), 7.8 (dd, J=7.8, 1.7 Hz, 1H), 8.0 (d, J=7.0 Hz, 2H); LC-MS, MS m/z 879 (M$^+$+H).

Preparation of Compound 3, Example 3

Compound 3

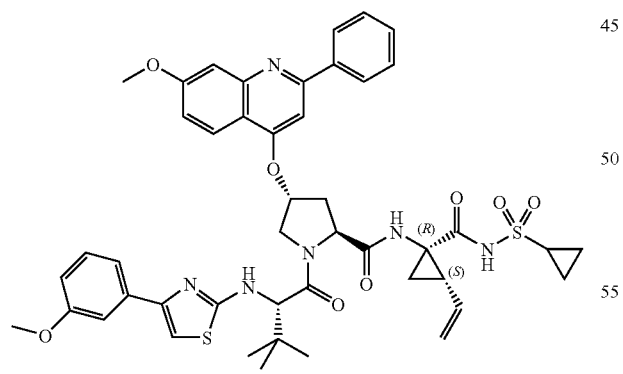

Compound 3 was prepared in 26.9% yield following the same procedure as described for the preparation of compound 1, except 3-methoxyphenacyl bromide was used instead of 2-bromo-acetophenone in step 7. $^1$H NMR (500 MHz, MeOH) δ ppm 1.1-1.1 (m, 3H), 1.2 (s, 9H), 1.2-1.3 (m, 2H), 1.4 (dd, J=9.5, 5.5 Hz, 1H), 1.9 (dd, J=8.1, 5.6 Hz, 1H), 2.2 (q, J=8.9 Hz, 1H), 2.4-2.4 (m, 1H), 2.6 (q, J=7.6 Hz, 1H), 2.9-3.0 (m, 1H), 3.5 (s, 3H), 4.0 (s, 3H), 4.3 (dd, J=12.1, 2.9 Hz, 1H), 4.6 (dd, J=10.5, 6.9 Hz, 1H), 5.1 (d, J=10.4 Hz, 2H), 5.3 (d, J=17.4 Hz, 1H), 5.7-5.8 (m, 1H), 6.0 (s, 1H), 6.4 (dd, J=8.1, 2.6 Hz, 1H), 6.8 (t, J=7.9 Hz, 1H), 7.0-7.0 (m, 2H), 7.1 (d, J=7.9 Hz, 1H), 7.3 (d, J=2.4 Hz, 1H), 7.6 (d, J=9.2 Hz, 1H), 7.6 (s, 1H), 7.7 (t, J=7.3 Hz, 2H), 7.8 (d, J=7.0 Hz, 1H), 8.0-8.0 (m, 2H); LC-MS, MS m/z 879 (M$^+$+H).

Preparation of Compound 4, Example 4

Compound 4

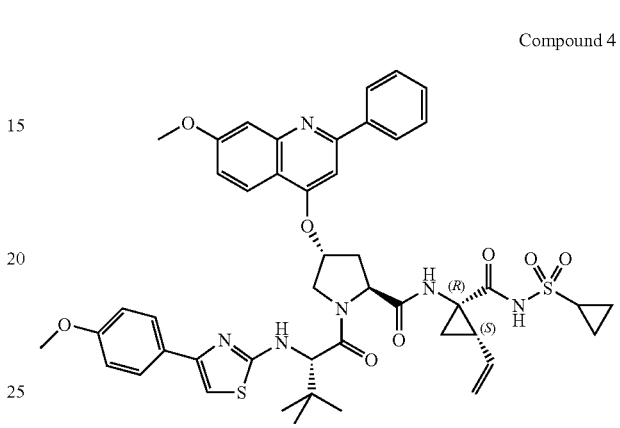

Compound 4 was prepared in 29.5% yield following the same procedure as described for the preparation of compound 1, except 4-methoxyphenacyl bromide was used instead of 2-bromo-acetophenone in step 7. $^1$H NMR (500 MHz, MeOH) δ ppm 1.0 (t, J=6.6 Hz, 1H), 1.1-1.1 (m, 3H), 1.2 (s, 9H), 1.2-1.3 (m, 2H), 1.4-1.5 (m, 1H), 1.9 (dd, J=8.1, 5.6 Hz, 1H), 2.2 (q, J=8.6 Hz, 1H), 2.4-2.4 (m, 1H), 2.6-2.6 (m, 1H), 2.9-3.0 (m, 1H), 3.5 (s, 3H), 4.0 (s, 3H), 4.2 (dd, J=12.2, 3.1 Hz, 1H), 4.6 (dd, J=10.4, 6.7 Hz, 1H), 5.1 (d, J=11.3 Hz, 1H), 5.1 (d, J=10.4 Hz, 1H), 5.3 (d, J=17.1 Hz, 1H), 5.7-5.8 (m, 1H), 6.0 (s, 1H), 6.5 (d, J=8.9 Hz, 2H), 7.1 (dd, J=9.3, 2.3 Hz, 1H), 7.3-7.4 (m, 3H), 7.6-7.6 (m, 2H), 7.7-7.7 (m, 2H), 7.8 (d, J=7.3 Hz, 1H), 8.0-8.0 (m, 2H); LC-MS, MS m/z 879 (M$^+$+H).

Preparation of Compound 5, Example 5

Compound 5

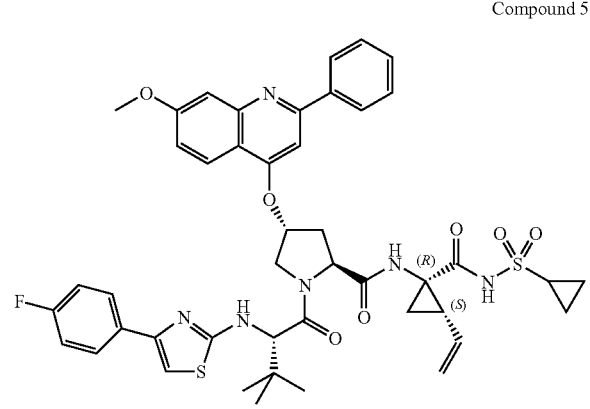

Compound 5 was prepared in 29.0% yield following the same procedure as described for the preparation of compound 1, except 4-fluorophenacyl bromide was used instead of 2-bromo-acetophenone in step 7. $^1$H NMR (500 MHz, MeOH) δ ppm 1.1-1.1 (m, 3H), 1.2 (s, 9H), 1.2-1.3 (m, 2H), 1.4 (dd, J=9.5, 5.5 Hz, 1H), 1.9 (dd, J=8.1, 5.6 Hz, 1H), 2.2 (q, J=8.9 Hz, 1H), 2.3-2.4 (m, 1H), 2.6-2.6 (m, 1H), 2.9-3.0 (m, 1H), 4.0 (s, 3H), 4.3 (dd, J=12.1, 2.9 Hz, 1H), 4.6 (dd, J=10.5, 6.9 Hz, 1H), 5.0 (d, J=12.5 Hz, 1H), 5.1 (dd, J=10.4, 1.2 Hz, 1H), 5.3 (dd, J=17.1, 1.2 Hz, 1H), 5.7-5.8 (m, 1H), 6.0 (s, 1H), 6.6 (t, J=8.9 Hz, 2H), 7.1 (dd, J=9.3, 2.3 Hz, 1H), 7.4 (d, J=2.1 Hz, 1H), 7.5 (dd, J=8.7, 5.3 Hz, 2H), 7.6 (d, J=8.2 Hz, 2H), 7.7 (t, J=7.5 Hz, 2H), 7.8 (d, J=7.3 Hz, 1H), 8.0 (d, J=7.3 Hz, 2H); LC-MS, MS m/z 867 (M$^+$+H).

Preparation of Compound 6, Example 6

Compound 6

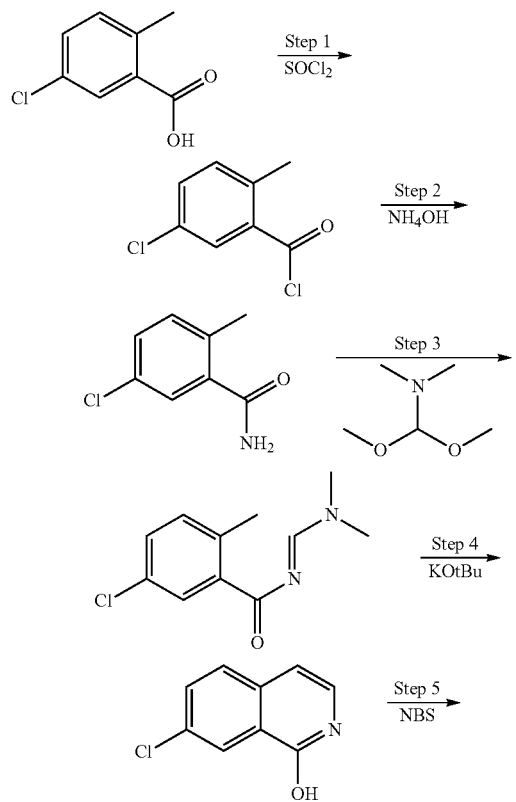

Scheme 1 of Example 6

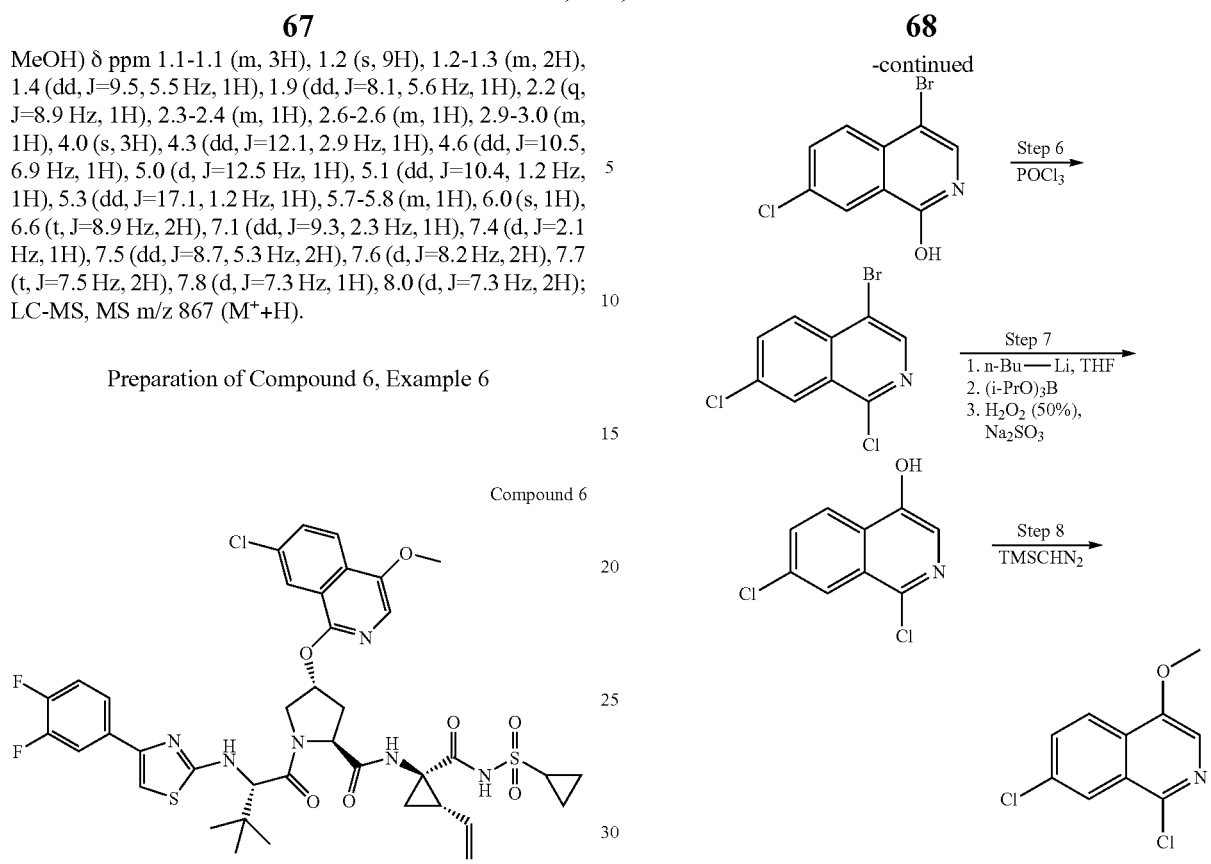

Step 1:

A slurry of 3-chloro-6-methylbezoic acid (17.0 g, 0.10 mol) in thionyl chloride (23.5 mL, 0.30 mol) was heated slowly to a gentle reflux and maintained at this temperature for 2 h. The reaction mixture was then cooled to RT and the excess thionyl chloride removed in vacuo. The residue was taken up in DCM (50 mL), and the solvent then removed in vacuo. (It should be noted that this process was repeated several times to ensure removal of residual thionyl chloride and HCl). The resulting product was then dissolved in THF (80 mL) which was used directly in the next reaction as described below.

Step 2:

To a solution of 30% ammonia (58 mL) in water (240 mL), cooled by salt-ice bath (−10° C.), was added dropwise a THF solution of the product of Step 1 above. After the addition was complete, the resulting reaction mixture (slurry) was stirred at −10° C. for 1 hr. The reaction mixture was then warmed to room temperature and decanted. The remaining solid in the reaction vessel was then triturated with water (50 mL). This process of trituration and decanting was then repeated. The remaining solid was then filtered and the filter cake washed with water. The solid was then dried in vacuo overnight to yield 13.8 g (82%) of desired product as a white crystalline material. $^1$H NMR (DMSO-d$_6$) δ ppm 2.33 (s, 3H), 7.24-7.27 (m, 1H), 7.35-7.38 (m, 2H), 7.44 (b, 1H), 7.80 (b, 1H); $^{13}$C NMR (100 MHz, DMSO-D$_6$) δ ppm 18.87, 126.64, 128.86, 129.81, 132.31, 134.19, 138.65, 169.41; LC-MS, MS m/z 170 (M$^+$+H).

Step 3:

A mixture of the product of Step 2 (11.5 g, 68 mmol), DMF-acetal (10.9 mL, 82 mmol), and THF (150 mL) was heated to reflux and maintained at this temperature for 2 hr. The reaction mixture was then cooled to room temperature and the volatiles were removed in vacuo. The resulting residue was recrystallized from hexane (150 mL) to yield 14.7 g (96%) of the desired product as white needles. $^1$H NMR (DMSO-d$_6$) δ 2.49-2.51 (m, 3H), 3.09 (s, 3H), 3.20 (s, 3H), 7.24, 7.27 (d, J=13.5 Hz, 1H), 7.37-7.41 (dd, J1=14 Hz, J2=4.5 Hz, 1H), 7.91, 7.92 (d, J=4.0 Hz, 1H), 8.55 (s, 1H); $^{13}$C NMR (100 MHz, DMSO-d$_6$) δ ppm 20.69, 35.09, 40.91, 129.50, 129.72, 132.98, 136.86, 138.87, 160.60, 177.04; LC-MS, MS m/z 225 (M$^+$+H).

Step 4:

A mixture of the product of Step 3 and KOtBu (14.7 g, 131 mmol) in THF (300 mL) was heated to reflux and maintained at this temperature for 2 hr (reaction mixture became a dark solution upon heating). The volume of the reaction mixture was then reduced by distilling off approximately 100 mL of solvent. The resulting solution was then carefully poured into water (1 L) and the resulting mixture was acidified with 1M HCl to pH=4. The mixture was then filtered, and the collected solid was washed thoroughly with water, then dried in vacuo overnight to yield 7.0 g (60%) of the desired product as a off-white powder. $^1$H NMR (400 Hz, CD$_3$OD) δ ppm 6.66 (d, J=7.05 Hz, 1H), 7.18 (d, J=7.05 Hz, 1H), 7.66 (s, 1H) 7.67 (d, J=2.01 Hz, 1H), 8.24 (d, J=2.27 Hz, 1H); $^{13}$C NMR (100 MHz, DMSO-d$_6$) δ ppm 104.05, 125.62, 127.21, 128.54, 129.52, 130.77, 132.43, 136.55, 160.72; LC-MS, MS m/z 180 (M$^+$+H).

Step 5:

A slurry of the product of Step 4 and NBS (39.747 g, 223.3 mmol) in MeCN (500 mL, anhydrous) was slowly heated to a gentle reflux over a period of approximately 2 h and maintained at a gentle reflux for 1.5 h. (This reaction can be monitored by LC/MS). The reaction mixture was then slowly cooled to room temperature over a period of 3 h and the observed solid was removed by simple filtration. The collected solid was washed with MeCN (100 mL×3) to provide 47 g of the desired product. This material was used in the next step without further purification.

$^1$H NMR (400 MHz, CD$_3$OD) δ ppm 7.46 (s, 1H), 7.81 (dd, J=8.40, 2.00 Hz, 1H), 7.88 (d, J=8.8 Hz, 1H), 8.27 (d, J=2.00 Hz, 1H); $^{13}$C NMR (100 MHz, DMSO-D$_6$) δ ppm 96.68, 126.34, 127.58, 127.71, 130.73, 132.20, 133.47, 134.46, 159.88; LC-MS, MS m/z 258 (M$^+$+H).

Step 6:

A heterogeneous solution of the product of Step 5 (47 g, 182 mmol) in POCl$_3$ (200 mL, 2.15 mol) was slowly heated to reflux over a period of 1 h. The reaction mixture was maintained at reflux for 4 h. The reaction mixture was then cooled to room temperature and concentrated in vacuo to remove excess POCl$_3$. The resulting residue was then taken up into 600 mL of CH$_2$Cl$_2$, cooled to at −35° C., then slowly treated with 1 N NaOH (400 mL) until the mixture was slightly basic (pH=8). The resulting organic layer was separated, washed with water, dried over MgSO$_4$, filtered, and concentrated in vacuo. The resulting residue was crystallized from EtOAc (approximately 50 mL) to give 32 g of desired product. The collected solid was washed with 10% EtOAc/Hexanes (3×50 mL).

The mother liquors were concentrated and purified by flash column chromatography (SiO$_2$, eluted with 16% EtOAc in hexanes) to give 4 g of the desired product as a solid. $^1$H NMR (400 MHz, CDCl$_3$) δ ppm 7.80 (dd, J=8.81, 2.01 Hz, 1H), 8.14 (d, J=9.06 Hz, 1H), 8.34 (d, J=1.76 Hz, 1H), 8.48 (s, 1H); $^{13}$C NMR (100 MHz, DMSO-D$_6$) δ ppm 118.39, 125.06, 127.59, 128.71, 133.89, 134.14, 134.93, 143.18, 148.98; LC-MS, MS m/z 275 (M$^+$+H).

Step 7:

To a slurry of the product of Step 6 (22.16 g, 80 mmol) in THF (500 mL) at −78° C. was added 100 mL of 1.6 M n-BuLi (in hexanes, 160 mmol) dropwise via cannula over 15 min (maintaining the internal temperature <−65° C.). The resulting solution was stirred for 0.5 h, after such time, (i-PrO)$_3$B (37 mL, 160 mmol) was added dropwise via syringe over 10 min (maintaining the internal temperature <−65° C.). The resulting reaction mixture was stirred for 0.5 h. After checking the reaction by LC/MS for completion, 80 ml of 30% H$_2$O$_2$ (776 mmol) was added dropwise via addition funnel over 10 min (the internal temperature rose to −60° C. during addition), followed by addition of 80 mL of 1 N NaOH (80 mmol). The cooling bath was removed, and the reaction mixture was allowed to warm to room temperature and stirred at room temperature for additional 1 h. After confirming the completion of the reaction by LC/MS, the reaction mixture was then cooled to −40° C., and a solution of 100 g of Na$_2$SO$_3$ (0.793 mole) in 400 mL of water was added dropwise via addition funnel as a means to quench excess H$_2$O$_2$ over 30 min (maintaining the internal temperature 5-10° C.). The resulting slurry was then neutralized with 6 N HCl (approximately 50 mL) at 0° C. till pH ~6, then diluted with 500 mL of EtOAc and decanted to a 2 L separatory funnel. To the remaining solid in the reaction vessel was added 500 mL of water and 300 mL of EtOAc, then neutralized with 6 N HCl (approximately 20 mL). The combined organic layers were washed with brine (3×300 mL), then water (3×200 mL), dried over MgSO$_4$, filtered, and concentrated to give a crude product which was triturated with 50 mL of EtOAc. The solid was collected by filtration, rinsed with EtOAc (3×25 mL) and dried to give desired product (2 runs: 12.0 g, 70% and 13.8 g, 81%). The filtrates were combined, concentrated and purified by flash column chromatography (SiO$_2$, eluted with 35% EtOAc in hexanes to give 2.1 g of product. Overall, 44.4 g of bromide gave 27.9 g (81%) of 4-OH product. $^1$H NMR (400 MHz, CD$_3$OD) δ ppm 4.05 (s, 3H), 7.4 (s, 1H), 7.76 (dd, J=8.8, 2, Hz, 1H), 8.16 (d, J=2 Hz, 1H), 8.23 (d, J=8.8 Hz, 1H); $^{13}$C NMR (100 MHz, DMSO-d$_6$) δ ppm 123.78, 124.66, 125.62, 127.03, 127.71, 130.72, 133.80, 137.63; 148.88; LC-MS, MS m/z 213 (M$^+$+H).

Step 8:

To a slurry of the product of Step 7 (16 g, 75.5 mmol) in MeOH-MeCN (30 mL/300 mL) at 0° C. was added dropwise 60 mL of 2 M solution of TMSCHN$_2$ in hexanes (120 mmol). The reaction mixture was allowed to warm to room temperature; then it was stirred for 14 h. The solution was then concentrated and the resulting solid was recrystallized from EtOAc (about 50 mL) to give 8.1 g of the desired product which was washed with 25% EtOAc in hexanes (3×20 mL). The mother liquors were concentrated and purified by flash column chromatography (SiO$_2$, eluted with 16% EtOAc in hexanes) to provide 3.2 g of the desired product as a solid. $^1$H NMR (400 MHz, CDCl$_3$) δ ppm 4.05 (s, 3H), 7.67 (dd, J=9.06, 2.01 Hz, 1H), 7.80 (s, 1H), 8.16 (d, J=8.81 Hz, 1H), 8.23 (d, J=2.01 Hz, 1H); $^{13}$C NMR (100 MHz, DMSO-d$_6$) δ ppm 56.68, 122.70, 123.99, 124.14, 126.67, 127.83, 131.43, 134.10, 139.75, 149.94; LC-MS, MS m/z 229 (M$^+$+H).

Scheme 2 of Example 6
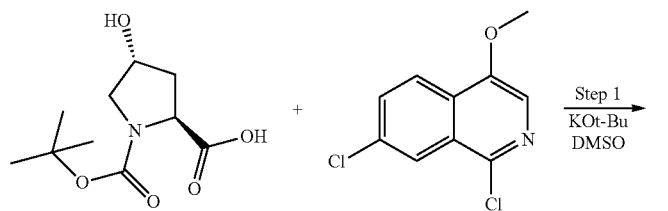
Step 1
KOt-Bu
DMSO
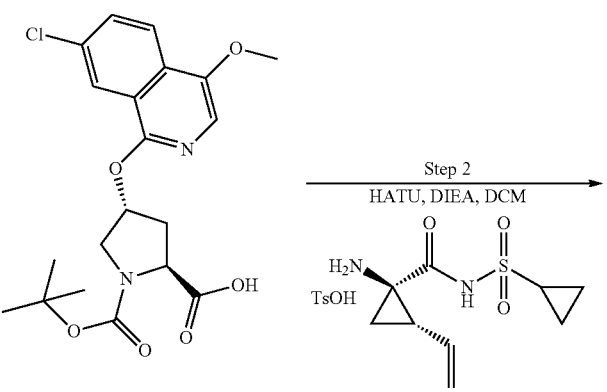
Step 2
HATU, DIEA, DCM
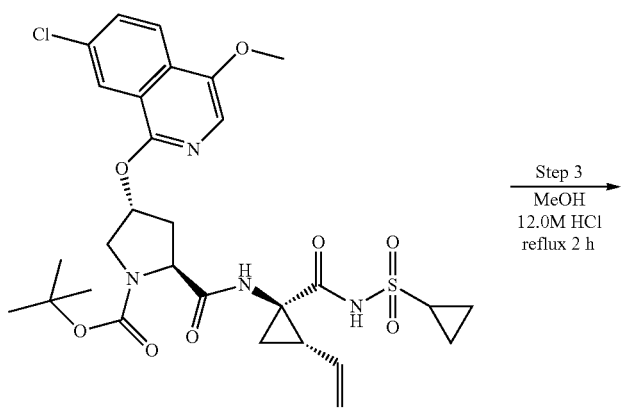
Step 3
MeOH
12.0M HCl
reflux 2 h
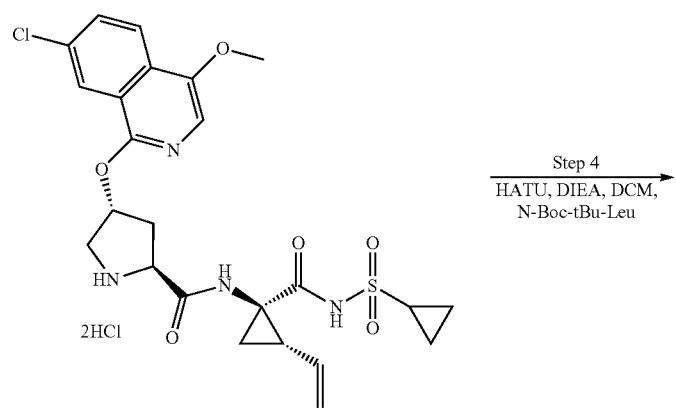
Step 4
HATU, DIEA, DCM,
N-Boc-tBu-Leu

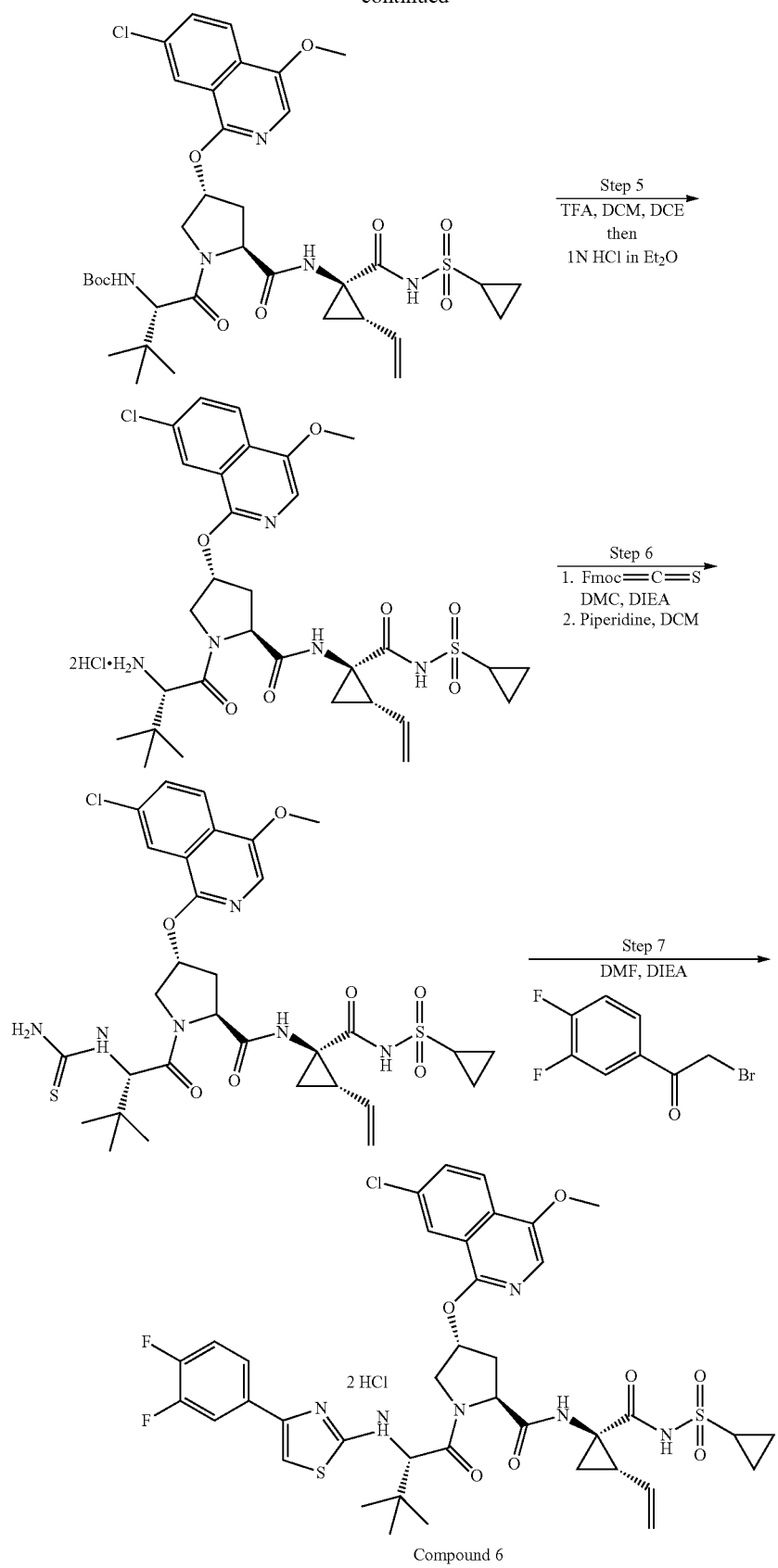
Compound 6

Step 1:
The product of Step 8, Scheme 1, Example 6 (0.452 g, 1.98 mmol), Boc-HYP-OH (0.508 g, 2.20 mmol), and potassium tert-butoxide (0.672 g, 6.0 mmol) in DMSO (20 mL) was stirred at room temperature for 4 hours. The mixture was quenched with water and neutralized with 1.0M aqueous HCl. The mixture was extracted with ethyl acetate and the organic was washed with brine, dried over anhydrous $MgSO_4$, filtered and concentrated to give a crude solid (0.844 g, quantitative) which was used in the next step without further purification.

Step 2:
To a solution of the product of step 1 (8.36 g, 19.8 mmol), (1R,2S)-1-amino-N-(cyclopropylsulfonyl)-2-vinylcyclopropanecarboxamide TsOH salt (9.64 g, 24 mmol), and $iPr_2EtN$ (17.4 mL, 100 mmol) in $CH_2Cl_2$ (200 mL) was added HATU (11.4 g, 31 mmol). The reaction mixture was stirred for 16 h, concentrated in vacuo and the residue dissolved in EtOAc (300 mL) and washed sequentially with 1 N HCl (3×50 mL), water (2×30 mL), and brine (2×50 mL). The organics were dried over $MgSO_4$, filtered, concentrated, and purified by flash column chromatography (SiO2, eluted with 25% acetone in hexanes) to provide 11.5 g of crude product. This compound was purified by crystallizing from MeOH (40 mL) to afford the desired product (11 g, 88% yield) as a crystalline solid. $^1$H NMR (400 MHz, $CD_3OD$) δ ppm 1.03-1.31 (m, 8H), 1.43 (s, 9H), 1.88 (dd, J=8.06, 5.54 Hz, 1H), 2.17-2.36 (m, 2H), 2.53 (dd, J=13.72, 6.42 Hz, 1H), 2.90-3.03 (m, 1H), 3.72-3.93 (m, 2H), 4.40 (dd, J=9.69, 6.92 Hz, 1H), 5.13 (d, J=10.32 Hz, 1H), 5.31 (d, J=17.12 Hz, 1H), 5.65-5.93 (m, 2H), 7.55 (s, 1H), 7.70 (dd, J=8.94, 2.14 Hz, 1H), 8.06 (d, J=2.01 Hz, 1H), 8.09 (d, J=8.81 Hz, 1H); $^{13}$C NMR (126 MHz, DMSO-$d_6$) δ ppm 5.47, 5.57, 5.75, 19.85, 22.38, 27.90, 27.99, 30.65, 30.72, 32.11, 33.81, 35.11, 36.30, 40.86, 41.59, 48.56, 52.39, 52.76, 56.24, 58.76, 59.21, 73.57, 74.06, 79.28, 80.06, 117.80, 119.16, 119.81, 119.88, 122.14, 123.48, 128.52, 131.00, 132.28, 133.38, 145.72, 151.77, 151.86, 154.06, 168.38, 169.13, 172.46, 173.27; LC-MS, MS m/z 635 ($M^+$+H).

Step 3:
A slurry of the product from step 2 (6.34 g, 10 mmol) in 50 mL of MeOH containing 3 mL of concentrated HCl was refluxed for 2 h. The solution was cooled to room temperature and concentrated in vacuo. The solid residue was taken up in dry $Et_2O$ (50 ml) and the solution concentrated in vacuo. This process, repeated five times to ensure complete removal of water and solubilized HCl, provided a bis-HCl salt product (6.07 g, 100% yield). $^1$H NMR (400 MHz, $CD_3OD$) δ ppm 0.96-1.21 (m, 3H), 1.22-1.30 (m, 1H), 1.38 (dd, J=9.57, 5.54 Hz, 1H), 1.95 (dd, J=8.06, 5.79 Hz, 1H), 2.25-2.46 (m, 2H), 2.83-3.08 (m, 2H), 3.75-3.90 (m, 2H), 4.01 (s, 3H), 4.70 (dd, J=10.32, 7.81 Hz, 1H), 5.10-5.20 (m, 1H), 5.33 (d, J=17.12 Hz, 1H), 5.58-5.76 (m, 1H), 5.88 (s, 1H), 7.57 (s, 1H), 7.74 (dd, J=8.81, 2.01 Hz, 1H), 8.12 (d, J=9.06 Hz, 1H), 8.28 (d, J=2.01 Hz, 1H); $^{13}$C NMR (101 MHz, $CD_3OD$) δ ppm 6.52, 6.65, 22.60, 31.99, 34.63, 37.04, 43.18, 52.95, 56.85, 60.56, 76.08, 119.06, 119.10, 121.65, 123.93, 124.63, 130.72, 132.37, 133.78, 134.76, 148.49, 153.02, 170.08, 170.67; LC-MS, MS m/z 535 ($M^+$+H).

Step 4:
To a solution of the product from step 3 (6.07 g, 10 mmol) in 100 mL of $CH_2Cl_2$, maintained at 0° C., was added 8.7 mL of $iPr_2EtN$ (50 mmol) followed by Boc-L-tert-leucine (2.772 g, 12 mmol) and HATU (5.7 g, 15 mmol). The reaction mixture was warmed to RT and stirred for 16 h before being concentrated in vacuo and the residue dissolved in EtOAc (300 mL). The EtOAc solution was washed sequentially with 1N HCl (3×50 mL), $H_2O$ (2×30 mL), and brine (2×50 mL). The organic phase was dried over $MgSO_4$, filtered, and concentrated in vacuo and the crude product obtained after purification by flash column chromatography ($SiO_2$, eluted with 33% acetone in hexanes) to provide a white solid product (7 g, 94% yield). $^1$H NMR (400 MHz, $CD_3OD$) δ ppm 1.00-1.06 (m, 11H), 1.16 (s, 9H), 1.14-1.24 (m, 2H), 1.44 (dd, J=9.32, 5.29 Hz, 1H), 1.88 (dd, J=8.06, 5.54 Hz, 1H), 2.17-2.39 (m, 2H), 2.59 (dd, J=13.85, 6.80 Hz, 1H), 2.87-3.02 (m, 1H), 4.00 (s, 3H), 4.01-4.14 (m, 1H), 4.17-4.24 (m, 1H), 4.43 (d, J=12.09 Hz, 1H), 4.52-4.65 (m, 1H), 5.12 (d, J=10.07 Hz, 1H), 5.30 (d, J=16.87 Hz, 1H), 5.65-5.91 (m, 2H), 7.56 (s, 1H), 7.68 (d, J=9.06 Hz, 1H), 8.05 (s, 1H), 8.09 (d, J=9.06 Hz, 1H). LC-MS, MS m/z 748 ($M^+$+H). Anal. Calcd for $C_{35}H_{46}ClN_5O_9S$: C, 55.84; H, 6.32; N, 9.10; S, 4.16. Found: C, 56.02; H, 6.31; N, 9.04.

Step 5:
To a solution of tert-butyl(S)-1-((2S,4R)-4-(7-chloro-4-methoxyisoquinolin-1-yloxy)-2-((1R,2S)-1-(cyclopropylsulfonylcarbamoyl)-2-vinylcyclopropylcarbamoyl)pyrrolidin-1-yl)-3,3-dimethyl-1-oxobutan-2-ylcarbamate, the product from step 4 (5.08 g, 6.79 mmol) in DCM (20 mL) and DCE (20.0 mL) was add TFA (20 mL, 260 mmol). The resulting light brown reaction mixture was stirred at 25° C. After 20 min at rt, reaction mixture was concentrated to light brown viscous oil, which was redissolved in DCE (30 mL) and reconcentrated to a light brown solid. The residue was dissolved in DCM (10 mL) and was added to a vigorously stirred solution of 1N HCl in $Et_2O$ (100 mL), the resulting off-white precipitate was obtained by vacuum filtration and washed with $Et_2O$ (50 mL) and was dried in a vacuum oven to afford (2S,4R)-1-((S)-2-amino-3,3-dimethylbutanoyl)-4-(7-chloro-4-methoxyisoquinolin-1-yloxy)-N-((1R,2S)-1-(cyclopropylsulfonylcarbamoyl)-2-vinylcyclopropyl)pyrrolidine-2-carboxamide, 2HCl (4.91 g, 6.81 mmol, 100% yield) as an off-white solid. $^1$H NMR (500 MHz, MeOD) δ ppm 1.0-1.1 (m, 3H), 1.2 (s, 9H), 1.2-1.3 (m, 3H), 1.4 (dd, J=9.5, 5.2 Hz, 1H), 1.9 (dd, J=7.9, 5.5 Hz, 1H), 2.3 (q, J=8.9 Hz, 1H), 2.3-2.4 (m, 1H), 2.7 (dd, J=14.0, 6.7 Hz, 1H), 2.9-3.0 (m, 1H), 3.3-3.3 (m, 1H), 3.5 (q, J=7.0 Hz, 1H), 4.0 (s, 3H), 4.1 (s, 1H), 4.1 (dd, J=12.4, 3.5 Hz, 1H), 4.4 (d, J=12.2 Hz, 1H), 4.7 (dd, J=10.4, 6.7 Hz, 1H), 5.1 (dd, J=10.4, 1.5 Hz, 1H), 5.3 (dd, J=17.2, 1.4 Hz, 1H), 5.7-5.7 (m, 1H), 5.9 (s, 1H), 7.5 (s, 1H), 7.8 (dd, J=8.9, 1.8 Hz, 1H), 8.1 (d, J=8.9 Hz, 1H), 8.3 (d, J=2.1 Hz, 1H). $^{13}$C NMR (MeOD) δ ppm 5.8, 5.8, 14.5, 22.4, 25.9, 31.3, 34.6, 34.9, 35.2, 41.8, 54.9, 56.3, 59.5, 60.6, 65.9, 77.8, 114.7, 117.8, 121.0, 123.7, 123.9, 130.4, 133.0, 133.1, 134.7, 147.8, 152.8, 168.1, 169.4, 173.4. LC-MS, MS m/z 648 ($M^+$+H).

Step 6:
To a solution of product of step 5, example 6, (1.53 g, 2.12 mmol) and N,N-diisopropylethylamine (1.11 mL, 6.37 mmol) in DCM (20 mL) was added Fmoc-isothiocyanate (0.895 g, 3.18 mmol). The resulting brown reaction mixture was stirred at 25° C. After 53 h, the reaction mixture was treated with piperidine (2 mL, 20.20 mmol) and stirred at 25° C. for an additional 6 h. The reaction mixture was diluted with DCM (50 mL) and washed with 3×50 mL 0.1N HCl. The organic layer was dried over $MgSO_4$ and concentrated to a brown solid which was purified by flash column chromatography ($SiO_2$, eluted with 95:5 DCM:MeOH) to give (2S,4R)-4-(7-chloro-4-methoxyisoquinolin-1-yloxy)-N-((1R,2S)-1-(cyclopropylsulfonylcarbamoyl)-2-vinylcyclopropyl)-1-((S)-3,3-dimethyl-2-thioureidobutanoyl)pyrrolidine-2-carboxamide (1.38 g, 1.951 mmol, 92% yield) as a light brown foamy solid product; but this material still contained about 33% of 1-((9H-fluoren-9-yl)methyl)piperidine by product and it was used in the next step without further purification. A small amount of an analytical sample was obtained by reverse phase HPLC. LC-MS, MS m/z 707 (M$^+$+H).

Step 7:

To a solution of product of step 6 (0.150 g, 0.212 mmol) and N,N-diisopropylethylamine (0.111 mL, 0.636 mmol) in DMF (2 mL) was added 2-bromo-1-(3,4-difluorophenyl)ethan-1-one (0.100 g, 0.424 mmol). The resulting reaction mixture was agitated at 25° C. After 17.5 h, the reaction mixture was added dropwise to a vigorously stirred solution of 1.0N HCl (5 mL), the resulting beige precipitate was filtered and washed with H$_2$O (3 mL). The crude product was purified by reverse phase HPLC using the following solvent system and conditions: solvent A=H$_2$O, solvent B=MeOH, both containing 0.1% TFA; 40% B to 100% B 20 mins, hold at 100% B 4 mins. After concentration of combined HPLC fractions, the resulting residue was redissolved into MeOH and treated with 1N aqueous HCl (2 mL) then it was re-concentrated and dried in a vacuum oven at 50° C. to give (2S,4R)-4-(7-chloro-4-methoxyisoquinolin-1-yloxy)-N-((1R,2S)-1-(cyclopropylsulfonylcarbamoyl)-2-vinylcyclopropyl)-1-((S)-2-(4-(3,4-difluorophenyl)thiazol-2-ylamino)-3,3-dimethylbutanoyl)pyrrolidine-2-carboxamide, 2HCl (76.9 mg, 0.084 mmol, 39.6% yield), compound 6, as light yellow solid. $^1$H NMR (500 MHz, MeOD) δ ppm 1.04-1.14 (m, 3H), 1.16 (s, 9H), 1.22 (s, 1H), 1.25 (d, J=4.9 Hz, 2H), 1.42 (dd, J=9.5, 5.5 Hz, 1H), 1.90 (dd, J=8.2, 5.5 Hz, 1H), 2.25 (q, J=8.9 Hz, 1H), 2.28-2.34 (m, 1H), 2.59 (dd, J=13.7, 7.3 Hz, 1H), 2.92-2.99 (m, 1H), 3.97 (s, 3H), 4.12 (dd, J=12.1, 3.5 Hz, 1H), 4.50 (d, J=11.9 Hz, 1H), 4.64-4.69 (m, 2H), 5.13 (dd, J=10.4, 1.5 Hz, 1H), 5.30 (dd, J=17.2, 1.4 Hz, 1H), 5.68-5.77 (m, 1H), 5.96 (s, 1H), 7.18-7.25 (m, 1H), 7.29-7.34 (m, 1H), 7.43-7.48 (m, 1H), 7.52 (s, 1H), 7.62 (dd, J=8.9, 2.1 Hz, 1H), 7.84 (d, J=1.8 Hz, 1H), 8.02 (d, J=9.2 Hz, 1H); LC-MS, MS m/z 843 (M$^+$+H).

Preparation of Compound 7, Example 7

Compound 7

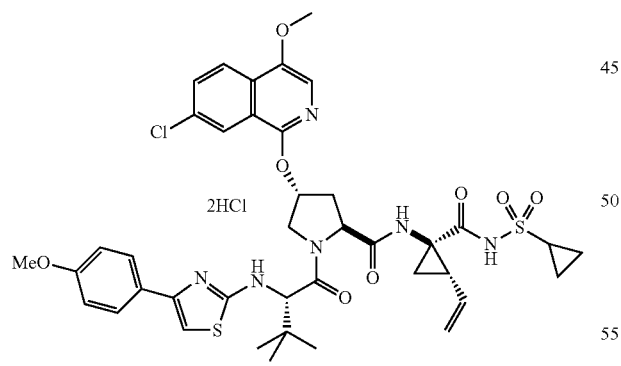

Compound 7 was prepared in 57.5% yield following the same procedure as described for the preparation of compound 6, except 2-bromo-4'-methoxyacetophenone was used instead of 2-bromo-1-(3,4-difluorophenyl)ethan-1-one in step 7. $^1$H NMR (500 MHz, MeOD) δ ppm 1.01-1.13 (m, 4H), 1.17 (s, 9H), 1.22-1.27 (m, 2H), 1.42 (dd, J=9.5, 5.5 Hz, 1H), 1.90 (dd, J=8.2, 5.5 Hz, 1H), 2.27 (q, J=8.9 Hz, 1H), 2.30-2.36 (m, 1H), 2.65 (dd, J=13.6, 7.2 Hz, 1H), 2.92-3.00 (m, 1H), 3.82 (s, 3H), 3.97 (s, 3H), 4.10 (dd, J=11.9, 2.7 Hz, 1H), 4.40 (d, J=12.5 Hz, 1H), 4.52 (s, 1H), 4.71 (dd, J=9.8, 7.3 Hz, 1H), 5.13 (dd, J=10.4, 1.5 Hz, 1H), 5.31 (dd, J=17.1, 1.2 Hz, 1H), 5.67-5.78 (m, 1H), 5.91 (s, 1H), 6.95 (d, J=8.5 Hz, 2H), 7.42 (d, J=8.5 Hz, 2H), 7.55 (s, 1H), 7.63 (dd, J=9.0, 2.0 Hz, 1H), 7.94 (d, J=2.1 Hz, 1H), 8.05 (d, J=8.9 Hz, 1H); LC-MS, MS m/z 837 (M$^+$+H).

Preparation of Compound 8, Example 8

Compound 8

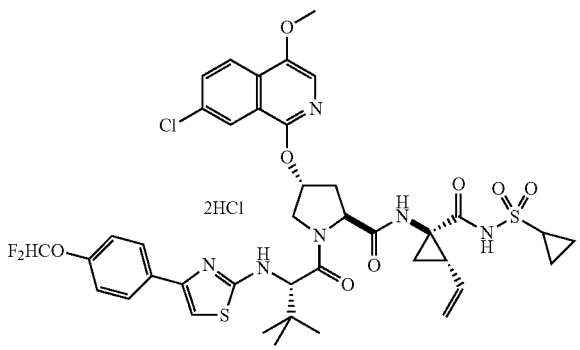

Compound 8 was prepared in 28.4% yield following the same procedure as described for the preparation of compound 6, except 2-bromo-1-(4-(difluoromethoxy)phenyl)ethanone was used instead of 2-bromo-1-(3,4-difluorophenyl)ethan-1-one in step 7. $^1$H NMR (500 MHz, MeOD) δ ppm 1.05-1.14 (m, 3H), 1.17 (s, 9H), 1.21 (s, 1H), 1.23-1.26 (m, 2H), 1.42 (dd, J=9.6, 5.3 Hz, 1H), 1.90 (dd, J=8.2, 5.5 Hz, 1H), 2.26 (q, J=8.9 Hz, 1H), 2.28-2.34 (m, 1H), 2.62 (dd, J=13.7, 7.3 Hz, 1H), 2.93-2.99 (m, 1H), 3.97 (s, 3H), 4.11 (dd, J=11.9, 3.4 Hz, 1H), 4.41 (d, J=12.2 Hz, 1H), 4.55 (s, 1H), 4.69 (dd, J=10.2, 7.2 Hz, 1H), 5.13 (dd, J=10.4, 1.5 Hz, 1H), 5.30 (dd, J=17.2, 1.4 Hz, 1H), 5.68-5.78 (m, 1H), 5.93 (s, 1H), 6.87 (t, J=73.4 Hz, 1H), 7.17 (d, J=8.9 Hz, 2H), 7.53 (s, 1H), 7.55 (s, 2H), 7.63 (dd, J=8.9, 2.1 Hz, 1H), 7.91 (d, J=2.1 Hz, 1H), 8.05 (d, J=8.9 Hz, 1H); LC-MS, MS m/z 873 (M$^+$+H).

Preparation of Compound 9, Example 9

Compound 9

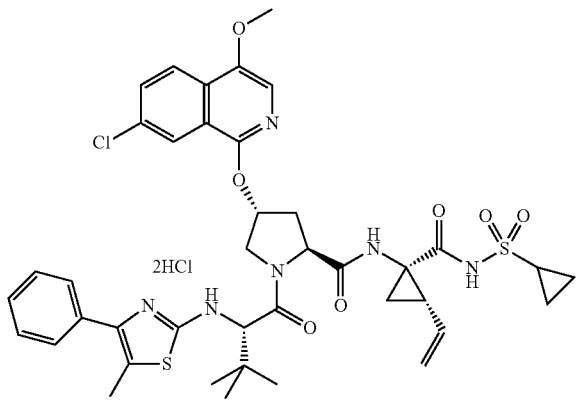

Scheme 1 of Example 9

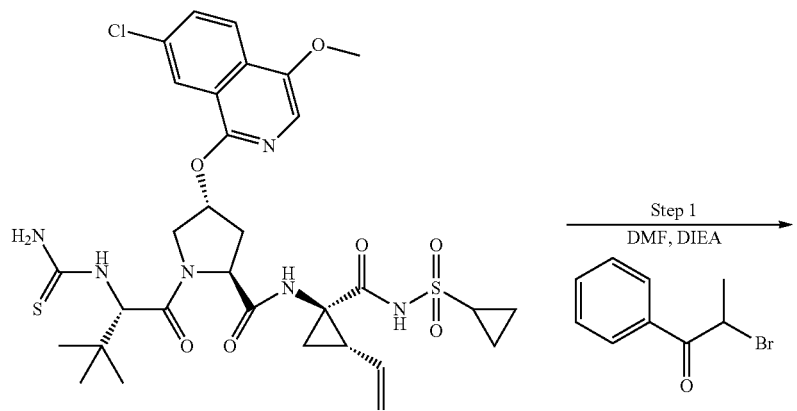

Product of step 6,
scheme 2 of example 6

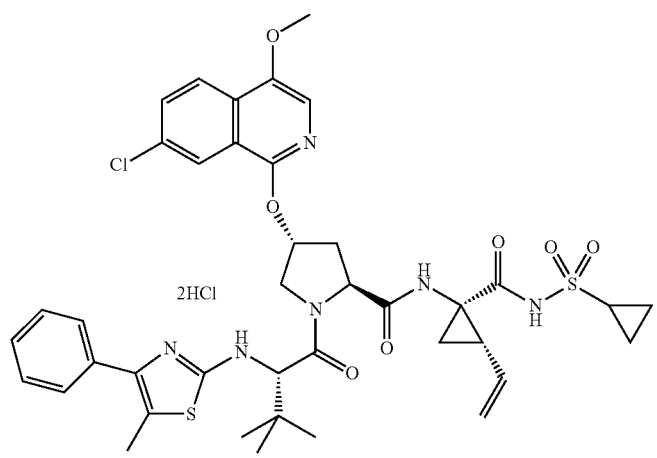

Compound 9

Step 1.

To light brown mixture of (2S,4R)-4-(7-chloro-4-methoxyisoquinolin-1-yloxy)-N-((1R, 2S)-1-(cyclopropylsulfonylcarbamoyl)-2-vinylcyclopropyl)-1-((S)-3,3-dimethyl-2-thioureidobutanoyl)pyrrolidine-2-carboxamide, the product of step 6, scheme 2 of example 6 (0.112 g, 0.158 mmol) and N,N-diisopropylethylamine (0.083 mL, 0.475 mmol) in DMF (1 mL) was added 2-bromopropiophenone (0.050 mL, 0.317 mmol). The resulting reaction mixture was stirred at 25° C. After 15 hr, the reaction mixture was diluted with MeOH (2 mL) and purified by reversed phase HPLC using the following solvent sytem and conditions: solvent A=H$_2$O, solvent B=MeOH, both containing 0.1% TFA; 20% B to 100% B 30 mins, hold at 100% B 4 mins. After concentration of combined HPLC fractions, each compound was redissolved into MeOH and treated with 1N aqueous HCl (2 mL). The sample was then concentrated and dried in a vacuum oven at 50° C. to afford (2S,4R)-4-(7-chloro-4-methoxyisoquinolin-1-yloxy)-N-((1R,2S)-1-(cyclopropylsulfonylcarbamoyl)-2-vinylcyclopropyl)-1-((S)-3,3-dimethyl-2-(5-methyl-4-phenylthiazol-2-ylamino)butanoyl)pyrrolidine-2-carboxamide, 2HCl, compound 9 (73.3 mg, 0.082 mmol, 51.8% yield) as a white bis-HCl-salt solid. $^1$H NMR (500 MHz, MeOD) δ ppm 1.07-1.11 (m, 2H), 1.14 (s, 9H), 1.23-1.26 (m, 2H), 1.42 (dd, J=9.5, 5.5 Hz, 1H), 1.91 (dd, J=8.2, 5.5 Hz, 1H), 2.03 (s, 3H), 2.24-2.34 (m, 2H), 2.64 (dd, J=13.7, 7.0 Hz, 1H), 2.92-2.99 (m, 1H), 3.97 (s, 3H), 4.09 (dd, J=12.2, 3.4 Hz, 1H), 4.28 (d, J=11.9 Hz, 1H), 4.43 (s, 1H), 4.71 (dd, J=10.1, 7.0 Hz, 1H), 5.14 (dd, J=10.4, 1.5 Hz, 1H), 5.31 (dd, J=17.1, 1.2 Hz, 1H), 5.69-5.78 (m, 1H), 5.89 (s, 1H), 7.31-7.34 (m, 2H), 7.47-7.50 (m, 3H), 7.56 (s, 1H), 7.69 (dd, J=8.9, 2.1 Hz, 1H), 7.99 (d, J=2.1 Hz, 1H), 8.10 (d, J=8.9 Hz, 1H), 9.24 (s, 1H); $^{13}$C NMR (MeOD) δ ppm 5.7, 5.8, 10.5, 22.4, 25.9, 31.2, 34.7, 35.0, 37.6, 41.7, 55.2, 55.9, 60.5, 65.6, 75.1, 115.7, 117.7, 118.9, 120.8, 122.4, 123.8, 128.1, 128.8, 129.2, 129.7, 130.2, 131.2, 133.2, 133.6, 135.0, 147.2, 152.4, 167.8, 168.7, 169.4, 173.8; LC-MS, MS m/z 821 (M$^+$+H).

Preparation of Compound 10, Example 10

Compound 10

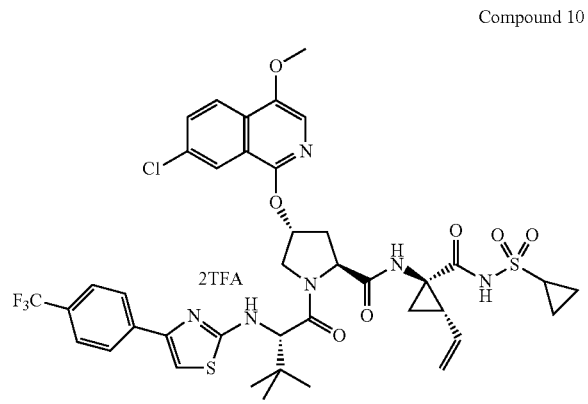

Scheme 1 of Example 10

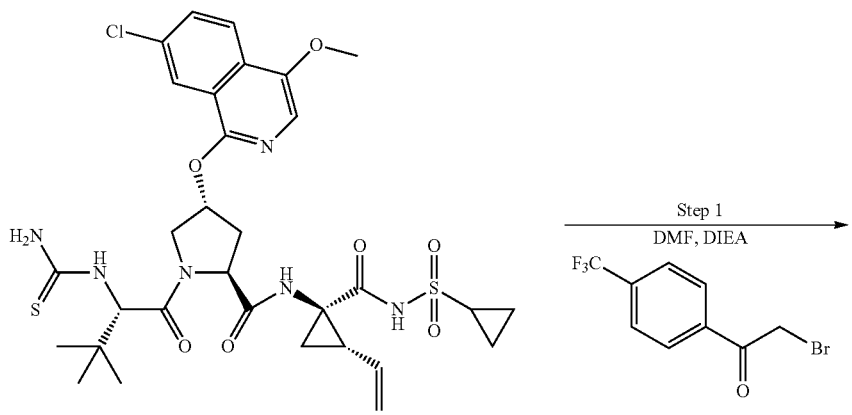

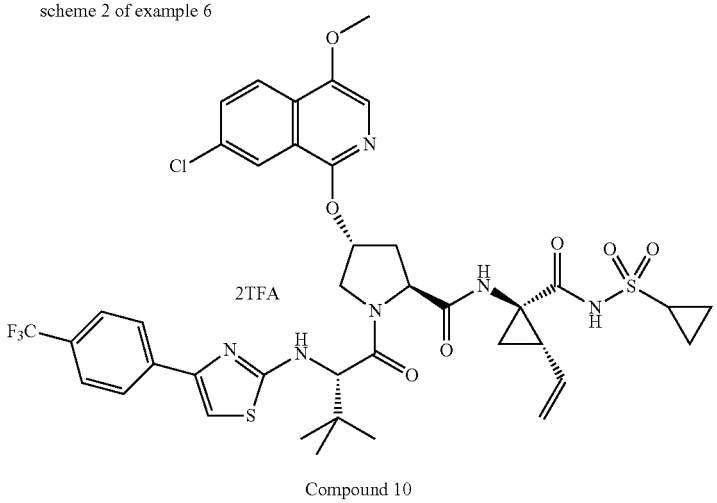

Compound 10

Step 1.

To a solution mixture of (2S,4R)-4-(7-chloro-4-methoxy-isoquinolin-1-yloxy)-N-((1R,2S)-1-(cyclopropylsulfonyl-carbamoyl)-2-vinylcyclopropyl)-1-((S)-3,3-dimethyl-2-thioureidobutanoyl)pyrrolidine-2-carboxamide, the product of step 6, scheme 2 of example 6 (0.150 g, 0.212 mmol) and N,N-diisopropylethylamine (0.111 mL, 0.636 mmol) in DMF (2 mL) was added 2-bromo-1-[4-(trifluoromethyl)phenyl]ethan-1-one (0.113 g, 0.424 mmol). The reaction vial was agitated at 25° C. overnight. After 18.0 h, the reaction mixture was added dropwise to a vigorously stirred solution of 1.0N HCl (5 mL), the resulting beige precipitate was filtered and washed with $H_2O$ (3 mL). The product was purified by reverse phase HPLC using the following solvent system and conditions: solvent A=$H_2O$, solvent B=MeOH, both containing 0.1% TFA; with 40% B to 100% B 20 mins, hold at 100% B 4 mins. After concentration of combined HPLC fractions, the product was then dried in a vacuum oven at 50° C. to afford (2S,4R)-4-(7-chloro-4-methoxyisoquinolin-1-yloxy)-N-((1R,2S)-1-(cyclopropylsulfonylcarbamoyl)-2-vinylcyclopropyl)-1-((S)-3,3-dimethyl-2-(4-(4-(trifluoromethyl)phenyl)thiazol-2-ylamino)butanoyl)pyrrolidine-2-carboxamide, 2TFA (97.3 mg, 0.088 mmol, 41.6% yield) as a yellow-green solid. $^1H$ NMR (500 MHz, MeOD) δppm 1.05-1.10 (m, 2H), 1.15 (s, 9H), 1.23-1.29 (m, 2H), 1.38 (dd, J=9.5, 5.5 Hz, 1H), 1.85 (dd, J=8.2, 5.5 Hz, 1H), 2.15-2.21 (m, 1H), 2.21-2.27 (m, 1H), 2.40 (dd, J=13.7, 6.7 Hz, 1H), 2.92-2.99 (m, 1H), 3.88 (s, 3H), 4.16 (dd, J=11.6, 3.7 Hz, 1H), 4.52 (dd, J=10.5, 6.9 Hz, 1H), 4.83 (s, 1H), 4.92 (d, J=11.9 Hz, 1H), 5.09 (dd, J=10.4, 1.5 Hz, 1H), 5.26 (dd, J=17.1, 1.2 Hz, 1H), 5.66-5.76 (m, 1H), 6.07 (s, 1H), 6.84 (s, 1H), 7.10 (d, J=8.2 Hz, 2H), 7.37 (s, 1H), 7.42 (d, J=2.1 Hz, 1H), 7.47 (dd, J=8.9, 2.1 Hz, 1H), 7.66 (d, J=8.2 Hz, 2H), 7.86 (d, J=8.9 Hz, 1H); $^{13}C$ NMR (MeOD) δ ppm 5.6, 5.8, 22.5, 26.3, 31.3, 34.9, 35.4, 35.5, 41.7, 55.2, 55.6, 60.1, 63.2, 74.2, 104.3, 117.6, 118.2, 120.7, 122.6, 123.1, 124.7, 124.7, 125.9, 129.4, 130.7, 133.1, 133.3138.1, 146.9, 152.1, 169.3, 169.7, 172.8, 174.3; LC-MS, MS m/z 875 ($M^++H$).

Preparation of Compound 11, Example 11

Compound 11

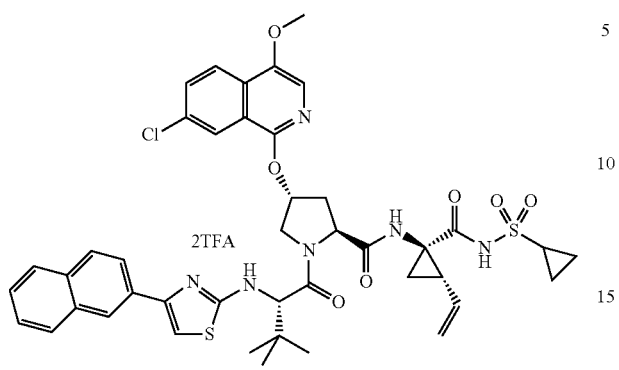

Compound 11 was prepared in 38.5% yield following the same procedure as described for the preparation of compound 10, except 2-bromo-2'-acetonaphthone was used instead of 2-bromo-1-[4-(trifluoromethyl)phenyl]ethan-1-one. $^1$H NMR (500 MHz, MeOD) δ ppm 1.05-1.10 (m, 2H), 1.19 (s, 9H), 1.26 (q, J=4.7 Hz, 2H), 1.31 (t, J=7.3 Hz, 1H), 1.39 (dd, J=9.5, 5.5 Hz, 1H), 1.86 (dd, J=7.9, 5.5 Hz, 1H), 2.18 (q, J=8.9 Hz, 1H), 2.22-2.29 (m, 1H), 2.39 (dd, J=13.6, 6.9 Hz, 1H), 2.85 (s, 1H), 2.92-2.99 (m, 1H), 3.72 (s, 3H), 4.22 (dd, J=11.6, 3.7 Hz, 1H), 4.53 (dd, J=10.5, 6.9 Hz, 1H), 5.01 (d, J=11.3 Hz, 1H), 5.09 (dd, J=10.4, 1.5 Hz, 1H), 5.26 (dd, J=17.2, 1.4 Hz, 1H), 5.66-5.77 (m, 1H), 6.12 (s, 1H), 7.16 (s, 1H), 7.18 (dd, J=8.1, 1.1 Hz, 1H), 7.21-7.26 (m, 1H), 7.32 (dd, J=8.9, 2.1 Hz, 1H), 7.36 (d, J=1.8 Hz, 1H), 7.39 (d, J=8.5 Hz, 1H), 7.45 (d, J=8.2 Hz, 1H), 7.49 (d, J=8.2 Hz, 1H), 7.56 (dd, J=8.5, 1.8 Hz, 1H), 7.64 (d, J=8.9 Hz, 1H), 8.02 (s, 1H); $^{13}$C NMR (MeOD) δ ppm 22.5, 26.3, 31.3, 34.9, 35.5, 35.6, 41.7, 42.8, 55.2, 55.4, 60.1, 63.5, 74.0, 91.9, 117.6, 117.7, 118.0, 120.5, 122.4, 122.7, 123.6, 124.7, 125.5, 125.8, 127.3, 127.5, 128.0, 129.1, 130.4, 131.4, 132.9, 132.9, 133.3, 133.4, 146.7, 152.0, 169.2, 169.7, 172.7, 174.3; LC-MS, MS m/z 857 (M$^+$+H).

Preparation of Compound 12, Example 12

Compound 12

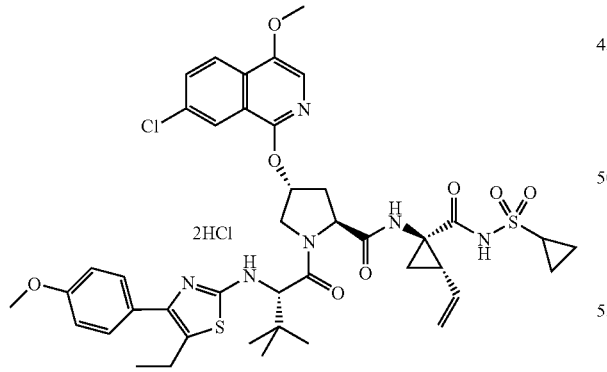

Compound 12 was prepared in 52% yield following the same procedure as described for the preparation of compound 9, except 2-Bromo-1-(4-methoxy-phenyl)-butan-1-one was used instead of 2-bromopropiophenone in step 1. $^1$H NMR (500 MHz, MeOD) δ ppm 1.0 (t, J=7.3 Hz, 3H), 1.0-1.1 (m, 2H), 1.1 (s, 9H), 1.2-1.3 (m, 2H), 1.9 (dd, J=8.1, 5.3 Hz, 1H), 2.2-2.4 (m, 3H), 2.4-2.5 (m, 1H), 2.6 (dd, J=13.7, 7.0 Hz, 1H), 2.9-3.0 (m, 1H), 3.8 (s, 3H), 4.0 (s, 3H), 4.1 (dd, J=11.9, 3.4 Hz, 1H), 4.3 (d, J=12.2 Hz, 1H), 4.4 (s, 1H), 4.7 (dd, J=9.8, 7.3 Hz, 1H), 5.1 (d, J=10.4 Hz, 1H), 5.3 (dd, J=17.4 Hz, 1H), 5.7-5.8 (m, 1H), 5.9 (s, 1H), 7.0 (d, J=8.5 Hz, 2H), 7.2 (d, J=8.5 Hz, 2H), 7.6 (s, 1H), 7.7 (dd, J=8.9, 2.1 Hz, 1H), 8.0 (d, J=2.1 Hz, 1H),8.1 (d, J=8.9 Hz, 1H), 9.2 (s, 1H). $^{13}$C NMR (126 MHz, MeOD) δ ppm 5.7, 5.8, 14.5, 19.5, 22.4, 25.9, 31.2, 34.7, 35.0, 37.6, 41.7, 55.0, 55.3, 55.9, 60.6, 65.7, 75.1, 114.6, 117.7, 118.9, 120.2, 120.8, 122.1, 122.4, 123.8, 129.7, 130.3, 131.2, 133.2, 133.6, 134.3, 147.2, 152.4, 161.6, 167.6, 168.7, 169.4, 173.8. LC-MS, MS m/z 865.3 (M$^+$+H).

Preparation of Compound 13, Example 13

Compound 13

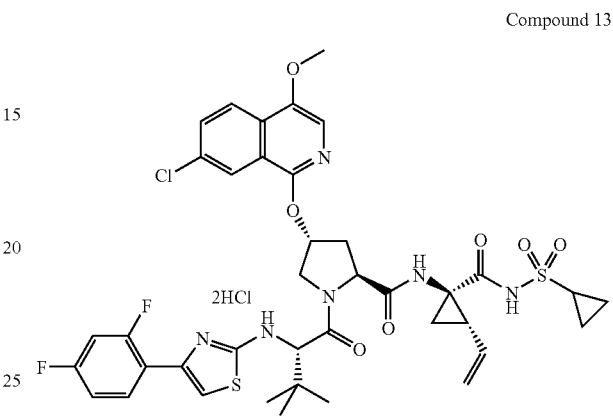

Compound 13 was prepared in 17% yield following the same procedure as described for the preparation of compound 9, except 2-bromo-2',4'-difluoroacetophenone was used instead of 2-bromopropiophenone in step 1. $^1$H NMR (500 MHz, MeOD) δ ppm 1.0-1.1 (m, 3H), 1.2 (s, 9H), 1.2 (s, 1H), 1.2-1.3 (m, 2H), 1.4 (dd, J=9.5, 5.2 Hz, 1H), 1.9 (dd, J=8.2, 5.5 Hz, 1H), 2.2 (q, J=8.8 Hz, 1H), 2.3-2.3 (m, 1H), 2.6 (dd, J=13.7, 7.0 Hz, 1H), 2.9-3.0 (m, 1H), 4.0 (s, 3H), 4.1 (dd, J=11.9, 3.4 Hz, 1H), 4.5 (d, J=11.9 Hz, 1H) 4.6-4.7 (m, 2H), 5.1 (dd, J=10.2, 1.7 Hz, 1H), 5.3 (dd, J=17.1, 1.5 Hz, 1H), 5.7-5.8 (m, 1H), 6.0 (s, 1H), 6.8-6.8 (m, 1H), 6.9-6.9 (m, 1H), 7.5 (s, 1H), 7.6 (dd, J=8.9, 2.1 Hz, 1H), 7.6-7.7 (m, 1H), 7.8 (d, J=2.1 Hz, 1H), 8.0 (d, J=9.2 Hz, 1H). $^{13}$C NMR (MeOD) δ ppm 5.6, 5.8, 22.5, 26.1, 31.2, 34.8, 35.1, 36.7, 41.7, 55.2, 55.8, 60.3, 64.8, 74.7, 104.3, 104.5, 111.7, 111.8, 111.9, 117.7, 118.1, 118.5, 120.8, 122.5, 123.5, 129.6, 130.8, 131.0, 133.2, 133.5, 147.1, 152.3, 159.4, 169.2, 169.5, 170.4, 174.0, 186.3. LC-MS, MS m/z 843.2 (M$^+$+H).

Preparation of Compound 14, Example 14

Compound 14

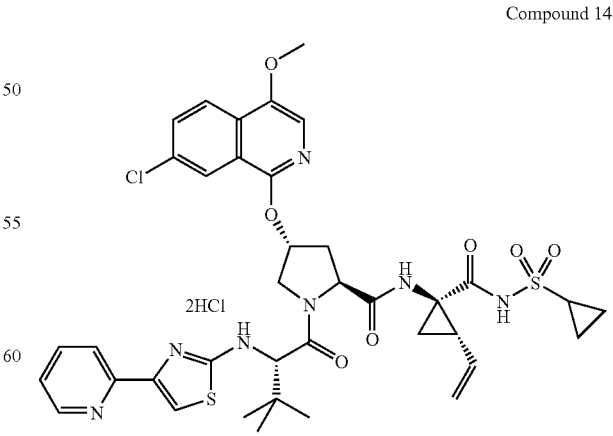

Compound 14 was prepared in 87% yield following the same procedure as described for the preparation of compound 9, except 2-bromo-1-(2-pyridinyl)-1-ethanone hydrobromide was used instead of 2-bromopropiophenone in step 1. $^1$H NMR (500 MHz, MeOD) δ ppm 1.1-1.1 (m, 2H), 1.1 (s, 9H), 1.2-1.3 (m, 2H), 1.4-1.4 (m, 1H), 1.9 (dd, J=8.2, 5.5 Hz, 1H), 2.2-2.3 (m, 2H), 2.4 (dd, J=13.6, 6.9 Hz, 1H), 2.9-3.0 (m, 1H), 3.9 (s, 3H), 4.0 (dd, J=11.9, 3.1 Hz, 1H), 4.6 (dd, J=10.5, 7.2 Hz, 1H), 4.7 (dd, J=12.1, 1.4 Hz, 1H), 4.9 (s, 1H), 5.1 (dd, J=10.4, 1.5 Hz, 1H), 5.3 (dd, J=17.2, 1.4 Hz, 1H), 5.7-5.8 (m, 1H), 6.1 (t, J=3.1 Hz, 1H), 7.4 (s, 1H), 7.5 (d, J=1.8 Hz, 1H), 7.5-7.5 (m, 1H), 7.6 (dd, J=9.2, 2.1 Hz, 1H), 7.6 (s, 1H), 7.9 (d, J=8.9 Hz, 1H), 8.0 (d, J=8.2 Hz, 1H), 8.1-8.2 (m, 1H), 8.2 (d, J=5.2 Hz, 1H). LC-MS, MS m/z 808.2 (M$^+$+H).

Preparation of Compound 15, Example 15

Compound 15

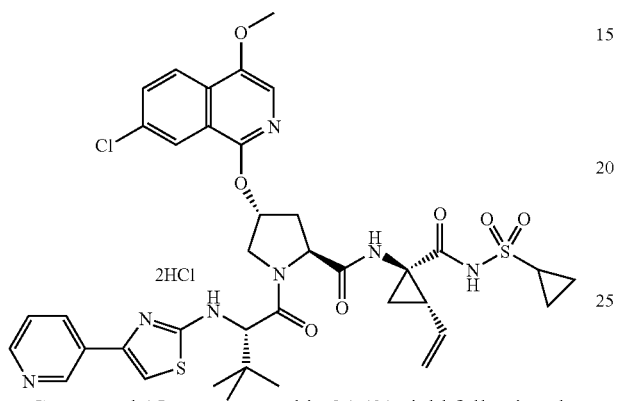

Compound 15 was prepared in 24.4% yield following the same procedure as described for the preparation of compound 9, except 3-(bromoacetyl)pyridine hydrobromide was used instead of 2-bromopropiophenone in step 1. $^1$H NMR (500 MHz, MeOD) δ ppm 1.1-1.1 (m, 3H), 1.2 (s, 9H), 1.2-1.3 (m, 2H), 1.4 (dd, J=9.5, 5.5 Hz, 1H), 1.9 (dd, J=7.9, 5.5 Hz, 1H), 2.2-2.3 (m, 2H), 2.4 (dd, J=13.6, 6.6 Hz, 1H), 3.0 (ddd, J=12.8, 8.1, 4.7 Hz, 1H), 3.9 (s, 3H), 4.1 (dd, J=11.7, 3.2 Hz, 1H), 4.5 (dd, J=10.7, 7.0 Hz, 1H), 4.9 (s, 1H), 5.1 (dd, J=10.4, 1.5 Hz, 1H), 5.3 (dd, J=17.1, 1.2 Hz, 1H), 5.7 (ddd, J=17.2, 10.3, 8.9 Hz, 1H), 6.1 (t, J=2.9 Hz, 1H), 7.3 (s, 1H), 7.3 (d, J=2.1 Hz, 1H), 7.4 (s, 1H), 7.6 (dd, J=8.9, 2.1 Hz, 1H), 7.6 (dd, J=8.2, 5.8 Hz, 1H), 7.9 (d, J=8.9 Hz, 1H), 8.2 (d, J=5.5 Hz, 1H), 8.7 (d, J=8.2 Hz, 1H), 8.9 (s, 1H). $^{13}$C NMR (MeOD) δ ppm 5.6, 5.8, 22.4, 26.2, 31.2, 34.9, 35.3, 41.7, 55.3, 55.9, 59.9, 63.1, 74.4, 108.9, 117.6, 118.8, 120.5, 122.2, 123.4, 127.0, 129.2, 131.0, 133.2, 133.3, 134.8, 138.2, 138.4, 141.9, 142.9, 146.7, 151.9, 169.6, 170.2, 172.6, 174.3. LC-MS, MS m/z 808.2 (M$^+$+H).

Preparation of Compound 16, Example 16

Compound 16

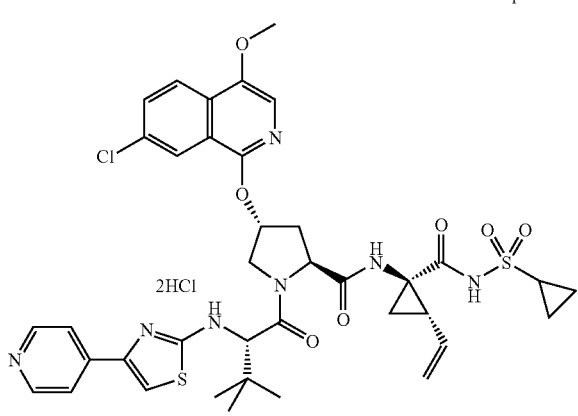

Compound 16 was prepared in 27.6% yield following the same procedure as described for the preparation of compound 9, except 2-bromo-1-(4-pyridinyl)-1-ethanone hydrobromide was used instead of 2-bromopropiophenone in step 1. $^1$H NMR (500 MHz, MeOD) δ ppm 1.1-1.1 (m, 2H), 1.1 (s, 9H), 1.2-1.3 (m, 2H), 1.4 (dd, J=9.5, 5.2 Hz, 1H), 1.9 (dd, J=7.9, 5.5 Hz, 1H), 2.2-2.3 (m, 2H), 2.4 (dd, J=13.6, 6.9 Hz, 1H), 3.0 (ddd, J=12.7, 8.1, 4.9 Hz, 1H), 3.9 (s, 3H), 4.1-4.1 (m, 1H), 4.5 (dd, J=10.7, 7.0 Hz, 1H), 4.9 (s, 1H), 5.1 (dd, J=10.4, 1.5 Hz, 1H), 5.3 (d, J=17.1 Hz, 1H), 5.7-5.8 (m, 1H), 6.2 (d, J=3.1 Hz, 1H), 7.4 (d, J=2.1 Hz, 1H), 7.4 (s, 1H), 7.5 (dd, J=8.9, 2.1 Hz, 1H), 7.7 (s, 1H), 7.9 (d, J=8.9 Hz, 1H), 8.0 (d, J=7.0 Hz, 2H), 8.2 (d, J=6.7 Hz, 2H). $^{13}$C NMR (MeOD) δ ppm 5.6, 5.8, 22.5, 26.2, 31.2, 34.9, 35.3, 35.3, 41.7, 55.4, 55.9, 60.0, 63.0, 74.3, 115.9, 117.6, 117.8, 118.8, 120.6, 122.4, 123.3, 129.2, 131.0, 133.2, 133.4, 140.7, 144.9, 146.7, 150.3, 152.0, 169.6, 169.9, 172.5, 174.3. LC-MS, MS m/z 808.2 (M$^+$+H). LC-MS, MS m/z 806.2 (M$^+$−H).

Preparation of Compound 17, Example 17

Compound 17

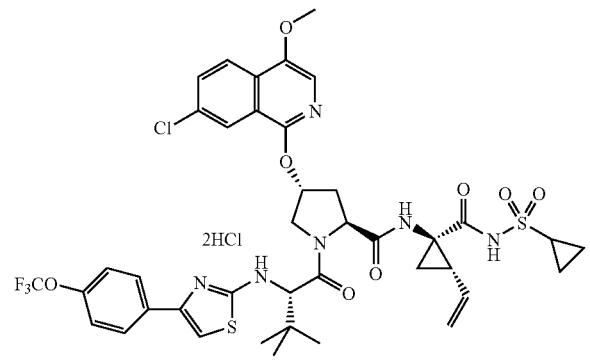

Compound 17 was prepared in 82% yield following the same procedure as described for the preparation of compound 9, except 2-bromo-1-[4-(trifluoromethoxy)phenyl]ethan-1-one was used instead of 2-bromopropiophenone in step 1. $^1$H NMR (500 MHz, MeOD) δ ppm 1.1-1.1 (m, 3H), 1.2 (s, 9H), 1.3 (dd, J=4.9, 2.7 Hz, 2H), 1.3-1.3 (m, 1H), 1.4 (dd, J=9.3, 5.3 Hz, 1H), 1.9 (dd, J=8.2, 5.5 Hz, 1H), 2.2-2.3 (m, 2H), 2.5 (dd, J=13.7, 7.0 Hz, 1H), 2.9-3.0 (m, 1H), 3.9 (s, 3H), 4.1 (dd, J=12.1, 3.5 Hz, 1H), 4.6 (d, J=12.2 Hz, 1H), 4.6-4.6 (m, 2H), 5.1 (dd, J=10.4, 1.5 Hz, 1H), 5.3 (dd, J=17.1, 1.2 Hz, 1H), 5.7-5.8 (m, 1H), 6.0 (s, 1H), 7.1 (d, J=8.2 Hz, 2H), 7.5 (s, 1H), 7.6-7.6 (m, 3H), 7.8 (d, J=1.8 Hz, 1H), 8.0 (d, J=8.9 Hz, 1H). LC-MS, MS m/z 891.2 (M$^+$+H).

Preparation of Compound 18, Example 18
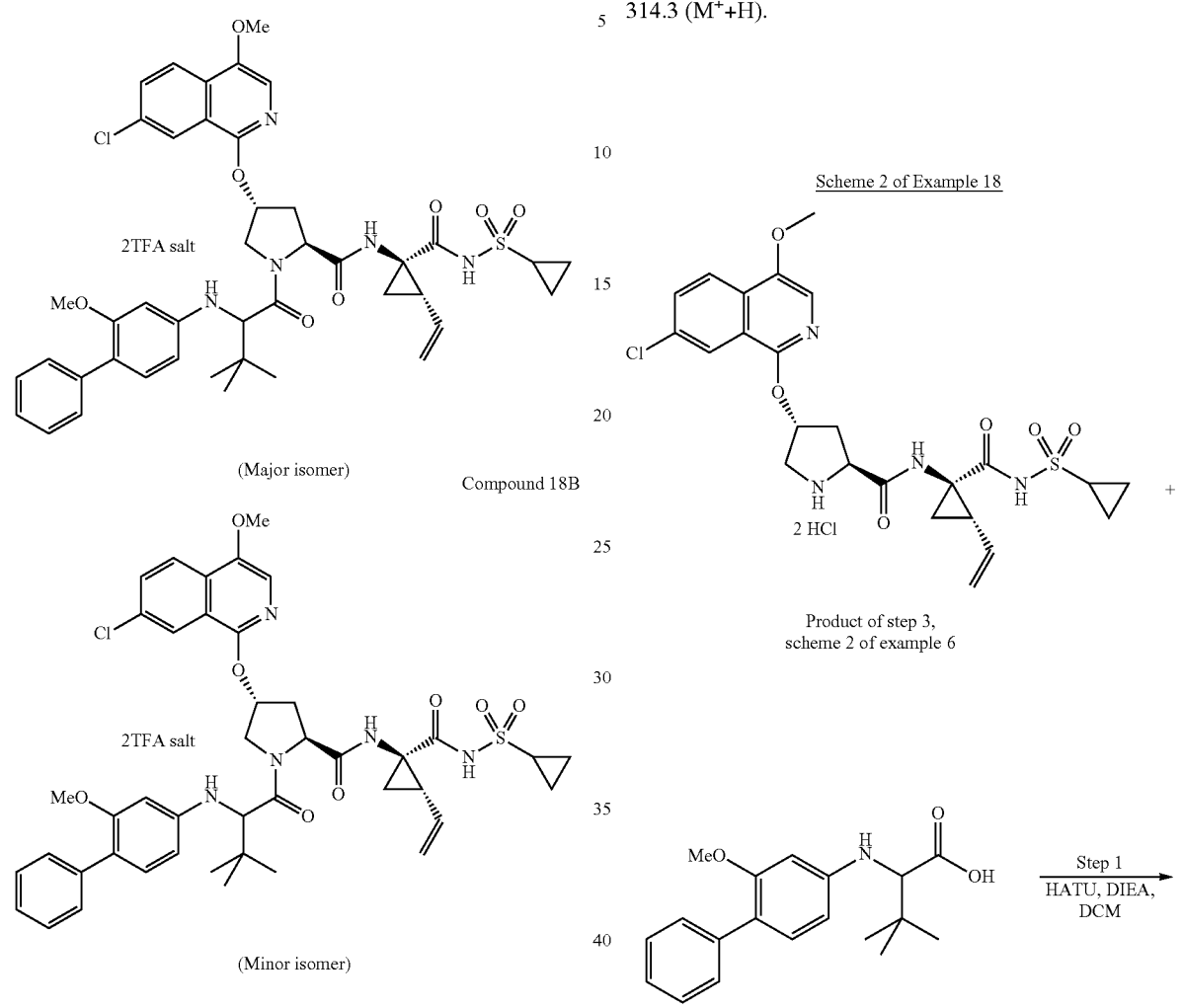
Step 1:
To a slurry mixture of 2-methoxybiphenyl-4-amine hydrochloride (1.0 g, 4.24 mmol) and sodium acetate (0.348 g, 4.24 mmol) in DCE (30 mL) was added 3,3-dimethyl-2-oxobutanoic acid (1.104 g, 8.49 mmol) and sodium cyanoborohydride (0.175 g, 2.79 mmol). The resulting light yellow reaction mixture was stirred at 25° C. overnight. LC-MS, MS m/z 314.3 (M$^+$+H).

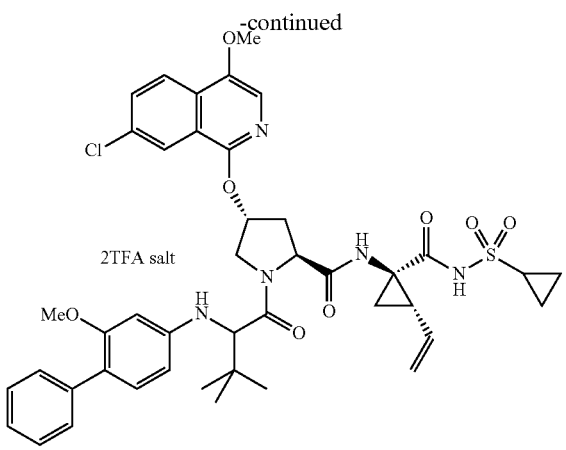

Compound 18B
(Isomer 2, minor isomer)

Step 1:

To a solution mixture of (2S,4R)-4-(7-chloro-4-methoxy-isoquinolin-1-yloxy)-N-((1R,2S)-1-(cyclopropylsulfonyl-carbamoyl)-2-vinylcyclopropyl)pyrrolidine-2-carboxamide, 2HCl (155.0 mg, 0.255 mmol) and DIEA (0.178 mL, 1.020 mmol) in DCM (2 mL) was added 2-(2-methoxybiphenyl-4-ylamino)-3,3-dimethylbutanoic acid (80 mg, 0.255 mmol) and HATU (126 mg, 0.331 mmol). The resulting brown reaction mixture was stirred at 25° C. After 6 hr, the reaction was concentrated and purified by reverse phase HPLC with the following condition: solvent A=$H_2O$, solvent B=MeCN, both containing 0.1% TFA; 15% B to 100% B 20 mins, hold at 100% B 4 mins. Concentration of the combined HPLC fractions and drying in vacuum oven at 25° C. gave 18A, (2S,4R)-4-(7-chloro-4-methoxyisoquinolin-1-yloxy)-N-((1R,2S)-1-(cyclopropylsulfonylcarbamoyl)-2-vinylcyclopropyl)-1-(2-(2-methoxybiphenyl-4-ylamino)-3,3-dimethylbutanoyl)pyrrolidine-2-carboxamide, 2TFA (104.4 mg, 0.095 mmol, 37.1% yield), (isomer 1 by HPLC) as light yellow solid, and 18B, (2S,4R)-4-(7-chloro-4-methoxy-isoquinolin-1-yloxy)-N-((1R,2S)-1-(cyclopropylsulfonyl-carbamoyl)-2-vinylcyclopropyl)-1-(2-(2-methoxybiphenyl-4-ylamino)-3,3-dimethylbutanoyl)pyrrolidine-2-carboxamide, 2TFA (75.8 mg, 0.067 mmol, 26.1% yield), (Isomer 2 by HPLC) as light greenish-yellow solid.

18A (isomer 1, HPLC): $^1$H NMR (500 MHz, MeOD) δ ppm 1.04-1.11 (m, 2H), 1.14 (s, 9H), 1.23-1.28 (m, 2H), 1.43 (dd, J=9.5, 5.5 Hz, 1H), 1.88 (dd, J=8.1, 5.6 Hz, 1H), 2.20-2.29 (m, 2H), 2.54 (dd, J=13.4, 6.7 Hz, 1H), 2.92-2.99 (m, 1H), 3.56 (s, 3H), 3.94 (s, 3H), 4.03 (s, 1H), 4.06 (dd, J=12.2, 3.1 Hz, 1H), 4.40 (d, J=12.2 Hz, 1H), 4.58 (dd, J=10.5, 6.9 Hz, 1H), 5.12 (d, J=10.4 Hz, 1H), 5.30 (d, J=17.1 Hz, 1H), 5.71 (s, 1H), 5.72-5.79 (m, 1H), 5.89 (d, J=7.9 Hz, 1H), 6.07 (d, J=8.2 Hz, 1H), 6.38 (s, 1H), 7.03 (d, J=7.3 Hz, 2H), 7.16 (t, J=7.0 Hz, 1H), 7.23 (t, J=7.5 Hz, 2H), 7.40 (dd, J=8.9, 2.1 Hz, 1H), 7.54 (s, 1H), 7.85 (d, J=1.8 Hz, 1H), 7.90 (d, J=8.9 Hz, 1H), 9.19 (s, 1H); $^{13}$C NMR (MeOD) δ ppm 5.6, 5.8, 22.5, 26.4, 31.3, 35.0, 35.7, 41.7, 42.8, 54.8, 55.8, 60.5, 63.6, 75.3, 99.7, 104.9, 117.6, 118.6, 120.7, 121.6, 122.4, 123.4), 125.7, 127.5, 129.2, 129.5, 130.6, 130.7, 131.1, 133.3, 133.5, 138.9, 147.1, 148.3, 152.6, 157.6, 169.7, 173.3, 174.5; LC-MS, MS m/z 830.3 (M$^+$+H).

18B (isomer 2, HPLC): $^1$H NMR (500 MHz, MeOD) δ ppm 0.98 (s, 9H), 1.01 (s, 1H), 1.01-1.05 (m, 1H), 1.20-1.26 (m, 2H), 1.35 (dd, J=9.6, 5.3 Hz, 1H), 1.85 (dd, J=8.1, 5.3 Hz, 1H), 2.22 (q, J=9.0 Hz, 1H), 2.29-2.35 (m, 1H), 2.57 (dd, J=13.9, 7.2 Hz, 1H), 2.79-2.86 (m, 1H), 3.74 (s, 3H), 3.99 (s, 3H), 4.05 (dd, J=11.9, 3.4 Hz, 1H), 4.17 (s, 1H), 4.44 (d, J=11.9 Hz, 1H), 4.56 (dd, J=9.9, 7.2 Hz, 1H), 5.11 (dd, J=10.4, 1.5 Hz, 1H), 5.30 (dd, J=17.2, 1.4 Hz, 1H), 5.74-5.81 (m, 1H), 5.82 (s, 1H), 6.40 (d, J=8.2 Hz, 1H), 6.46 (s, 1H), 7.03 (d, J=8.2 Hz, 1H), 7.16 (t, J=7.3 Hz, 1H), 7.27 (t, J=7.6 Hz, 2H), 7.38 (d, J=7.3 Hz, 2H), 7.57 (s, 1H), 7.68 (dd, J=8.9, 2.1 Hz, 1H), 8.01 (d, J=1.8 Hz, 1H), 8.09 (d, J=8.9 Hz, 1H), 9.35 (s, 1H); $^{13}$C NMR (MeOD) δ ppm 5.4, 5.8, 23.6, 26.1, 31.2, 34.4, 34.5, 36.5, 41.5, 54.1, 55.1, 55.8, 60.2, 62.4, 75.2, 98.8, 117.5, 117.8, 118.8, 120.7, 120.8, 122.5, 123.6, 125.7, 127.7, 129.2, 129.6, 131.0, 131.1, 133.3, 133.5, 139.5, 147.1, 149.2, 152.5, 157.8, 169.8, 173.8, 174.8; LC-MS, MS m/z 830.3 (M$^+$+H).

Preparation of Compound 19, Example 19

Compound 19

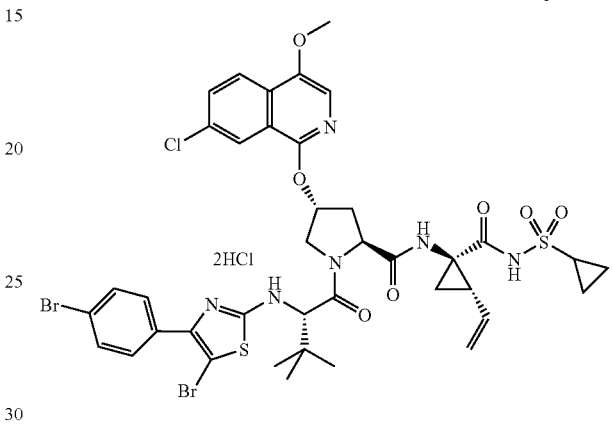

Compound 19 was prepared in 59% yield following the same procedure as described for the preparation of compound 9, except p,alpha,alpha-tribromoacetophenone was used instead of 2-bromopropiophenone in step 1. $^1$H NMR (500 MHz, MeOD) δ ppm 1.1-1.1 (m, 4H), 1.2 (s, 9H), 1.2-1.3 (m, 3H), 1.4 (dd, J=9.5, 5.5 Hz, 1H), 1.9 (dd, J=8.1, 5.3 Hz, 1H), 2.2-2.3 (m, 2H), 2.5 (dd, J=13.6, 6.9 Hz, 1H), 2.9 (none, 1H), 2.9-3.0 (m, 1H), 4.0 (s, 3H), 4.0 (d, J=4.9 Hz, 1H), 4.1 (dd, J=11.7, 3.5 Hz, 1H), 4.6 (dd, J=10.4, 7.0 Hz, 1H), 5.1 (dd, J=10.4, 1.5 Hz, 1H), 5.3 (dd, J=17.1, 1.2 Hz, 1H), 5.7-5.8 (m, 1H), 6.0 (s, 1H), 7.2 (d, J=8.2 Hz, 2H), 7.4 (d, J=8.5 Hz, 2H), 7.4 (s, 1H), 7.5 (dd, J=9.2, 2.1 Hz, 1H), 7.6 (d, J=1.8 Hz, 1H), 8.0 (d, J=8.9 Hz, 1H).

Preparation of Compound 20, Example 20

Compound 20

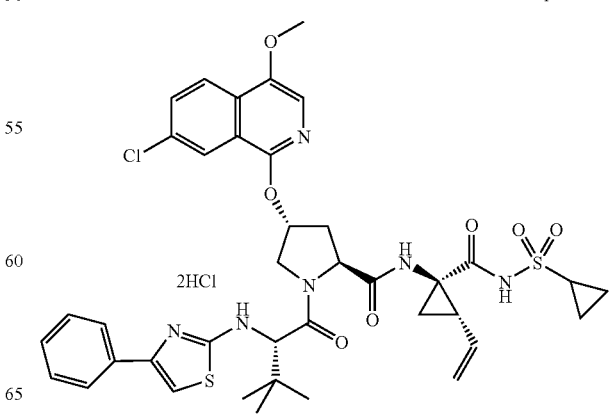

Compound 20 was prepared in 51% yield following the same procedure as described for the preparation of compound 9, except 2-bromoacetophenone was used instead of 2-bromopropiophenone in step 1. ¹H NMR (500 MHz, MeOD) δ ppm 1.1-1.1 (m, 2H), 1.2 (s, 9H), 1.2-1.2 (m, 1H), 1.2 (d, J=3.7 Hz, 2H), 1.4 (dd, J=9.3, 5.3 Hz, 1H), 1.9 (dd, J=7.9, 5.5 Hz, 1H), 2.3-2.3 (m, 2H), 2.6 (dd, J=13.7, 7.0 Hz, 1H), 3.0 (dq, J=8.4, 4.1 Hz, 1H), 4.0 (s, 3H), 4.1 (dd, J=12.2, 3.1 Hz, 1H), 4.4 (d, J=12.2 Hz, 1H), 4.5 (s, 1H), 4.7 (dd, J=10.1, 7.3 Hz, 1H), 5.1 (dd, J=10.2, 1.4 Hz, 1H), 5.3 (dd, J=17.1, 1.2 Hz, 1H), 5.7-5.8 (m, 1H), 5.9 (s, 1H), 7.4-7.5 (m, 3H), 7.5-7.5 (m, 2H), 7.6 (s, 1H), 7.6 (dd, J=8.9, 2.1 Hz, 1H), 7.9 (d, J=1.8 Hz, 1H), 8.1 (d, J=8.9 Hz, 1H). LC-MS, MS m/z 807.2 (M⁺+H).

Preparation of Compound 21, Example 21

Compound 21

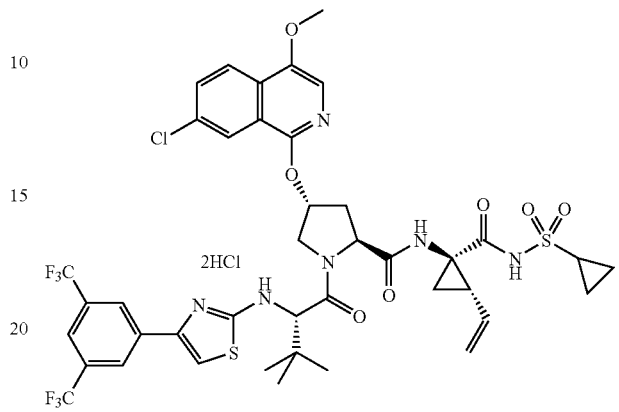

Compound 21 was prepared in 36% yield following the same procedure as described for the preparation of compound 9, except 2-bromo-4'-cyanoacetophenone was used instead of 2-bromopropiophenone in step 1. ¹H NMR (500 MHz, MeOD) δ ppm 1.1-1.1 (m, 2H), 1.2 (s, 9H), 1.2-1.3 (m, 2H), 1.4 (dd, J=9.5, 5.5 Hz, 1H), 1.9 (dd, J=8.2, 5.5 Hz, 1H), 2.2-2.3 (m, 2H), 2.5 (dd, J=13.6, 6.9 Hz, 1H), 2.9-3.0 (m, 1H), 4.0 (s, 3H), 4.1 (dd, J=11.9, 3.7 Hz, 1H), 4.6 (dd, J=10.5, 6.9 Hz, 1H), 4.7 (d, J=11.6 Hz, 1H), 4.8 (s, 1H), 5.1 (dd, J=10.4, 1.5 Hz, 1H), 5.3 (dd, J=17.1, 1.2 Hz, 1H), 5.7 (ddd, J=17.1, 10.4, 8.9 Hz, 1H), 6.1 (s, 1H), 7.3 (d, J=7.3 Hz, 2H), 7.5 (s, 1H), 7.5-7.6 (m, 2H), 7.6 (d, J=8.5 Hz, 2H), 8.0 (d, J=9.2 Hz, 1H). LC-MS, MS m/z 832.2 (M⁺+H).

Preparation of Compound 22, Example 22

Compound 22

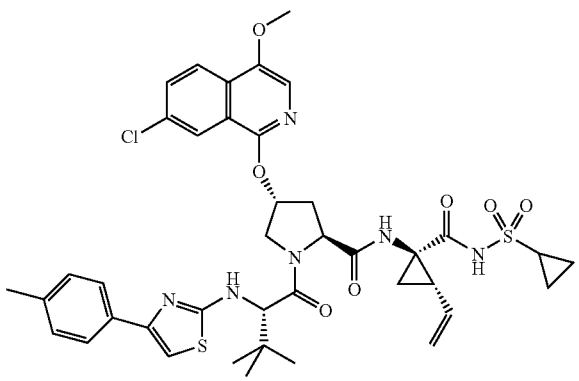

Compound 22 was prepared in 69% yield following the same procedure as described for the preparation of compound 9, except 3',5'-bis(trifluoromethyl)-2-bromoacetophenone was used instead of 2-bromopropiophenone in step 1. ¹H NMR (500 MHz, MeOD) δ ppm 1.1-1.1 (m, 2H), 1.2 (s, 9H), 1.2-1.3 (m, 2H), 1.4 (dd, J=9.5, 5.5 Hz, 1H), 1.9 (dd, J=8.2, 5.5 Hz, 1H), 2.2 (q, J=9.2 Hz, 1H), 2.2-2.3 (m, 1H), 2.5 (dd, J=14.0, 7.0 Hz, 1H), 3.0 (ddd, J=12.8, 8.1, 4.7 Hz, 1H), 3.9 (s, 3H), 4.2 (dd, J=11.6, 3.4 Hz, 1H), 4.4 (dd, J=10.7, 6.7 Hz, 1H), 4.9 (s, 1H), 5.0 (d, J=11.0 Hz, 1H), 5.1 (dd, J=10.4, 1.5 Hz, 1H), 5.2 (dd, J=17.1, 1.5 Hz, 1H), 5.7 (ddd, J=17.2, 10.3, 8.9 Hz, 1H), 6.0 (t, J=3.1 Hz, 1H), 7.2 (s, 1H), 7.3 (d, J=2.1 Hz, 1H), 7.3 (s, 1H), 7.4 (s, 1H), 7.5 (dd, J=8.9, 2.1 Hz, 1H), 7.9 (d, J=8.9 Hz, 1H), 8.2 (s, 2H). LC-MS, MS m/z 943.0 (M⁺+H).

Preparation of Compound 23, Example 23

Compound 23

Scheme 1 of Example 23

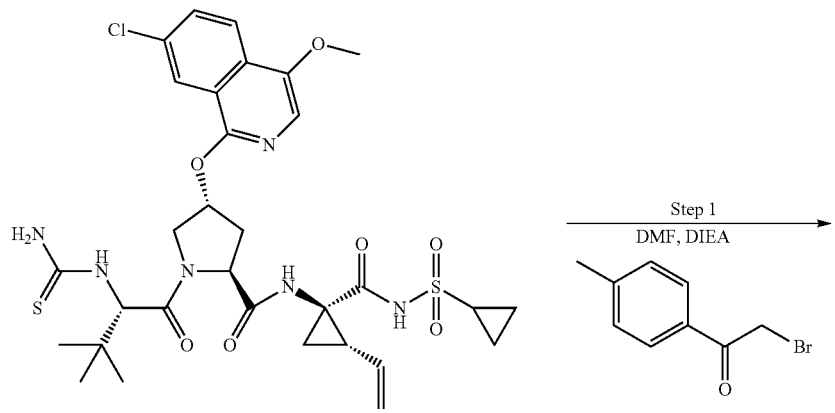

Product of step 6,
scheme 2 of example 6

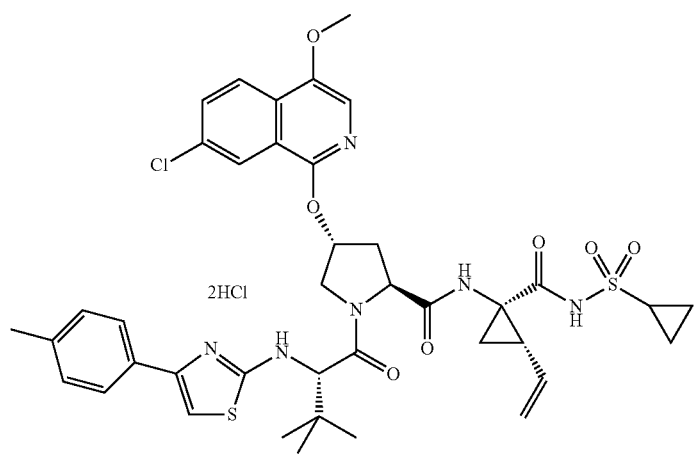

Compound 23

Step 1.

To a solution of (2S,4R)-4-(7-chloro-4-methoxyisoquinolin-1-yloxy)-N-((1R,2S)-1-(cyclopropylsulfonylcarbamoyl)-2-vinylcyclopropyl)-1-((s)-3,3-dimethyl-2-thioureidobutanoyl)pyrrolidine-2-carboxamide (80 mg, 113 umol) and N,N-diisopropylethylamine (43.9 mg, 339 umol) in DMF (1.2 mL) were added 2-bromo-4'-methylacetophenone (226 umol). After stirring at room temperature for 60 hr, the reaction mixture was purified by reversed phase HPLC using solvent sytem and conditions as the following: solvent A=5:95 MeCN:H$_2$O, solvent B=95:5 MeCN:H$_2$O, both containing 10 mM NH$_4$OAc; 0% B to 100% B 8 mins, hold at 100% B 1 min. The combined HPLC fractions were combined, concentrated and dried under vacuo to afford compound 23. LC-MS, MS m/z 820.9 (M$^+$+H).

Preparation of Compound 24, Example 24

Compound 24

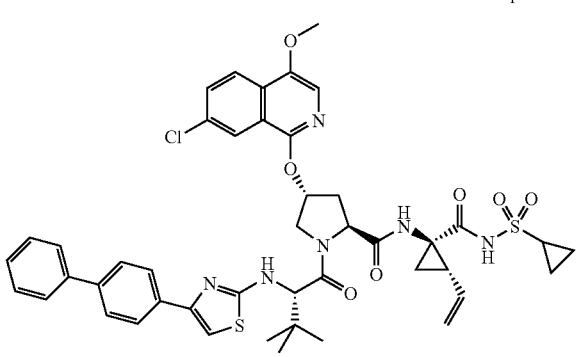

Compound 24 was prepared following the same procedure as described for the preparation of compound 23, except 2-bromo-4'-phenylacetophenone was used instead of 2-bromo-4'-methylacetophenone in step 1. LC-MS, MS m/z 882.9 (M$^+$+H).

Preparation of Compound 25, Example 25

Compound 25

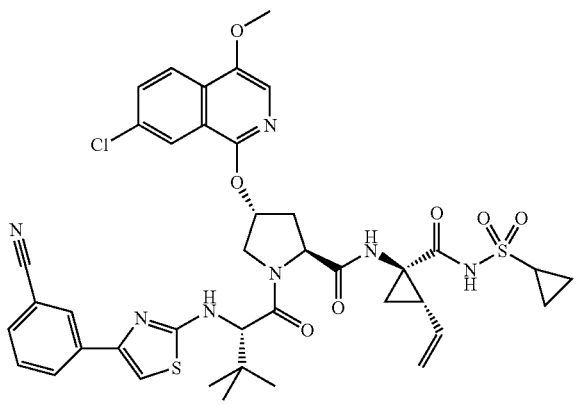

Compound 25 was prepared following the same procedure as described for the preparation of compound 23, except 3-(2-bromoacetyl)benzonitrile was used instead of 2-bromo-4'-methylacetophenone in step 1. LC-MS, MS m/z 831.8 (M$^+$+H).

Preparation of Compound 26, Example 26

Compound 26

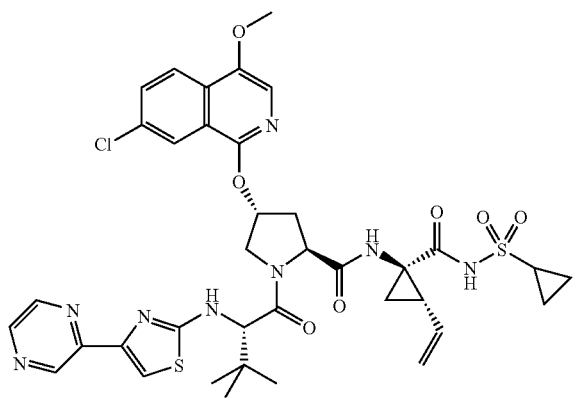

Compound 27 was prepared following the same procedure as described for the preparation of compound 23, except 2-bromo-1-pyrazin-2-yl-ethanone was used instead of 2-bromo-4'-methylacetophenone in step 1. $^1$H NMR (600 MHz, DMSO_CDCl3) δ ppm 1.03-1.12 (m, 2H), 1.16 (s, 9H), 1.38 (t, J=7.03 Hz, 1H), 1.76 (d, J=6.44 Hz, 1H), 2.14-2.30 (m, 2H), 2.43 (dd, J=13.48, 6.44 Hz, 1H), 2.96-3.05 (m, 1H), 3.96 (s, 3H), 4.22 (dd, J=11.42, 3.81 Hz, 1H), 4.46 (dd, J=9.96, 7.03 Hz, 1H), 4.76 (d, J=9.37 Hz, 1H), 4.83 (d, J=11.72 Hz, 1H), 5.12 (d, J=9.96 Hz, 1H), 5.24 (d, J=17.58 Hz, 1H), 6.03 (br. s., 1H), 7.53 (s, 1H), 7.61 (dd, J=9.08, 2.05 Hz, 1H), 7.95 (dd, J=14.94, 9.08 Hz, 2H), 7.99 (s, 1H), 8.05 (br. s., 1H), 8.27 (s, 2H), 8.87 (br. s., 1H), 8.92 (s, 1H), 10.43 (br. s., 1H). LC-MS, MS m/z 808.9 (M$^+$+H).

Preparation of Compound 27, Example 27

Compound 27

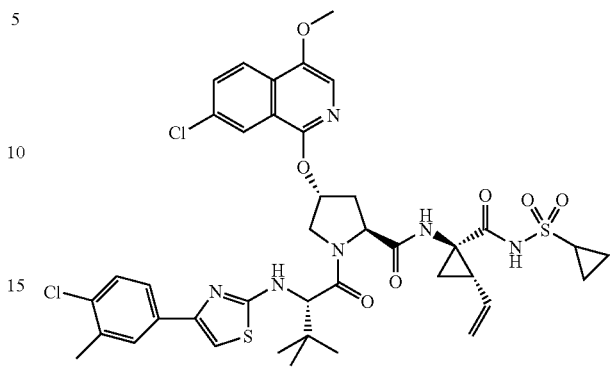

Compound 27 was prepared following the same procedure as described for the preparation of compound 23, except 4-chloro-3-methylphenacyl chloride was used instead of 2-bromo-4'-methylacetophenone in step 1. $^1$H NMR (600 MHz, DMSO_CDCl3) δ ppm 0.99-1.12 (m, 3H), 1.17 (s, 9H), 1.33-1.41 (m, 2H), 1.75 (d, J=5.27 Hz, 1H), 1.92 (s, 3H), 2.13-2.24 (m, 2H), 2.34 (dd, J=13.48, 6.44 Hz, 1H), 2.96-3.05 (m, 1H), 3.99 (s, 3H), 4.21 (dd, J=11.13, 3.52 Hz, 1H), 4.41 (dd, J=10.55, 7.03 Hz, 1H), 4.70 (d, J=9.37 Hz, 1H), 4.94 (d, J=11.72 Hz, 1H), 5.11 (d, J=11.13 Hz, 1H), 5.24 (d, J=16.41 Hz, 1H), 5.66 (t, J=18.16 Hz, 1H), 6.10 (br. s., 1H), 6.76 (d, J=8.79 Hz, 1H), 6.90 (s, 1H), 7.30 (s, 1H), 7.43 (d, J=7.03 Hz, 1H), 7.54-7.63 (m, 2H), 7.79 (d, J=9.37 Hz, 1H), 7.97 (d, J=8.79 Hz, 2H), 8.27 (s, 2H), 8.88 (s, 1H), 10.39 (s, 1H). LC-MS, MS m/z 882.9 (M$^+$+H).

Preparation of Compound 28, Example 28

Compound 28

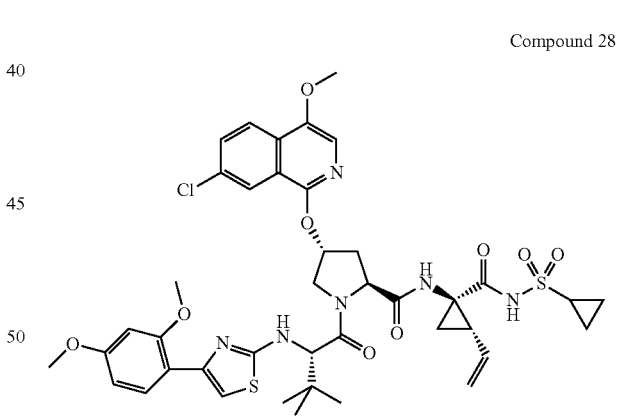

Compound 28 was prepared following the same procedure as described for the preparation of compound 23, except 2-bromo-2',4'-dimethoxyacetophenone was used instead of 2-bromo-4'-methylacetophenone in step 1. $^1$H NMR (600 MHz, DMSO_CDCl3) δ ppm 1.09 (d, J=3.52 Hz, 3H), 1.15 (s, 8H), 1.38 (t, J=4.69 Hz, 1H), 1.76 (dd, J=7.62, 5.27 Hz, 1H), 2.21 (ddd, J=17.87, 9.37, 9.08 Hz, 2H), 2.34-2.42 (m, 1H), 2.61 (t, J=5.57 Hz, 1H), 2.98 (dd, J=8.50, 3.81 Hz, 1H), 3.81 (s, 3H), 3.98 (s, 3H), 4.02 (d, J=4.10 Hz, 1H), 4.21 (dd, J=11.72, 4.10 Hz, 1H), 4.48 (dd, J=9.96, 7.03 Hz, 1H), 4.62 (d, J=9.37 Hz, 1H), 4.75 (d, J=11.72 Hz, 1H), 5.12 (d, J=11.13 Hz, 1H), 5.25 (d, J=16.41 Hz, 1H), 5.62-5.72 (m, 1H), 5.95 (d, J=7.62 Hz, 1H), 6.04 (br. s., 1H), 6.27 (s, 1H), 6.80 (s, 1H), 7.52-7.58 (m, 2H), 7.67 (d, J=8.79 Hz, 1H), 7.86 (d, J=8.79

Hz, 1H), 7.99 (s, 2H), 8.27 (s, 2H), 8.92 (s, 1H), 10.44 (s, 1H). LC-MS, MS m/z 866.9 (M++H).

Preparation of Compound 29, Example 29

Compound 29

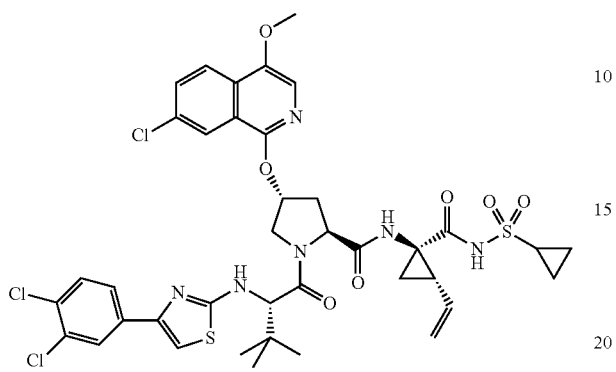

Compound 29 was prepared following the same procedure as described for the preparation of compound 23, except 3,4-dichlorophenacyl bromide was used instead of 2-bromo-4'-methylacetophenone in step 1. $^1$H NMR (600 MHz, DMSO_CDCl3) δ ppm 1.04-1.12 (m, 3H), 1.17 (s, 9H), 1.33-1.45 (m, 2H), 1.75 (dd, J=7.62, 5.27 Hz, 1H), 2.15-2.25 (m, 2H), 2.36 (dd, J=13.18, 6.74 Hz, 1H), 2.98 (dd, J=8.50, 3.81 Hz, 1H), 3.98 (s, 3H), 4.20 (dd, J=11.72, 3.52 Hz, 1H), 4.42 (dd, J=10.55, 6.44 Hz, 1H), 4.71 (d, J=9.37 Hz, 1H), 4.89 (d, J=11.13 Hz, 1H), 5.11 (d, J=11.13 Hz, 1H), 5.24 (d, J=16.99 Hz, 1H), 5.65 (dd, J=17.28, 9.67 Hz, 1H), 6.10 (br. s., 1H), 6.96 (d, J=8.20 Hz, 1H), 7.08 (s, 1H), 7.30 (s, 1H), 7.55 (d, J=1.76 Hz, 2H), 7.61 (dd, J=8.79, 1.76 Hz, 1H), 7.82 (s, 1H), 7.89 (d, J=9.37 Hz, 1H), 7.96 (d, J=8.79 Hz, 1H), 7.99 (s, 1H), 8.27 (s, 2H), 8.87 (s, 1H), 10.40 (s, 1H). LC-MS, MS m/z 876.8 (M++H).

Preparation of Compound 30, Example 30

Compound 30

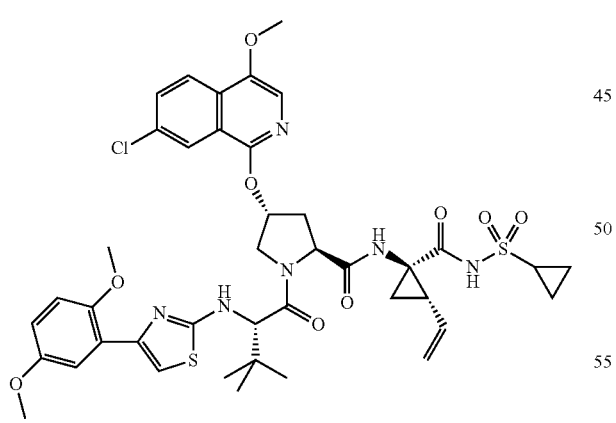

Compound 30 was prepared following the same procedure as described for the preparation of compound 23, except 2-bromo-1-(2,5-dimethoxyphenyl)ethanone was used instead of 2-bromo-4'-methylacetophenone in step 1. $^1$H NMR (600 MHz, DMSO_CDCl3) δ ppm 1.09 (dd, J=6.15, 2.64 Hz, 3H), 1.16 (s, 9H), 1.35-1.41 (m, 1H), 1.75 (dd, J=7.91, 5.57 Hz, 1H), 2.15-2.26 (m, 2H), 2.42 (dd, J=13.77, 6.74 Hz, 1H), 2.61 (t, J=5.57 Hz, 1H), 2.98 (dd, J=8.20, 3.52 Hz, 1H), 3.80 (s, 3H), 3.95 (s, 3H), 4.20 (dd, J=11.42, 3.81 Hz, 1H), 4.45 (dd, J=9.96, 7.03 Hz, 1H), 4.66 (d, J=8.79 Hz, 1H), 4.79 (d, J=11.13 Hz, 1H), 5.12 (d, J=11.72 Hz, 1H), 5.25 (d, J=17.58 Hz, 1H), 5.62-5.71 (m, 1H), 5.99 (br. s., 1H), 6.37 (dd, J=8.50, 2.64 Hz, 1H), 6.68 (d, J=8.79 Hz, 1H), 7.02 (s, 0H), 7.44-7.52 (m, 2H), 8.27 (s, 2H), 8.90 (s, 1H), 10.41 (s, 1H). LC-MS, MS m/z 866.8 (M++H).

Preparation of Compound 31, Example 31

Compound 31

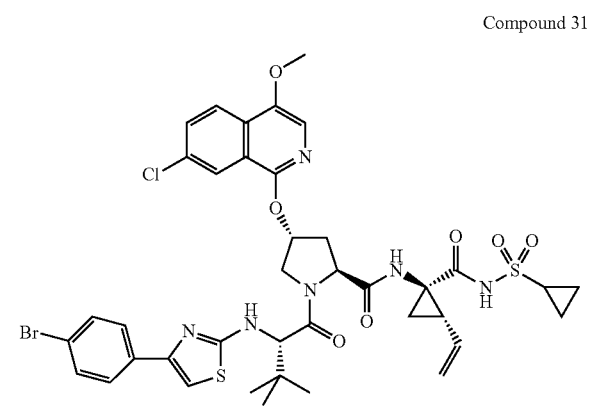

Compound 31 was prepared following the same procedure as described for the preparation of compound 23, except 4-bromo-phenacyl bromide was used instead of 2-bromo-4'-methylacetophenone in step 1. $^1$H NMR (600 MHz, DMSO_CDCl3) δ ppm 1.03-1.12 (m, 2H), 1.15 (s, 9H), 1.38 (dd, J=9.08, 4.98 Hz, 1H), 1.75 (br. s., 1H), 2.11-2.29 (m, 1H), 2.33-2.42 (m, 1H), 2.92-3.02 (m, 1H), 3.99 (s, 3H), 4.06 (q, J=5.27 Hz, 2H), 4.22 (dd, J=10.55, 2.93 Hz, 1H), 4.47 (d, J=16.41 Hz, 1H), 4.69 (d, J=9.37 Hz, 1H), 4.78 (d, J=11.13 Hz, 1H), 5.04-5.16 (m, 1H), 5.24 (d, J=16.40 Hz, 1H), 5.67 (dd, J=19.63, 9.08 Hz, 1H), 6.05 (br. s., 1H), 6.89 (s, 1H), 6.96 (d, J=8.20 Hz, 1H), 7.46 (br. s., 1H), 7.53 (d, J=8.79 Hz, 2H), 7.58 (s, 1H), 7.65 (dd, J=9.08, 2.05 Hz, 1H), 7.80 (d, J=9.37 Hz, 1H), 8.00 (d, J=9.37 Hz, 1H), 8.28 (s, 2H), 8.89 (br. s., 1H), 10.44 (br. s., 1H). LC-MS, MS m/z 884.8 (M++H).

Preparation of Compound 32 Example 32

Compound 32

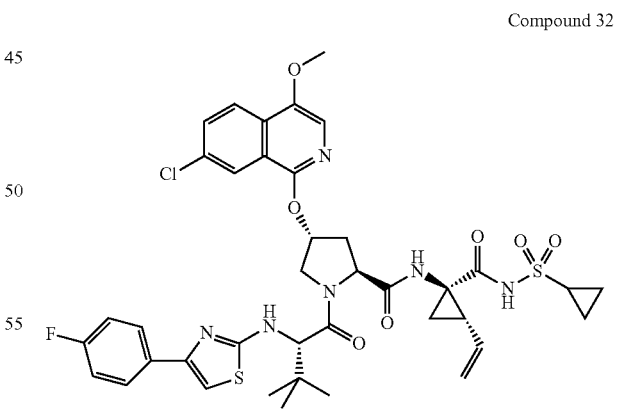

Compound 32 was prepared following the same procedure as described for the preparation of compound 23, except 2-chloro-4'-fluoroacetophenone was used instead of 2-bromo-4'-methylacetophenone in step 1. $^1$H NMR (600 MHz, DMSO_CDCl3) δ ppm 1.04-1.12 (m, 2H), 1.15 (s, 9H), 1.38 (dd, J=8.79, 5.27 Hz, 1H), 1.72-1.79 (m, 1H), 2.14-2.31 (m, 2H), 2.40 (dd, J=13.48, 6.44 Hz, 1H), 3.97 (s, 3H), 4.06 (q, J=5.27 Hz, 1H), 4.22 (dd, J=11.13, 2.93 Hz, 1H), 4.47 (d, J=4.46 Hz, 1H), 4.70 (d, J=9.37 Hz, 1H), 4.73-4.80 (m, 1H), 5.12 (d, J=8.79 Hz, 1H), 5.25 (d, J=15.82 Hz, 1H), 5.62-5.74 (m, 1H), 6.02 (br. s., 1H), 6.65 (t, J=8.50 Hz, 1H), 7.57 (s, 1H), 7.63 (dd, J=8.50, 5.57 Hz, 2H), 7.75 (d, J=9.37 Hz, 1H), 7.99 (d, J=9.37 Hz, 1H), 8.28 (s, 2H), 8.89 (br. s., 1H), 10.44 (br. s., 1H). LC-MS, MS m/z 824.9 (M$^+$+H).

Preparation of Compound 33, Example 33

Compound 33

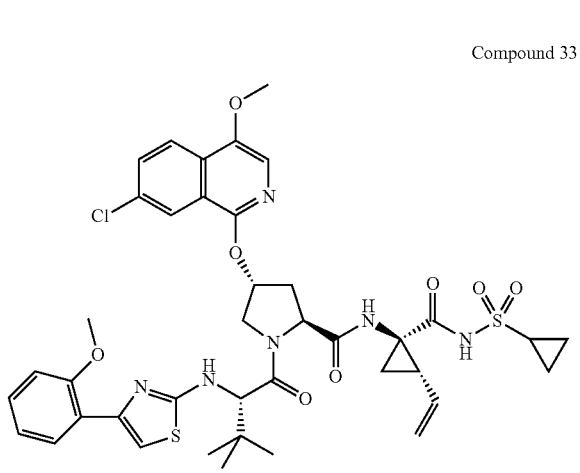

Compound 33 was prepared following the same procedure as described for the preparation of compound 23, except 2-bromo-2'-methoxyacetophenone was used instead of 2-bromo-4'-methylacetophenone in step 1. $^1$H NMR (600 MHz, DMSO_CDCl3) δ ppm 1.06-1.13 (m, 3H), 1.15 (s, 9H), 1.39 (dd, J=8.50, 4.98 Hz, 1H), 1.76 (d, J=1.76 Hz, 1H), 2.24 (d, J=15.82 Hz, 1H), 2.41 (dd, J=13.48, 7.03 Hz, 1H), 3.24 (d, J=4.69 Hz, 2H), 3.84 (s, 3H), 3.96 (s, 3H), 4.06 (q, J=5.27 Hz, 1H), 4.23 (d, J=7.62 Hz, 1H), 4.48 (d, J=16.41 Hz, 01H), 4.64 (d, J=9.37 Hz, 1H), 4.71 (d, J=6.44 Hz, 1H), 5.12 (d, J=9.96 Hz, 1H), 5.25 (d, J=17.58 Hz, 1H), 5.67 (t, J=14.35 Hz, 1H), 5.97 (br. s., 1H), 6.47 (t, J=7.32 Hz, 1H), 6.79 (d, J=7.62 Hz, 1H), 6.86 (br. s., 1H), 6.95 (s, 1H), 7.56 (d, J=9.37 Hz, 1H), 7.68 (d, J=9.37 Hz, 1H), 7.99 (t, J=8.79 Hz, 1H), 8.28 (s, 2H), 8.90 (br. s., 1H), 10.44 (br. s., 1H). LC-MS, MS m/z 836.9 (M$^+$+H).

Preparation of Compound 34, Example 34

Compound 34

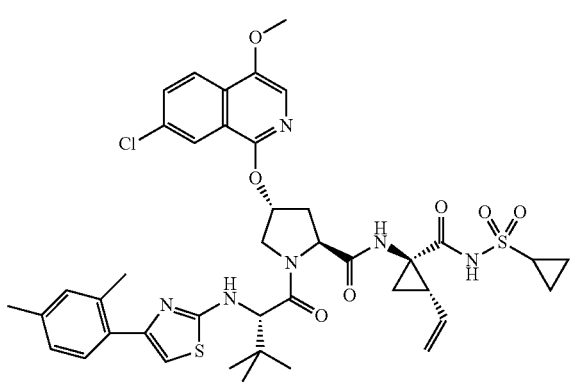

Compound 34 was prepared following the same procedure as described for the preparation of compound 23, except 2-bromo-1-(2,4-dimethylphenyl)ethan-1-one was used instead of 2-bromo-4'-methylacetophenone in step 1. LC-MS, MS m/z 834.9 (M$^+$+H).

Preparation of Compound 35, Example 35

Compound 35

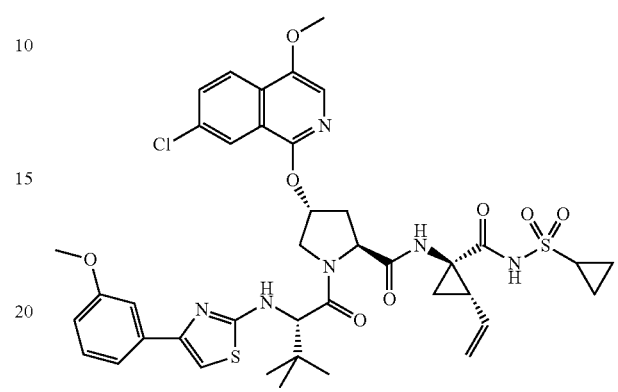

Compound 35 was prepared following the same procedure as described for the preparation of compound 23, except 2-bromo-3'-methoxyacetophenone was used instead of 2-bromo-4'-methylacetophenone in step 1. $^1$H NMR (600 MHz, DMSO_CDCl3) δ ppm 1.06-1.13 (m, 2H), 1.15 (s, 9H), 1.39 (dd, J=8.50, 4.98 Hz, 1H), 1.76 (d, J=1.76 Hz, 1H), 2.24 (d, J=15.82 Hz, 1H), 2.41 (dd, J=13.48, 7.03 Hz, 1H), 3.24 (d, J=4.69 Hz, 3H), 3.84 (s, 3H), 3.96 (s, 3H), 4.06 (q, J=5.27 Hz, 1H), 4.23 (d, J=7.62 Hz, 1H), 4.48 (d, J=16.41 Hz, 1H), 4.64 (d, J=9.37 Hz, 1H), 4.71 (d, J=6.44 Hz, 1H), 5.12 (d, J=9.96 Hz, 1H), 5.25 (d, J=17.58 Hz, 1H), 5.67 (t, J=14.35 Hz, 1H), 5.97 (br. s., 1H), 6.47 (t, J=7.32 Hz, 1H), 6.79 (d, J=7.62 Hz, 1H), 6.86 (br. s., 1H), 6.95 (s, 1H), 7.56 (d, J=9.37 Hz, 1H), 7.68 (d, J=9.37 Hz, 1H), 7.99 (t, J=8.79 Hz, 1H), 8.28 (s, 2H), 8.90 (br. s., 1H), 10.44 (br. s., 1H). LC-MS, MS m/z 837.4 (M$^+$+H).

Preparation of Compound 36, Example 36

Compound 36

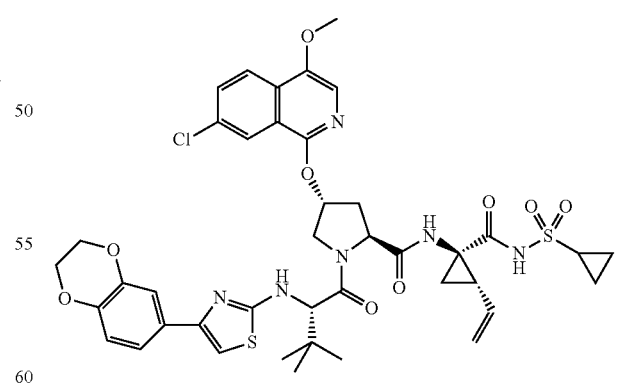

Compound 36 was prepared following the same procedure as described for the preparation of compound 23, except 2-bromo-1-(2,3-dihydro-1,4-benzodioxin-6-yl)ethan-1-one was used instead of 2-bromo-4'-methylacetophenone in step 1. $^1$H NMR (600 MHz, DMSO_CDCl3) δ ppm 1.03-1.12 (m, 3H), 1.16 (s, 9H), 1.38 (dd, J=8.79, 5.27 Hz, 1H), 1.74 (br. s., 1H), 2.14-2.27 (m, 2H), 2.38 (dd, J=12.89, 6.44 Hz, 1H), 3.24 (d, J=5.27 Hz, 3H), 3.72 (br. s., 1H), 3.86 (d, J=6.44 Hz, 1H), 3.98 (s, 3H), 4.06 (q, J=5.08 Hz, 2H), 4.22 (dd, J=11.43, 3.81 Hz, 1H), 4.42 (t, J=8.20 Hz, 1H), 4.66 (d, J=8.79 Hz, 1H), 4.86 (d, J=9.96 Hz, 1H), 5.11 (d, J=10.55 Hz, 1H), 5.24 (d, J=17.58 Hz, 1H), 6.03 (br. s., 1H), 6.34 (d, J=8.20 Hz, 1H), 6.67 (s, 1H), 7.12 (d, J=8.20 Hz, 1H), 7.20 (s, 1H), 7.48 (br. s., 1H), 7.59 (s, 1H), 7.62-7.70 (m, 2H), 8.00 (d, J=8.79 Hz, 1H), 8.28 (s, 2H), 8.88 (br. s., 1H), 10.42 (br. s., 1H). LC-MS, MS m/z 864.9 (M$^+$+H).

Preparation of Compound 37, Example 37

Compound 37

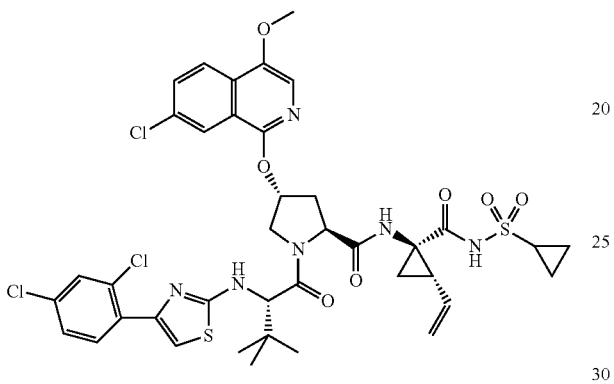

Compound 37 was prepared following the same procedure as described for the preparation of compound 23, except 2,2',4'-trichloroacetophenone was used instead of 2-bromo-4'-methylacetophenone in step 1. $^1$H NMR (600 MHz, DMSO_CDCl3) δ ppm 1.02-1.12 (m, 3H), 1.15 (s, 9H), 1.39 (dd, J=9.37, 5.27 Hz, 1H), 1.65-1.81 (m, 1H), 2.22 (t, J=16.11 Hz, 2H), 2.36 (dd, J=13.77, 6.74 Hz, 1H), 2.92-3.02 (m, 1H), 3.99 (s, 3H), 4.06 (q, J=5.27 Hz, 2H), 4.19 (d, J=8.20 Hz, 1H), 4.50 (t, J=7.91 Hz, 1H), 4.61 (d, J=9.37 Hz, 2H), 5.12 (d, J=9.37 Hz, 1H), 5.26 (d, J=16.40 Hz, 1H), 5.60-5.72 (m, 1H), 6.03 (br. s., 1H), 6.78 (d, J=8.20 Hz, 1H), 7.04 (s, 1H), 7.13 (br. s., 1H), 7.53 (br. s., 1H), 7.57 (s, 1H), 7.71 (d, J=2.34 Hz, 1H), 7.82 (t, J=8.50 Hz, 2H), 8.03 (d, J=8.79 Hz, 1H), 8.28 (s, 2H), 8.93 (br. s., 1H), 10.45 (br. s., 1H). LC-MS, MS m/z 874.8 (M$^+$+H).

Preparation of Compound 38, Example 38

Compound 38

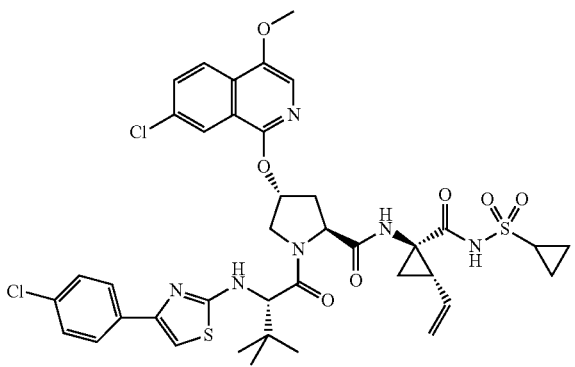

Compound 38 was prepared following the same procedure as described for the preparation of compound 23, except 2-bromo-4'-chloroacetophenone was used instead of 2-bromo-4'-methylacetophenone in step 1. $^1$H NMR (600 MHz, DMSO_CDCl3) δ ppm 1.04-1.12 (m, 3H), 1.15 (s, 9H), 1.38 (dd, J=9.08, 4.98 Hz, 1H), 1.75 (br. s., 1H), 2.13-2.29 (m, 2H), 2.38 (dd, J=12.89, 6.44 Hz, 2H), 3.98 (s, 3H), 4.07 (q, J=5.27 Hz, 2H), 4.22 (d, J=8.79 Hz, 1H), 4.48 (d, J=5.86 Hz, 1H), 4.69 (d, J=8.79 Hz, 1H), 4.73-4.81 (m, 1H), 5.12 (br. s., 1H), 5.24 (d, J=16.99 Hz, 1H), 5.68 (br. s., 1H), 6.05 (br. s., 1H), 6.84 (d, J=8.20 Hz, 1H), 6.87 (br. s., 1H), 7.54-7.60 (m, 3H), 7.65 (d, J=8.79 Hz, 1H), 7.79 (d, J=9.37 Hz, 1H), 7.99 (d, J=8.79 Hz, 1H), 8.28 (s, 2H), 8.89 (br. s., 1H), 10.44 (br. s., 1H). LC-MS, MS m/z 840.9 (M$^+$+H).

Preparation of Compound 39, Example 39

Compound 39

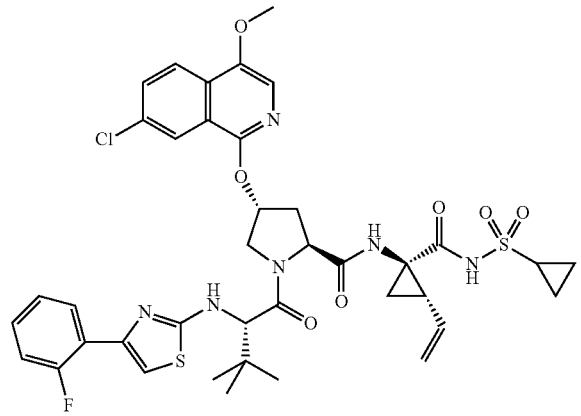

Compound 39 was prepared following the same procedure as described for the preparation of compound 23, except 2-fluorophenacyl bromide was used instead of 2-bromo-4'-methylacetophenone in step 1. $^1$H NMR (600 MHz, DMSO_CDCl3) δ ppm 1.08 (d, J=7.03 Hz, 3H), 1.15 (s, 9H), 1.38 (dd, J=8.79, 4.69 Hz, 1H), 1.75 (br. s., 1H), 2.18-2.29 (m, 1H), 2.38-2.44 (m, 1H), 2.98 (br. s., 1H), 3.96 (s, 3H), 4.07 (q, J=4.88 Hz, 2H), 4.22 (dd, J=11.43, 3.22 Hz, 1H), 4.47 (t, J=8.50 Hz, 1H), 4.70 (d, J=9.37 Hz, 1H), 4.74 (d, J=9.96 Hz, 1H), 5.12 (d, J=9.96 Hz, 1H), 5.25 (d, J=17.58 Hz, 1H), 6.00 (br. s., 1H), 6.65 (t, J=7.03 Hz, 1H), 6.80 (s, 1H), 6.84-6.94 (m, 2H), 7.51 (br. s., 1H), 7.54 (s, 1H), 7.65 (dd, J=8.79, 1.76 Hz, 1H), 7.79 (d, J=9.37 Hz, 1H), 7.92 (t, J=7.91 Hz, 1H), 7.97 (d, J=8.79 Hz, 1H), 8.28 (s, 2H), 8.89 (br. s., 1H), 10.44 (br. s., 1H). LC-MS, MS m/z 824.9 (M$^+$+H).

Preparation of Compound 40, Example 40

Compound 40

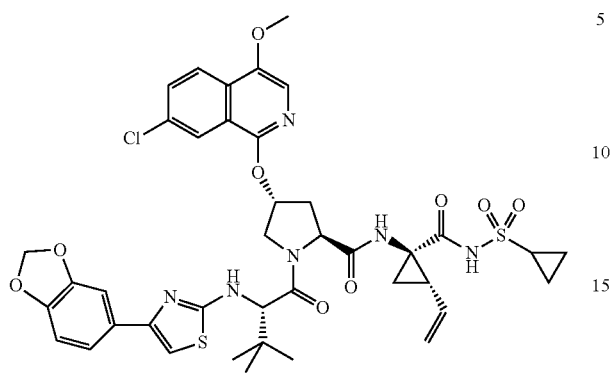

Compound 40 was prepared following the same procedure as described for the preparation of compound 23, except 1-(1,3-benzodioxol-5-yl)-2-bromoethan-1-one was used instead of 2-bromo-4'-methyacetophenone in step 1. $^1$H NMR (600 MHz, DMSO_CDCl3) δ ppm 1.06 (t, 3H), 1.15 (s, 9H), 1.38 (dd, J=9.08, 4.98 Hz, 1H), 1.75 (br. s., 1H), 2.22 (d, J=15.23 Hz, 2H), 2.32-2.41 (m, 1H), 2.98 (br. s., 1H), 3.98 (s, 3H), 4.06 (q, J=5.27 Hz, 2H), 4.22 (d, J=7.62 Hz, 1H), 4.45 (d, J=16.99 Hz, 1H), 4.67 (d, J=8.79 Hz, 1H), 4.79 (d, J=11.13 Hz, 1H), 5.11 (d, J=9.37 Hz, 1H), 5.24 (d, J=14.65 Hz, 1H), 5.56 (br. s., 1H), 5.74 (s, 1H), 6.06 (br. s., 1H), 6.33 (d, J=7.62 Hz, 1H), 6.68 (s, 1H), 7.09-7.21 (m, 1H), 7.50 (br. s., 1H), 7.58 (s, 1H), 7.64-7.71 (m, 2H), 8.00 (d, J=8.79 Hz, 1H), 8.28 (s, 2H), 8.89 (br. s., 1H), 10.43 (br. s., 1H). LC-MS, MS m/z 850.9 (M$^+$+H).

Preparation of Compound 41, Example 41

Compound 41

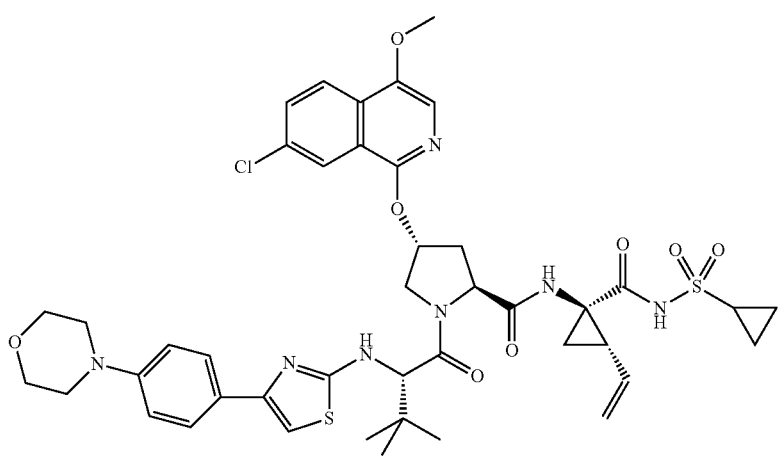

Compound 41 was prepared following the same procedure as described for the preparation of compound 23, except 2-bromo-1-(4-morpholinophenyl)-1-ethanone was used instead of 2-bromo-4'-methylacetophenone in step 1. $^1$H NMR (600 MHz, DMSO_CCDl3) δ ppm 1.04-1.11 (m, 4H), 1.16 (s, 9H), 1.38 (dd, J=9.37, 5.27 Hz, 1H), 1.74 (br. s., 1H), 2.15-2.29 (m, 2H), 2.35 (d, J=6.44 Hz, 2H), 2.65-2.70 (m, 2H), 2.71-2.78 (m, 2H), 2.98 (br. s., 2H), 3.60-3.69 (m, 4H), 3.79 (br. s., H), 3.99 (s, 3H), 4.02 (d, J=5.86 Hz, 1H), 4.07 (d, J=4.69 Hz, 4H), 4.27 (dd, J=11.13, 4.10 Hz, 1H), 4.45 (d, J=8.79 Hz, 1H), 4.65 (d, J=8.79 Hz, 1H), 4.87 (d, J=11.72 Hz, 1H), 5.11 (d, J=11.13 Hz, 1H), 5.24 (d, J=16.99 Hz, 1H), 5.68 (qt, 1H), 6.03 (br. s., 1H), 6.34 (d, J=8.20 Hz, 2H), 6.62 (s, 1H), 7.53 (d, J=8.20 Hz, 2H), 7.59-7.68 (m, 2H), 8.00 (d, J=8.79 Hz, 1H), 8.28 (s, 2H), 8.90 (br. s., 1H), 10.45 (br. s., 1H). LC-MS, MS m/z 891.9 (M$^+$+H).

Preparation of Compound 42, Example 42

Compound 42

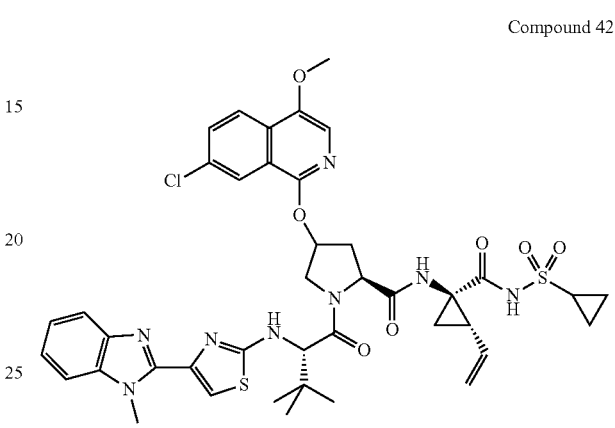

Compound 42 was prepared following the same procedure as described for the preparation of compound 23, except 2-bromo-1-(1-methyl-1H-benzimidazol-2-yl)-1-ethanone was used instead of 2-bromo-4'-methylacetophenone in step 1. $^1$H NMR (600 MHz, DMSO_CDCl3) δ ppm 1.09 (br. s., 2H), 1.13 (s, 9H), 1.16-1.21 (m, 2H), 1.42 (dd, J=8.79, 5.27 Hz, 1H), 1.79 (d, J=1.17 Hz, 1H), 2.18-2.33 (m, 2H), 2.50 (dd, J=13.48, 7.03 Hz, 1H), 3.00 (br. s., 1H), 3.72 (s, 3H), 3.96 (s, 3H), 4.06 (q, J=4.88 Hz, 2H), 4.20 (dd, J=11.13, 2.93 Hz, 1H), 4.43 (d, J=11.13 Hz, 1H), 4.59 (t, J=8.50 Hz, 1H), 4.74 (d, J=9.37 Hz, 1H), 5.15 (d, J=9.96 Hz, 1H), 5.29 (d, J=16.99 Hz, 1H), 5.70 (br. s., 1H), 5.86 (br. s., 1H), 7.08 (s, 1H), 7.14-7.21 (m, 2H), 7.25 (d, J=6.44 Hz, 1H), 7.33 (s, 1H), 7.51 (d, J=6.44 Hz, 1H), 7.63 (dd, J=8.79, 2.34 Hz, 1H), 7.74 (s, 1H), 7.89 (d, J=8.79 Hz, 1H), 8.00 (d, J=9.37 Hz, 1H), 8.28 (s, 2H), 8.97 (br. s., 1H), 10.46 (br. s., 1H). LC-MS, MS m/z 860.9 (M$^+$+H).

Preparation of Compound 43, Example 43

Compound 43

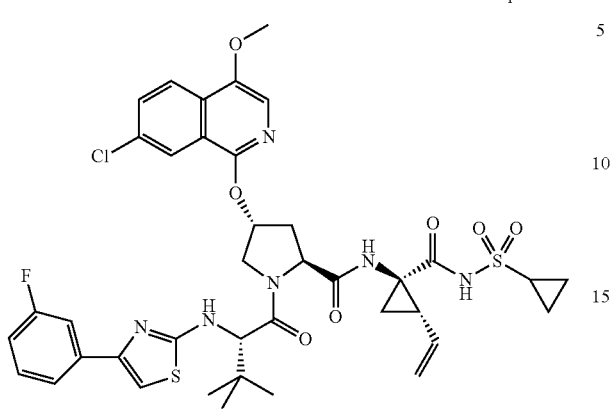

Compound 43 was prepared following the same procedure as described for the preparation of compound 23, except 3-fluorophenacyl bromide was used instead of 2-bromo-4'-methylacetophenone in step 1. $^1$H NMR (600 MHz, DMSO_CDCl3) δ ppm 0.99-1.13 (m, 2H), 1.16 (s, 9H), 1.38 (dd, J=9.37, 5.27 Hz, 1H), 1.75 (br. s., 1H), 2.09-2.28 (m, 1H), 2.35-2.47 (m, 1H), 3.96 (s, 3H), 4.06 (d, J=5.27 Hz, 2H), 4.23 (dd, J=11.13, 3.52 Hz, 1H), 4.44 (t, J=7.91 Hz, 1H), 4.71 (d, J=9.37 Hz, 1H), 4.80 (d, J=12.30 Hz, 1H), 5.12 (d, J=9.37 Hz, 1H), 5.24 (d, J=16.40 Hz, 1H), 6.02 (br. s., 1H), 6.93 (d, J=7.03 Hz, 2H), 7.43 (d, J=10.55 Hz, 1H), 7.48 (d, J=7.03 Hz, 1H), 7.55 (s, 1H), 7.64 (d, J=8.79 Hz, 1H), 7.81 (d, J=9.37 Hz, 1H), 7.97 (d, J=9.37 Hz, 1H), 8.28 (s, 2H), 8.88 (br. s., 1H), 10.42 (br. s., 1H). LC-MS, MS m/z 824.9 (M$^+$+H).

Preparation of Compound 44, Example 44

Compound 44

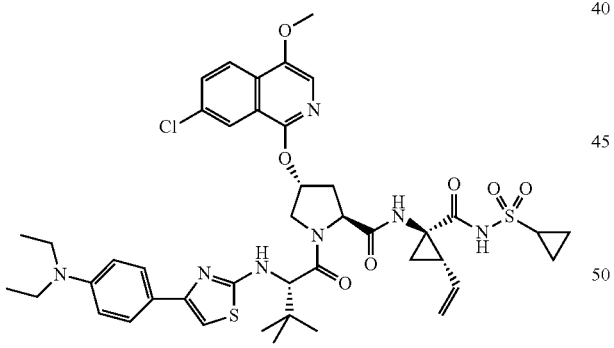

Compound 44 was prepared following the same procedure as described for the preparation of compound 23, except α-bromo-4-(diethylamino)acetophenone was used instead of 2-bromo-4'-methylacetophenone in step 1. $^1$H NMR (600 MHz, DMSO_CDCl3) δ ppm 0.86 (t, J=6.74 Hz, 6H), 1.05-1.11 (m, 4H), 1.16 (s, 9H), 1.37 (dd, J=9.08, 4.98 Hz, 1H), 1.74 (d, J=6.44 Hz, 1H), 2.21 (dd, J=17.58, 9.37 Hz, 2H), 2.35 (dd, J=13.18, 6.74 Hz, 1H), 2.93-3.10 (m, 6H), 3.96 (s, 3H), 4.07 (d, J=5.27 Hz, 3H), 4.24 (dd, J=11.72 Hz, 1H), 4.42 (dd, J=9.37, 7.03 Hz, 1H), 4.64 (d, J=9.37 Hz, 1H), 4.92 (d, J=11.13 Hz, 1H), 5.11 (d, J=10.55 Hz, 1H), 5.24 (d, J=17.58 Hz, 1H), 5.63-5.72 (m, 1H), 6.02 (br. s., 1H), 6.14 (d, J=8.79 Hz, 2H), 6.47 (s, 1H), 7.50 (d, J=8.20 Hz, 2H), 7.57 (d, J=9.37 Hz, 2H), 7.59 (s, 1H), 7.64 (dd, J=9.08, 2.05 Hz, 1H), 7.97 (d, J=8.79 Hz, 1H), 8.28 (s, 2H), 8.88 (br. s., 1H), 10.43 (br. s., 1H). LC-MS, MS m/z 877.9 (M$^+$+H).

Preparation of Compound 45, Example 45

Compound 45

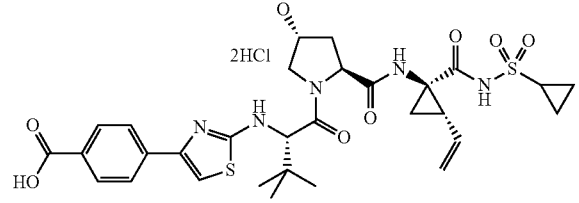

Compound 45 was prepared following the same procedure as described for the preparation of compound 23, except 2-bromo-2-phenylacetophenone was used instead of 2-bromo-4'-methylacetophenone in step 1. $^1$H NMR (600 MHz, DMSO_CDCl3) δ ppm 1.04-1.13 (m, 3H), 1.16 (s, 9H), 1.18 (br. s., 2H), 1.39 (dd, J=9.08, 4.98 Hz, 1H), 1.76 (t, J=5.86 Hz, 1H), 2.24 (dd, J=16.40, 9.37 Hz, 2H), 2.40 (dd, J=12.60, 7.32 Hz, 1H), 2.99 (br. s., 1H), 3.98 (s, 3H), 4.06 (q, J=4.88 Hz, 2H), 4.24 (dd, J=11.13, 4.10 Hz, 1H), 4.50 (d, J=15.82 Hz, 1H), 4.70 (d, J=9.37 Hz, 2H), 5.13 (d, J=10.55 Hz, 1H), 5.26 (d, J=16.99 Hz, 1H), 5.62-5.72 (m, 1H), 5.95 (br. s., 1H), 6.71-6.86 (m, 3H), 7.15 (d, J=7.03 Hz, 1H), 7.27 (d, J=7.03 Hz, 5H), 7.62 (s, 1H), 7.69 (d, J=8.79 Hz, 1H), 7.72 (s, 1H), 7.87 (d, J=9.37 Hz, 1H), 8.03 (d, J=8.79 Hz, 1H), 8.28 (s, 2H), 8.90 (br. s., 1H), 10.45 (br. s., 1H). LC-MS, MS m/z 882.9 (M$^+$+H).

Preparation of Compound 46, Example 46

Compound 46

Compound 46 was prepared following the same procedure as described for the preparation of compound 9, except 4-(2-bromoacetyl)benzoic acid was used instead of 2-bromopropiophenone in step 1. $^1$H NMR (500 MHz, MeOD) δ ppm 1.06-1.11 (m, 2H), 1.12-1.19 (m, 9H), 1.22-1.29 (m, 3H), 1.41 (dd, J=9.3, 5.3 Hz, 1H), 1.88 (dd, J=8.2, 5.5 Hz, 1H), 2.19-2.28 (m, 2H), 2.39-2.46 (m, 1H), 2.83-2.87 (m, 1H), 2.95 (tt, J=8.7, 4.5 Hz, 1H), 3.90 (s, 3H), 4.15 (dd, J=11.4, 3.5 Hz, 1H), 4.57 (dd, J=10.5, 6.9 Hz, 1H), 5.11 (dd, J=10.5, 1.4 Hz, 1H), 5.28 (d, J=17.4 Hz, 1H), 5.68-5.77 (m, 1H), 6.06-6.11 (m, 1H), 7.38 (s, 1H), 7.51 (ddd, J=8.5, 5.8, 2.4 Hz, 4H), 7.55-7.61 (m, 2H), 7.89 (d, J=8.9 Hz, 1H). LC-MS, MS m/z 851.2 (M⁺+H).

Preparation of Compound 47, Example 47

Compoound 47

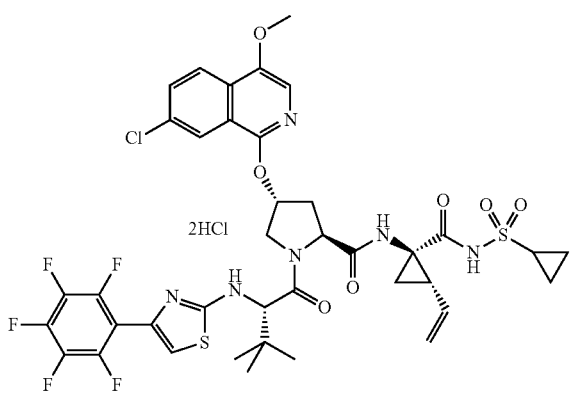

Compound 47 was prepared in 41% yield following the same procedure as described for the preparation of compound 9, except 2,3,4,5,6-pentafluorophenacyl bromide was used instead of 2-bromopropiophenone in step 1. ¹H NMR (500 MHz, MeOD) δ ppm 1.04-1.10 (m, 2H), 1.15 (s, 9H), 1.21-1.28 (m, 2H), 1.40 (dd, J=9.5, 5.5 Hz, 1H), 1.87 (dd, J=8.2, 5.5 Hz, 1H), 2.17-2.26 (m, 2H), 2.35-2.43 (m, 1H), 2.95 (td, J=8.4, 4.0 Hz, 1H), 3.98 (s, 3H), 4.10 (dd, J=11.4, 3.8 Hz, 1H), 4.56 (dd, J=10.4, 6.7 Hz, 1H), 4.64 (s, 1H), 4.72 (d, J=11.6 Hz, 1H), 5.11 (dd, J=10.4, 1.5 Hz, 1H), 5.27 (dd, J=17.1, 1.2 Hz, 1H), 5.72 (ddd, J=17.1, 10.2, 9.0 Hz, 1H), 6.04 (s, 1H), 6.85 (s, 1H), 7.49 (s, 1H), 7.59-7.65 (m, 2H), 8.00 (d, J=8.9 Hz, 1H). ¹³C NMR (126 MHz, MeOD) δ ppm 5.6, 5.8, 22.5, 26.2, 31.2, 34.9, 35.5, 35.7, 41.7, 42.8, 54.9, 55.8, 60.2, 63.7, 74.4, 117.6, 118.5, 120.6, 122.3, 123.3, 129.3, 130.9, 133.3, 133.5, 146.9, 152.2, 168.7, 169.6, 172.3, 174.2. LC-MS, MS m/z 897.2 (M⁺+H).

Preparation of Compound 48, Example 48

Compound 48

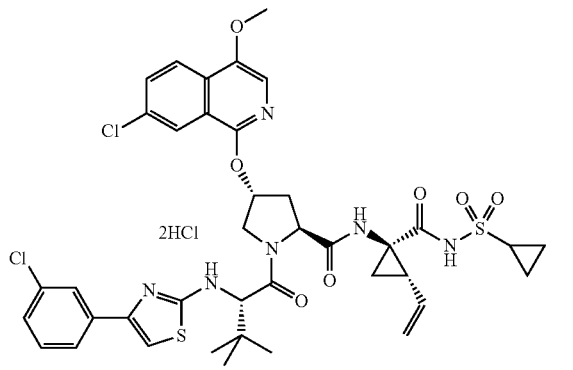

Compound 48 was prepared in 31.5% yield following the same procedure as described for the preparation of compound 9, except 3-chlorophenacyl bromide was used instead of 2-bromopropiophenone in step 1. ¹H NMR (500 MHz, MeOD) δ ppm 1.06-1.11 (m, 2H), 1.16 (s, 9H), 1.24-1.27 (m, 2H), 1.41 (dd, J=9.5, 5.2 Hz, 1H), 1.88 (dd, J=8.2, 5.5 Hz, 1H), 2.20-2.30 (m, 2H), 2.51 (dd, J=13.7, 6.7 Hz, 1H), 2.96 (ddd, J=12.7, 8.0, 4.9 Hz, 1H), 3.93 (s, 3H), 4.15 (dd, J=11.6, 3.7 Hz, 1H), 4.56 (dd, J=10.4, 7.0 Hz, 1H), 4.68-4.72 (m, 2H), 5.11 (dd, J=10.2, 1.7 Hz, 1H), 5.28 (dd, J=17.1, 1.2 Hz, 1H), 5.73 (ddd, J=17.2, 10.2, 9.2 Hz, 1H), 6.00 (t, J=3.2 Hz, 1H), 7.01-7.04 (m, 1H), 7.08 (t, J=7.8 Hz, 1H), 7.43 (d, J=7.9 Hz, 2H), 7.53-7.57 (m, 2H), 7.62 (d, J=1.8 Hz, 1H), 7.96 (d, J=8.9 Hz, 1H). ¹³C NMR (126 MHz, MeOD) δ ppm 5.6, 5.8, 22.5, 26.1, 31.2, 34.9, 35.3, 36.1, 41.7, 55.1, 55.7, 60.2, 64.1, 74.5, 117.6, 118.4, 120.8, 122.6, 123.3, 124.1, 125.9, 127.8, 129.5, 129.8, 130.9, 133.2, 134.4, 147.0, 148.8, 152.2, 163.2, 169.6, 169.7, 171.6, 174.1, 178.4. LC-MS, MS m/z 841.2 (M⁺+H).

Preparation of Compound 49, Example 49

Compound 49

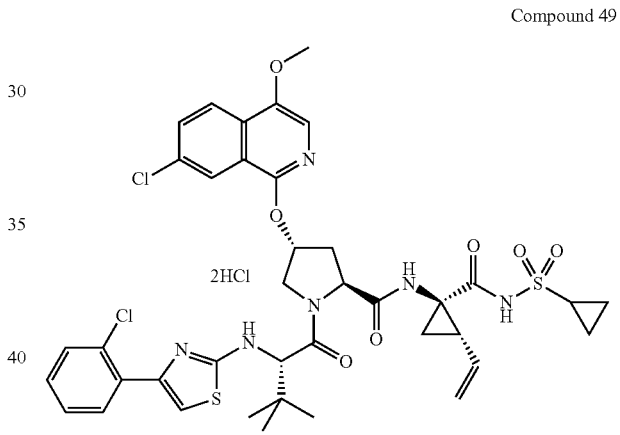

Compound 49 was prepared in 28.9% yield following the same procedure as described for the preparation of compound 9, except 2-chlorophenacyl bromide was used instead of 2-bromopropiophenone in step 1. ¹H NMR (500 MHz, MeOD) δ ppm 1.06-1.12 (m, 3H), 1.14 (s, 9H), 1.25 (dd, J=4.9, 2.7 Hz, 2H), 1.42 (dd, J=9.5, 5.5 Hz, 1H), 1.89 (dd, J=8.2, 5.5 Hz, 1H), 2.22-2.32 (m, 2H), 2.56 (dd, J=13.6, 7.2 Hz, 1H), 2.96 (ddd, J=12.8, 8.1, 4.7 Hz, 1H), 3.95 (s, 3H), 4.13 (dd, J=11.7, 3.8 Hz, 1H), 4.38 (d, J=11.9 Hz, 1H), 4.58 (s, 1H), 4.63 (dd, J=10.1, 7.3 Hz, 1H), 5.13 (dd, J=10.4, 1.5 Hz, 1H), 5.30 (dd, J=17.1, 1.2 Hz, 1H), 5.73 (ddd, J=17.2, 10.3, 8.9 Hz, 1H), 5.90 (s, 1H), 6.77 (s, 1H), 7.21 (t, J=7.5 Hz, 1H), 7.26-7.31 (m, 1H), 7.36 (d, J=7.3 Hz, 1H), 7.48 (s, 1H), 7.50 (dd, J=7.6, 1.5 Hz, 1H), 7.66 (dd, J=8.9, 2.1 Hz, 1H), 7.89 (d, J=2.1 Hz, 1H), 8.06 (d, J=8.9 Hz, 1H). ¹³C NMR (126 MHz, MeOD) δ ppm 5.6, 5.8, 22.5, 26.1, 31.2, 34.8, 35.1, 37.0, 41.7, 55.1, 55.8, 60.4, 64.6, 74.7, 117.6, 118.7, 120.8, 122.6, 123.6, 127.2, 129.6, 130.0, 130.3, 130.6, 131.1, 131.5, 132.7, 133.2, 133.5, 147.1, 152.4, 168.8, 169.5, 170.1, 174.0, 181.3. LC-MS, MS m/z 841.2 (M⁺+H).

Preparation of Compound 50, Example 50

Compound 50

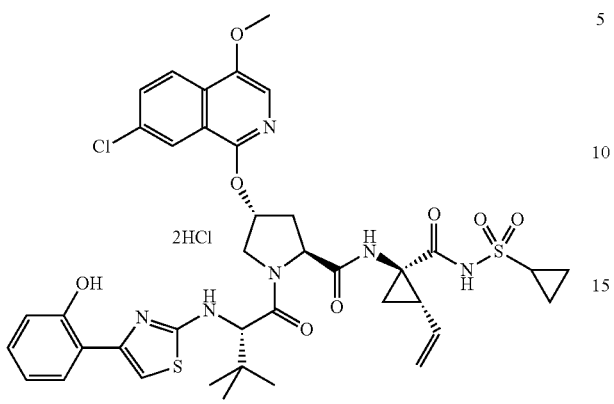

Compound 50 was prepared in 41.6% yield following the same procedure as described for the preparation of compound 9, except 2-bromo-2'-hydroxyacetophenone was used instead of 2-bromopropiophenone in step 1. $^1$H NMR (500 MHz, MeOD) δ ppm 1.06-1.11 (m, 2H), 1.15 (s, 9H), 1.24 (dd, J=4.9, 2.7 Hz, 2H), 1.42 (dd, J=9.5, 5.5 Hz, 1H), 1.90 (dd, J=8.2, 5.5 Hz, 1H), 2.22-2.28 (m, 1H), 2.28-2.33 (m, 1H), 2.63 (dd, J=13.7, 7.3 Hz, 1H), 2.92-2.98 (m, J=8.2, 8.2, 4.9, 4.7 Hz, 1H), 3.98 (s, 3H), 4.07 (dd, J=12.2, 3.1 Hz, 1H), 4.24 (s, 1H), 4.35 (d, J=11.9 Hz, 1H), 4.69 (dd, J=10.1, 7.3 Hz, 1H), 5.13 (dd, J=10.4, 1.5 Hz, 1H), 5.30 (dd, J=17.2, 1.4 Hz, 1H), 5.73 (ddd, J=17.1, 10.4, 8.9 Hz, 1H), 5.90 (s, 1H), 6.90 (t, J=7.8 Hz, 2H), 7.23-7.27 (m, 1H), 7.43 (d, J=7.9 Hz, 1H), 7.56 (s, 1H), 7.59 (dd, J=8.9, 2.1 Hz, 1H), 7.91 (d, J=2.1 Hz, 1H), 8.04 (d, J=8.9 Hz, 1H). $^{13}$C NMR (126 MHz, MeOD) δ ppm 5.6, 5.8, 22.4, 25.9, 31.2, 34.8, 34.9, 36.8, 41.7, 55.2, 55.9, 60.4, 66.2, 74.9, 116.7, 117.7, 118.9, 120.4, 120.8, 122.3, 123.8, 127.6, 129.6, 131.0, 131.4, 133.2, 133.6, 147.2, 152.2, 154.6, 159.0, 169.4, 169.5, 169.7, 172.4, 173.9. LC-MS, MS m/z 823.2 (M$^+$+H).

Preparation of Compound 51, Example 51

Compound 51

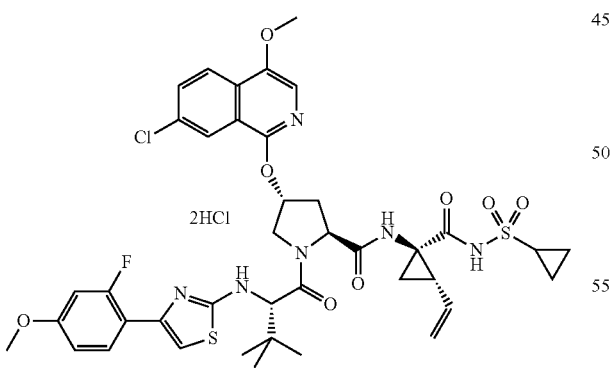

Compound 51 was prepared in 36.2% yield following the same procedure as described for the preparation of compound 9, except 2-fluoro-4-methoxyphenacyl bromide was used instead of 2-bromopropiophenone in step 1. $^1$H NMR (500 MHz, MeOD) δ ppm 1.04-1.11 (m, 3H), 1.15 (s, 9H), 1.21-1.26 (m, 2H), 1.41 (dd, J=9.5, 5.5 Hz, 1H), 1.89 (dd, J=8.1, 5.6 Hz, 1H), 2.21-2.30 (m, 2H), 2.54 (dd, J=13.7, 6.7 Hz, 1H), 2.96 (ddd, J=12.7, 8.1, 4.9 Hz, 1H), 3.73 (s, 3H), 3.96 (s, 3H), 4.12 (dd, J=11.7, 3.5 Hz, 1H), 4.52 (d, J=11.6 Hz, 1H), 4.56 (s, 1H), 4.62 (dd, J=10.4, 7.0 Hz, 1H), 5.12 (d, J=10.4 Hz, 1H), 5.29 (d, J=17.4 Hz, 1H), 5.73 (dt, J=17.2, 9.6 Hz, 1H), 5.98 (s, 1H), 6.53-6.63 (m, 2H), 7.46-7.52 (m, 2H), 7.60 (dd, J=8.9, 2.1 Hz, 1H), 7.76 (s, 1H), 8.01 (d, J=8.9 Hz, 1H). $^{13}$C NMR (126 MHz, MeOD) δ ppm 5.6, 5.8, 22.5, 26.0, 31.2, 34.8, 35.2, 36.6, 41.7, 42.8, 55.2, 55.3, 55.8, 60.4, 64.8, 74.6, 101.8, 102.0, 110.5, 117.6, 118.6, 120.8, 122.5, 123.5, 129.5, 129.9, 129.9, 131.0, 133.2, 133.4, 147.1, 152.3, 161.8, 169.2, 169.5, 170.5, 174.0 LC-MS, MS m/z 855.2 (M$^+$+H).

Preparation of Compound 52, Example 52

Compound 52

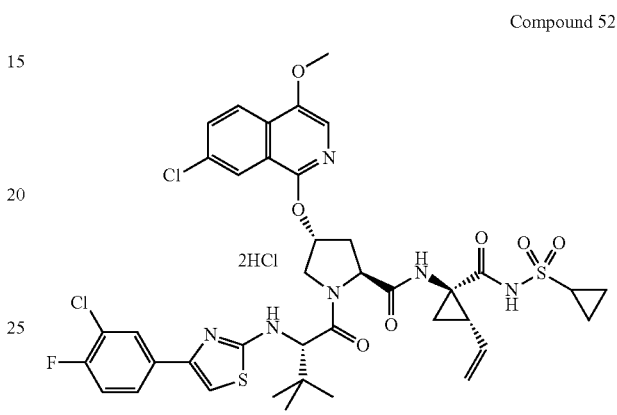

Compound 52 was prepared in 21.2% yield following the same procedure as described for the preparation of compound 9, except 2-bromo-1-(3-chloro-4-fluorophenyl)ethanone was used instead of 2-bromopropiophenone in step 1. $^1$H NMR (500 MHz, MeOD) δ ppm 1.04-1.11 (m, 3H), 1.15 (s, 9H), 1.22-1.29 (m, 2H), 1.41 (dd, J=9.5, 5.5 Hz, 1H), 1.87 (dd, J=8.2, 5.5 Hz, 1H), 2.18-2.26 (m, 2H), 2.42-2.50 (m, 1H), 2.91-2.98 (m, 1H), 3.94 (s, 3H), 4.14 (dd, J=11.7, 3.5 Hz, 1H), 4.55 (dd, J=10.7, 7.0 Hz, 1H), 4.70-4.76 (m, 2H), 5.11 (dd, J=10.4, 1.5 Hz, 1H), 5.27 (dd, J=17.1, 1.2 Hz, 1H), 5.73 (ddd, J=17.1, 10.4, 8.9 Hz, 1H), 6.06 (d, J=2.7 Hz, 1H), 6.86 (t, J=8.9 Hz, 1H), 7.38-7.45 (m, 2H), 7.51-7.57 (m, 2H), 7.60 (dd, J=7.2, 2.3 Hz, 1H), 7.95 (d, J=9.5 Hz, 1H). $^{13}$C NMR (126 MHz, MeOD) δ ppm 5.6, 5.8, 22.5, 26.2, 31.2, 34.9, 35.4, 35.8, 41.7, 55.2, 55.7, 60.2, 63.8, 74.3, 116.2, 116.4, 117.6, 118.3, 120.5, 120.6, 120.7, 122.5, 123.3, 123.6, 125.9, 125.9, 128.0, 128.5, 129.4, 130.8, 133.2, 133.2, 147.0, 152.1, 169.6, 169.6, 172.0, 174.2. LC-MS, MS m/z 859.2 (M$^+$+H).

Preparation of Compound 53, Example 53

Compound 53

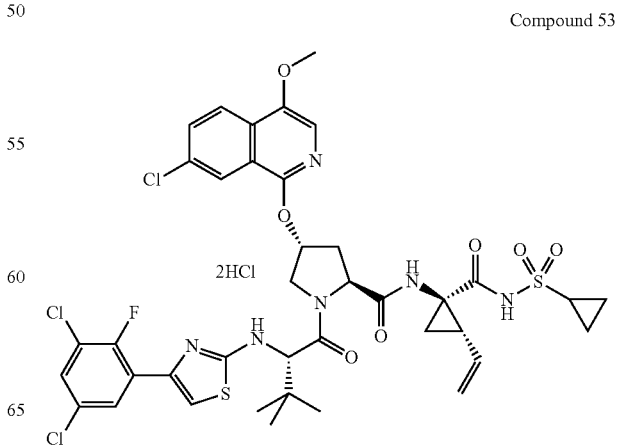

Compound 53 was prepared in 15.3% yield following the same procedure as described for the preparation of compound 9, except 2-bromo-1-(3,5-dichloro-2-fluorophenyl)ethanone was used instead of 2-bromopropiophenone in step 1. ¹H NMR (500 MHz, MeOD) δ ppm 1.07-1.11 (m, 2H), 1.14 (s, 9H), 1.23-1.27 (m, 2H), 1.42 (dd, J=9.5, 5.5 Hz, 1H), 1.89 (dd, J=8.2, 5.5 Hz, 1H), 2.23-2.33 (m, 2H), 2.57 (dd, J=13.7, 7.3 Hz, 1H), 2.92-2.99 (m, 1H), 3.98 (s, 4H), 4.16 (dd, J=11.7, 4.1 Hz, 1H), 4.27 (d, J=11.9 Hz, 1H), 4.56 (s, 1H), 4.63 (dd, J=9.9, 7.2 Hz, 1H), 5.13 (dd, J=10.1, 1.5 Hz, 1H), 5.27-5.34 (m, 1H), 5.74 (ddd, J=17.1, 10.4, 8.9 Hz, 1H), 5.83 (s, 1H), 6.67 (s, 1H), 7.27-7.35 (m, 2H), 7.50 (s, 1H), 7.70 (dd, J=8.9, 2.1 Hz, 1H), 7.98 (d, J=2.1 Hz, 1H), 8.11 (d, J=8.9 Hz, 1H). ¹³C NMR (126 MHz, MeOD) δ ppm 5.6, 5.8, 15.1, 22.5, 26.1, 31.2, 34.8, 35.1, 37.1, 41.7, 55.0, 55.8, 60.4, 64.3, 74.8, 105.9, 108.7, 117.6, 117.8, 118.7, 120.8, 122.6, 123.7, 129.1, 129.2, 131.1, 133.2, 133.5, 147.2, 148.1, 148.4, 148.4, 152.5, 165.7, 169.5, 170.2, 173.9, 178.4. LC-MS, MS m/z 895.1 (M⁺+H).

Preparation of Compound 54, Example 54

Compound 54

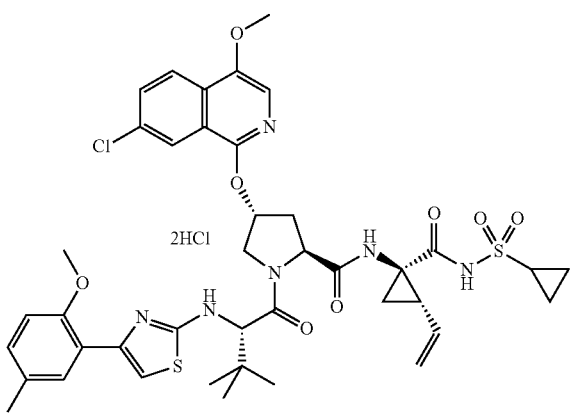

Compound 54 was prepared in 40.2% yield following the same procedure as described for the preparation of compound 9, except 2-bromo-1-(2-methoxy-5-methyl-phenyl)-ethanone was used instead of 2-bromopropiophenone in step 1. ¹H NMR (500 MHz, MeOD) δ ppm 1.06-1.11 (m, 2H), 1.16 (s, 9H), 1.24 (dd, J=4.6, 2.4 Hz, 2H), 1.42 (dd, J=9.5, 5.5 Hz, 1H), 1.90 (dd, J=7.9, 5.5 Hz, 1H), 2.24 (s, 3H), 2.30 (ddd, J=13.9, 10.1, 4.1 Hz, 2H), 2.61 (dd, J=13.7, 7.3 Hz, 1H), 2.96 (ddd, J=12.7, 8.0, 4.9 Hz, 1H), 3.87 (s, 3H), 3.99 (s, 3H), 4.09 (dd, J=12.1, 3.2 Hz, 1H), 4.35 (s, 1H), 4.44 (d, J=12.2 Hz, 1H), 4.66 (dd, J=10.2, 7.2 Hz, 1H), 5.13 (dd, J=10.2, 1.7 Hz, 1H), 5.30 (dd, J=17.1, 1.2 Hz, 1H), 5.73 (ddd, J=17.2, 10.3, 8.9 Hz, 1H), 5.92 (s, 1H), 6.96 (d, J=8.5 Hz, 1H), 7.16 (d, J=7.9 Hz, 1H), 7.36 (d, J=0.9 Hz, 1H), 7.56 (s, 1H), 7.58 (dd, J=8.9, 2.1 Hz, 1H), 7.85 (d, J=1.5 Hz, 1H), 8.03 (d, J=8.9 Hz, 1H). ¹³C NMR (126 MHz, MeOD) δ ppm 5.6, 5.8, 19.4, 22.5, 25.9, 31.1, 34.8, 35.0, 36.9, 41.6, 55.1, 55.3, 55.8, 60.3, 65.7, 74.8, 111.8, 117.7, 118.7, 120.7, 122.4, 123.7, 129.2, 129.5, 130.7, 131.0, 133.2, 133.4, 147.1, 150.7, 152.2, 154.6, 160.2, 169.5, 173.9, 176.8, 179.5, 185.7, 191.1. LC-MS, MS m/z 851.2 (M⁺+H).

Preparation of Compound 55, Example 55

Compound 55

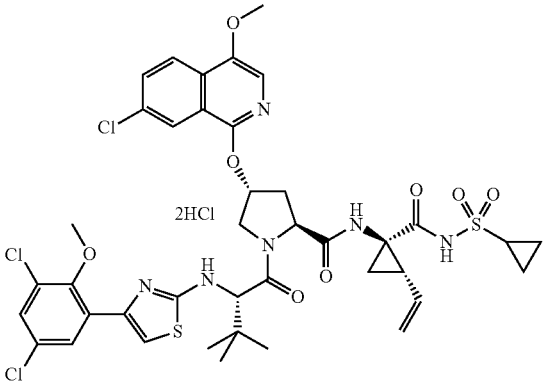

Compound 55 was prepared in 37.9% yield following the same procedure as described for the preparation of compound 9, except 2-bromo-1-(3,5-dichloro-2-methoxyphenyl)ethanone was used instead of 2-bromopropiophenone in step 1. ¹H NMR (500 MHz, MeOD) δ ppm 1.06-1.11 (m, 2H), 1.16 (s, 9H), 1.23-1.27 (m, 2H), 1.42 (dd, J=9.5, 5.5 Hz, 1H), 1.89 (dd, J=7.9, 5.5 Hz, 1H), 2.20-2.26 (m, 1H), 2.26-2.32 (m, 1H), 2.55 (dd, J=13.6, 6.9 Hz, 1H), 2.96 (ddd, J=12.8, 8.1, 4.7 Hz, 1H), 3.61 (s, 3H), 3.96 (s, 3H), 4.17 (dd, J=11.9, 3.7 Hz, 1H), 4.55 (d, J=11.6 Hz, 1H), 4.60 (dd, J=10.4, 7.0 Hz, 1H), 4.68 (s, 1H), 5.12 (dd, J=10.4, 1.5 Hz, 1H), 5.29 (dd, J=17.1, 1.2 Hz, 1H), 5.73 (ddd, J=17.2, 10.2, 9.2 Hz, 1H), 5.97 (s, 1H), 7.24 (d, J=2.4 Hz, 1H), 7.48 (s, 1H), 7.58 (dd, J=8.9, 2.1 Hz, 1H), 7.62 (d, J=2.4 Hz, 1H), 7.72 (d, J=2.1 Hz, 1H), 7.99 (d, J=9.2 Hz, 1H). ¹³C NMR (126 MHz, MeOD) δ ppm 5.6, 5.8, 22.6, 26.1, 31.2, 34.9, 35.2, 36.5, 41.6, 55.1, 55.7, 59.9, 60.3, 64.1, 74.6, 117.6, 118.5, 120.7, 122.5, 123.4, 128.3, 129.4, 129.5, 129.7, 130.9, 133.2, 147.0, 152.1, 152.3, 152.5, 168.6, 169.6, 171.0, 174.0, 175.5, 181.0. LC-MS, MS m/z 907.1 (M⁺+H). LC-MS, MS m/z 905.2 (M⁺−H).

Preparation of Compound 56, Example 56

Compound 56

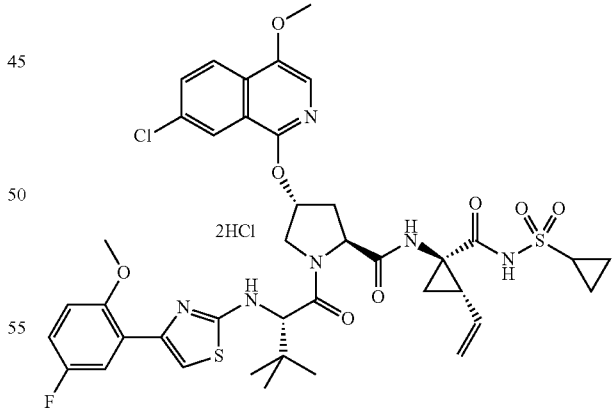

Compound 56 was prepared in 40.9% yield following the same procedure as described for the preparation of compound 9, except 2-bromo-1-(5-fluoro-2-methoxyphenyl)ethanone was used instead of 2-bromopropiophenone in step 1. ¹H NMR (500 MHz, MeOD) δ ppm 1.06-1.11 (m, 2H), 1.16 (s, 9H), 1.22-1.26 (m, 2H), 1.42 (dd, J=9.5, 5.5 Hz, 1H), 1.90 (dd, J=8.1, 5.3 Hz, 1H), 2.23-2.31 (m, 2H), 2.59 (dd, J=13.9, 6.9 Hz, 1H), 2.95 (td, J=8.3, 4.1 Hz, 1H), 3.87 (s, 3H), 3.97 (s, 3H), 4.10 (dd, J=11.9, 3.4 Hz, 1H), 4.40-4.48 (m, 2H), 4.65

(dd, J=10.1, 7.3 Hz, 1H), 5.13 (dd, J=10.4, 1.5 Hz, 1H), 5.29 (d, J=17.1 Hz, 1H), 5.68-5.77 (m, 1H), 5.94 (s, 1H), 7.03 (d, J=4.6 Hz, 2H), 7.35 (dd, J=9.5, 2.1 Hz, 1H), 7.52 (s, 1H), 7.58 (dd, J=8.9, 2.1 Hz, 1H), 7.81 (s, 1H), 8.01 (d, J=8.9 Hz, 1H). $^{13}$C NMR (126 MHz, MeOD) δ ppm 5.6, 5.8, 22.5, 25.9, 31.2, 34.8, 35.0, 36.8, 41.6, 55.1, 55.7, 60.3, 65.4, 74.7, 113.0, 113.1, 115.2, 115.4, 116.9, 117.7, 118.6, 120.7, 122.4, 123.6, 129.5, 130.9, 133.2, 133.4, 147.1, 148.6, 152.2, 153.1, 154.6, 156.2, 158.1, 168.9, 169.5, 169.9, 172.8, 173.9. LC-MS, MS m/z 855.1 (M$^+$+H). LC-MS, MS m/z 853.2 (M$^+$–H).

Preparation of Compound 57, Example 57

Compound 57

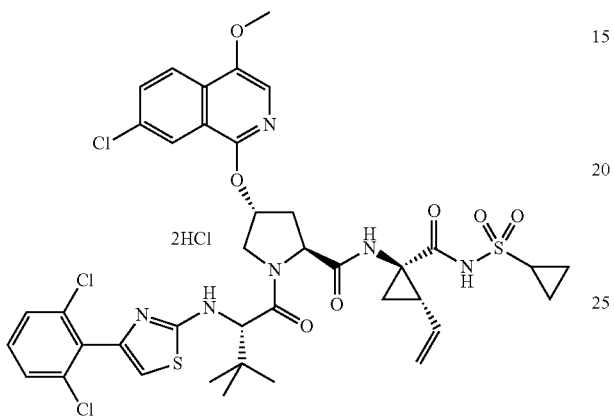

Compound 57 was prepared in 8.9% yield following the same procedure as described for the preparation of compound 9, except 2-bromo-1-(2,6-dichlorophenyl)ethanone was used instead of 2-bromopropiophenone in step 1. $^1$H NMR (500 MHz, MeOD) δ ppm 1.06-1.11 (m, 3H), 1.12-1.16 (m, 9H), 1.25 (dd, J=4.6, 2.7 Hz, 2H), 1.42 (dd, J=9.6, 5.3 Hz, 1H), 1.89 (dd, J=8.2, 5.5 Hz, 1H), 2.25-2.33 (m, 2H), 2.56 (dd, J=13.6, 7.2 Hz, 1H), 2.96 (ddd, J=12.8, 8.1, 4.7 Hz, 1H), 3.98 (s, 3H), 4.15 (dd, J=11.7, 4.1 Hz, 1H), 4.23-4.29 (m, 1H), 4.57 (s, 1H), 4.62 (dd, J=9.8, 7.0 Hz, 1H), 5.13 (dd, J=10.4, 1.5 Hz, 1H), 5.30 (dd, J=17.2, 1.4 Hz, 1H), 5.74 (ddd, J=17.1, 10.2, 9.0 Hz, 1H), 5.83 (s, 1H), 6.59 (s, 1H), 7.28 (dd, J=15.6, 8.5 Hz, 1H), 7.33 (s, 3H), 7.49 (s, 1H), 7.70 (dd, J=8.9, 2.1 Hz, 1H), 7.99 (d, J=1.8 Hz, 1H), 8.11 (d, J=9.2 Hz, 1H). LC-MS, MS m/z 877.2 (M$^+$+H). LC-MS, MS m/z 875.1 (M$^+$–H).

Preparation of Compound 58, Example 58

Compound 58

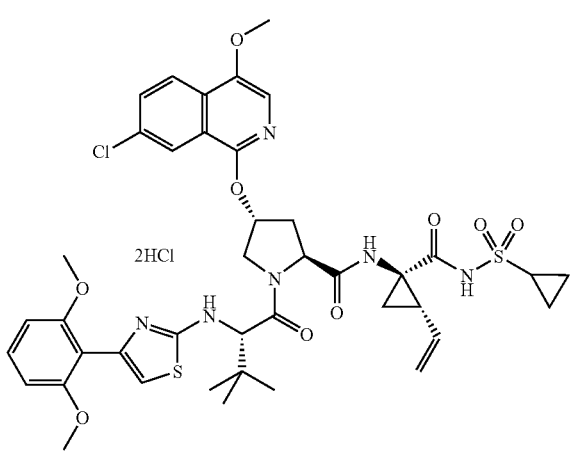

Compound 58 was prepared in 50.5% yield following the same procedure as described for the preparation of compound 9, except 2-bromo-1-(2,6-dimethoxyphenyl)ethanone was used instead of 2-bromopropiophenone in step 1. $^1$H NMR (500 MHz, MeOD) δ ppm 1.06-1.13 (m, 3H), 1.16 (s, 9H), 1.23 (d, J=4.6 Hz, 2H), 1.43 (dd, J=9.5, 5.5 Hz, 1H), 1.91 (dd, J=8.2, 5.5 Hz, 1H), 2.25-2.34 (m, 2H), 2.65 (dd, J=13.6, 7.2 Hz, 1H), 2.95 (tt, J=8.1, 4.7 Hz, 1H), 3.85 (s, 6H), 4.00 (s, 3H), 4.08 (dd, J=12.2, 3.4 Hz, 1H), 4.27-4.35 (m, 2H), 4.70 (dd, J=10.2, 7.2 Hz, 1H), 5.13 (dd, J=10.4, 1.5 Hz, 1H), 5.31 (dd, J=17.2, 1.4 Hz, 1H), 5.73 (ddd, J=17.2, 10.2, 9.2 Hz, 1H), 5.87 (s, 1H), 6.65 (s, 1H), 6.79 (d, J=8.5 Hz, 2H), 7.42 (t, J=8.4 Hz, 1H), 7.58 (s, 1H), 7.64 (dd, J=8.9, 2.1 Hz, 1H), 7.99 (d, J=1.8 Hz, 1H), 8.07 (d, J=8.9 Hz, 1H). $^{13}$C NMR (126 MHz, MeOD) δ ppm 5.6, 5.8, 22.5, 25.9, 31.2, 34.8, 34.9, 37.3, 41.7, 55.0, 55.7, 55.8, 60.5, 65.9, 75.0, 104.6, 105.7, 117.7, 118.9, 120.8, 122.4, 123.8, 129.6, 131.1, 132.3, 133.2, 133.5, 147.2, 152.3, 158.6, 168.3, 168.8, 169.4, 173.9, 182.6. LC-MS, MS m/z 867.2 (M$^+$+H). LC-MS, MS m/z 865.2 (M$^+$–H).

Preparation of Compound 59, Example 59

Compound 59

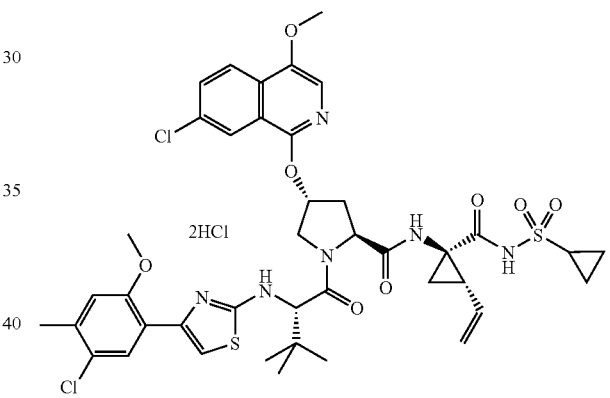

Compound 59 was prepared in 45.8% yield following the same procedure as described for the preparation of compound 9, except 2-bromo-1-(5-chloro-2-methoxy-4-methylphenyl)ethanone was used instead of 2-bromopropiophenone in step 1. $^1$H NMR (500 MHz, MeOD) δ ppm 1.06-1.11 (m, 2H), 1.16 (s, 9H), 1.24 (dd, J=4.0, 3.1 Hz, 2H), 1.41 (dd, J=9.5, 5.5 Hz, 1H), 1.89 (dd, J=7.9, 5.5 Hz, 1H), 2.21 (none, 1H), 2.25 (s, 3H), 2.27-2.32 (m, 1H), 2.56 (dd, J=13.4, 7.0 Hz, 1H), 2.96 (tt, J=8.0, 4.8 Hz, 1H), 3.87 (s, 3H), 3.98 (s, 3H), 4.11 (dd, J=12.1, 3.2 Hz, 1H), 4.46 (s, 1H), 4.53 (d, J=11.9 Hz, 1H), 4.62 (dd, J=10.2, 7.2 Hz, 1H), 5.12 (d, J=10.4 Hz, 1H), 5.29 (d, J=16.8 Hz, 1H), 5.73 (ddd, J=17.2, 10.3, 8.9 Hz, 1H), 5.97 (s, 1H), 6.90 (s, 1H), 7.52 (s, 1H), 7.55-7.59 (m, 2H), 7.74 (s, 1H), 8.00 (d, J=8.9 Hz, 1H). $^{13}$C NMR (126 MHz, MeOD) δ ppm 5.6, 5.8, 19.2, 22.5, 26.0, 31.2, 34.8, 35.1, 36.7, 41.6, 55.1, 55.5, 55.8, 60.3, 74.6, 114.1, 117.6, 118.6, 120.7, 122.4, 123.4, 125.9, 128.8, 129.5, 130.9, 133.2, 133.3, 145.7, 147.0, 152.2, 155.3, 161.9, 169.5, 170.2, 173.9. LC-MS, MS m/z 885.2 (M$^+$+H).

Preparation of Compound 60, Example 60

Compound 60

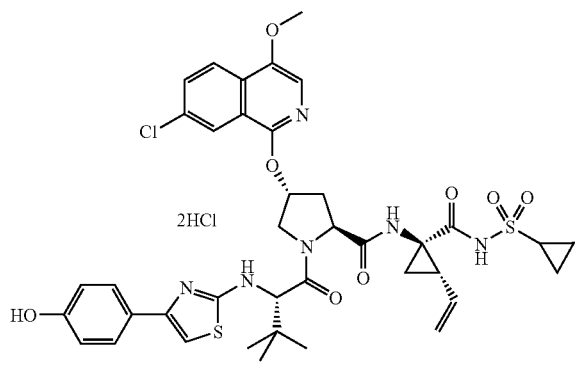

Compound 60 was prepared in 44.3% yield following the same procedure as described for the preparation of compound 9, except 2-bromo-1-(4-hydroxyphenyl)ethanone was used instead of 2-bromopropiophenone in step 1. $^1$H NMR (400 MHz, MeOD) δ ppm 1.04-1.11 (m, 3H), 1.15 (s, 9H), 1.21-1.26 (m, 2H), 1.42 (dd, J=9.3, 5.5 Hz, 1H), 1.90 (dd, J=8.1, 5.5 Hz, 1H), 2.21-2.33 (m, 2H), 2.62 (dd, J=13.7, 7.2 Hz, 1H), 2.95 (ddd, J=12.8, 8.1, 4.8 Hz, 1H), 3.96 (s, 3H), 4.09 (dd, J=12.0, 3.4 Hz, 1H), 4.34 (d, J=11.8 Hz, 1H), 4.43 (s, 1H), 4.67 (dd, J=10.3, 7.3 Hz, 1H), 5.13 (dd, J=10.3, 1.5 Hz, 1H), 5.30 (dd, J=17.1, 1.5 Hz, 1H), 5.73 (ddd, J=17.2, 10.3, 8.8 Hz, 1H), 5.91 (s, 1H), 6.80 (d, J=8.8 Hz, 2H), 7.31 (d, J=8.6 Hz, 2H), 7.55 (s, 1H), 7.62 (dd, J=8.9, 2.1 Hz, 1H), 7.91 (d, J=2.0 Hz, 1H), 8.06 (d, J=8.8 Hz, 1H. LC-MS, MS m/z 823.2 (M$^+$+H).

Preparation of Compound 61, Example 61

Compound 61

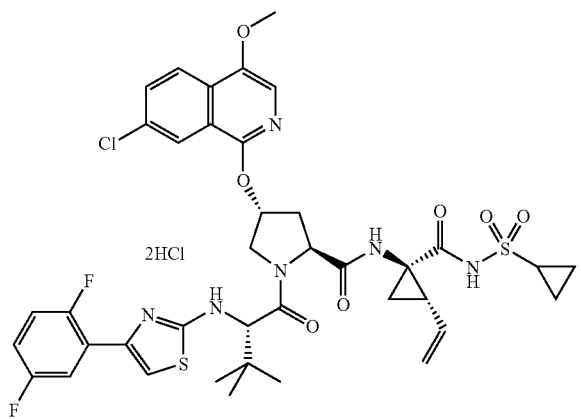

Compound 61 was prepared in 50.0% yield following the same procedure as described for the preparation of compound 9, except 2,5-difluorophenacyl bromide was used instead of 2-bromopropiophenone in step 1. $^1$H NMR (400 MHz, MeOD) δ ppm 1.05-1.11 (m, 2H), 1.15 (s, 9H), 1.22-1.27 (m, 2H), 1.41 (dd, J=9.4, 5.4 Hz, 1H), 1.88 (dd, J=8.1, 5.5 Hz, 1H), 2.19-2.31 (m, 2H), 2.52 (dd, J=13.7, 6.9 Hz, 1H), 2.91-2.99 (m, 1H), 3.93 (s, 3H), 4.14 (dd, J=11.8, 3.5 Hz, 1H), 4.55-4.62 (m, 2H), 4.68 (s, 1H), 5.11 (dd, J=10.4, 1.6 Hz, 1H), 5.28 (dd, J=17.1, 1.3 Hz, 1H), 5.73 (ddd, J=17.1, 10.3, 8.8 Hz, 1H), 6.00 (s, 1H), 6.82-6.88 (m, 1H), 6.98 (ddd, J=10.6, 9.1, 4.4 Hz, 1H), 7.40 (ddd, J=9.3, 5.9, 3.1 Hz, 1H), 7.44 (s, 1H), 7.56 (dd, J=8.9, 2.1 Hz, 1H), 7.68 (d, J=2.0 Hz, 1H), 7.95 (d, J=9.1 Hz, 1H). $^{13}$C NMR (101 MHz, MeOD) δ ppm 5.6, 5.8, 22.6, 26.1, 31.2, 34.9, 35.2, 36.3, 41.6, 55.1, 55.7, 60.2, 64.1, 74.6, 108.1, 109.6, 115.3, 117.6, 118.2, 120.7, 122.5, 123.4, 130.9, 133.2, 133.3, 133.4, 144.1, 152.2, 159.4, 160.4, 165.8, 169.6, 174.1, 176.1, 179.3, 183.4, 186.0. LC-MS, MS m/z 843.2 (M$^+$–H).

Preparation of Compound 62, Example 62

Compound 62

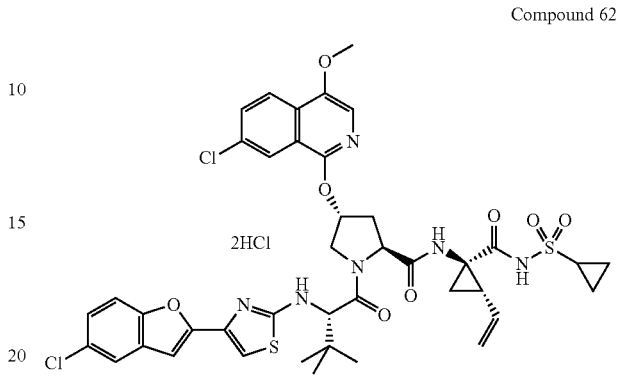

Compound 62 was prepared in 46.9% yield following the same procedure as described for the preparation of compound 9, except 2-bromo-1-(5-chloro-1-benzofuran-2-yl)ethanone was used instead of 2-bromopropiophenone in step 1. $^1$H NMR (400 MHz, MeOD) δ ppm 1.05-1.11 (m, 2H), 1.17 (s, 9H), 1.22-1.28 (m, 2H), 1.39 (dd, J=9.4, 5.4 Hz, 1H), 1.86 (dd, J=8.1, 5.5 Hz, 1H), 2.18-2.28 (m, 2H), 2.36-2.43 (m, 1H), 2.92-2.99 (m, 1H), 3.85 (s, 3H), 4.15 (dd, J=11.6, 3.5 Hz, 1H), 4.54 (dd, J=10.6, 6.8 Hz, 1H), 4.80 (s, 1H), 4.98 (d, J=11.3 Hz, 1H), 5.09 (dd, J=10.3, 1.8 Hz, 1H), 5.26 (dd, J=17.1, 1.5 Hz, 1H), 5.71 (ddd, J=17.1, 10.3, 8.8 Hz, 1H), 6.19 (t, J=3.0 Hz, 1H), 6.60 (s, 1H), 6.89 (d, J=2.3 Hz, 1H), 7.03-7.07 (m, 1H), 7.09-7.13 (m, 1H), 7.35 (s, 1H), 7.37 (dd, J=8.9, 2.1 Hz, 1H), 7.46 (d, J=2.0 Hz, 1H), 7.70 (d, J=8.8 Hz, 1H). LC-MS, MS m/z 881.1 (M$^+$+H).

Preparation of Compound 63, Example 63

Compound 63

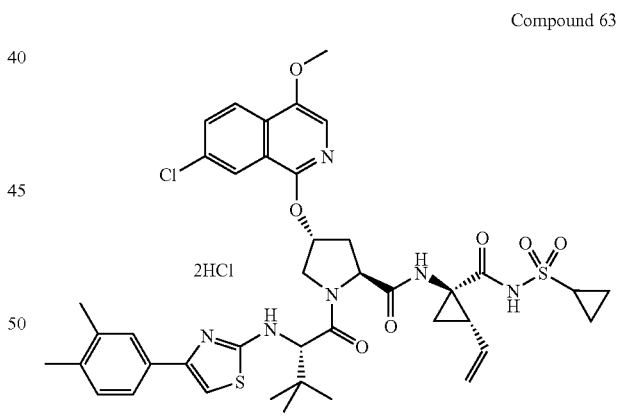

Compound 63 was prepared in 42.7% yield following the same procedure as described for the preparation of compound 9, except 2-bromo-1-(3,4-dimethyl-phenyl)-ethanone was used instead of 2-bromopropiophenone in step 1. $^1$H NMR (400 MHz, MeOD) δ ppm 1.05-1.12 (m, 2H), 1.16 (s, 9H), 1.22-1.25 (m, 2H), 1.41 (dd, J=9.4, 5.4 Hz, 1H), 1.89 (dd, J=8.1, 5.5 Hz, 1H), 2.22 (s, 6H), 2.24-2.33 (m, 2H), 2.59 (dd, J=13.8, 7.3 Hz, 1H), 2.95 (ddd, J=12.8, 8.1, 4.8 Hz, 1H), 3.96 (s, 3H), 4.11 (dd, J=12.1, 3.5 Hz, 1H), 4.41 (d, J=12.1 Hz, 1H), 4.49 (s, 1H), 4.66 (dd, J=10.2, 7.2 Hz, 1H), 5.12 (dd, J=10.3, 1.5 Hz, 1H), 5.29 (dd, J=17.1, 1.3 Hz, 1H), 5.73 (ddd, J=17.2, 10.3, 9.1 Hz, 1H), 5.93 (s, 1H), 7.08-7.13 (m, 1H), 7.19 (dd, J=7.8, 1.8 Hz, 1H), 7.26 (s, 1H), 7.54 (s, 1H), 7.60 (dd, J=8.9, 2.1 Hz, 1H), 7.85 (d, J=2.0 Hz, 1H), 8.04 (d, J=9.1

Hz, 1H). ¹³C NMR (101 MHz, MeOD) δ ppm 2.1, 5.6, 5.8, 18.6, 18.8, 22.5, 25.9, 31.2, 34.8, 35.0, 37.2, 41.6, 55.1, 55.8, 60.4, 62.7, 65.6, 74.5, 74.8, 117.7, 118.7, 120.8, 122.4, 123.6, 127.2, 129.6, 130.2, 131.0, 132.3, 133.2, 133.4, 137.7, 147.1, 152.3, 173.8. LC-MS, MS m/z 835.2 (M⁺+H).

Preparation of Compound 64, Example 64

Compound 64

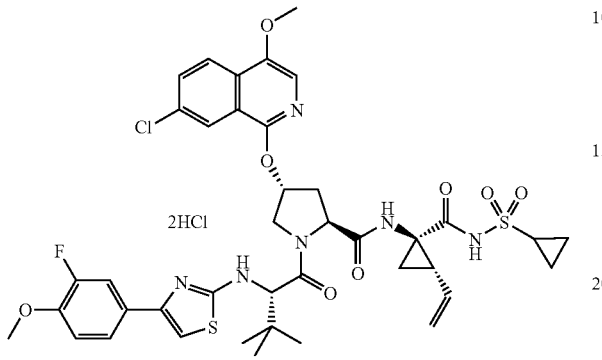

Compound 64 was prepared in 34.1% yield following the same procedure as described for the preparation of compound 9, except 3-fluoro-4-methoxyphenacyl bromide was used instead of 2-bromopropiophenone in step 1. ¹H NMR (400 MHz, MeOD) δ ppm 1.06-1.11 (m, 2H), 1.16 (s, 9H), 1.24 (ddd, J=7.5, 5.0, 4.8 Hz, 2H), 1.41 (dd, J=9.6, 5.5 Hz, 1H), 1.89 (dd, J=8.2, 5.4 Hz, 1H), 2.21-2.32 (m, 2H), 2.57 (dd, J=13.8, 7.1 Hz, 1H), 2.91-2.99 (m, J=8.6, 4.2, 4.0, 4.0 Hz, 1H), 3.83 (s, 3H), 3.95 (s, 3H), 4.11 (dd, J=12.0, 3.4 Hz, 1H), 4.46 (d, J=12.1 Hz, 1H), 4.57 (s, 1H), 4.65 (dd, J=10.3, 7.1 Hz, 1H), 5.12 (dd, J=10.3, 1.5 Hz, 1H), 5.29 (dd, J=17.1, 1.3 Hz, 1H), 5.67-5.78 (m, 1H), 5.96 (s, 1H), 6.98 (t, J=8.8 Hz, 1H), 7.20-7.27 (m, 2H), 7.51 (s, 1H), 7.60 (dd, J=8.9, 2.1 Hz, 1H), 7.81 (d, J=2.0 Hz, 1H), 8.01 (d, J=9.1 Hz, 1H). ¹³C NMR (101 MHz, MeOD) δ ppm 5.6, 5.8, 22.5, 23.7, 26.0, 31.2, 34.8, 35.1, 37.0, 41.6, 55.2, 55.8, 60.4, 64.5, 65.2, 67.7, 74.8, 78.5, 113.7, 114.0, 117.7, 118.5, 120.8, 122.4, 122.6, 123.6, 129.5, 131.0, 133.2, 147.1, 152.2, 158.7, 169.5, 169.9, 173.9, 175.3, 180.3 LC-MS, MS m/z 855.2 (M⁺+H).

Preparation of Compound 65, Example 65

Compound 65

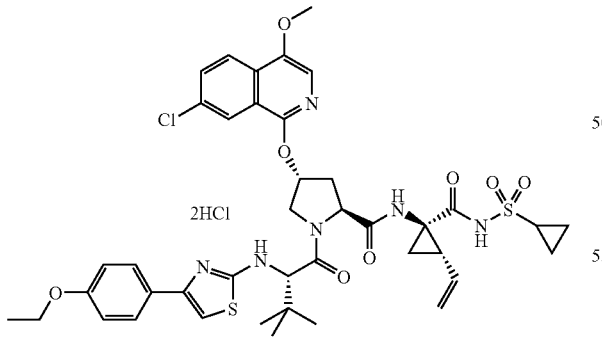

Compound 65 was prepared in 49.0% yield following the same procedure as described for the preparation of compound 9, except 2-bromo-1-(4-ethoxyphenyl)ethanone was used instead of 2-bromopropiophenone in step 1. ¹H NMR (400 MHz, MeOD) δ ppm 1.06-1.11 (m, 2H), 1.15 (s, 9H), 1.22-1.26 (m, 2H), 1.37 (t, J=6.9 Hz, 3H), 1.41 (dd, J=9.4, 5.4 Hz, 1H), 1.90 (dd, J=8.1, 5.5 Hz, 1H), 2.21-2.33 (m, 2H), 2.59 (dd, J=13.7, 7.2 Hz, 1H), 2.95 (ddd, J=12.7, 8.1, 4.9 Hz, 1H), 3.96 (s, 3H), 3.97-4.04 (m, 2H), 4.10 (dd, J=12.1, 3.3 Hz, 1H), 4.40 (d, J=11.8 Hz, 1H), 4.48 (s, 1H), 4.66 (dd, J=10.1, 7.3 Hz, 1H), 5.12 (dd, J=10.4, 1.6 Hz, 1H), 5.29 (dd, J=17.1, 1.3 Hz, 1H), 5.73 (ddd, J=17.2, 10.3, 8.8 Hz, 1H), 5.93 (s, 1H), 6.87 (d, J=8.8 Hz, 2H), 7.37-7.41 (m, 2H), 7.54 (s, 1H), 7.61 (dd, J=8.9, 2.1 Hz, 1H), 7.87 (d, J=2.0 Hz, 1H), 8.05 (d, J=8.8 Hz, 1H). ¹³C NMR (101 MHz, MeOD) δ ppm 4.7, 5.6, 5.8, 14.0, 22.6, 25.9, 31.2, 34.8, 35.0, 37.2, 41.6, 55.1, 55.8, 60.4, 63.8, 65.5, 74.8, 89.5, 96.8, 115.0, 117.7, 118.7, 120.4, 120.8, 121.6, 122.4, 123.7, 124.8, 127.7, 129.6, 131.1, 133.2, 133.5, 160.7, 172.9, 173.9, 190.8. LC-MS, MS m/z 851.2 (M⁺+H).

Preparation of Compound 66, Example 66

Compound 66

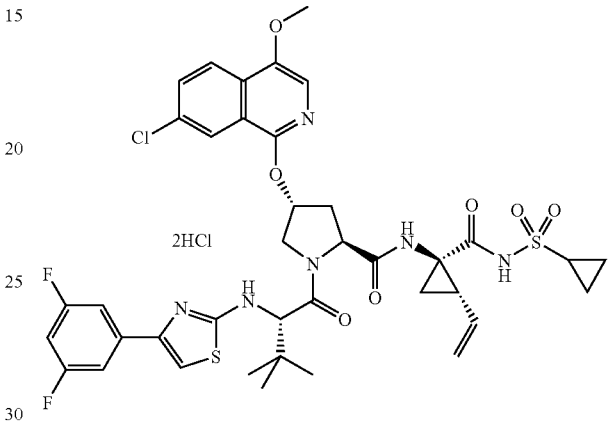

Compound 66 was prepared in 34.6% yield following the same procedure as described for the preparation of compound 9, except 3,5-difluorophenacyl bromide was used instead of 2-bromopropiophenone in step 1. ¹H NMR (400 MHz, MeOD) δ ppm 1.05-1.11 (m, 2H), 1.15 (s, 9H), 1.22-1.27 (m, 2H), 1.40 (dd, J=9.4, 5.4 Hz, 1H), 1.87 (dd, J=8.1, 5.5 Hz, 1H), 2.18-2.30 (m, 2H), 2.50 (dd, J=13.7, 6.9 Hz, 1H), 2.92-2.99 (m, 1H), 3.93 (s, 3H), 4.14 (dd, J=11.8, 3.5 Hz, 1H), 4.57 (dd, J=10.6, 7.1 Hz, 1H), 4.66 (d, J=11.6 Hz, 1H), 4.73 (s, 1H), 5.11 (dd, J=10.3, 1.5 Hz, 1H), 5.28 (dd, J=17.2, 1.4 Hz, 1H), 5.72 (ddd, J=17.2, 10.3, 8.9 Hz, 1H), 6.02 (t, J=3.0 Hz, 1H), 6.57-6.63 (m, 1H), 7.09 (dd, J=8.7, 2.1 Hz, 2H), 7.43 (s, 1H), 7.56 (dd, J=8.9, 2.1 Hz, 1H), 7.62 (d, J=2.0 Hz, 1H), 7.95 (d, J=9.1 Hz, 1H). LC-MS, MS m/z 843.2 (M⁺+H).

Preparation of Compound 67, Example 67

Compound 67

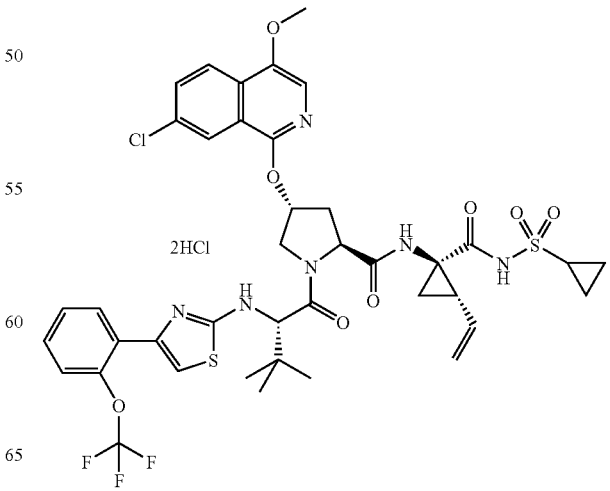

Compound 67 was prepared in 42.7% yield following the same procedure as described for the preparation of compound 9, except 2-(trifluoromethoxy)phenacyl bromide was used instead of 2-bromopropiophenone in step 1. $^1$H NMR (400 MHz, MeOD) δ ppm 1.06-1.11 (m, 2H), 1.15 (s, 9H), 1.22-1.27 (m, 2H), 1.41 (dd, J=9.6, 5.5 Hz, 1H), 1.89 (dd, J=8.2, 5.4 Hz, 1H), 2.22-2.33 (m, 2H), 2.57 (dd, J=13.7, 7.2 Hz, 1H), 2.96 (ddd, J=12.7, 8.1, 4.7 Hz, 1H), 3.94 (s, 3H), 4.13 (dd, J=11.8, 3.8 Hz, 1H), 4.36 (d, J=11.8 Hz, 1H), 4.61 (s, 1H), 4.64 (dd, J=10.1, 7.1 Hz, 1H), 5.12 (dd, J=10.3, 1.8 Hz, 1H), 5.30 (dd, J=17.1, 1.5 Hz, 1H), 5.73 (ddd, J=17.2, 10.3, 8.8 Hz, 1H), 5.90 (s, 1H), 7.28-7.37 (m, 2H), 7.43-7.47 (m, 1H), 7.48 (s, 1H), 7.60 (dd, J=7.8, 1.5 Hz, 1H), 7.64 (dd, J=8.9, 2.1 Hz, 1H), 7.90 (d, J=2.0 Hz, 1H), 8.04 (d, J=8.8 Hz, 1H). LC-MS, MS m/z 891.2 (M$^+$+H).

Preparation of Compound 68, Example 68

Compound 68

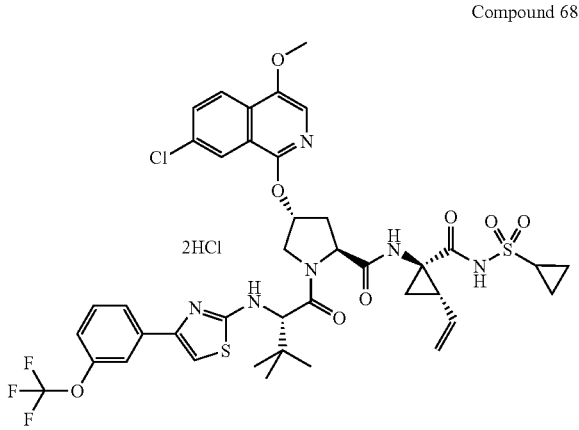

Compound 68 was prepared in 34.2% yield following the same procedure as described for the preparation of compound 9, except 3-(trifluoromethoxy)phenacyl bromide was used instead of 2-bromopropiophenone in step 1. $^1$H NMR (400 MHz, MeOD) δ ppm 1.06-1.11 (m, 2H), 1.16 (s, 9H), 1.22-1.27 (m, 2H), 1.41 (dd, J=9.6, 5.5 Hz, 1H), 1.88 (dd, J=8.1, 5.5 Hz, 1H), 2.19-2.31 (m, 2H), 2.55 (dd, J=13.67, 7.1 Hz, 1H), 2.92-2.99 (m, 1H), 3.93 (s, 3H), 4.13 (dd, J=11.8, 3.5 Hz, 1H), 4.55-4.62 (m, 2H), 4.64 (s, 1H), 5.11 (dd, J=10.4, 1.6 Hz, 1H), 5.28 (dd, J=17.1, 1.3 Hz, 1H), 5.72 (ddd, J=17.1, 10.3, 8.8 Hz, 1H), 5.95 (s, 1H), 7.10 (d, J=8.1 Hz, 1H), 7.31 (t, J=8.1 Hz, 1H), 7.47 (s, 2H), 7.51 (dd, J=7.8, 1.0 Hz, 1H), 7.56 (dd, J=8.8, 2.0 Hz, 1H), 7.72 (d, J=2.0 Hz, 1H), 7.99 (d, J=8.8 Hz, 1H). LC-MS, MS m/z 891.2 (M$^+$+H).

Preparation of Compound 69, Example 69

Compound 69

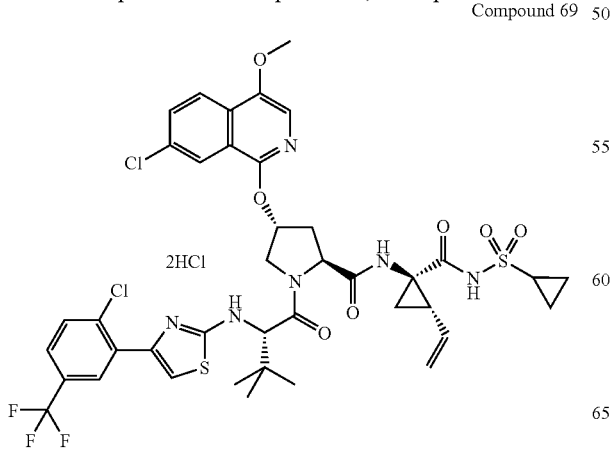

Compound 69 was prepared in 54.5% yield following the same procedure as described for the preparation of compound 9, except 2'-chloro-5'-(trifluoromethyl)phenacyl bromide was used instead of 2-bromopropiophenone in step 1. $^1$H NMR (400 MHz, MeOD) δ ppm 1.08 (ddd, J=7.7, 3.4, 3.2 Hz, 2H), 1.15 (s, 9H), 1.22-1.27 (m, 2H), 1.40 (dd, J=9.4, 5.4 Hz, 1H), 1.88 (dd, J=8.1, 5.5 Hz, 1H), 2.20-2.31 (m, 2H), 2.55 (dd, J=13.6, 7.1 Hz, 1H), 2.92-2.99 (m, 1H), 3.93 (s, 3H), 4.13 (dd, J=11.6, 3.8 Hz, 1H), 4.48 (d, J=11.8 Hz, 1H), 4.59 (dd, J=10.3, 7.1 Hz, 1H), 4.64 (s, 1H), 5.11 (dd, J=10.3, 1.5 Hz, 1H), 5.28 (dd, J=17.1, 1.3 Hz, 1H), 5.67-5.77 (m, 1H), 5.89 (s, 1H), 7.03 (s, 1H), 7.45 (s, 1H), 7.53 (s, 2H), 7.63 (dd, J=8.9, 2.1 Hz, 1H), 7.78 (d, J=2.0 Hz, 1H), 7.97 (s, 1H), 8.03 (d, J=8.8 Hz, 1H). LC-MS, MS m/z 909.0 (M$^+$+H).

Preparation of Compound 70, Example 70

Compound 70

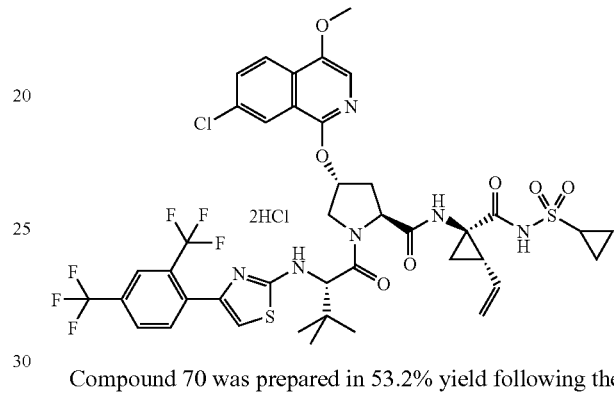

Compound 70 was prepared in 53.2% yield following the same procedure as described for the preparation of compound 9, except 2,4-bis(trifluoromethyl)phenacyl bromide was used instead of 2-bromopropiophenone in step 1. $^1$H NMR (400 MHz, MeOD) δ ppm 1.06-1.11 (m, 2H), 1.13 (s, 9H), 1.21 (s, 1H), 1.24 (dd, J=4.7, 2.6 Hz, 2H), 1.41 (dd, J=9.4, 5.4 Hz, 1H), 1.89 (dd, J=8.2, 5.4 Hz, 1H), 2.21-2.32 (m, 2H), 2.55 (dd, J=13.7, 7.2 Hz, 1H), 2.92-2.99 (m, 1H), 3.95 (s, 3H), 4.12 (dd, J=11.8, 4.0 Hz, 1H), 4.34 (d, J=11.8 Hz, 1H), 4.61 (s, 1H), 4.63 (dd, J=10.1, 7.1 Hz, 1H), 5.12 (dd, J=10.3, 1.5 Hz, 1H), 5.29 (dd, J=17.2, 1.4 Hz, 1H), 5.73 (ddd, J=17.2, 10.3, 8.8 Hz, 1H), 5.88 (s, 1H), 6.72 (s, 1H), 7.49 (s, 1H), 7.65 (d, J=8.1 Hz, 1H), 7.68 (dd, J=8.9, 2.1 Hz, 1H), 7.82 (d, J=7.8 Hz, 1H), 7.93 (d, J=1.8 Hz, 1H), 7.97 (s, 1H), 8.07 (d, J=9.1 Hz, 1H). LC-MS, MS m/z 943.0 (M$^+$+H).

Preparation of Compound 71, Example 71

Compound 71

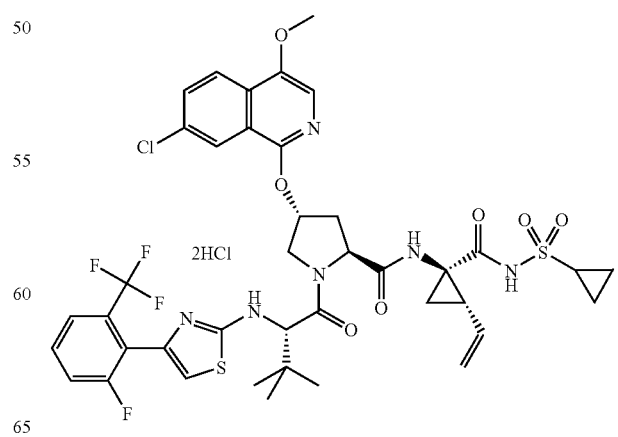

Compound 71 was prepared in 34.0% yield following the same procedure as described for the preparation of compound 9, except 2-fluoro-6-(trifluoromethyl)phenacyl bromide was used instead of 2-bromopropiophenone in step 1. $^1$H NMR (400 MHz, MeOD) δ ppm 1.08 (ddd, J=8.3, 6.3, 3.8 Hz, 3H), 1.13 (s, 9H), 1.22-1.27 (m, 2H), 1.41 (dd, J=9.4, 5.4 Hz, 1H), 1.89 (dd, J=8.1, 5.5 Hz, 1H), 2.22-2.33 (m, 2H), 2.60 (dd, J=13.8, 7.1 Hz, 1H), 2.95 (ddd, J=12.7, 8.1, 4.7 Hz, 1H), 3.97 (s, 3H), 4.11-4.22 (m, 2H), 4.55 (s, 1H), 4.64 (dd, J=9.8, 7.3 Hz, 1H), 5.13 (dd, J=10.3, 1.5 Hz, 1H), 5.30 (dd, J=17.1, 1.3 Hz, 1H), 5.72 (ddd, J=17.2, 10.3, 8.8 Hz, 1H), 5.84 (s, 1H), 6.80 (s, 1H), 7.47 (t, J=8.8 Hz, 1H), 7.50 (s, 1H), 7.63 (d, J=7.8 Hz, 1H), 7.68-7.73 (m, 2H), 8.01 (d, J=2.0 Hz, 1H), 8.10 (d, J=9.1 Hz, 1H). LC-MS, MS m/z 893.2 (M$^+$+H).

Preparation of Compound 72, Example 72

Compound 72

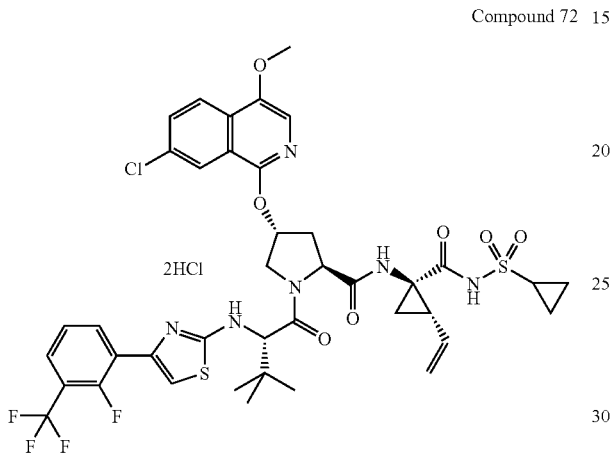

2HCl

Compound 72 was prepared in 57.3% yield following the same procedure as described for the preparation of compound 9, except 2-fluoro-3-(trifluoromethyl)phenacyl bromide was used instead of 2-bromopropiophenone in step 1. $^1$H NMR (400 MHz, MeOD) δ ppm 1.08 (ddd, J=10.1, 5.1, 2.9 Hz, 2H), 1.15 (s, 9H), 1.22-1.27 (m, 2H), 1.40 (dd, J=9.4, 5.4 Hz, 1H), 1.87 (dd, J=8.3, 5.5 Hz, 1H), 2.18-2.30 (m, 2H), 2.49 (dd, J=13.6, 7.1 Hz, 1H), 2.92-2.99 (m, 1H), 3.91 (s, 3H), 4.13 (dd, J=11.8, 3.5 Hz, 1H), 4.58 (dd, J=10.3, 7.1 Hz, 1H), 4.64 (d, J=11.8 Hz, 1H), 4.74 (s, 1H), 5.11 (dd, J=10.4, 1.6 Hz, 1H), 5.28 (dd, J=17.1, 1.3 Hz, 1H), 5.72 (ddd, J=17.2, 10.3, 8.8 Hz, 1H), 6.01 (t, J=3.0 Hz, 1H), 6.99 (t, J=7.9 Hz, 1H), 7.35 (t, J=6.9 Hz, 1H), 7.40 (s, 1H), 7.54 (dd, J=8.8, 2.3 Hz, 1H), 7.60 (d, J=1.8 Hz, 1H), 7.92 (d, J=9.1 Hz, 1H), 7.94-7.98 (m, 1H). LC-MS, MS m/z 893.2 (M$^+$+H).

Preparation of Compound 73, Example 73

Compound 73

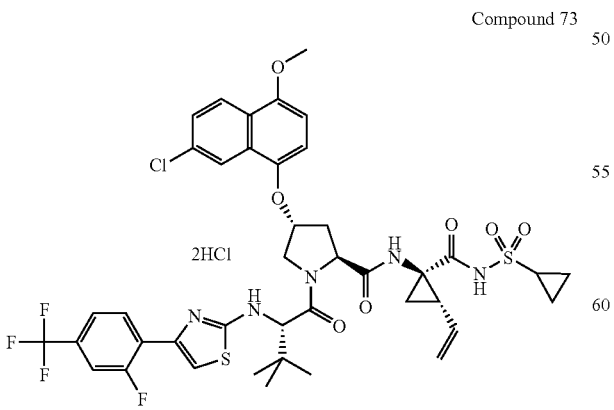

2HCl

Compound 73 was prepared in 55.6% yield following the same procedure as described for the preparation of compound 9, except 2-fluoro-4-(trifluoromethyl)phenacyl bromide was used instead of 2-bromopropiophenone in step 1. $^1$H NMR (400 MHz, MeOD) d ppm 1.05-1.11 (m, 2H), 1.16 (s, 9H), 1.22-1.27 (m, 2H), 1.40 (dd, J=9.6, 5.3 Hz, 1H), 1.87 (dd, J=8.2, 5.4 Hz, 1H), 2.17-2.29 (m, 2H), 2.47 (dd, J=13.7, 6.9 Hz, 1H), 2.96 (ddd, J=12.8, 8.1, 4.8 Hz, 1H), 3.92 (s, 3H), 4.14 (dd, J=11.8, 3.5 Hz, 1H), 4.56 (dd, J=10.6, 7.1 Hz, 1H), 4.69-4.76 (m, 2H), 5.10 (dd, J=10.3, 1.5 Hz, 1H), 5.27 (dd, J=17.2, 1.4 Hz, 1H), 5.72 (ddd, J=17.2, 10.3, 8.9 Hz, 1H), 6.04 (s, 1H), 7.09 (d, J=8.1 Hz, 1H), 7.19 (d, J=11.3 Hz, 1H), 7.42 (s, 1H), 7.53-7.58 (m, 2H), 7.88-7.96 (m, 2H). LC-MS, MS m/z 893.2 (M$^+$+H).

Preparation of Compound 74, Example 74

Compound 74

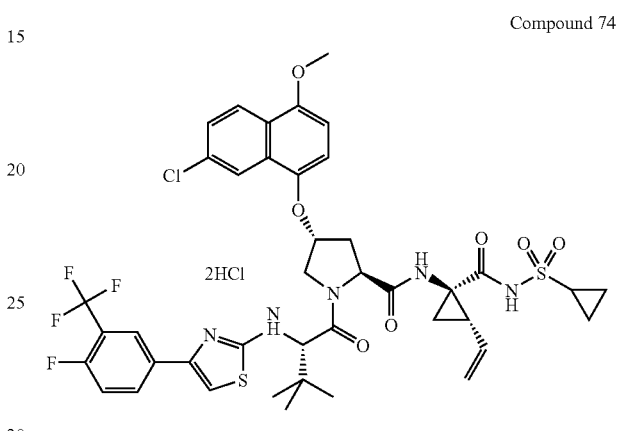

2HCl

Compound 74 was prepared in 38.5% yield following the same procedure as described for the preparation of compound 9, except 4-fluoro-3-(trifluoromethyl)phenacyl bromide was used instead of 2-bromopropiophenone in step 1. $^1$H NMR (400 MHz, MeOD) δ ppm 1.05-1.11 (m, 2H), 1.16 (s, 9H), 1.22-1.27 (m, 2H), 1.39 (dd, J=9.4, 5.4 Hz, 1H), 1.87 (dd, J=8.1, 5.5 Hz, 1H), 2.17-2.29 (m, 2H), 2.49 (dd, J=13.6, 7.1 Hz, 1H), 2.92-2.99 (m, 1H), 3.93 (s, 3H), 4.14 (dd, J=11.6, 3.5 Hz, 1H), 4.53 (dd, J=10.6, 7.1 Hz, 1H), 4.72-4.78 (m, 2H), 5.10 (dd, J=10.3, 1.5 Hz, 1H), 5.27 (dd, J=17.2, 1.4 Hz, 1H), 5.72 (ddd, J=17.2, 10.3, 9.1 Hz, 1H), 5.99 (t, J=2.9 Hz, 1H), 7.01 (t, J=9.6 Hz, 1H), 7.44 (s, 1H), 7.51-7.56 (m, 2H), 7.77-7.82 (m, 1H), 7.87 (dd, J=6.8, 2.0 Hz, 1H), 7.95 (d, J=9.6 Hz, 1H). LC-MS, MS m/z 893.2 (M$^+$+H).

Preparation of Compound 75, Example 75

Compound 75

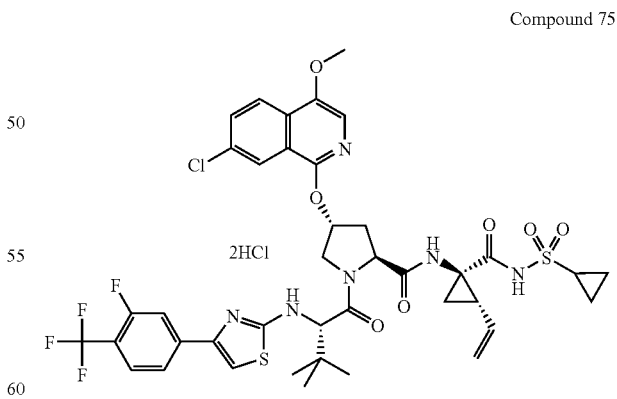

2HCl

Compound 75 was prepared in 53.4% yield following the same procedure as described for the preparation of compound 9, except 3-fluoro-4-(trifluoromethyl)phenacyl bromide was used instead of 2-bromopropiophenone in step 1. $^1$H NMR (400 MHz, MeOD) δ ppm 1.05-1.11 (m, 2H), 1.16 (s, 9H), 1.25 (td, J=4.9, 2.5 Hz, 2H), 1.39 (dd, J=9.4, 5.4 Hz, 1H), 1.86 (dd, J=8.2, 5.4 Hz, 1H), 2.16-2.28 (m, 2H), 2.43 (dd, J=13.7, 6.9 Hz, 1H), 2.92-2.99 (m, 1H), 3.91 (s, 3H), 4.15 (dd, J=11.7, 3.4 Hz, 1H), 4.53 (dd, J=10.6, 7.1 Hz, 1H), 4.79-4.83 (m, 2H), 5.10 (dd, J=10.3, 1.5 Hz, 1H), 5.26 (dd, J=17.1, 1.3 Hz, 1H), 5.71 (ddd, J=17.2, 10.3, 8.8 Hz, 1H), 6.08 (s, 1H), 7.19 (t, J=7.9 Hz, 1H), 7.41-7.48 (m, 4H), 7.52 (dd, J=8.9, 2.1 Hz, 1H), 7.91 (d, J=8.8 Hz, 1H). LC-MS, MS m/z 893.2 (M⁺+H).

Preparation of Compound 76, Example 76

Compound 76

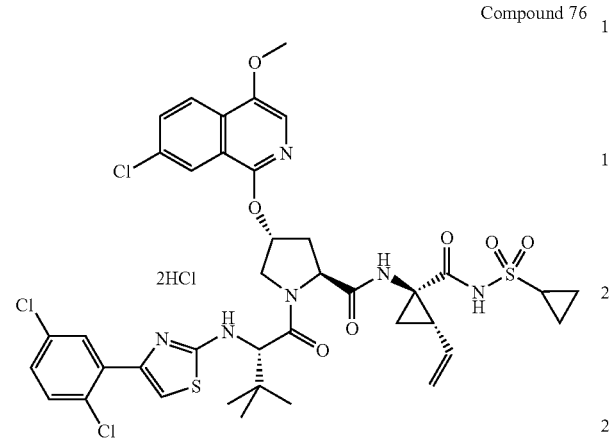

Compound 76 was prepared in 49.3% yield following the same procedure as described for the preparation of compound 9, except 2-bromo-1-(2,5-dichlorophenyl)ethanone was used instead of 2-bromopropiophenone in step 1. ¹H NMR (400 MHz, MeOD) δ ppm 1.06-1.11 (m, 2H), 1.15 (s, 9H), 1.25 (ddd, J=7.5, 5.0, 4.8 Hz, 2H), 1.41 (dd, J=9.6, 5.3 Hz, 1H), 1.89 (dd, J=8.1, 5.5 Hz, 1H), 2.21-2.32 (m, 2H), 2.57 (dd, J=13.6, 7.1 Hz, 1H), 2.95 (ddd, J=12.8, 8.0, 4.7 Hz, 1H), 3.96 (s, 3H), 4.14 (dd, J=11.8, 3.8 Hz, 1H), 4.41 (d, J=11.8 Hz, 1H), 4.58-4.65 (m, 2H), 5.12 (dd, J=10.3, 1.5 Hz, 1H), 5.29 (dd, J=17.1, 1.3 Hz, 1H), 5.67-5.77 (m, 1H), 5.92 (s, 1H), 6.94 (s, 1H), 7.25-7.30 (m, 1H), 7.31-7.36 (m, 1H), 7.49 (s, 1H), 7.60 (d, J=2.5 Hz, 1H), 7.64 (dd, J=8.9, 2.1 Hz, 1H), 7.84 (d, J=2.0 Hz, 1H), 8.04 (d, J=9.1 Hz, 1H). LC-MS, MS m/z 877.1 (M⁺+H).

Preparation of Compound 77, Example 77

Compound 77

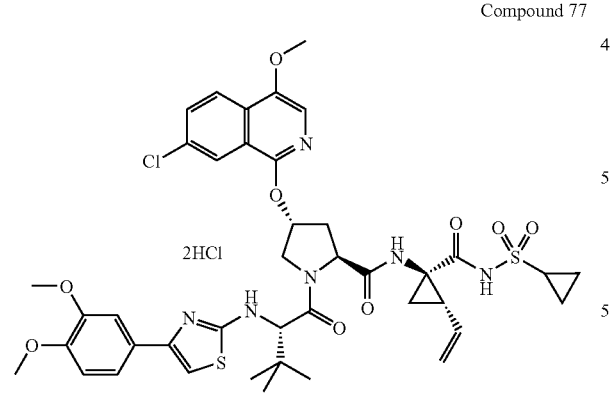

Compound 77 was prepared in 49.2% yield following the same procedure as described for the preparation of compound 9, except 2-bromo-1-(3,4-dimethoxyphenyl)ethanone was used instead of 2-bromopropiophenone in step 1. ¹H NMR (400 MHz, MeOD) δ ppm 1.04-1.11 (m, 3H), 1.16 (s, 9H), 1.21-1.26 (m, 2H), 1.41 (dd, J=9.4, 5.4 Hz, 1H), 1.89 (dd, J=8.1, 5.5 Hz, 1H), 2.21-2.33 (m, 2H), 2.59 (dd, J=13.6, 7.1 Hz, 1H), 2.95 (ddd, J=12.7, 8.1, 4.7 Hz, 1H), 3.80 (s, 3H), 3.82 (s, 3H), 3.96 (s, 3H), 4.10 (dd, J=12.0, 3.1 Hz, 1H), 4.45 (d, J=12.1 Hz, 1H), 4.50 (s, 1H), 4.66 (dd, J=10.2, 7.2 Hz, 1H), 5.12 (dd, J=10.3, 1.5 Hz, 1H), 5.25-5.34 (m, 1H), 5.67-5.78 (m, 1H), 5.94 (s, 1H), 6.87 (d, J=8.3 Hz, 1H), 7.02-7.08 (m, 2H), 7.53 (s, 1H), 7.60 (dd, J=8.8, 2.3 Hz, 1H), 7.84 (d, J=2.0 Hz, 1H), 8.03 (d, J=8.8 Hz, 1H). LC-MS, MS m/z 867.2 (M⁺+H).

Preparation of Compound 78, Example 78

Compound 78

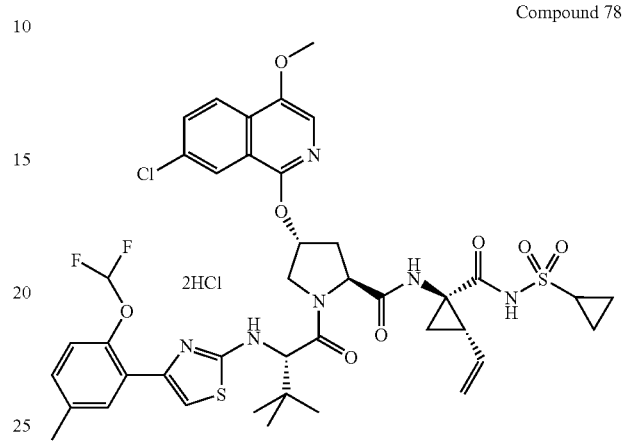

Compound 78 was prepared in 54.2% yield following the same procedure as described for the preparation of compound 9, except 2-bromo-1-[2-(difluoromethoxy)-5-methylphenyl]ethanone was used instead of 2-bromopropiophenone in step 1. ¹H NMR (400 MHz, MeOD) δ ppm 1.06-1.11 (m, 2H), 1.16 (s, 9H), 1.22-1.27 (m, 2H), 1.41 (dd, J=9.4, 5.4 Hz, 1H), 1.89 (dd, J=8.2, 5.4 Hz, 1H), 2.20-2.25 (m, 1H), 2.26 (s, 3H), 2.28-2.33 (m, 1H), 2.59 (dd, J=13.7, 7.2 Hz, 1H), 2.92-2.99 (m, J=8.6, 4.2, 4.0, 4.0 Hz, 1H), 3.95 (s, 3H), 4.12 (dd, J=12.0, 3.7 Hz, 1H), 4.40 (d, J=12.1 Hz, 1H), 4.54 (s, 1H), 4.64 (dd, J=10.1, 7.1 Hz, 1H), 5.12 (dd, J=10.3, 1.5 Hz, 1H), 5.29 (dd, J=17.2, 1.4 Hz, 1H), 5.72 (ddd, J=17.2, 10.3, 9.1 Hz, 1H), 5.91 (s, 1H), 6.75 (t, J=73.4 Hz, 1H), 7.09 (d, J=8.3 Hz, 1H), 7.22 (dd, J=8.4, 1.6 Hz, 1H), 7.37 (d, J=1.5 Hz, 1H), 7.51 (s, 1H), 7.63 (dd, J=8.9, 2.1 Hz, 1H), 7.89 (d, J=2.0 Hz, 1H), 8.05 (d, J=8.8 Hz, 1H). LC-MS, MS m/z 887.2 (M⁺+H).

Preparation of Compound 79, Example 79

Compound 79

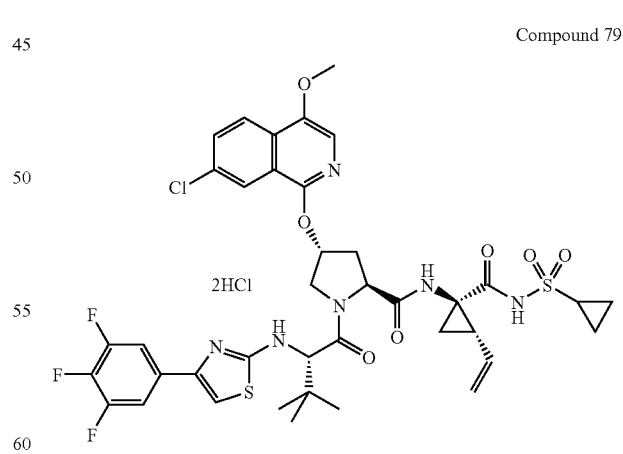

Compound 79 was prepared in 48.6% yield following the same procedure as described for the preparation of compound 9, except 3,4,5-trifluorophenacyl bromide was used instead of 2-bromopropiophenone in step 1. ¹H NMR (400 MHz, MeOD) δ ppm 1.05-1.11 (m, 2H), 1.14 (s, 9H), 1.25 (td, J=4.8, 2.4 Hz, 2H), 1.40 (dd, J=9.4, 5.4 Hz, 1H), 1.87 (dd, J=8.3, 5.5 Hz, 1H), 2.18-2.29 (m, 2H), 2.46 (dd, J=13.7, 6.9

Hz, 1H), 2.95 (ddd, J=12.7, 8.1, 4.7 Hz, 1H), 3.94 (s, 3H), 4.13 (dd, J=11.8, 3.5 Hz, 1H), 4.57 (dd, J=10.6, 6.8 Hz, 1H), 4.69 (d, J=11.8 Hz, 1H), 4.78 (s, 1H), 5.10 (dd, J=10.3, 1.5 Hz, 1H), 5.27 (dd, J=17.1, 1.5 Hz, 1H), 5.72 (ddd, J=17.1, 10.3, 8.8 Hz, 1H), 6.07-6.11 (m, 1H), 7.19 (dd, J=9.2, 6.7 Hz, 2H), 7.44 (s, 1H), 7.54-7.58 (m, 2H), 7.94 (d, J=9.6 Hz, 1H). LC-MS, MS m/z 861.2 (M$^+$+H).

Preparation of Compound 80, Example 80

Compound 80

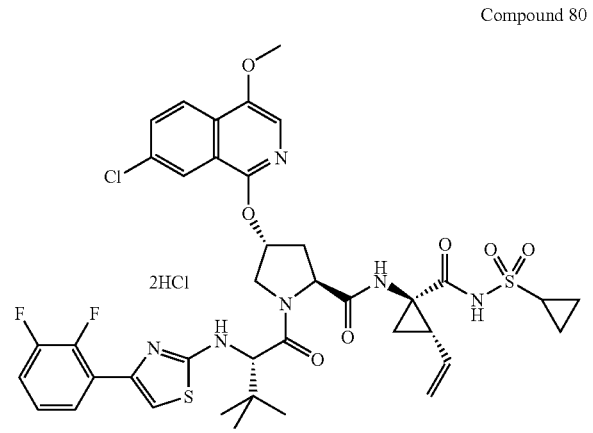

Compound 80 was prepared in 51.4% yield following the same procedure as described for the preparation of compound 9, except 2,3-difluorophenacyl bromide was used instead of 2-bromopropiophenone in step 1. $^1$H NMR (400 MHz, MeOD) δ ppm 1.08 (ddd, J=7.8, 4.8, 2.5 Hz, 2H), 1.15 (s, 9H), 1.25 (dt, J=6.5, 4.2 Hz, 2H), 1.41 (dd, J=9.4, 5.4 Hz, 1H), 1.88 (dd, J=8.1, 5.5 Hz, 1H), 2.20-2.31 (m, 2H), 2.53 (dd, J=13.7, 6.9 Hz, 1H), 2.92-2.99 (m, 1H), 3.94 (s, 3H), 4.12 (dd, J=11.8, 3.5 Hz, 1H), 4.54 (d, J=1.8 Hz, 1H), 4.60 (dd, J=10.3, 7.1 Hz, 1H), 4.65 (s, 1H), 5.11 (dd, J=10.3, 1.5 Hz, 1H), 5.29 (dd, J=17.1, 1.3 Hz, 1H), 5.73 (ddd, J=17.2, 10.3, 9.1 Hz, 1H), 5.97 (s, 1H), 6.90-6.96 (m, 1H), 7.03-7.10 (m, 1H), 7.39-7.43 (m, 1H), 7.44 (s, 1H), 7.59 (dd, J=8.8, 2.3 Hz, 1H), 7.72 (d, J=2.0 Hz, 1H), 7.99 (d, J=9.1 Hz, 1H). LC-MS, MS m/z 843.2 (M$^+$+H).

Preparation of Compound 81 Example 81

Compound 81

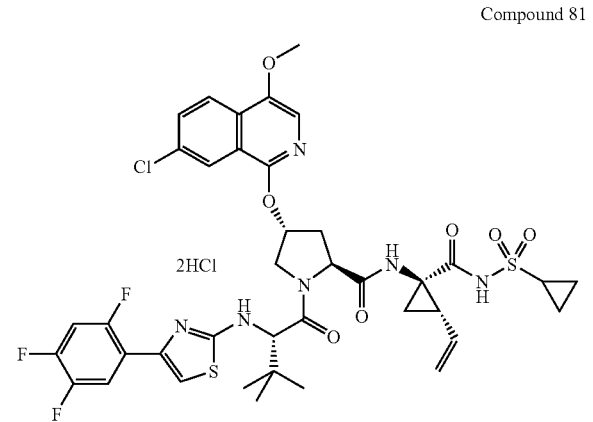

Compound 81 was prepared in 42.0% yield following the same procedure as described for the preparation of compound 9, except 2,4,5-trifluorophenacyl bromide was used instead of 2-bromopropiophenone in step 1. $^1$H NMR (400 MHz, MeOD) δ ppm 1.05-1.11 (m, 2H), 1.14 (s, 9H), 1.25 (dt, J=7.3, 2.1 Hz, 2H), 1.41 (dd, J=9.4, 5.4 Hz, 1H), 1.88 (dd, J=8.1, 5.5 Hz, 1H), 2.19-2.30 (m, 2H), 2.49 (dd, J=13.7, 6.9 Hz, 1H), 2.92-2.99 (m, 1H), 3.94 (s, 3H), 4.13 (dd, J=11.6, 3.5 Hz, 1H), 4.56-4.63 (m, 2H), 4.72 (s, 1H), 5.11 (dd, J=10.3, 1.8 Hz, 1H), 5.28 (dd, J=17.1, 1.3 Hz, 1H), 5.72 (ddd, J=17.2, 10.3, 9.1 Hz, 1H), 6.06 (t, J=3.0 Hz, 1H), 6.97 (td, J=10.6, 6.5 Hz, 1H), 7.44 (s, 1H), 7.51-7.59 (m, 2H), 7.61 (d, J=2.0 Hz, 1H), 7.94 (d, J=9.1 Hz, 1H). LC-MS, MS m/z 861.2 (M$^+$+H).

Preparation of Compound 82, Example 82

Compound 82

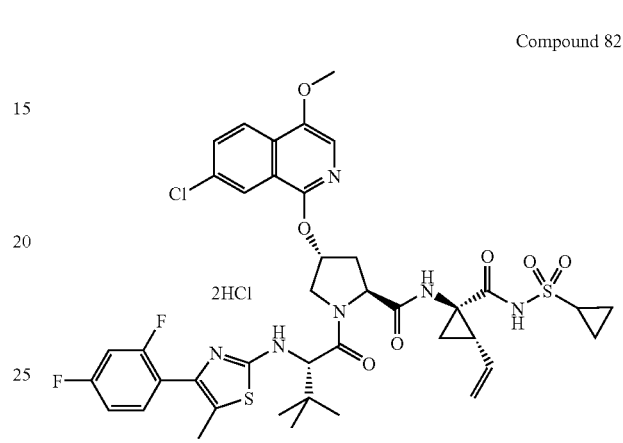

Compound 82 was prepared in 64.4% yield following the same procedure as described for the preparation of compound 9, except 2-bromo-1-(2,4-difluorophenyl)propan-1-one bromide was used instead of 2-bromopropiophenone in step 1. $^1$H NMR (400 MHz, MeOD) δ ppm 1.05-1.10 (m, 2H), 1.13 (s, 9H), 1.21-1.26 (m, 2H), 1.42 (dd, J=9.4, 5.4 Hz, 1H), 1.90 (dd, J=8.2, 5.4 Hz, 1H), 1.98 (s, 3H), 2.22-2.33 (m, 2H), 2.61 (dd, J=13.6, 7.1 Hz, 1H), 2.95 (ddd, J=12.7, 8.0, 4.8 Hz, 1H), 3.97 (s, 3H), 4.10 (dd, J=12.0, 3.7 Hz, 1H), 4.27 (d, J=12.1 Hz, 1H), 4.47 (s, 1H), 4.67 (dd, J=10.1, 7.1 Hz, 1H), 5.13 (dd, J=10.3, 1.5 Hz, 1H), 5.30 (dd, J=17.2, 1.4 Hz, 1H), 5.73 (ddd, J=17.2, 10.3, 8.8 Hz, 1H), 5.86 (s, 1H), 7.02-7.11 (m, 2H), 7.34-7.40 (m, 1H), 7.53 (s, 1H), 7.69 (dd, J=8.8, 2.0 Hz, 1H), 7.99 (d, J=2.0 Hz, 1H), 8.09 (d, J=8.8 Hz, 1H). LC-MS, MS m/z 857.2 (M$^+$+H).

Preparation of Compound 83, Example 83

Compound 83

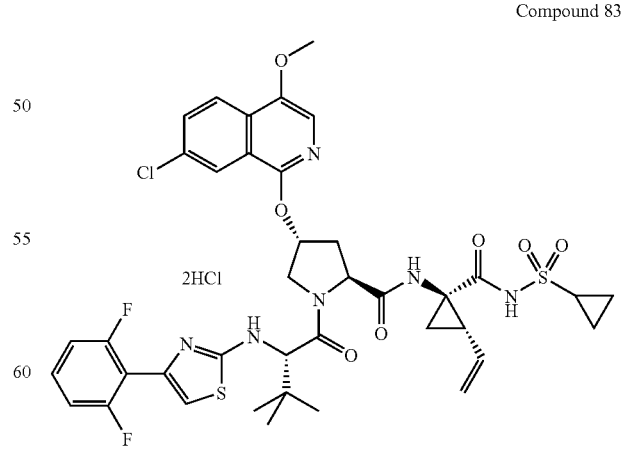

Compound 83 was prepared in 62.9% yield following the same procedure as described for the preparation of compound 9, except 2-bromo-2',6'-difluoroaceyophenone was used instead of 2-bromopropiophenone in step 1. $^1$H NMR (400

MHz, MeOD) δ ppm 1.05-1.11 (m, 2H), 1.15 (s, 9H), 1.21-1.26 (m, 2H), 1.41 (dd, J=9.4, 5.4 Hz, 1H), 1.89 (dd, J=8.2, 5.4 Hz, 1H), 2.22-2.33 (m, 2H), 2.59 (dd, J=13.7, 7.2 Hz, 1H), 2.95 (ddd, J=12.7, 8.1, 4.7 Hz, 1H), 3.97 (s, 3H), 4.12 (dd, J=12.0, 3.9 Hz, 1H), 4.35 (d, J=11.8 Hz, 1H), 4.52 (s, 1H), 4.64 (dd, J=10.1, 7.1 Hz, 1H), 5.12 (dd, J=10.3, 1.5 Hz, 1H), 5.30 (dd, J=17.1, 1.5 Hz, 1H), 5.73 (ddd, J=17.1, 10.3, 8.8 Hz, 1H), 5.88 (s, 1H), 6.84 (s, 1H), 7.01 (t, J=8.6 Hz, 2H), 7.43 (ddd, J=14.8, 8.4, 6.3 Hz, 1H), 7.52 (s, 1H), 7.65 (dd, J=8.8, 2.3 Hz, 1H), 7.94 (d, J=2.0 Hz, 1H), 8.06 (d, J=8.8 Hz, 1H). LC-MS, MS m/z 843.2 (M$^+$+H).

1.53 Hz, 1H), 5.32 (dd, J=17.09, 1.22 Hz, 1H), 5.78 (ddd, J=17.09, 10.22, 9.00 Hz, 1H), 7.16-7.23 (m, 2H), 7.28 (t, J=7.63 Hz, 1H), 7.43-7.49 (m, 1H), 7.49-7.54 (m, 2H), 7.64 (d, J=2.14 Hz, 1H), 7.79 (d, J=8.85 Hz, 1H). LC-MS, MS m/z 878 (M+H)$^+$.

Preparation of Compound 85, Example 85

Compound 85

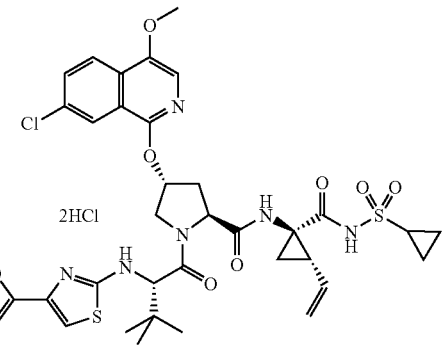

2HCl

Preparation of Compound 84, Example 84

Compound 84

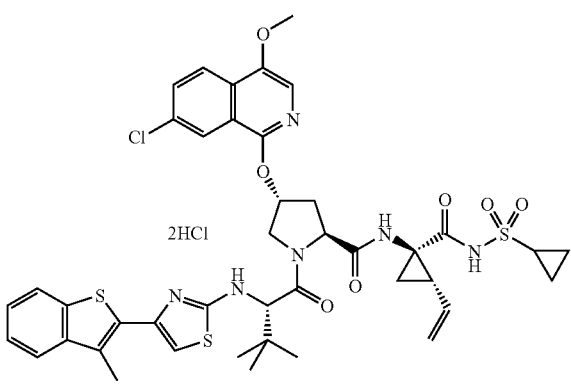

2HCl

Compound 84 was prepared in 34.1% yield following a similar procedure as described for the preparation of compound 9, except 2-Bromo-1-(3-methylbenzo[b]thiophen-2-yl)ethan-1-one was used instead of 2-bromopropiophenone in step 1, $^1$H NMR (500 MHz, MeOD) δ ppm 1.09-1.15 (m, 3H), 1.18 (s, 9H), 1.25-1.33 (m, 3H), 1.46 (dd, J=9.46, 5.49 Hz, 1H), 1.92 (dd, J=8.24, 5.49 Hz, 1H), 2.22-2.30 (m, 2H), 2.31 (s, 3H), 2.46 (dd, J=13.43, 7.02 Hz, 1H), 2.95-3.04 (m, 1H), 3.70 (s, 3H), 4.19 (dd, J=11.60, 3.66 Hz, 1H), 4.64 (dd, J=10.38, 7.02 Hz, 1H), 4.82 (br. s., 1H), 5.15 (dd, J=10.38, Compound 85 was prepared in 43.1% yield following a similar procedure as described for the preparation of compound 9, except 2-Bromo-1-(3-phenylisoxazol-5-yl)ethan-1-one was used instead of 2-bromopropiophenone in step 1. $^1$H NMR (500 MHz, MeOD) δ ppm 1.08-1.14 (m, 2H), 1.21 (s, 9H), 1.26-1.32 (m, 2H), 1.42 (dd, J=9.31, 5.34 Hz, 1H), 1.88 (dd, J=8.24, 5.49 Hz, 1H), 2.21 (q, J=8.85 Hz, 1H), 2.24-2.31 (m, 1H), 2.43 (dd, J=13.43, 6.41 Hz, 1H), 2.96-3.03 (m, 1H), 3.74 (s, 3H), 4.20 (dd, J=11.60, 3.36 Hz, 1H), 4.53 (dd, J=10.68, 6.41 Hz, 1H), 4.86 (s, 1H), 5.09-5.15 (m, 2H), 5.28 (dd, J=17.24, 1.07 Hz, 1H), 5.74 (ddd, J=17.17, 10.15, 9.00 Hz, 1H), 6.21 (br. s., 1H), 6.68 (s, 1H), 7.22-7.39 (m, 5H), 7.46-7.53 (m, 2H), 7.78 (d, J=9.77 Hz, 1H). LC-MS, MS m/z 875 (M+H)$^+$.

Preparation of Compound 86, Example 86

Compound 86

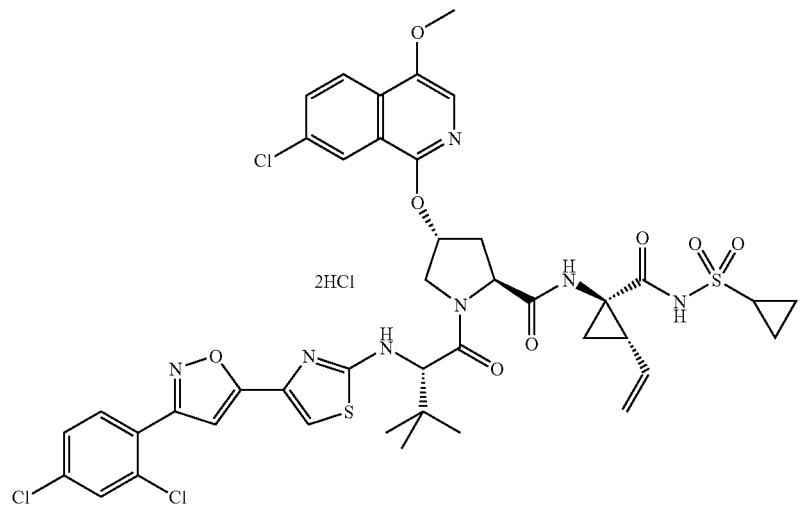

2HCl

Compound 86 was prepared in 61.2% yield following a similar procedure as described for the preparation of compound 9, except 2-bromo-1-(3-(2,4-dichlorophenyl)isoxazol-5-yl)ethanone was used instead of 2-bromopropiophenone in step 1. ¹H NMR (500 MHz, MeOD) δ ppm 1.06-1.14 (m, 2H), 1.22 (s, 9H), 1.25-1.32 (m, 2H), 1.39 (dd, J=9.46, 5.49 Hz, 1H), 1.86 (dd, J=8.09, 5.34 Hz, 1H), 2.18 (q, J=8.85 Hz, 1H), 2.21-2.29 (m, 1H), 2.40 (dd, J=13.28, 6.56 Hz, 1H), (dd, J=10.68, 6.71 Hz, 1H), 4.83 (s, 1H), 4.99 (d, J=11.60 Hz, 1H), 5.14 (dd, J=10.38, 1.53 Hz, 1H), 5.30 (d, J=17.09 Hz, 1H), 5.70-5.83 (m, 2H), 6.16 (br. s., 1H), 6.68 (s, 1H), 6.97-7.06 (m, 2H), 7.14 (td, J=7.63, 1.22 Hz, 1H), 7.23 (d, J=7.93 Hz, 1H), 7.34 (s, 1H), 7.40 (dd, J=8.85, 2.14 Hz, 1H), 7.57 (d, J=1.83 Hz, 1H), 7.74 (d, J=8.85 Hz, 1H). LC-MS, MS m/z 848 (M+H)⁺.

Preparation of Compound 88, Example 88

Compound 88

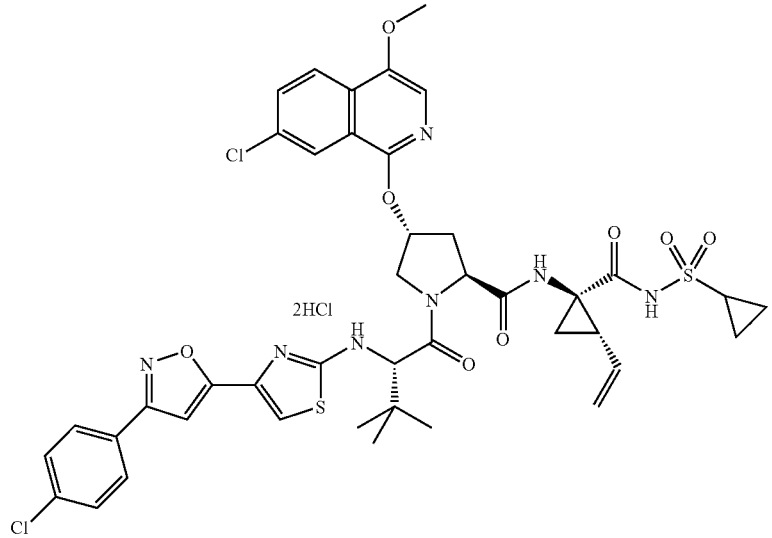

2.93-3.02 (m, 1H), 3.93 (s, 3H), 4.24 (dd, J=11.29, 3.66 Hz, 1H), 4.46 (dd, J=10.68, 6.71 Hz, 1H), 4.79 (s, 1H), 5.11 (d, J=10.68 Hz, 2H), 5.26 (d, J=17.09 Hz, 1H), 5.73 (dt, J=17.17, 9.58 Hz, 1H), 6.11 (br. s., 1H), 6.93 (s, 1H), 7.03 (d, J=8.55 Hz, 1H), 7.14-7.22 (m, 1H), 7.31 (d, J=1.83 Hz, 1H), 7.38 (s, 1H), 7.47-7.54 (m, 2H), 7.85 (d, J=9.46 Hz, 1H). LC-MS, MS m/z 944 (M+H)⁺.

Preparation of Compound 87, Example 87

Compound 87

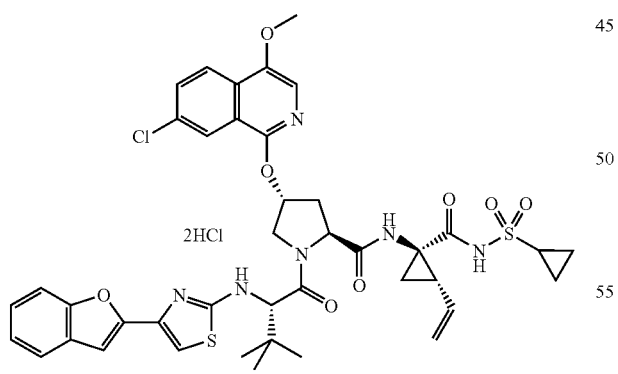

Compound 87 was prepared in 40.4% yield following a similar procedure as described for the preparation of compound 9, except 1-(benzofuran-2-yl)-2-bromoethanone was used instead of 2-bromopropiophenone in step 1. ¹H NMR (500 MHz, MeOD) δ ppm 1.06-1.15 (m, 2H), 1.20 (s, 9H), 1.26-1.33 (m, 2H), 1.44 (dd, J=9.46, 5.49 Hz, 1H), 1.90 (dd, J=7.93, 5.49 Hz, 1H), 2.19-2.34 (m, 2H), 2.46 (dd, J=13.58, 6.87 Hz, 1H), 2.95-3.03 (m, 1H), 3.79 (s, 3H), 4.02 (dt, J=6.49, 3.32 Hz, 1H), 4.20 (dd, J=11.75, 3.51 Hz, 1H), 4.58

Compound 88 was prepared in 59.9% yield following a similar procedure as described for the preparation of compound 9, except 2-bromo-1-(3-(4-chlorophenyl)isoxazol-5-yl)ethanone was used instead of 2-bromopropiophenone in step 1. ¹H NMR (500 MHz, MeOD) δ ppm 1.08-1.13 (m, 2H), 1.22 (s, 9H), 1.26-1.32 (m, 2H), 1.41 (dd, J=9.46, 5.49 Hz, 1H), 1.87 (dd, J=8.24, 5.49 Hz, 1H), 2.16-2.30 (m, 2H), 2.35-2.41 (m, 1H), 2.95-3.03 (m, 1H), 3.81 (s, 3H), 4.21 (dd, J=11.60, 3.66 Hz, 1H), 4.50 (dd, J=10.83, 6.56 Hz, 1H), 4.84 (s, 1H), 5.09-5.18 (m, 2H), 5.27 (dd, J=17.24, 1.07 Hz, 1H), 5.74 (ddd, J=17.09, 10.07, 9.16 Hz, 1H), 6.25 (br. s., 1H), 6.70 (s, 1H), 7.20-7.29 (m, 5H), 7.43 (d, J=1.83 Hz, 1H), 7.47 (dd, J=8.85, 2.14 Hz, 1H), 7.75 (d, J=8.85 Hz, 1H), LC-MS, MS m/z 909 (M+H)⁺.

Preparation of Compound 89, Example 89

Compound 89

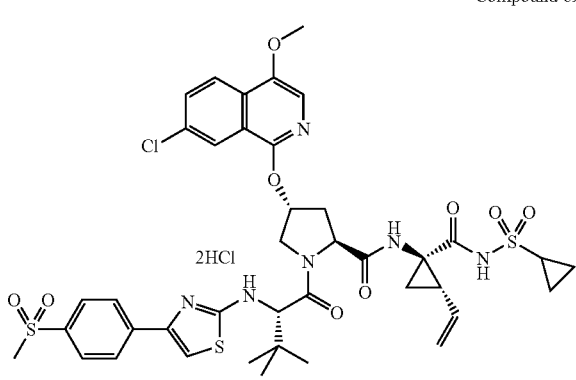

Compound 89 was prepared in 14.2% yield following a similar procedure as described for the preparation of compound 9, except 2-bromo-1-(4-(methylsulfonyl)phenyl)ethanone was used instead of 2-bromopropiophenone in step 1. ¹H NMR (500 MHz, MeOD) δ ppm 1.09-1.15 (m, 2H), 1.20 (s, 9H), 1.25-1.33 (m, 2H), 1.43 (dd, J=9.46, 5.49 Hz, 1H), 1.90 (dd, J=7.93, 5.49 Hz, 1H), 2.18-2.30 (m, 2H), 2.44 (dd, J=13.73, 6.41 Hz, 1H), 2.81 (s, 3H), 2.96-3.03 (m, 1H), 3.93 (s, 3H), 4.19 (dd, J=11.60, 3.36 Hz, 1H), 4.53 (dd, J=10.68, 7.02 Hz, 1H), 4.92 (s, 1H), 5.02 (d, J=10.99 Hz, 1H), 5.13 (dd, J=10.53, 1.37 Hz, 1H), 5.29 (dd, J=17.24, 1.07 Hz, 1H), 5.75 (ddd, J=17.09, 10.22, 9.00 Hz, 1H), 6.12 (t, J=3.05 Hz, 1H), 7.39-7.47 (m, 4H), 7.52 (dd, J=8.85, 2.14 Hz, 1H), 7.81 (d, J=8.55 Hz, 2H), 7.91 (d, J=8.85 Hz, 1H). LC-MS, MS m/z 886 (M+H)⁺.

Preparation of Compound 90, Example 90

Compound 90

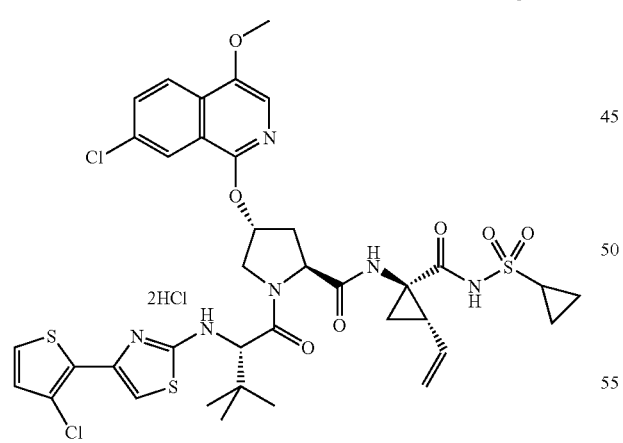

Compound 90 was prepared in 47.3% yield following a similar procedure as described for the preparation of compound 9, except 2-bromo-1-(3-chlorothiophen-2-yl)ethanone was used instead of 2-bromopropiophenone in step 1. ¹H NMR (500 MHz, MeOD) δ ppm 1.09-1.14 (m, 2H), 1.16 (s, 9H), 1.26-1.33 (m, 2H), 1.45 (dd, J=9.46, 5.49 Hz, 1H), 1.91 (dd, J=7.93, 5.49 Hz, 1H), 2.22-2.36 (m, 2H), 2.52 (dd, J=13.58, 6.87 Hz, 1H), 2.96-3.03 (m, 1H), 3.98 (s, 3H), 4.19 (dd, J=11.60, 3.97 Hz, 1H), 4.60 (dd, J=10.07, 7.02 Hz, 1H), 4.76 (s, 1H), 4.80 (d, J=11.60 Hz, 1H), 5.15 (dd, J=10.22, 1.37 Hz, 1H), 5.32 (dd, J=17.09, 1.22 Hz, 1H), 5.77 (ddd, J=17.09, 10.22, 9.00 Hz, 1H), 6.05 (br. s., 1H), 6.64 (d, J=5.49 Hz, 1H), 6.83 (d, J=5.49 Hz, 1H), 7.44 (s, 1H), 7.61 (dd, J=8.85, 2.14 Hz, 1H), 7.68 (d, J=1.83 Hz, 1H), 8.00 (d, J=8.85 Hz, 1H). LC-MS, MS m/z 848 (M+H)⁺.

Preparation of Compound 91, Example 91

Compound 91

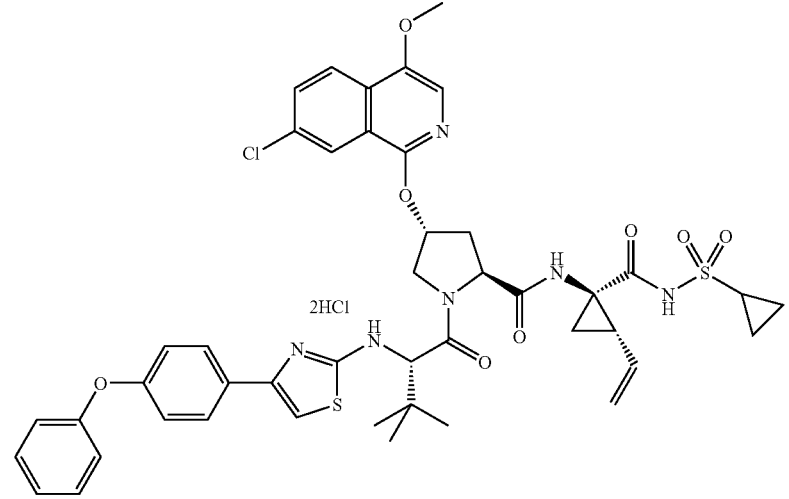

Compound 91 was prepared in 31.8% yield following a similar procedure as described for the preparation of compound 9, except 2-bromo-1-(4-phenoxyphenyl)ethanone was used instead of 2-bromopropiophenone in step 1. ¹H NMR (500 MHz, MeOD) δ ppm 1.08-1.15 (m, 2H), 1.20 (s, 9H), 1.26-1.31 (m, 2H), 1.44 (dd, J=9.46, 5.49 Hz, 1H), 1.92 (dd, J=8.24, 5.49 Hz, 1H), 2.21-2.35 (m, 2H), 2.57 (dd, J=13.43, 7.02 Hz, 1H), 2.95-3.03 (m, 1H), 3.99 (s, 3H), 4.17 (dd, J=11.90, 3.66 Hz, 1H), 4.61 (dd, J=10.22, 7.17 Hz, 1H), 4.65-4.71 (m, 2H), 5.15 (dd, J=10.38, 1.22 Hz, 1H), 5.32 (dd, J=17.09, 1.22 Hz, 1H), 5.76 (ddd, J=17.17, 10.15, 9.00 Hz, 1H), 5.99 (br. s., 1H), 6.78 (d, J=8.55 Hz, 2H), 6.86 (d, J=7.63 Hz, 2H), 7.15 (t, J=7.32 Hz, 1H), 7.35 (t, J=8.09 Hz, 2H), 7.52-7.57 (m, 3H), 7.62 (dd, J=8.85, 2.14 Hz, 1H), 7.75 (d, J=1.83 Hz, 1H), 8.06 (d, J=8.85 Hz, 1H). LC-MS, MS m/z 900 (M+H)⁺.

Preparation of Compound 92, Example 92

Compound 92

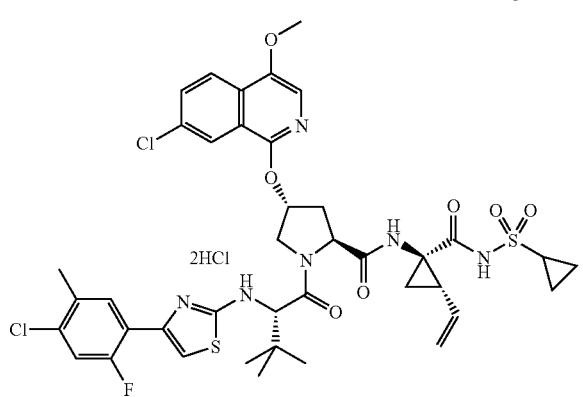

Compound 92 was prepared in 21.9% yield following a similar procedure as described for the preparation of compound 9, except 2-bromo-1-(4-chloro-2-fluoro-5-methylphenyl)ethanone was used instead of 2-bromopropiophenone in step 1. $^1$H NMR (500 MHz, MeOD) δ ppm 1.09-1.14 (m, 2H), 1.21 (s, 9H), 1.27-1.32 (m, 2H), 1.43 (dd, J=9.46, 5.49 Hz, 1H), 1.87-1.93 (m, 4H), 2.19-2.31 (m, 2H), 2.40-2.47 (m, 1H), 2.94-3.03 (m, 1H), 3.99 (s, 3H), 4.20 (dd, J=11.60, 3.36 Hz, 1H), 4.54 (dd, J=10.68, 6.71 Hz, 1H), 4.85 (s, 1H), 4.98 (d, J=11.29 Hz, 1H), 5.13 (dd, J=10.38, 1.22 Hz, 1H), 5.29 (dd, J=17.09, 1.22 Hz, 1H), 5.75 (ddd, J=17.09, 10.22, 9.00 Hz, 1H), 6.18 (t, J=2.75 Hz, 1H), 6.76 (d, J=11.29 Hz, 1H), 7.40 (d, J=2.14 Hz, 1H), 7.45 (s, 1H), 7.54 (dd, J=8.85, 2.14 Hz, 1H), 7.76 (d, J=8.55 Hz, 1H), 7.96 (d, J=8.85 Hz, 1H). LC-MS, MS m/z 874 (M+H)$^+$.

Preparation of Compound 93, Example 93

Compound 93

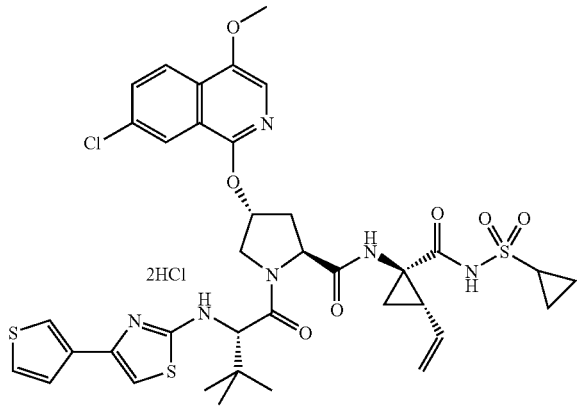

Compound 93 was prepared in 41.7% yield following a similar procedure as described for the preparation of compound 9, except 2-bromo-1-(thiophen-3-yl)ethanone was used instead of 2-bromopropiophenone in step 1. $^1$H NMR (500 MHz, MeOD) δ ppm 1.09-1.15 (m, 2H), 1.19 (s, 9H), 1.25-1.31 (m, 2H), 1.45 (dd, J=9.46, 5.49 Hz, 1H), 1.93 (dd, J=7.93, 5.49 Hz, 1H), 2.23-2.37 (m, 2H), 2.61 (dd, J=13.73, 7.02 Hz, 1H), 2.95-3.03 (m, 1H), 4.00 (s, 3H), 4.17 (dd, J=11.90, 3.36 Hz, 1H), 4.54-4.62 (m, 2H), 4.67 (dd, J=10.22, 7.17 Hz, 1H), 5.16 (dd, J=10.53, 1.37 Hz, 1H), 5.33 (dd, J=17.09, 1.22 Hz, 1H), 5.77 (ddd, J=17.17, 10.15, 9.00 Hz, 1H), 5.96 (br. s., 1H), 7.26 (dd, J=5.04, 1.07 Hz, 1H), 7.38 (dd, J=4.73, 2.90 Hz, 1H), 7.54-7.59 (m, 2H), 7.62 (dd, J=8.85, 2.14 Hz, 1H), 7.85 (d, J=2.14 Hz, 1H), 8.06 (d, J=8.85 Hz, 1H). LC-MS, MS m/z 814 (M+H)$^+$.

Preparation of Compound 94, Example 94

Compound 94

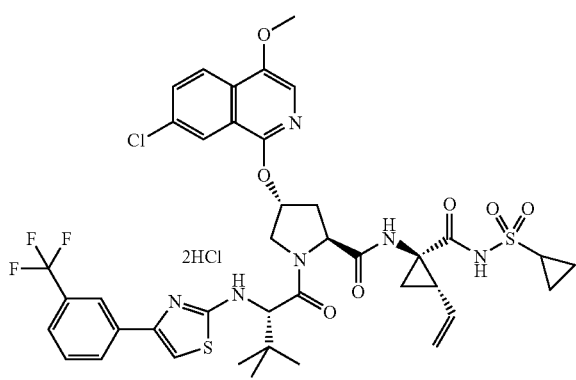

Compound 94 was prepared in 37.8% yield following a similar procedure as described for the preparation of compound 9, except 2-bromo-1-(3-(trifluoromethyl)phenyl)ethanone was used instead of 2-bromopropiophenone in step 1. $^1$H NMR (500 MHz, MeOD) δ ppm 1.09-1.15 (m, 2H), 1.20 (s, 9H), 1.26-1.32 (m, 2H), 1.43 (dd, J=9.46, 5.49 Hz, 1H), 1.91 (dd, J=8.24, 5.49 Hz, 1H), 2.17-2.33 (m, 2H), 2.53 (dd, J=13.43, 7.02 Hz, 1H), 2.95-3.03 (m, 1H), 3.94 (s, 3H), 4.19 (dd, J=11.60, 3.36 Hz, 1H), 4.55 (dd, J=10.53, 6.87 Hz, 1H), 4.80 (s, 1H), 4.84 (br. s., 1H), 5.14 (dd, J=10.38, 1.22 Hz, 1H), 5.30 (dd, J=16.94, 1.07 Hz, 1H), 5.70-5.81 (m, 1H), 6.01 (br. s., 1H), 7.21-7.31 (m, 2H), 7.44 (s, 1H), 7.52-7.56 (m, 2H), 7.82 (d, J=7.32 Hz, 1H), 7.92 (s, 1H), 7.95 (d, J=9.77 Hz, 1H). LC-MS, MS m/z 876 (M+H)$^+$.

Preparation of Compound 95, Example 95

Compound 95

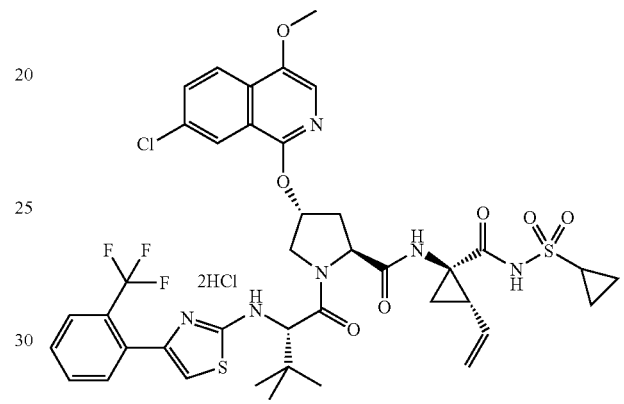

Compound 95 was prepared in 67.9% yield following a similar procedure as described for the preparation of compound 9, except 2-bromo-1-(2-(trifluoromethyl)phenyl)ethanone was used instead of 2-bromopropiophenone in step 1. $^1$H NMR (500 MHz, MeOD) δ ppm 1.09-1.14 (m, 2H), 1.16 (s, 9H), 1.27-1.31 (m, 2H), 1.45 (dd, J=9.46, 5.49 Hz, 1H), 1.92 (dd, J=7.93, 5.49 Hz, 1H), 2.24-2.36 (m, 2H), 2.56 (dd, J=13.43, 7.02 Hz, 1H), 2.95-3.03 (m, 1H), 4.00 (s, 3H), 4.16 (dd, J=11.90, 3.97 Hz, 1H), 4.42 (d, J=11.60 Hz, 1H), 4.60-4.66 (m, 2H), 5.16 (dd, J=10.38, 1.22 Hz, 1H), 5.33 (dd, J=17.24, 1.07 Hz, 1H), 5.77 (ddd, J=17.17, 9.99, 9.16 Hz, 1H), 5.88 (br. s., 1H), 7.37-7.47 (m, 3H), 7.50 (s, 1H), 7.61 (d, J=7.32 Hz, 1H), 7.71 (dd, J=8.85, 2.14 Hz, 1H), 7.93 (d, J=1.83 Hz, 1H), 8.11 (d, J=8.85 Hz, 1H). LC-MS, MS m/z 876 (M+H)$^+$.

Preparation of Compound 96, Example 96

Compound 96

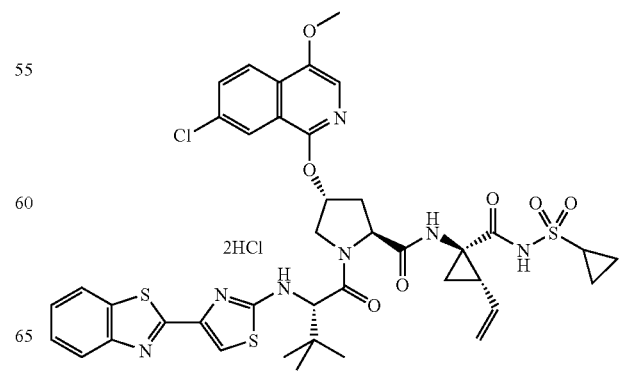

Compound 96 was prepared in 71.1% yield following a similar procedure as described for the preparation of compound 9, except 1-(benzo[d]thiazol-2-yl)-2-bromoethanone was used instead of 2-bromopropiophenone in step 1. $^1$H NMR (500 MHz, MeOD) δ ppm 1.08-1.15 (m, 2H), 1.19 (s, 9H), 1.26-1.33 (m, 2H), 1.45 (dd, J=9.46, 5.49 Hz, 1H), 1.91 (dd, J=7.93, 5.49 Hz, 1H), 2.21-2.35 (m, 2H), 2.46 (dd, J=13.43, 7.02 Hz, 1H), 2.95-3.04 (m, 1H), 3.67 (s, 3H), 4.20 (dd, J=11.44, 2.90 Hz, 1H), 4.63 (dd, J=10.07, 7.02 Hz, 1H), 4.90 (s, 1H), 5.15 (d, J=10.38 Hz, 1H), 5.31 (d, J=17.09 Hz, 1H), 5.76 (dt, J=17.09, 9.46 Hz, 1H), 6.23 (br. s., 1H), 7.23 (s, 1H), 7.31-7.40 (m, 1H), 7.43 (dd, J=8.85, 1.83 Hz, 1H), 7.46-7.52 (m, 2H), 7.60 (d, J=7.93 Hz, 1H), 7.67 (d, J=8.85 Hz, 1H), 7.73 (d, J=8.24 Hz, 1H). LC-MS, MS m/z 865 (M+H)$^+$.

Preparation of Compound 97, Example 97

Compound 97

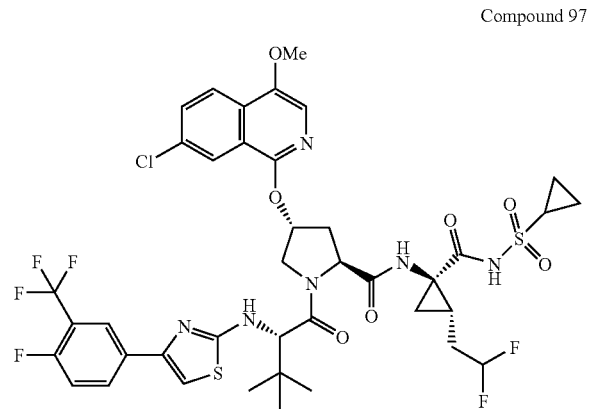

Scheme 1

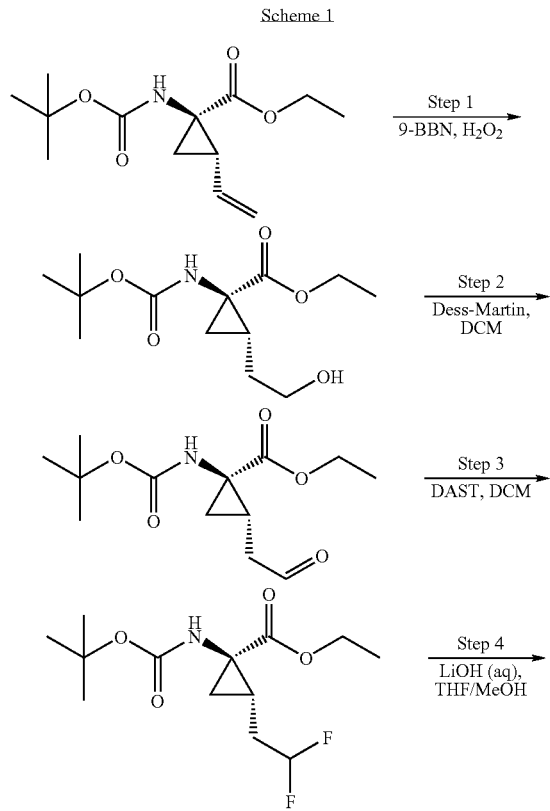

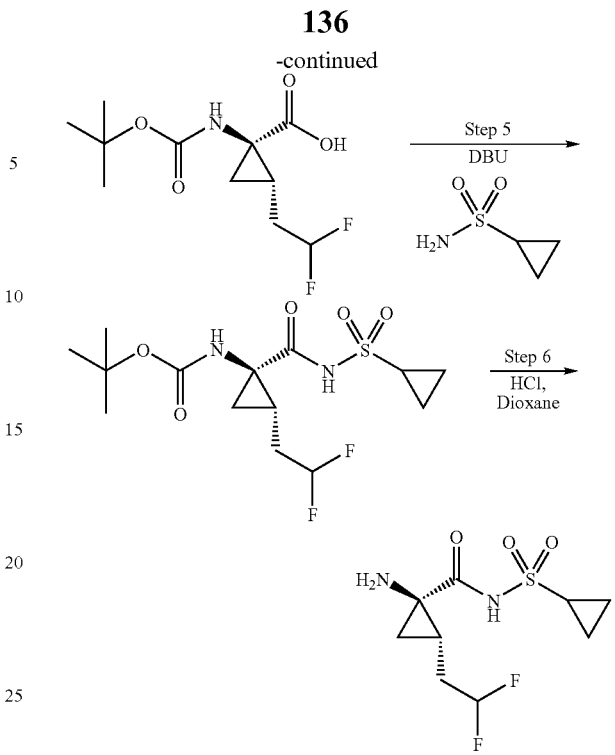

Step 1.

To a solution of (1R,2S)-ethyl 1-(tert-butoxycarbonylamino)-2-vinylcyclopropanecarboxylate (15.3 g, 59.9 mmol) in THF (100 ml) was added 9-BBN (180 ml, 90 mmol) dropwise at 0° C. The formed solution was stirred at room temperature for 2 hr. The final solution was cooled back to 0° C. while 3 M aqueous solution of sodium acetate (180 ml, 540 mmol) was added. To this well stirred mixture, Hydrogen peroxide (89 ml, 30%, 869 mmol) was added dropwise (Caution should be exercised since the addition was exothermic). The formed warm two layer mixture was stirred overnight. The upper organic layer was separated and the aqueous layer was extracted with EtOAc. The combined organic layers were washed with brine, dried over MgSO$_4$, filtered, and evaporated. The residue was purified by silica gel column, eluted with 4:1, 3:1, 2:1, then 3:2 Hexane-EtOAc to afford the desired product (1R,2S)-ethyl 1-(tert-butoxycarbonylamino)-2-(2-hydroxyethyl)cyclopropanecarboxylate (11.50 g, 42.1 mmol, 70.2% yield) as a viscous oil, which solidified upon standing on the bench. $^1$H NMR (CDCl$_3$) δ 1.18-1.21 (m, 1H), 1.25 (t, J=7 Hz, 3H), 1.35-1.40 (m, 1H), 1.44 (s, 9H), 1.61-1.65 (m, 1H), 1.70-1.75 (m, 1H), 1.91-1.98 (m, 1H), 3.61-3.65 (m, 1H), 3.71-3.75 (m, 1H), 4.10-4.21 (m, 2H), 5.17 (b, 1H).

Step 2.

To a solution of (1R,2S)-ethyl 1-(tert-butoxycarbonylamino)-2-(2-hydroxyethyl)cyclopropanecarboxylate (9.70 g, 35.5 mmol) in DCM (300 ml) at 0° C. was added Dess-Martin periodinane (18.06 g, 42.6 mmol). The formed slurry was stirred at room temperature overnight. The reaction mixture was filtered through celite. The resulting filtrated was concentrated and this process was repeated one more time. Residue was purified by a silica gel column, eluted with 8:1, 4:1, 3:1, then 2:1 heaxane-EtOAc to yield (1R,2S)-ethyl 1-(tert-butoxycarbonylamino)-2-(2-oxoethyl)cyclopropanecarboxylate (6.15 g, 22.67 mmol, 63.9% yield) as a colorless oil. $^1$H NMR (CDCl$_3$) δ 1.24 (t, J=7 Hz, 3H), 1.40-1.45 (m, 11H), 1.65-1.69 (m, 1H), 2.75-2.80 (m, 2H), 4.09-4.19 (m, 2H), 5.17 (b, 1H), 9.76 (s, 1H).

Step 3.

To a solution of (1R,2S)-ethyl 1-(tert-butoxycarbonylamino)-2-(2-oxoethyl)cyclopropanecarboxylate (4.10 g, 15.11 mmol) in DCM (50 ml) at 0° C. was added (DIETHYLAMINO)SULFUR TRIFLUORIDE (7.99 ml, 60.4 mmol). The formed light yellow solution was stirred at room temperature overnight. The final solution was diluted with DCM, cooled, carefully quenched with conc. ammonium chloride. The separated organic layer was washed with 5% citric acid twice, 0.5 M NaOH three times, and brine, respectively, dired over MgSO4, evaporated in vacuo. The residue was purified by Biotage column, eluted with gradient 5% to 40% EtOAc-Hexane to yield (1R,2S)-ethyl 1-(tert-butoxycarbonylamino)-2-(2,2-difluoroethyl)cyclopropanecarboxylate (1.65 g, 5.63 mmol, 37.2% yield) as a light yellow oil. 500 mg of starting material (12%) was also recovered. $^1$H NMR (CDCl$_3$) δ 1.26 (t, J=7 Hz, 3H), 1.35-1.39 (m, 1H), 1.44 (s, 9H), 1.46-1.50 (m, 1H), 1.55-1.60 (m, 1H), 2.18-2.24 (m, 2H), 4.15-4.21 (m, 2H), 5.17 (b, 1H), 5.73, 5.85, 5.99 (b, 1H).
Step 4.

To a solution of (1R,2S)-ethyl 1-(tert-butoxycarbonylamino)-2-(2,2-difluoroethyl)cyclopropanecarboxylate (1.14 g, 3.89 mmol) in THF (10 mL) and MeOH (10.00 mL) was added a premade solution of lithium hydroxide monohydrate (0.489 g, 11.66 mmol) in water (10.00 mL). The formed cloudy solution was stirred at room temperature overnight. The volatiles were removed in vacuo and the residue was taken up in water, acidified with 5% citric acid, extracted with EtOAc. The separated organic layer was washed with brine, dired over MgSO$_4$, and evaporated in vacuo. The dark residue was triturated with hexane to yield 665 mg of light yellow solid. The filtrated was concentrated to a dark residue (300 mg) which was purified by Biotage column, eluted with gradient 5% to 10% DCM-MeOH to yield additional 250 mg of the desired product as a light yellow solid. Total, (1R,2S)-1-(tert-butoxycarbonylamino)-2-(2,2-difluoroethyl)cyclopropanecarboxylic acid (915 mg, 3.45 mmol, 89% yield). $^1$H NMR (CD$_3$OD) δ 1.25-1.28 (m, 1H), 1.42-1.43 (m, 10H), 1.46-1.53 (m, 1H), 2.12-2.14 (m, 2H), 5.73, 5.85, 6.00 (b, 1H).
Step 5.

To a solution of (1R,2S)-1-(tert-butoxycarbonylamino)-2-(2,2-difluoroethyl)cyclopropanecarboxylic acid (665 mg, 2.507 mmol) in THF (20 mL) was added CDI (528 mg, 3.26 mmol) and the formed solution was stirred at rt for 3 h. Cyclopropanesulfonamide (395 mg, 3.26 mmol) and DBU (0.756 mL, 5.01 mmol) were added and the mixture was stirred at rt overnight. The reaction was diluted with EtOAc and washed with 1.0M HCl solution. The aqueous layer was extracted with EtOAc and the combined organics were washed with 5% citric acid, brine, dried over MgSO$_4$, filtered and evaporated to give crude material. The crude product was purified on the Biotage (acetone/hexanes 5-30%) to give the pure product tert-butyl (1R,2S)-1-(cyclopropylsulfonylcarbamoyl)-2-(2,2-difluoroethyl)cyclopropylcarbamate (783 mg, 1.913 mmol, 76% yield) as a white solid. $^1$H NMR (500 MHz, MeOD) δ 1.01-1.15 (m, 2H), 1.16-1.35 (m, 2H), 1.49 (s, 10H), 1.58-1.77 (m, 2H), 1.92-2.19 (m, 2H), 2.90-2.99 (m, 1H), 5.80-6.10 (m, 1H).
Step 6.

A solution of 4.0M HCl in dioxane (10.5 ml, 42.0 mmol) was added to tert-butyl (1R,2S)-1-(cyclopropylsulfonylcarbamoyl)-2-(2,2-difluoroethyl)cyclopropylcarbamate (770 mg, 2.090 mmol) and the resulting mixture was stirred at rt overnight. The reaction was concentrated and dried under vacuum to afford the desired product (1R,2S)-1-amino-N-(cyclopropylsulfonyl)-2-(2,2-difluoroethyl)cyclopropanecarboxamide, HCl, 0.6 dioxane (746 mg, 1.877 mmol, 90% yield) as a light yellow foam. $^1$HNMR spectrum showed it contained 0.6 mole equivalents of 1,4-dioxane as solvate. $^1$H NMR (500 MHz, MeOD) δ 1.07-1.20 (m, 2H), 1.21-1.39 (m, 2H), 1.61 (dd, J=10.22, 7.48 Hz, 1H), 1.78-1.88 (m, 1H), 1.94 (t, J=7.78 Hz, 1H), 2.07-2.30 (m, 2H), 3.00-3.13 (m, 1H), 5.89-6.24 (m, 1H).

Scheme 2

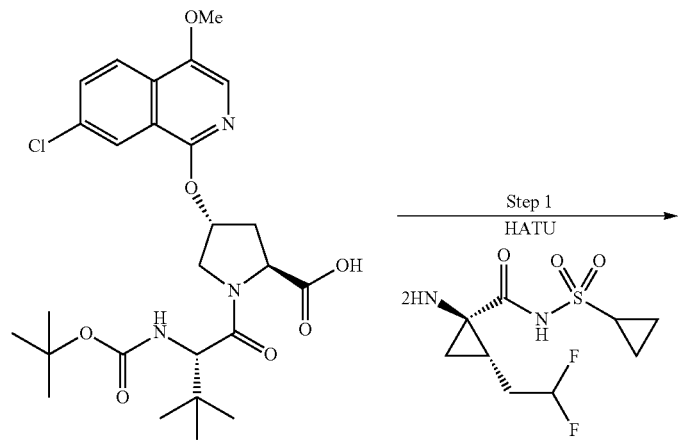

-continued
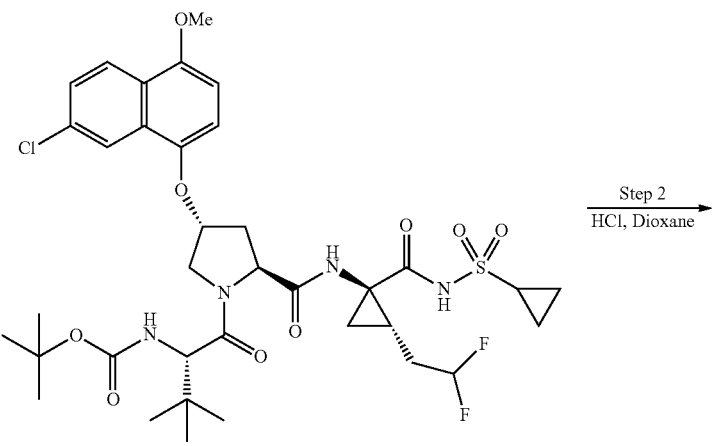
Step 2
HCl, Dioxane
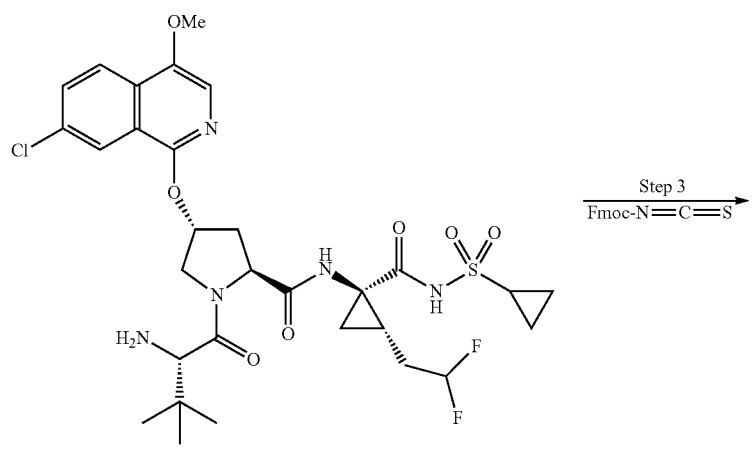
Step 3
Fmoc-N=C=S
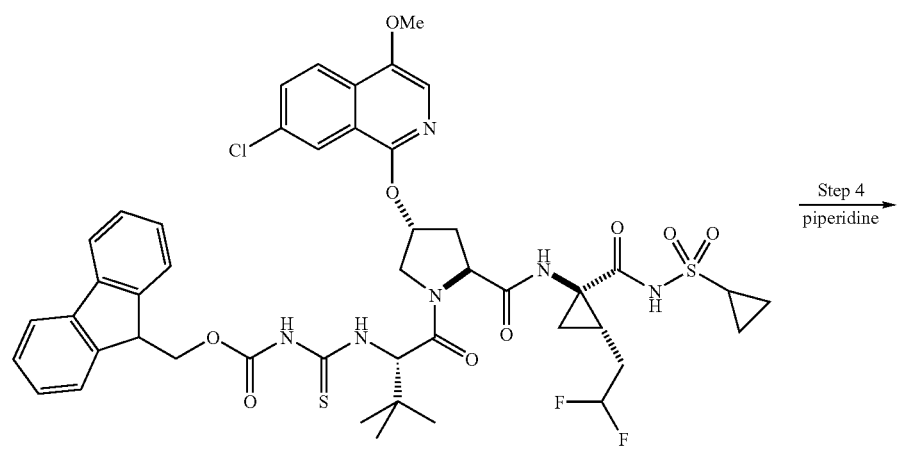
Step 4
piperidine -continued

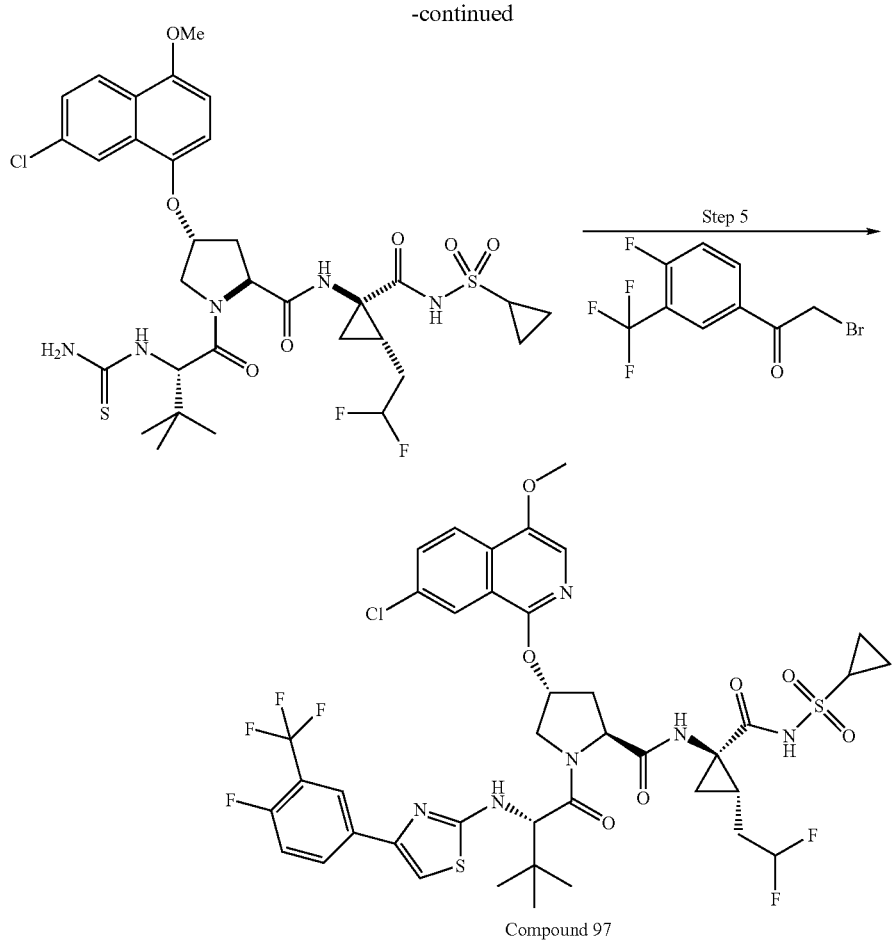

Compound 97

Step 1:

To a slurry of (2S,4R)-1-((S)-2-(tert-butoxycarbonylamino)-3,3-dimethylbutanoyl)-4-(7-chloro-4-methoxyisoquinolin-1-yloxy)pyrrolidine-2-carboxylic acid (500 mg, 0.933 mmol), (1R,2S)-1-amino-N-(cyclopropylsulfonyl)-2-(2,2-difluoroethyl)cyclopropanecarboxamide, HCl, 0.6dioxane (334 mg, 0.933 mmol), and HATU (426 mg, 1.119 mmol) in $CH_2Cl_2$ (10 ml) at 0° C. was added N,N-diisopropylethylamine (0.487 ml, 2.80 mmol). The formed light yellow solution was stirred at 0° C. to r.t overnight. Reaction mixture was diluted with EtOAc (50 mL), washed with 5% citric acid, brine, dried over $MgSO_4$, filtered, and concentrated. The crude product was dissolved in a small amount of DCM and charged to a Biotage silica gel cartridge which was eluted with 5-40% gradient hexane-acetone to yield tert-butyl(S)-1-((2S,4R)-4-(7-chloro-4-methoxyisoquinolin-1-yloxy)-2-((1R,2S)-1-(cyclopropylsulfonylcarbamoyl)-2-(2,2-difluoroethyl)cyclopropylcarbamoyl)pyrrolidin-1-yl)-3,3-dimethyl-1-oxobutan-2-ylcarbamate (655 mg, 0.816 mmol, 88% yield) as a white foam. $^1$H NMR (500 MHz, MeOD) δ 0.98-1.23 (m, 21H), 1.23-1.44 (m, 3H), 1.70 (d, J=3.36 Hz, 2H), 2.12-2.39 (m, 3H), 2.61 (dd, J=13.73, 6.71 Hz, 1H), 2.90-2.99 (m, 1H), 4.03 (s, 3H), 4.05-4.13 (m, 1H), 4.22 (d, J=9.46 Hz, 1H), 4.46 (d, J=11.29 Hz, 1H), 4.61 (dd, J=10.38, 7.02 Hz, 1H), 5.77-6.13 (m, 2H), 6.60 (br. s., 1H), 7.60 (s, 1H), 7.71 (d, J=8.85 Hz, 1H), 7.99-8.19 (m, 2H). LC-MS (retention time: 3.25 min, Method A), MS m/z 786.2 (M++H).

LC/MS Conditions for Method A.
Start % B=0
Final % B=100
Gradient Time=3 min
Stop Time=4 min
Flow Rate=4 ml/min
Wavelength=220
Solvent A=90% Water-10% Methanol-0.1% TFA
Solvent B=10% Water-90% Methanol-0.1% TFA
Column 3=(3) PHENOMENEX-LUNA 4.6×50 mm S10

Step 2:

A solution of 4.0M HCl in dioxane (3.665 mL, 14.66 mmol) was added to tert-butyl(S)-1-((2S,4R)-4-(7-chloro-4-methoxyisoquinolin-1-yloxy)-2-((1R,2S)-1-(cyclopropylsulfonylcarbamoyl)-2-(2,2-difluoroethyl)cyclopropylcarbamoyl)pyrrolidin-1-yl)-3,3-dimethyl-1-oxobutan-2-ylcarbamate (592 mg, 0.753 mmol) and stirred at rt overnight. The reaction was concentrated and dried under vacuum to afford the desired product (2S,4R)-1-((S)-2-amino-3,3-dimethylbutanoyl)-4-(7-chloro-4-methoxyisoquinolin-1-yloxy)-N-((1R,2S)-1-(cyclopropylsulfonylcarbamoyl)-2-(2,2-difluoroethyl)cyclopropyl)pyrrolidine-2-carboxamide, 2 HCl, 0.13dioxane (593 mg, 0.693 mmol, 92% yield) as a light yellow powder. $^1$HNMR spectrum showed it contained 0.13 mole equivalents of 1,4-dioxane as solvate. $^1$H NMR (500 MHz, MeOD) δ 1.05-1.23 (m, 10H), 1.23-1.41 (m, 3H), 1.60-1.84 (m, 2H), 2.10-2.27 (m, 2H), 2.28-2.42 (m, 1H), 2.66 (dd, J=13.73, 6.71 Hz, 1H), 2.93-3.06 (m, 1H), 4.03 (s, 3H), 4.09 (s, 1H), 4.15 (dd, J=12.05, 3.81 Hz, 1H), 4.28 (d, J=11.90 Hz, 1H), 4.65-4.79 (m, 1H), 5.77-6.14 (m, 2H), 7.61 (s, 1H), 7.76 (dd, J=8.85, 2.14 Hz, 1H), 8.09-8.22 (m, 2H), 9.30 (s, 1H). LC-MS (retention time: 2.47 min, Method A), MS m/z 686.1 (M++H).

Step 3:

To a solution of (2S,4R)-1-((S)-2-amino-3,3-dimethylbutanoyl)-4-(7-chloro-4-methoxyisoquinolin-1-yloxy)-N-((1R,2S)-1-(cyclopropylsulfonylcarbamoyl)-2-(2,2-difluoroethyl)cyclopropyl)pyrrolidine-2-carboxamide, 2 HCl (207 mg, 0.273 mmol) and N,N-diisopropylethylamine (0.142 mL, 0.818 mmol) in DCM (5 mL) was added Fmoc-isothiocyanate (97 mg, 0.327 mmol). The resulting brown reaction mixture was stirred at 25° C. for 2 h. The reaction mixture was washed with 0.1 M HCl. The organic layer was washed with brine, dried over MgSO$_4$ and concentrated to a brown foam (11.6 g). This product was purified by flash column chromatography (SiO$_2$, eluted with gradient 5%~50% acetone-hexane) to afford (2S,4R)-1-((S)-2-(3-(((9H-fluoren-9-yl)methoxy)carbonyl)thioureido)-3,3-dimethylbutanoyl)-4-(7-chloro-4-methoxyisoquinolin-1-yloxy)-N-((1R,2S)-1-(cyclopropylsulfonylcarbamoyl)-2-(2,2-difluoroethyl)cyclopropyl)pyrrolidine-2-carboxamide (190 mg, 0.177 mmol, 64.8% yield) as white solid. $^1$H NMR (500 MHz, MeOD) δ 1.01 (m., 2H), 1.10-1.18 (s, 9H), 1.18-1.29 (m, 2H), 1.28-1.42 (m, 1H), 1.58-1.76 (m, 2H), 2.13-2.26 (m, 2H), 2.26-2.41 (m, 1H), 2.65 (m, 1H), 2.96 (m, 1H), 3.95-4.10 (m, 4H), 4.29 (t, J=6.87 Hz, 1H), 4.39-4.46 (m, 1H), 4.46-4.55 (m, 1H), 4.66 (dd, J=10.68, 6.71 Hz, 1H), 4.79 (s, 1H), 5.80 (m, 1H), 5.82-6.10 (m, 1H), 7.33 (t, J=7.63 Hz, 2H), 7.42 (t, J=7.48 Hz, 2H), 7.57 (s, 1H), 7.68 (d, J=8.55 Hz, 2H), 7.82 (d, J=7.32 Hz, 2H), 8.03-8.18 (m, 2H). LC (retention time: 3.44 min, Method A).

Step 4:

To a solution of (2S,4R)-1-((S)-2-(3-(((9H-fluoren-9-yl)methoxy)carbonyl)thioureido)-3,3-dimethylbutanoyl)-4-(7-chloro-4-methoxyisoquinolin-1-yloxy)-N-((1R,2S)-1-(cyclopropylsulfonylcarbamoyl)-2-(2,2-difluoroethyl)cyclopropyl)pyrrolidine-2-carboxamide (184 mg, 0.190 mmol) in DCM (2 mL) was added piperidine (0.2 mL, 2.020 mmol). The formed light yellow solution was stirred at 25° C. After 2 h, solvent and excess piperidine were removed under reduced pressure using a roto-evaporator. The resulting yellow solid was taken up in DCM and washed with 0.1N HCl. The organic layer was washed with brine, dried over MgSO$_4$ and concentrated to a light yellow solid. Purification by Biotage column, eluted with gradient 0-5% MeOH-DCM failed to seperate the desired product from by product, therefore the formed product in this step was used as crude for future reactions. LC-MS (retention time: 2.89 min, Method A), MS m/z 745.2 (M++H).

Step 5:

To a solution of (2S,4R)-4-(7-chloro-4-methoxyisoquinolin-1-yloxy)-N-((1R,2S)-1-(cyclopropylsulfonylcarbamoyl)-2-(2,2-difluoroethyl)cyclopropyl)-1-((S)-3,3-dimethyl-2-thioureidobutanoyl)pyrrolidine-2-carboxamide (30 mg, 0.040 mmol) and N,N-diisopropylethylamine (0.014 mL, 0.081 mmol) in DMF (1 mL) was added 2-bromo-1-(4-fluoro-3-(trifluoromethyl)phenyl)ethanone (22.95 mg, 0.081 mmol). The formed light yellow solution was stirred at 25° C. After 3 h, the reaction mixture was diluted with MeOH (1 mL) and purified by reverse phase HPLC using solvent system and conditions as the following: solvent A=H$_2$O, solvent B=MeOH, both containing 0.1% TFA; 15% B to 100% B 15 mins, hold at 100% B 5 mins. The combined HPLC fractions was concentrated to almost dryness, filtered, washed the cake with water. The collected cake was dried in vacuo overnight to afford the desired product (2S,4R)-4-(7-chloro-4-methoxyisoquinolin-1-yloxy)-N-((1R,2S)-1-(cyclopropylsulfonylcarbamoyl)-2-(2,2-difluoroethyl)cyclopropyl)-1-((S)-2-(4-(4-fluoro-3-(trifluoromethyl)phenyl)thiazol-2-ylamino)-3,3-dimethylbutanoyl)pyrrolidine-2-carboxamide (26 mg, 0.027 mmol, 65.9% yield) as an off-white solid. $^1$H NMR (500 MHz, MeOD) δ 1.10-1.15 (m, 2H), 1.18 (s, 9H), 1.24-1.42 (m, 3H), 1.61-1.75 (m, 2H), 2.09-2.32 (m, 3H), 2.45 (dd, J=13.73, 6.71 Hz, 1H), 2.92-3.10 (m, 1H), 3.95 (s, 3H), 4.18 (dd, J=11.44, 3.51 Hz, 1H), 4.51 (dd, J=10.83, 6.87 Hz, 1H), 4.87-4.93 (m, 1H), 4.99 (d, J=10.99 Hz, 1H), 5.74-6.05 (m, 1H), 6.08 (br. s., 1H), 6.75-6.91 (m, 2H), 7.37 (d, J=1.83 Hz, 1H), 7.42 (s, 1H), 7.52 (dd, J=8.85, 2.14 Hz, 1H), 7.82 (ddd, J=8.39, 2.44, 2.29 Hz, 1H), 7.86-8.00 (m, 2H). LC (retention time: 3.34 min, Method A).

Preparation of Compound 98, Example 98

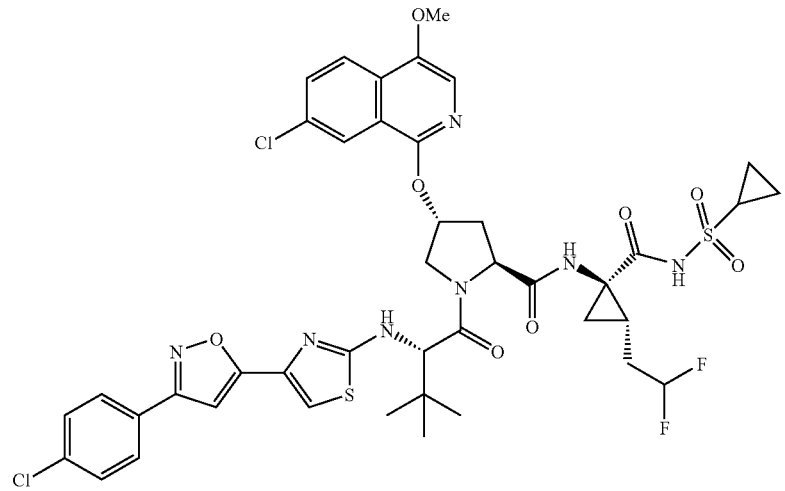

Compound 98

Compound 98 was prepared in 41.5% yield following the same procedure as described for the preparation of compound 97, except 2-bromo-1-(3-(4-chlorophenyl)isoxazol-5-yl)ethanone was used instead of -bromo-1-(4-fluoro-3-(trifluoromethyl)phenyl)ethanone in step 5. $^1$H NMR (500 MHz, MeOD) δ 1.06-1.17 (m, 2H), 1.19-1.26 (m, 9H), 1.25-1.40 (m, 3H), 1.56-1.75 (m, 2H), 2.11-2.29 (m, 3H), 2.36 (dd, J=13.58, 6.26 Hz, 1H), 2.96-3.07 (m, 1H), 3.81 (s, 3H), 4.21 (dd, J=11.60, 3.66 Hz, 1H), 4.52 (dd, J=10.99, 6.71 Hz, 1H), 4.77-4.86 (m, 1H), 5.14 (d, J=11.29 Hz, 1H), 5.75-6.10 (m, 1H), 6.19-6.32 (m, 1H), 6.70 (s, 1H), 7.14 (s, 1H), 7.19-7.33 (m, 5H), 7.40-7.51 (m, 2H), 7.75 (d, J=8.85 Hz, 1H). LC (retention time: 3.35 min, Method A).

Preparation of Compound 99, Example 99

Compound 99

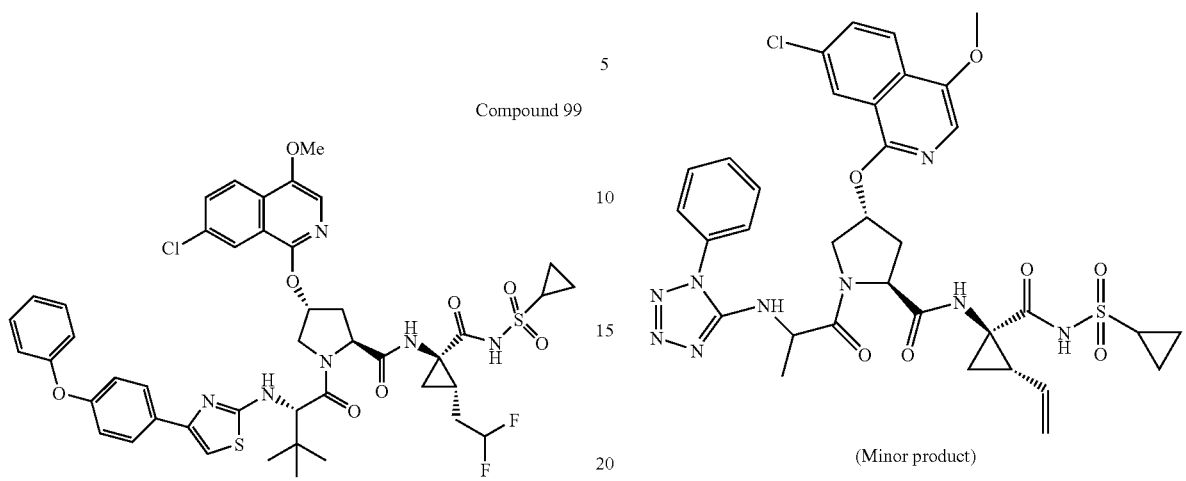

Compound 99 was prepared in 41.6% yield following the same procedure as described for the preparation of compound 97, except 2-bromo-1-(4-phenoxyphenyl)ethanone was used instead of -bromo-1-(4-fluoro-3-(trifluoromethyl)phenyl)ethanone in step 5. $^1$H NMR (500 MHz, MeOD) δ ppm 1.13 (dd, J=8.09, 2.59 Hz, 2H), 1.15-1.24 (m, 9H), 1.24-1.41 (m, 3H), 1.57-1.76 (m, 2H), 2.07-2.33 (m, 3H), 2.45 (dd, J=13.73, 6.71 Hz, 1H), 2.94-3.07 (m, 1H), 3.97 (s, 3H), 4.19 (dd, J=11.44, 3.51 Hz, 1H), 4.52 (dd, J=10.53, 6.87 Hz, 1H), 4.77-4.86 (m, 1H), 4.97 (t, J=11.60 Hz, 1H), 5.72-6.10 (m, 2H), 6.53 (d, J=8.85 Hz, 2H), 6.60-6.74 (m, 3H), 7.02-7.13 (m, 1H), 7.27 (t, J=7.63 Hz, 2H), 7.46 (s, 1H), 7.53-7.67 (m, 4H), 8.01 (d, J=8.85 Hz, 1H). LC (retention time: 3.46 min, Method A).

Preparation of Compound 100, Example 100

Compounds 100A

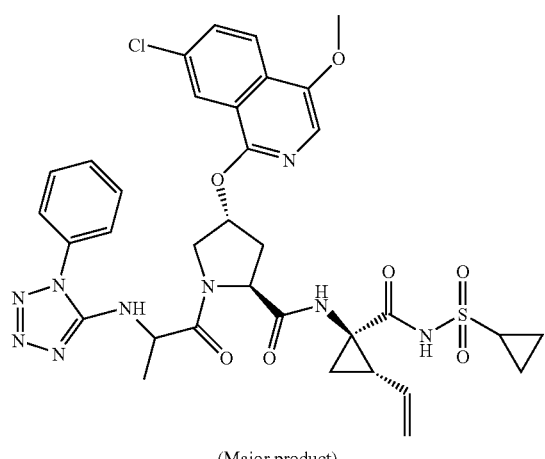

(Major product)

Compounds 100B

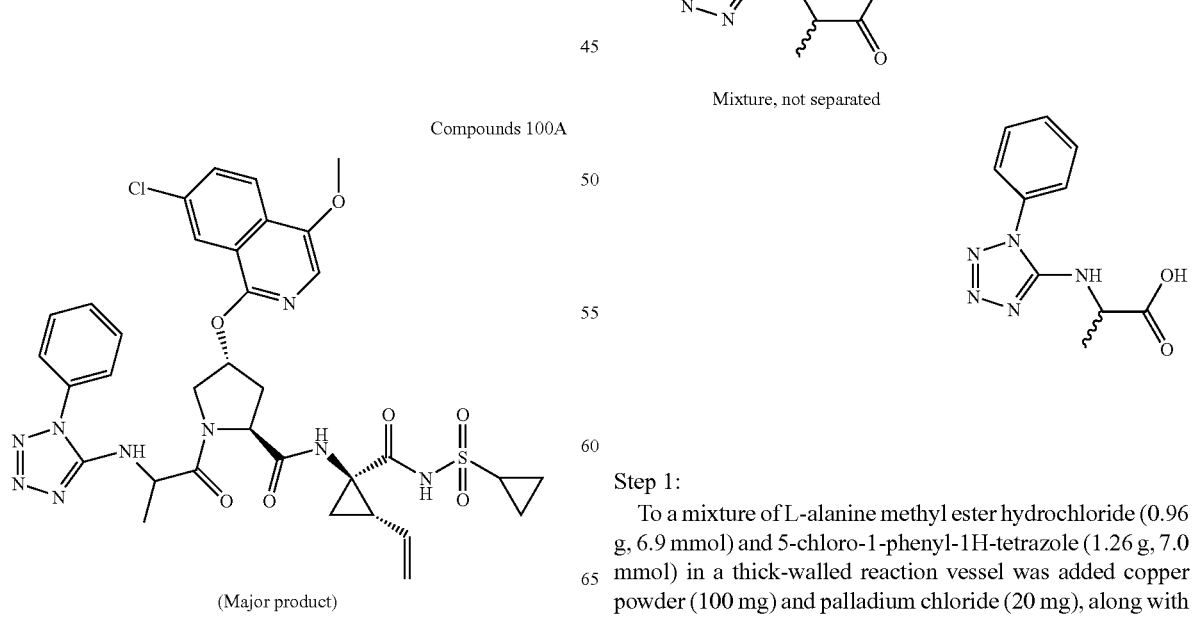

(Minor product)

Scheme 1 of Example 100

Step 1:
To a mixture of L-alanine methyl ester hydrochloride (0.96 g, 6.9 mmol) and 5-chloro-1-phenyl-1H-tetrazole (1.26 g, 7.0 mmol) in a thick-walled reaction vessel was added copper powder (100 mg) and palladium chloride (20 mg), along with anhydrous potassium carbonate (1.0 mg) in dry dioxane (30 mL). The suspension was warmed to 120° C. forming a greenish mixture. The green color did not stay for long (less than 20 minutes at 120° C.) before the solution phase changed back into very light yellow. Heating continued overnight. A pair of very similar products were formed from the reaction as monitored by TLC (20% ethyl acetate v/v in hexanes, eluted twice). LCMS showed a pair of barely separated peaks of the same molecular weight. The reaction mixture was washed with 1N HCl, organic residue was extracted into ethyl acetate (2×25 mL). The crude product was partitioned over a normal phase silica gel column to give 198 mg (12%) of a mixture of two components, in addition to the unreacted starting materials. LCMS [Phenomenex-Luna 4.6×50 mm S10, 0% B to 70% B in 4 minutes at flow rate 4 mL/minute] Rt=2.79 and 2.96 minutes, both gave the same [M+H]$^+$=248.18. Partial NMR chemical shifts are recorded as follows: $^1$H NMR (400 MHz, CHLOROFORM-D) δ ppm 1.53 (d, J=7.05 Hz, 3H, for MeCH), 3.74 (s, 3H, for MeO) for the major isomer (53%); 1.83 (d, J=7.05 Hz, 3H, MeCH), 3.77 (s, 3H, MeO) for the minor isomer (47%). This mixture was used in the next step without further separation.

Step 2:

The mixed tetrazole derivatives from step 1 (198 mg, 0.8 mmol) was suspended into methanol (2 mL) at room temperature. Sodium hydroxide solution (1.0 N, 0.4 mL) was added, mixture stirred for an hour forming a clear solution. It was extracted with ether (2×5 mL), the aqueous phase was neutralized with 1 N HCl. The free acids were extracted into ether, concentrated under high vacuum to give 92.3 mg (49.5%) of the desired carboxylic acids.

Scheme 2 of Example 100

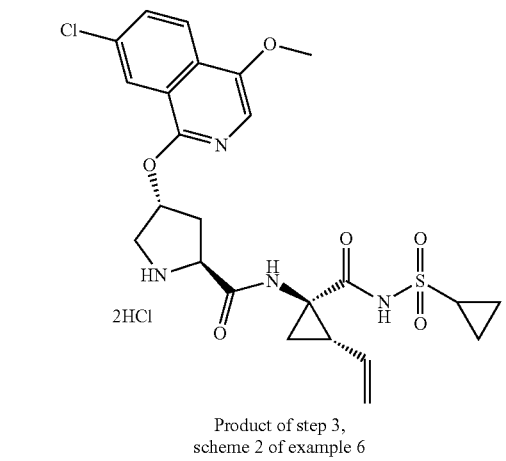

Product of step 3, scheme 2 of example 6

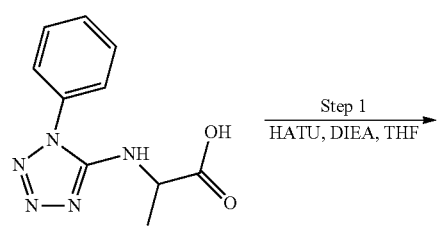

Step 1
HATU, DIEA, THF

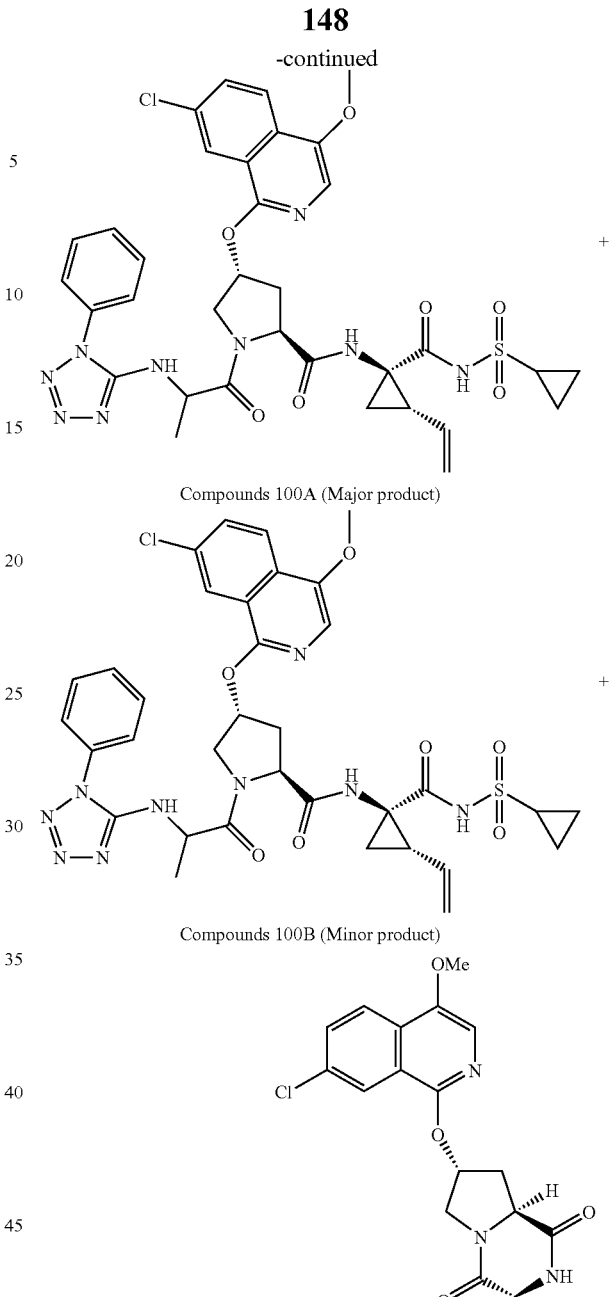

Step 1:

The product of step 2, scheme 1 of example 100 (46 mg, 0.2 mmol, mixture of isomers) was mixed with the product of step 3, scheme 2 of example 6 (105 mg, 0.2 mmol, along with HATU (225 mg, 0.59 mmol) in dry THF (4 mL) under nitrogen. To this mixture at room temperature was added Hünig's base (50 µL, 0.3 mmol), stirring continued overnight. The thick suspension was diluted with 0.5 N HCl, organic residues were extracted into ethyl acetate (3×5 mL). The crude product was purified on a preparative HPLC [YMC combiprep ODS 30×50 mm S5, 30% B to 100% B in 12 minutes at flow rate 40 mL/minute] to give two major fractions at RT 9.6 and 10.1 minutes. The faster fraction (35 mg) was the by-product derived from the cyclization of the starting material (the product of step 3, scheme 2 of example 6) under the reaction conditions. The slower fraction was the desired product (58 mg, 39%, mixture of 100A and 100B). LCMS [Phenomenex- Luna 4.6×50 mm S10, eluted with 40% B to 100% B in 4 minutes at flow rate 4 mL/minute] Rt=3.313, [M+H]+= 750.33. Partial NMR chemical shifts are recorded as: $^1$H NMR (400 MHz, CHLOROFORM-D) δ ppm 1.45 (d, J=6.80 Hz, 3H, for MeCH), 3.976 (s, 3H, for MeO) for the major isomer (~⅔); 1.33 (d, J=6.80 Hz 3H, MeCH), 3.984 (s, 3H, MeO) for the minor isomer (~⅓).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Buldi, J. Proc. Natl. Acad. Sci. U.S.A. 94(16),8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J Virol. 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride (MgCl$_2$), 1 µg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% TritonX-100, 10 mM βMB). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 μM final concentration (from a 2 mM stock solution in DMSO stored at −20° C.). HCV NS3/4A protease type 1a (1b), 2-3 nM final concentration (from a 5 μM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 μg/ml Bovine Serum Albumin (Sigma) to the assay buffer and reducing the end protease concentration to 300 pM.

The assay was performed in a 96-well polystyrene black plate from Falcon. Each well contained 25 μl NS3/4A protease complex in assay buffer, 50 μl of a compound of the present disclosure in 10% DMSO/assay buffer and 25 μl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nM at 25° C. Reactions were generally followed for approximately 15 min.

The percent inhibition was calculated with the following equation:

$$100 - [(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y = A + ((B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using a fluorometric Amino-Methyl-Coumarin (AMC) substrate specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

Compound concentrations varied from 100 to 0.4 μM depending on their potency. The enzyme assays were each initiated by addition of substrate to enzyme-inhibitor pre-incubated for 10 min at room temperature and hydrolysis to 15% conversion as measured on cytofluor.

The final conditions for each assay were as follows:
50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with 5 μM LLVY-AMC and 1 nM Chymotrypsin.
50 mM Tris-HCl, pH 8.0, 50 mM NaCl, 0.1 mM EDTA, 3% DMSO, 0.02% Tween-20, 5 μM succ-AAPV-AMC and 20 nM HNE or 8 nM PPE;
100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 μM Z-FR-AMC diluted in $H_2O$.

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Assession number:AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamar Blue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 μl). The cells were lysed with 25 μl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 μM final from a 2 mM stock in 100% DMSO. The plate was then placed into the Cytofluor 4000 instrument which had been set to 340 nm excitation/490 nm emission, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, *J. Virol.* 75(10):4614-4624 (2001)). The replicon construct described for our FRET assay was modified by inserting cDNA encoding a humanized form of the Renilla luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, Science 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for Renilla Luciferase activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 min to 2 h at room temperature. Dual-Glo Stop & Glo Reagent (50 µl) was then added to each well, and plates were rocked again for an additional 10 min to 2 h at room temperature. Plates were read on a Packard TopCount NXT using a luminescence program. The percentage inhibition was calculated using the formula below:

% control=average luciferase signal in experimental wells (+compound) average luciferase signal in DMSO control wells (−compound)

The values were graphed and analyzed using XLfit to obtain the $EC_{50}$ value.
Representative compounds of the disclosure were assessed in the HCV enzyme assays, HCV replicon cell assay and/or in several of the outlined specificity assays. For example, Compound 68 was found to have an $IC_{50}$ of 4 nanomolar (nM) against the NS3/4A BMS strain in the enzyme assay. Similar potency values were obtained with the published H177 ($IC_{50}$ of 1.9 nM) and J4L6S ($IC_{50}$ of 0.9 nM) strains. The $EC_{50}$ value in the replicon FRET assay was 5.7 nM and 2 nM in the replicon Luciferase assay. In the specificity assays, the same compound was found to have the following activity: HLE>50 µM; PPE>50 µM; Chymotrypsin=3 µM; Cathepsin B 15 µM. These results indicate this family of compounds is highly specific for the NS3 protease and many of these members inhibit HCV replicon replication.
The compounds of the current disclosure were tested and found to have activities in the ranges as follow:
$IC_{50}$ Activity Range (for compounds tested): A is >200 nM; B is 20-200 nM; C is 1-20 nM.
$EC_{50}$ Activity Ranges (NS3/4A BMS Strain): A is >200 nM; B is 50-200 nM; C is 1-50 nM.

TABLE 2

| Example Number | IC50 Range | EC50 Range |
| --- | --- | --- |
| 1 | C | C |
| 2 | C | C |
| 3 | C | C |
| 4 | C | C |
| 5 | C | C |
| 6 | C | C |
| 7 | C | C |
| 8 | C | C |
| 9 | C | C |
| 10 | C | C |
| 11 | C | C |
| 12 | C | C |
| 13 | C | C |
| 14 | C | C |
| 15 | C | C |
| 16 | 1.00 nM | 6.57 nM |
| 17 | 11.00 nM | 8.95 nM |
| 18A | 54.00 nM | 78.11 nM |
| 18B | 2500.00 nM | — |
| 19 | C | C |
| 20 | 3.00 nM | 3.9 nM |
| 21 | C | C |
| 22 | C | C |
| 23 | B | C |
| 24 | B | C |
| 25 | C | C |
| 26 | C | C |
| 27 | 2.00 nM | 5.26 nM |
| 28 | C | C |
| 29 | C | C |
| 30 | C | C |
| 31 | C | C |
| 32 | C | C |
| 33 | 9.00 nM | 6.84 nM |
| 34 | C | C |
| 35 | C | C |
| 36 | C | C |
| 37 | B | C |
| 38 | C | C |
| 39 | C | C |
| 40 | C | C |
| 41 | C | C |
| 42 | C | C |
| 43 | C | C |
| 44 | C | C |
| 45 | C | C |
| 46 | C | C |
| 47 | C | C |
| 48 | C | C |
| 49 | C | C |
| 50 | 39.00 nM | 18.93 nM |
| 51 | C | C |
| 52 | C | C |
| 53 | 17.00 nM | 20.30 nM |
| 54 | C | C |
| 55 | C | C |
| 56 | C | C |
| 57 | C | C |
| 58 | C | C |
| 59 | C | C |
| 60 | C | — |
| 61 | C | — |
| 62 | C | |
| 63 | C | |
| 64 | C | |
| 65 | C | |
| 66 | C | |
| 67 | B | |
| 68 | C | |
| 69 | C | |
| 70 | 89.00 nM | — |
| 71 | B | — |
| 72 | C | — |
| 73 | C | — |
| 74 | 2.00 nM | — |
| 75 | C | — |
| 76 | C | — |
| 77 | C | — |
| 78 | C | — |
| 79 | C | — |

TABLE 2-continued

| Example Number | IC50 Range | EC50 Range |
| --- | --- | --- |
| 80 | C | — |
| 81 | C | — |
| 82 | C | — |
| 83 | C | — |
| 84 | C | |
| 85 | C | C |
| 86 | 2.00 nM | |
| 87 | C | |
| 88 | C | |
| 89 | C | |
| 90 | C | |
| 91 | C | |
| 92 | C | C |
| 93 | C | C |
| 94 | C | |
| 95 | 17.00 nM | |
| 96 | C | |
| 97 | C | C |
| 98 | C | C |
| 99 | B | B |
| 100 | 795.0 nM | 334.4 nM |

It will be evident to one skilled in the art that the present disclosure is not limited to the foregoing illustrative examples, and that it can be embodied in other specific forms without departing from the essential attributes thereof It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (II)

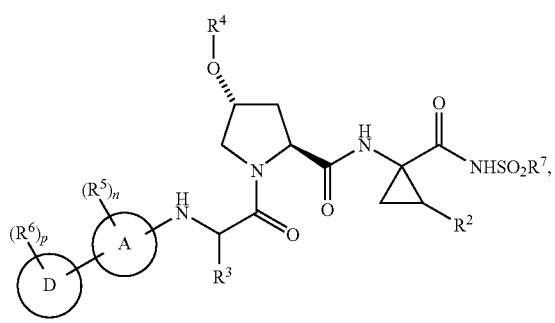

(II)

or a pharmaceutically acceptable salt thereof, wherein n is 0, 1, 2, 3, or 4;

p is 0, 1, 2, 3, 4, or 5;

A is a five- or six-membered partially or fully unsaturated ring optionally containing one, two, three, or four heteroatoms selected from nitrogen, oxygen, and sulfur;

D is a five- to eight-membered partially or fully unsaturated ring optionally containing one, two, three, or four heteroatoms selected from nitrogen, oxygen, and sulfur; wherein the five- to eight-membered ring is optionally fused to a second five- to eight-membered partially or fully unsaturated ring optionally containing one, two, three, or four heteroatoms selected from nitrogen, oxygen, and sulfur;

$R^2$ is selected from hydrogen, alkenyl, alkyl, and cycloalkyl, wherein the alkenyl, alkyl, and cycloalkyl are optionally substituted with halo;

$R^3$ is alkyl;

$R^4$ is heterocyclyl;

each $R^5$ is independently selected from alkoxy, alkoxycarbonyl, alkyl, alkylcarbonyl, alkylsulfanyl, aryl, carboxy, cyano, cycloalkyl, cycloalkyloxy, halo, haloalkyl, haloalkoxy, heterocyclyl, hydroxy, —$NR^cR^d$, $(NR^eR^f)$carbonyl, $(NR^eR^f)$sulfonyl, and oxo; provided that when A is a six-membered substituted ring all $R^5$ groups on the ring other than those where $R^5$ is fluoro must be in the meta and/or para positions relative to the ring's point of attachment to the parent molecular moiety;

each $R^6$ is independently selected from alkoxy, alkoxycarbonyl, alkyl, alkylcarbonyl, alkylsulfanyl, alkylsulfonyl, aryl, aryloxy, carboxy, cyano, cycloalkyl, cycloalkyloxy, halo, haloalkoxy, haloalkyl, heterocyclyl, hydroxy, —$NR^cR^d$, $(NR^eR^f)$carbonyl, $(NR^eR^f)$sulfonyl, and oxo;

$R^7$ is cycloalkyl;

$R^a$ and $R^b$ are independently selected from hydrogen, alkoxy, alkyl, aryl, arylalkyl, cycloalkyl, (cycloalkyl)alkyl, haloalkoxy, haloalkyl, heterocyclyl, and heterocyclylalkyl; or $R^a$ and $R^b$ together with the nitrogen atom to which they are attached form a four to seven-membered monocyclic heterocyclic ring;

$R^c$ and $R^d$ are independently selected from hydrogen, alkoxyalkyl, alkoxycarbonyl, alkyl, alkylcarbonyl, arylalkyl, haloalkoxyalkyl, haloalkoxycarbonyl, haloalkyl, and $(NR^eR^f)$carbonyl; and $R^e$ and $R^f$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

2. A compound of claim 1, or a pharmaceutically acceptable salt thereof, wherein n is 0 or 1;

p is 0, 1, 2, 3, 4, or 5;

A is a five- or six-membered partially or fully unsaturated ring optionally containing one, two, three, or four heteroatoms selected from nitrogen, oxygen, and sulfur;

D is a five- to eight-membered partially or fully unsaturated ring optionally containing one, two, three, or four heteroatoms selected from nitrogen, oxygen, and sulfur; wherein the five- to eight-membered ring is optionally fused to a second five- to eight-membered partially or fully unsaturated ring optionally containing one, two, three, or four heteroatoms selected from nitrogen, oxygen, and sulfur;

$R^2$ is alkenyl;

$R^3$ is alkyl;

$R^4$ is heterocyclyl;

each $R^5$ is independently selected from alkoxy, alkyl, and aryl; provided that when A is a six-membered substituted ring all $R^5$ groups on the ring other must be in the meta and/or para positions relative to the ring's point of attachment to the parent molecular moiety;

each $R^6$ is independently selected from alkoxy, alkyl, alkylsulfonyl, aryloxy, carboxy, cyano, halo, haloalkoxy, haloalkyl, heterocyclyl, hydroxy, and —$NR^cR^d$;

$R^7$ is cycloalkyl; and $R^c$ and $R^d$ are each alkyl.

3. A compound of claim 2, or a pharmaceutically acceptable salt thereof, wherein $R^4$ is heterocyclyl wherein the heterocyclyl is isoquinolinyl.

4. A compound selected from
Compound 1
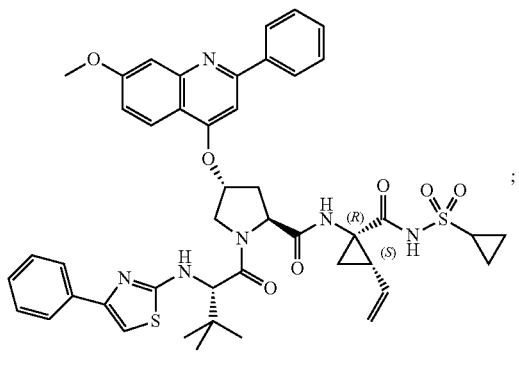
Compound 2
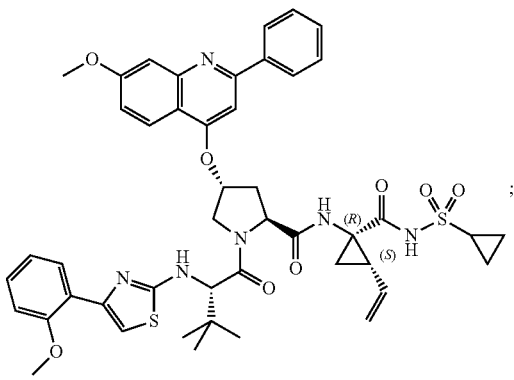
Compound 3
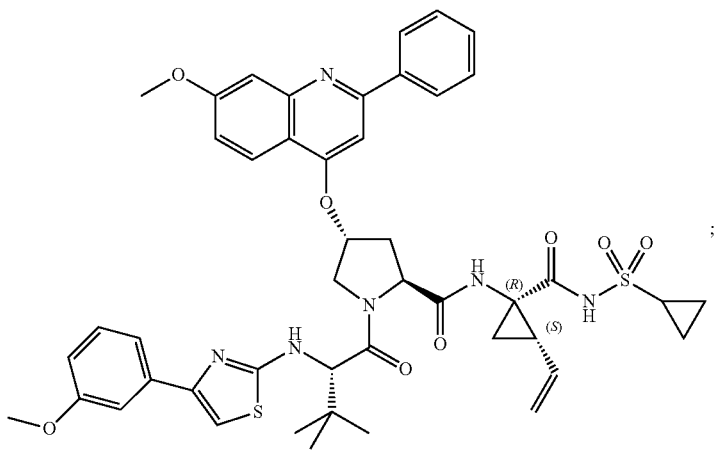
Compound 4
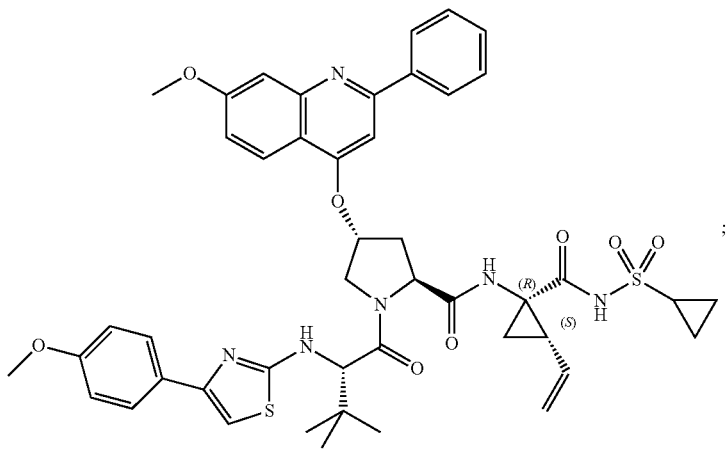

-continued
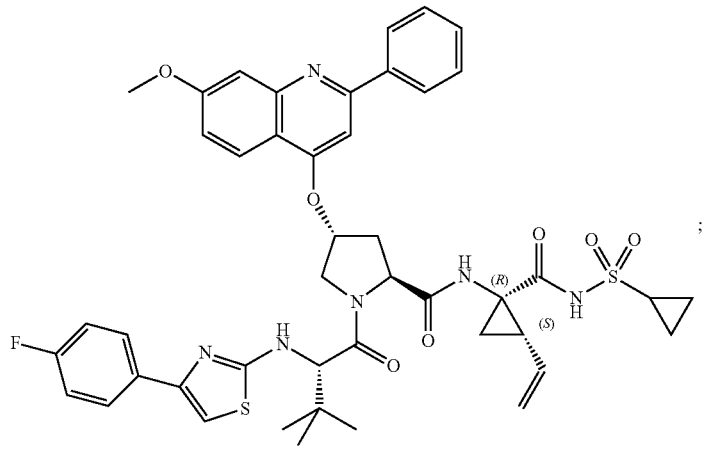
Compound 5
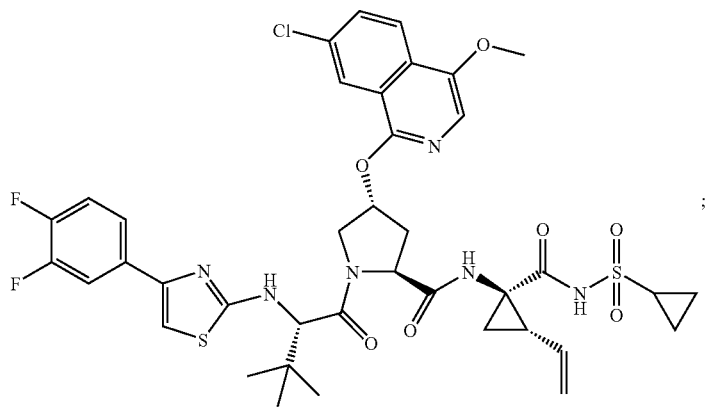
Compound 6
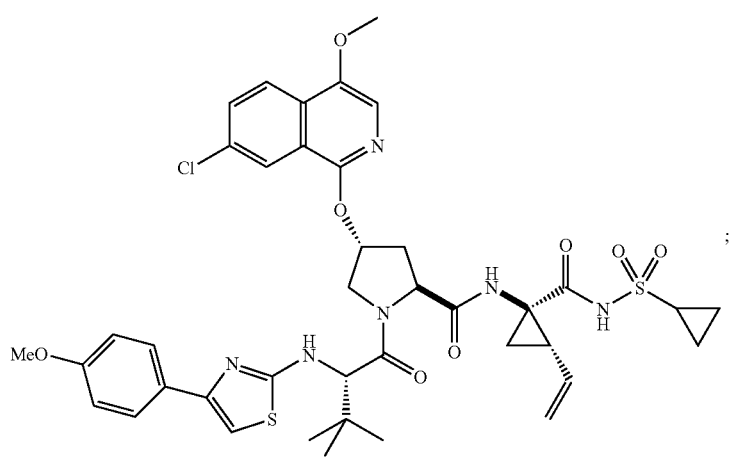
Compound 7

-continued
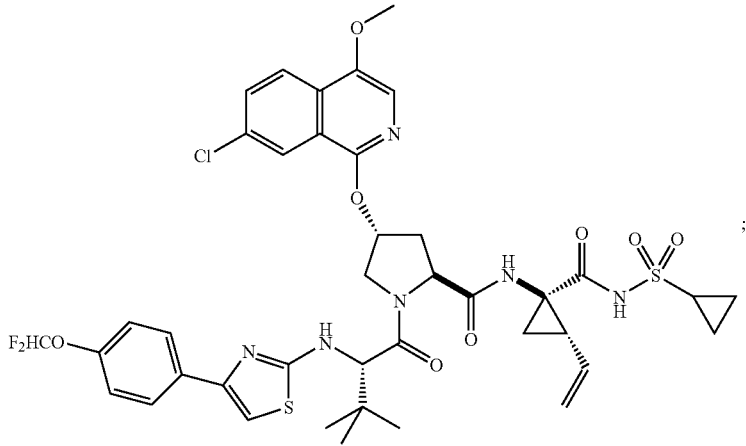
Compound 8
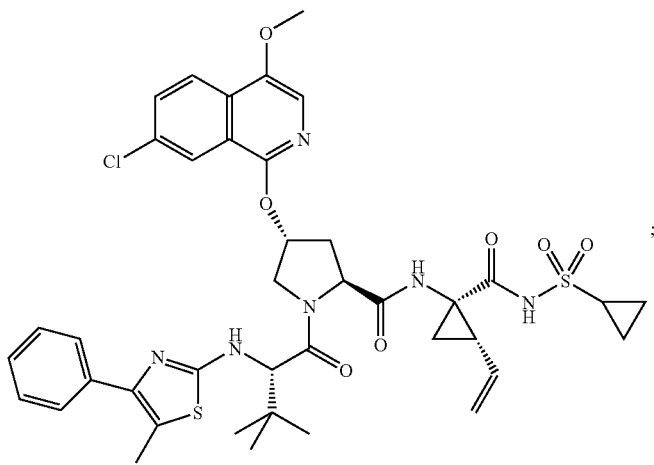
Compound 9
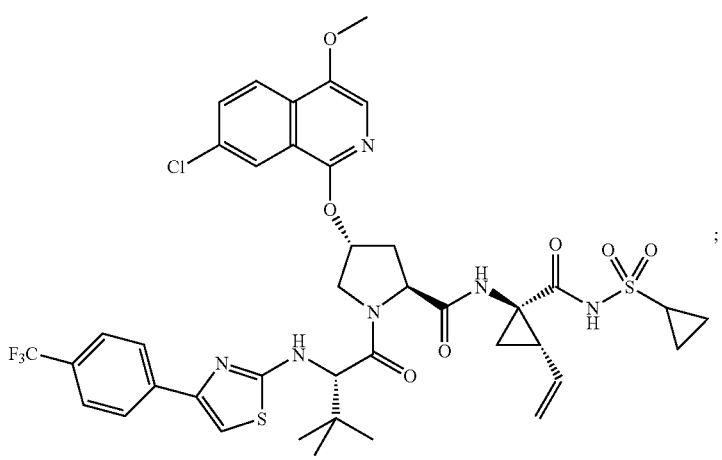
Compound 10

-continued
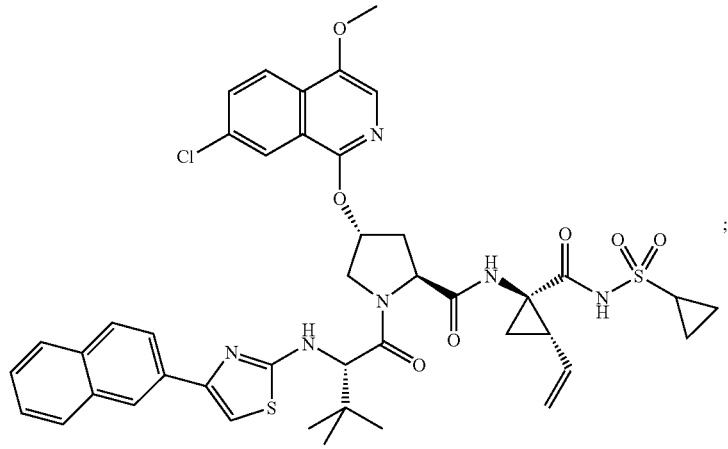
Compound 11
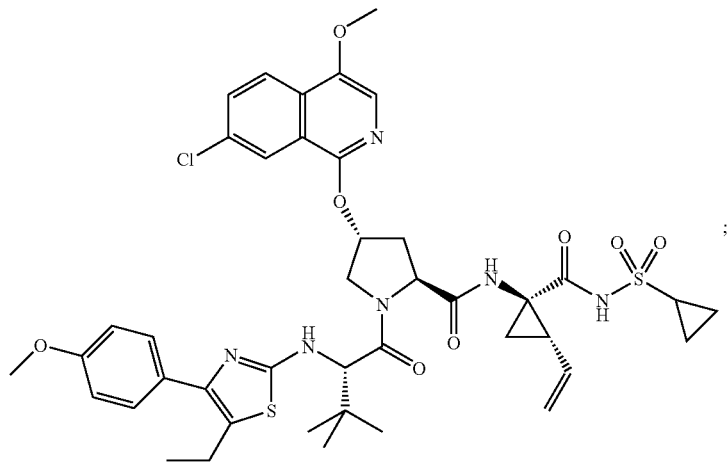
Compound 12
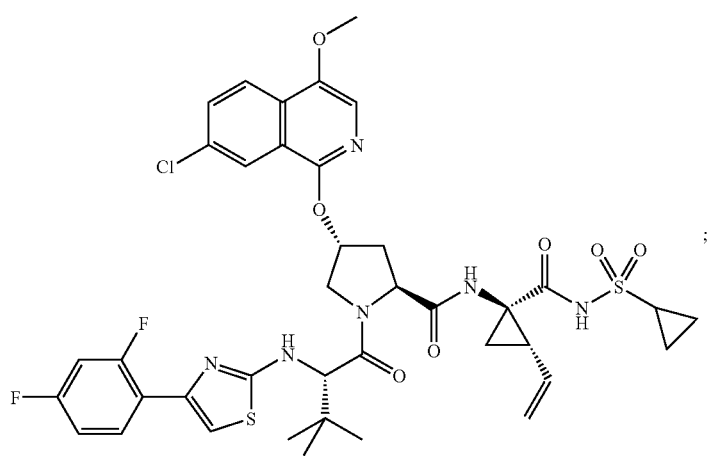
Compound 13

-continued
Compound 14
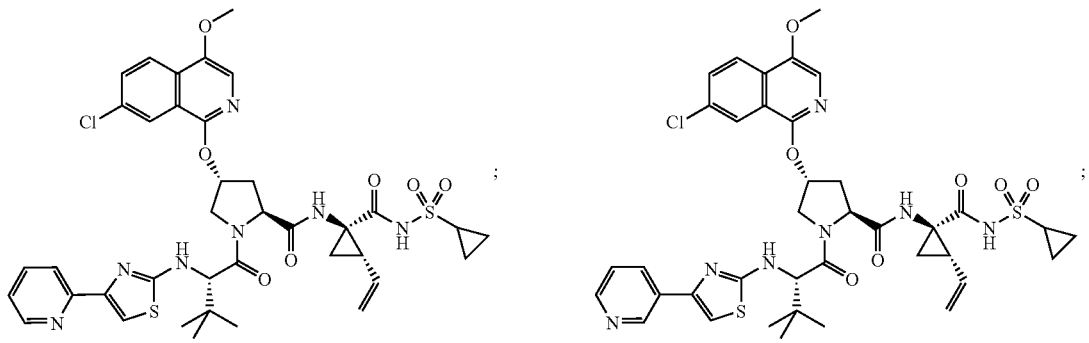
Compound 15
Compound 16
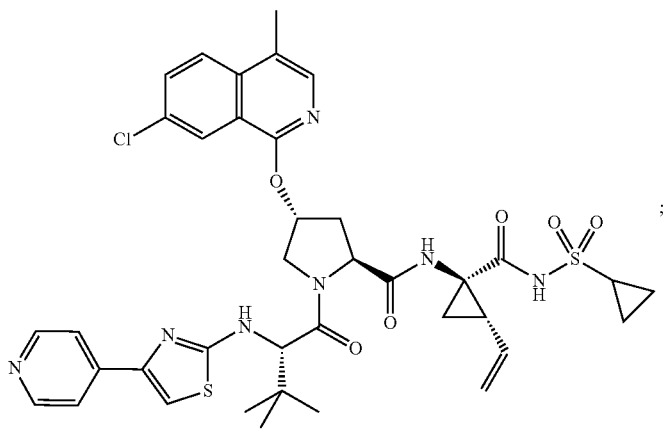
Compound 17
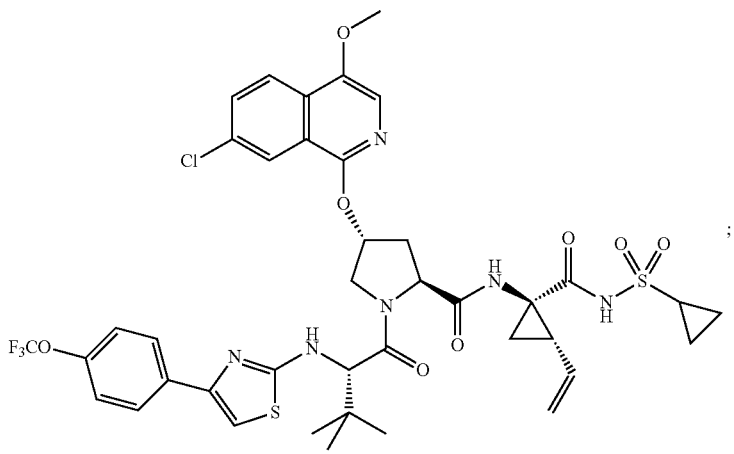
Compound 18A
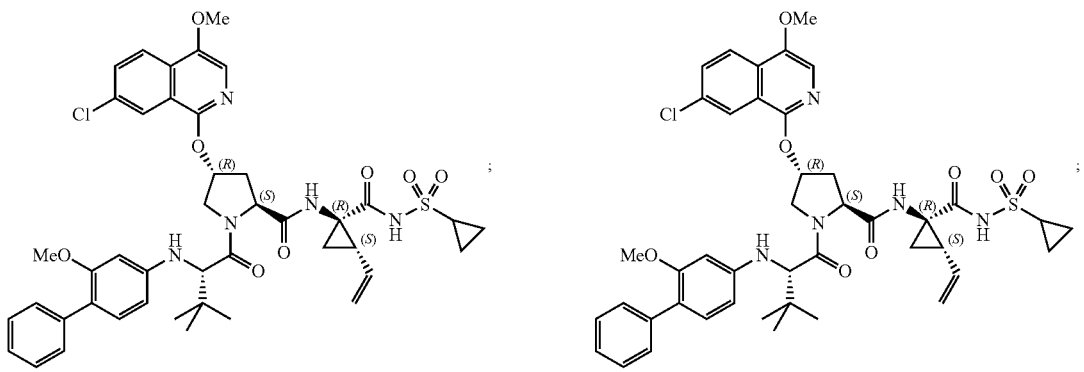
Compound 18B -continued
Compound 19
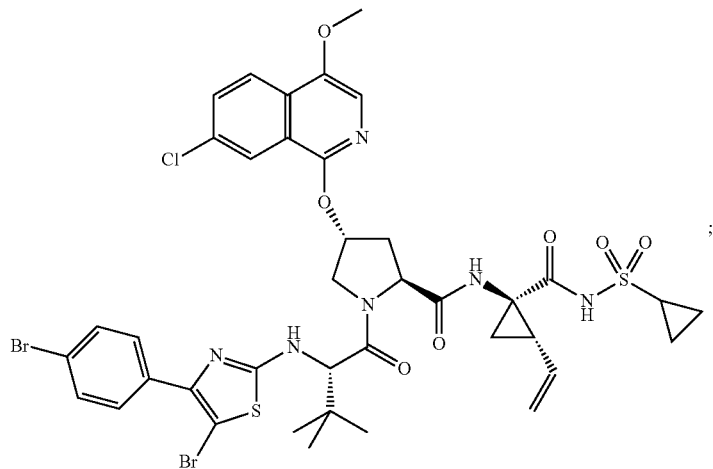
Compound 20
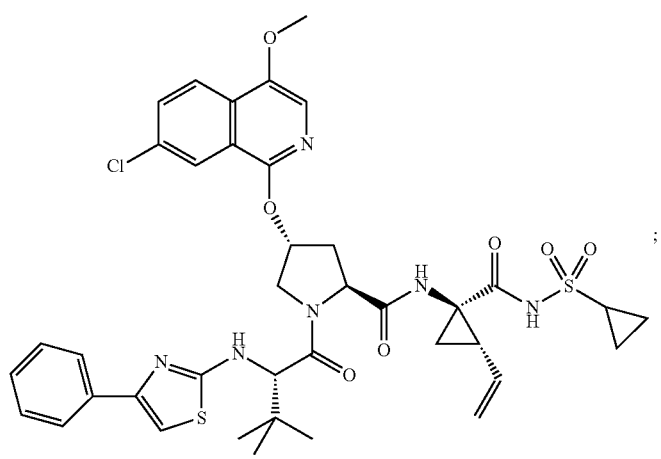
Compound 21
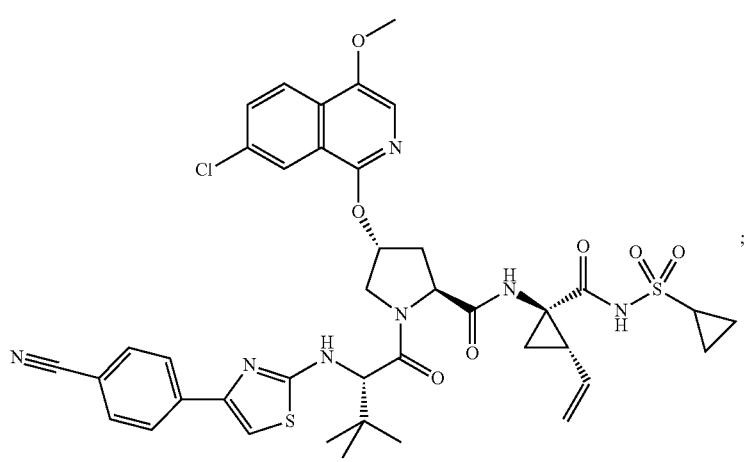

Compound 22
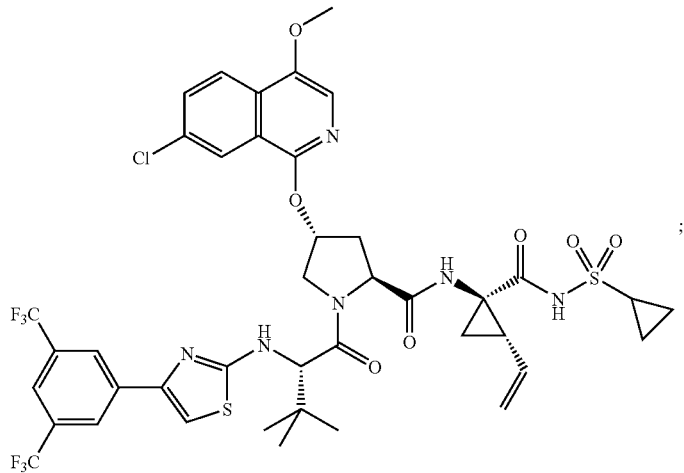
Compound 23
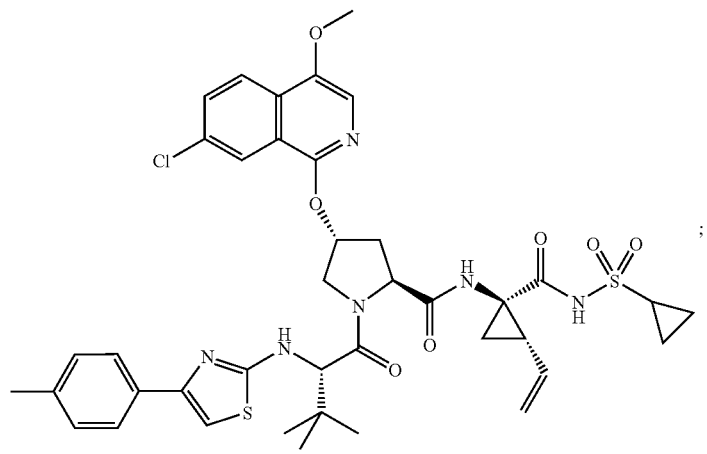
Compound 24
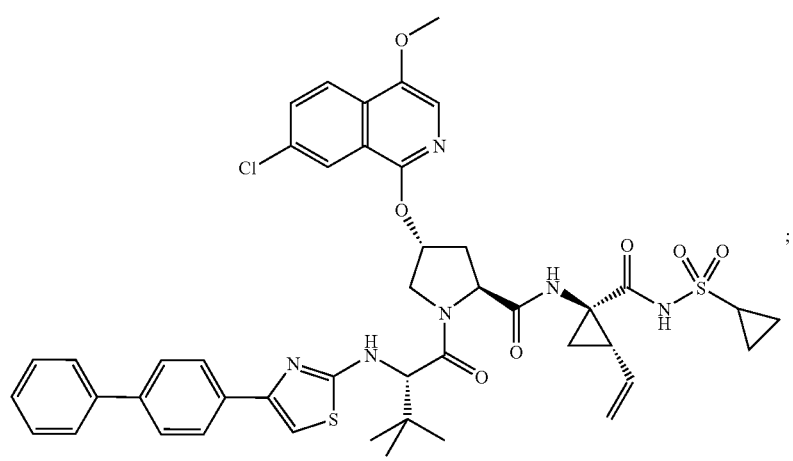

-continued
Compound 25
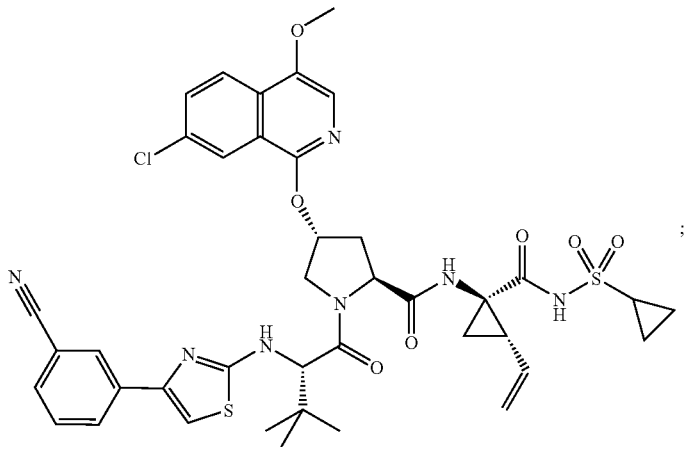
Compound 26
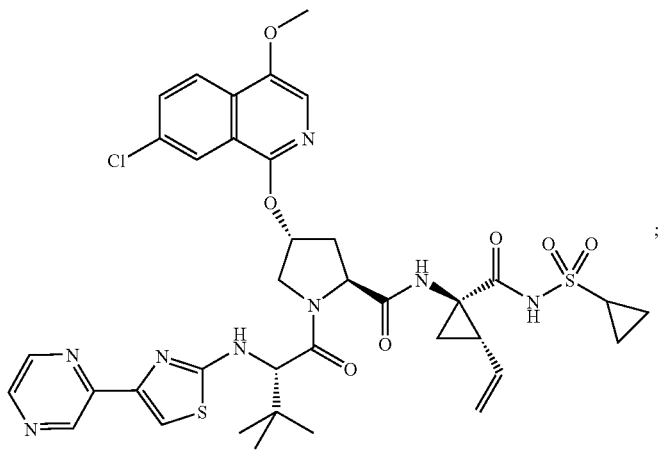
Compound 27
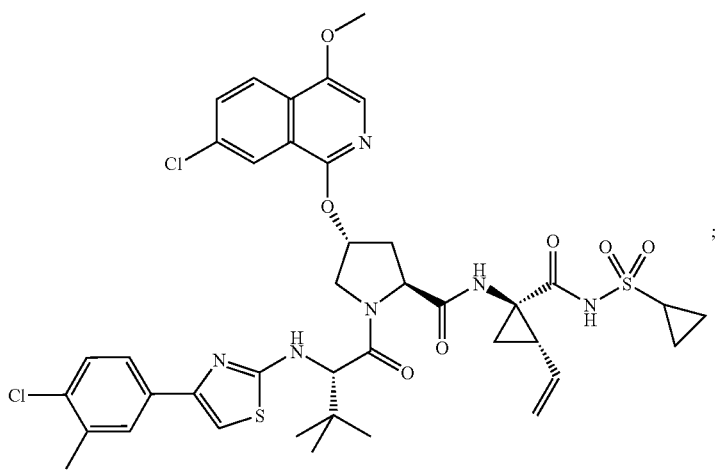

-continued
Compound 28
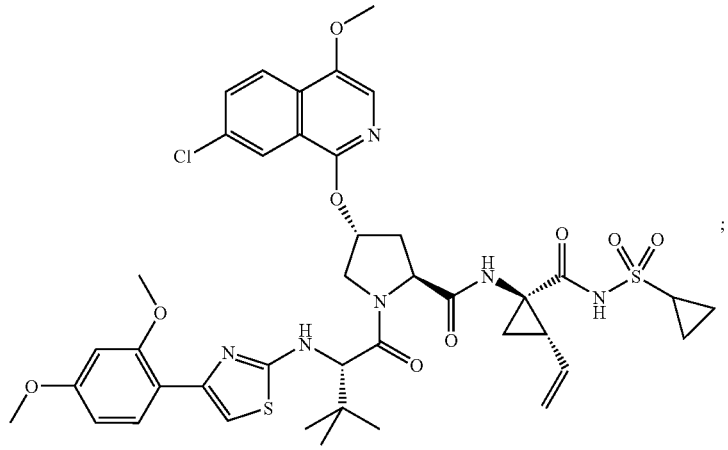
Compound 29
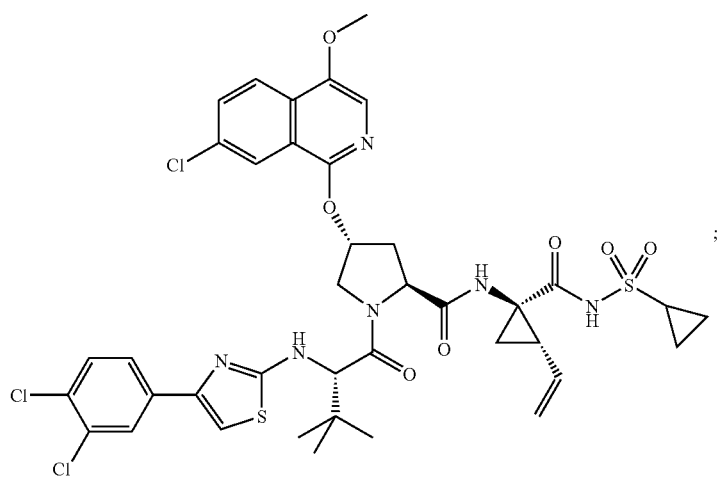
Compound 30
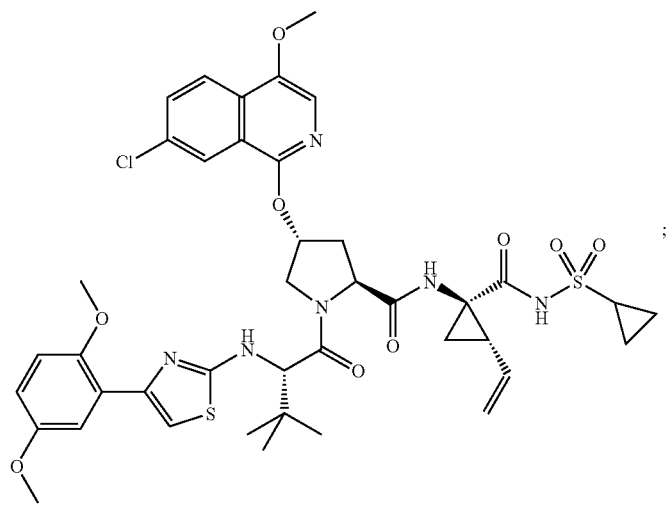

Compound 31
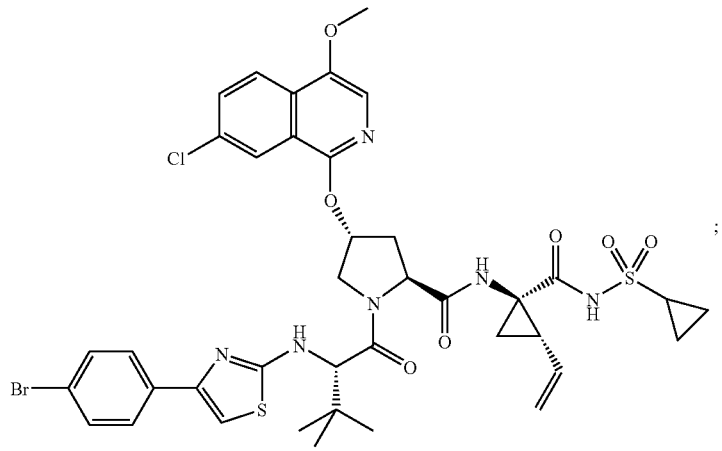
Compound 32
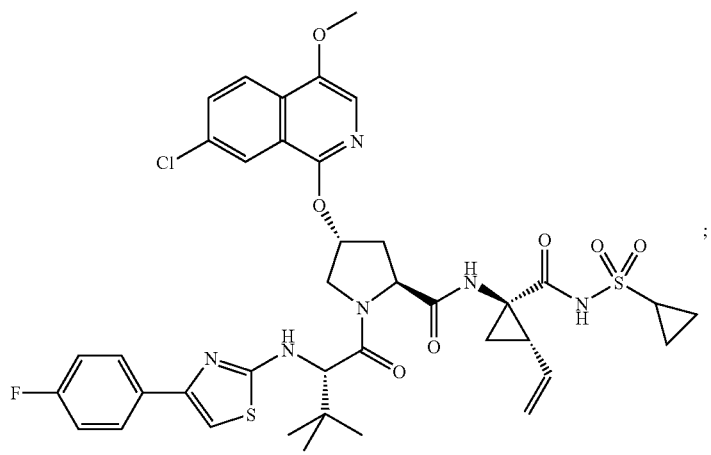
Compound 33
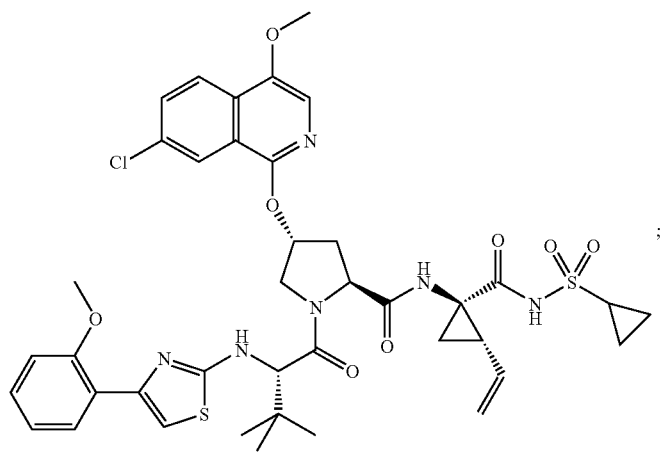

Compound 34
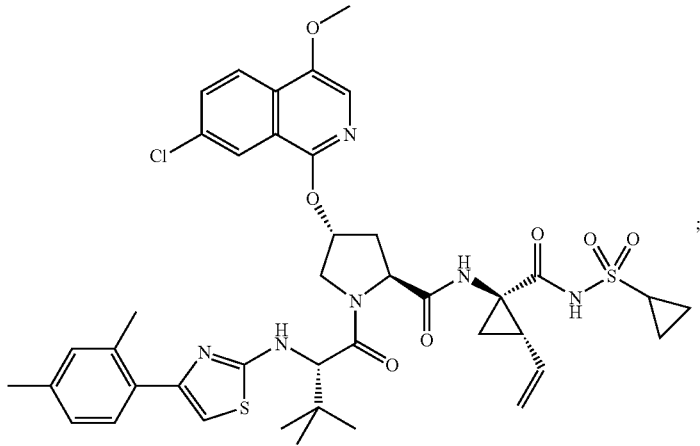
Compound 35
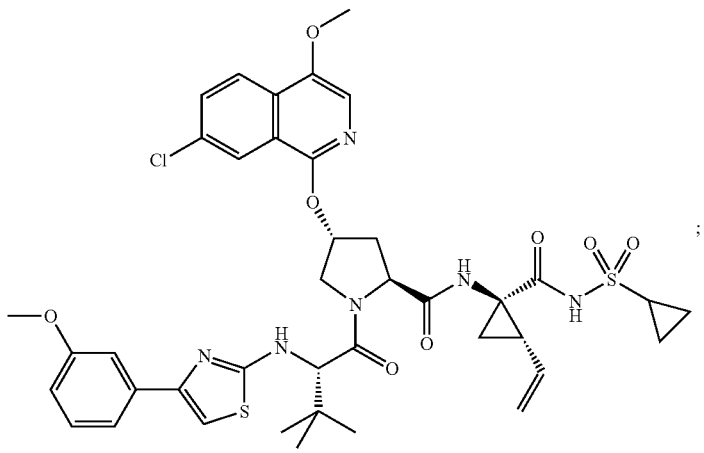
Compound 36
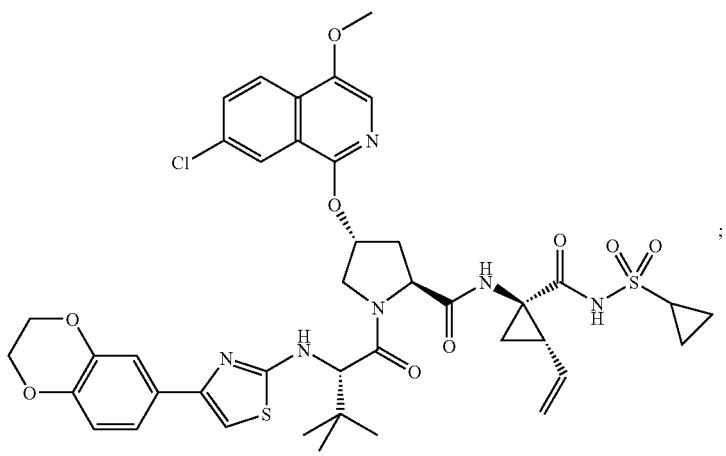

-continued
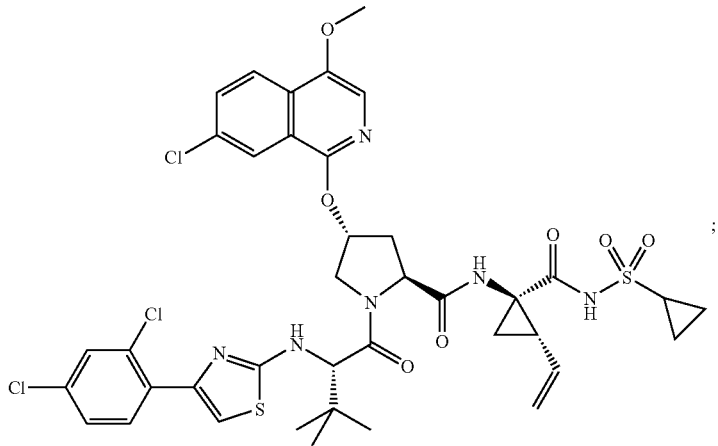
Compound 37
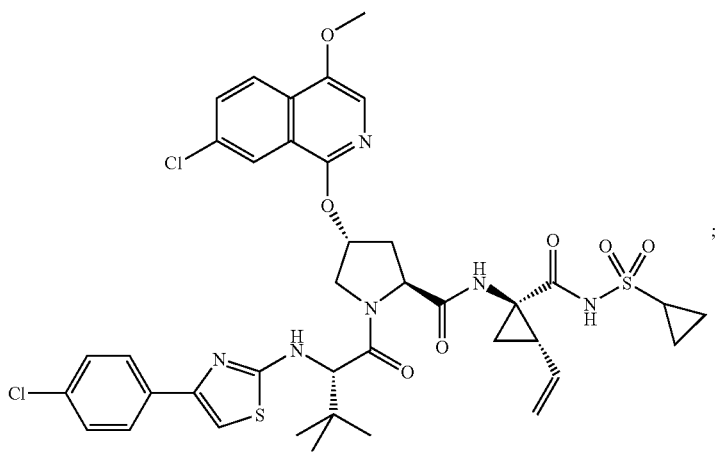
Compound 38
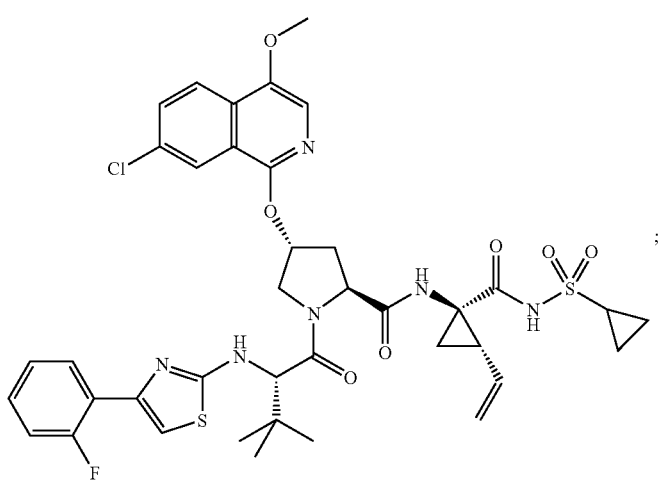
Compound 39

-continued
Compound 40
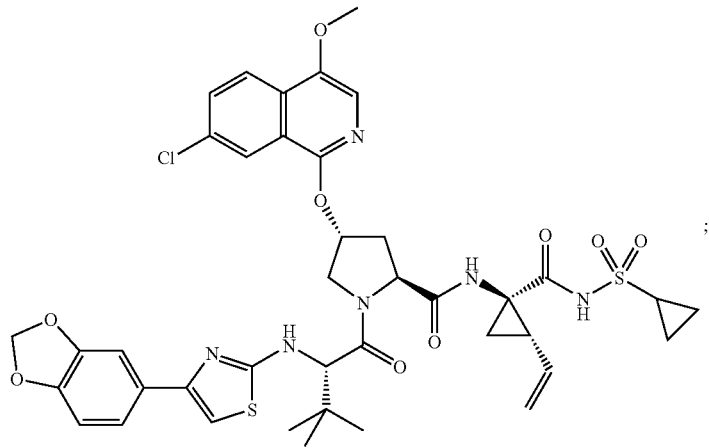
Compound 41
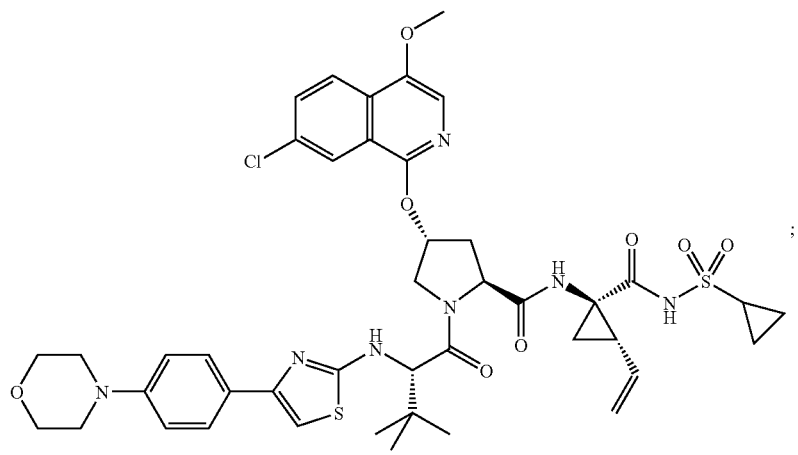
Compound 42
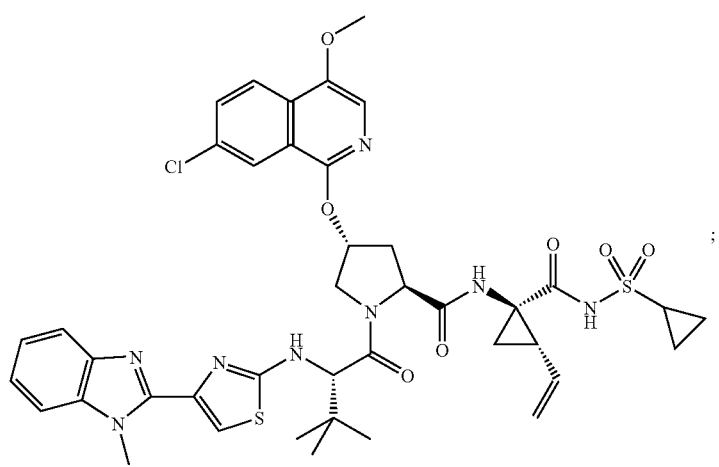

Compound 43
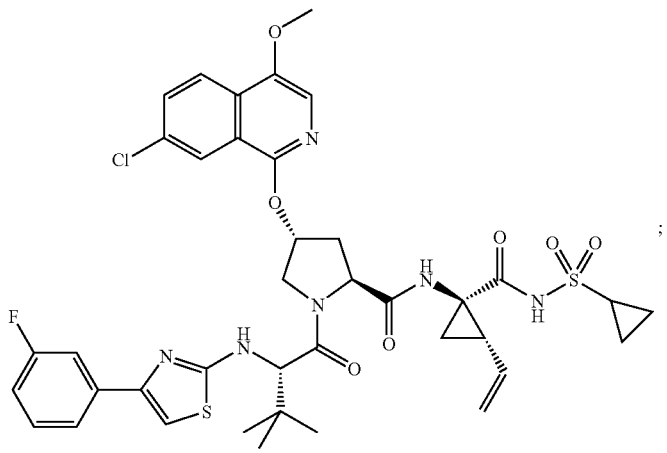
Compound 44
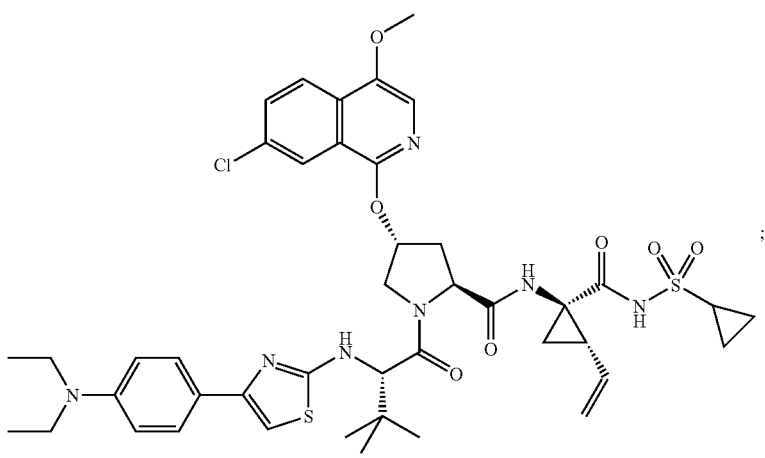
Compound 45
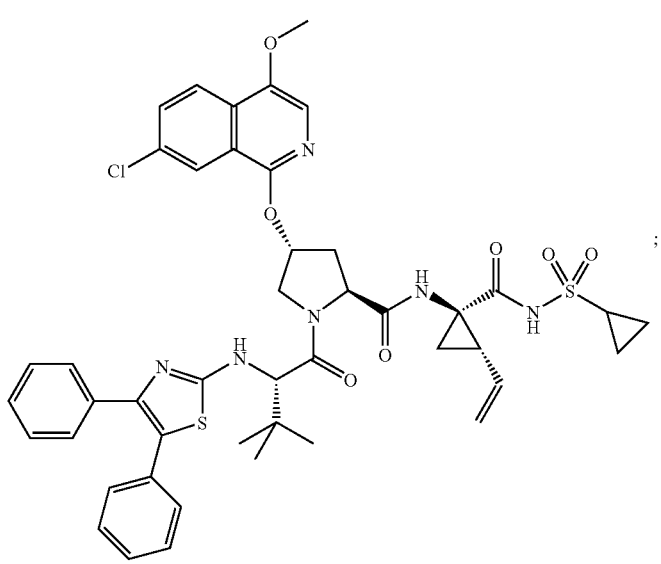

-continued
Compound 46
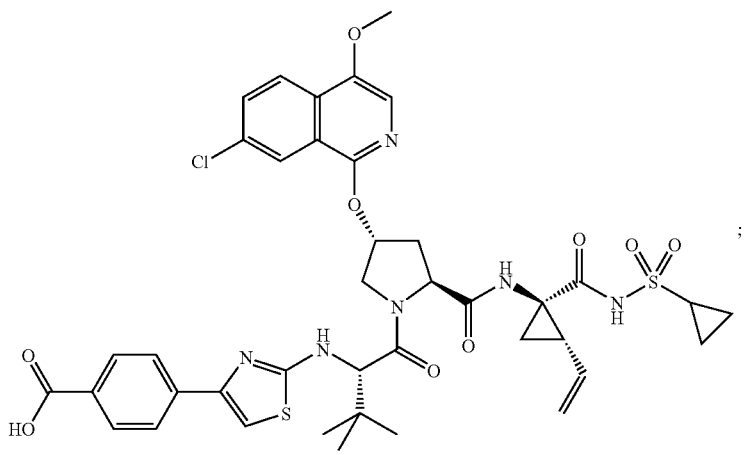
Compound 47
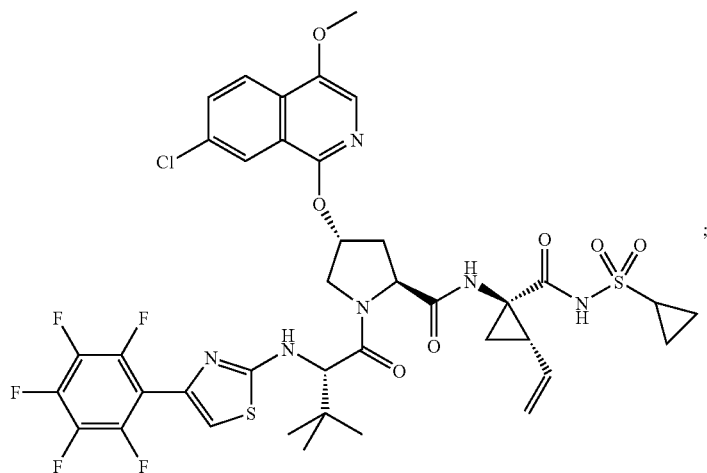
Compound 48
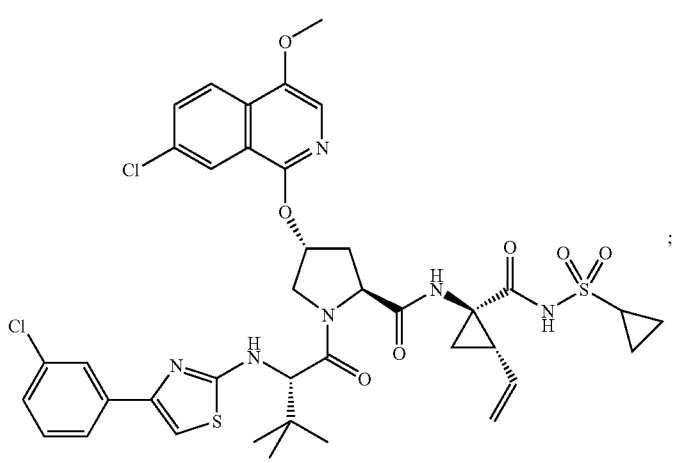

Compound 49
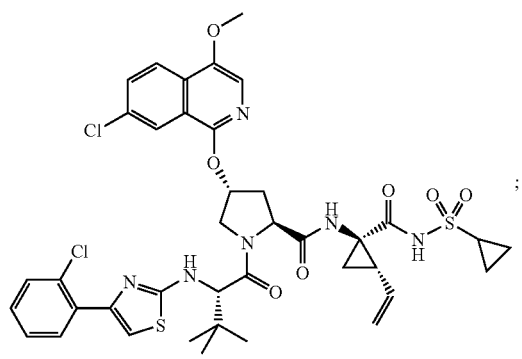
Compound 50
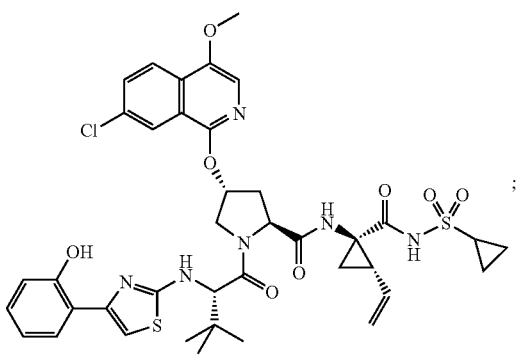
Compound 51
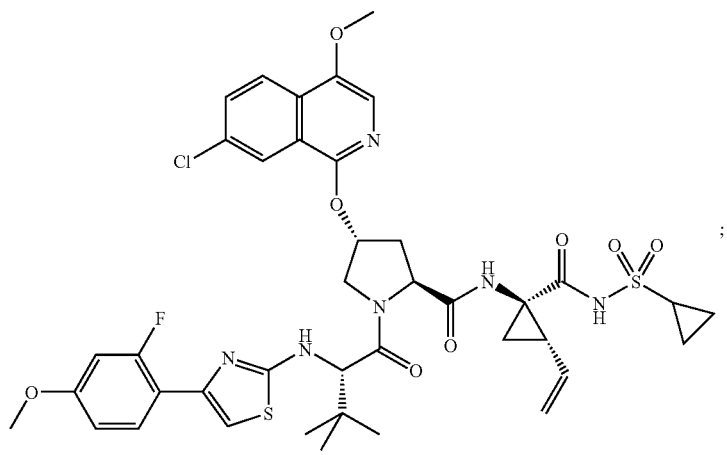
Compound 52
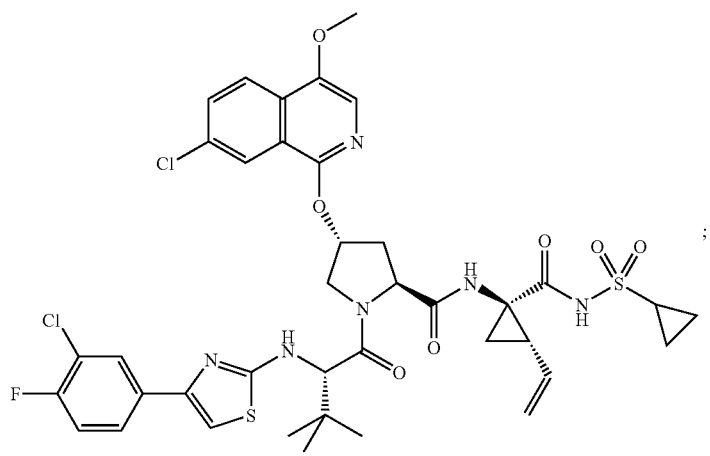
Compound 53
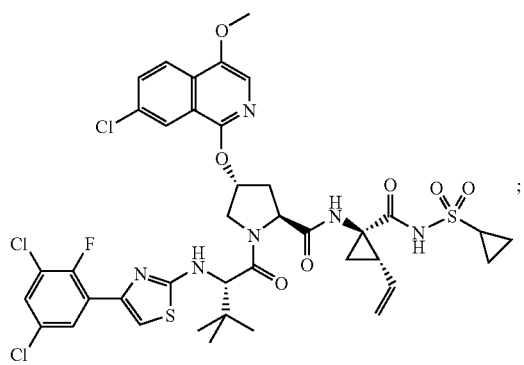
Compound 54
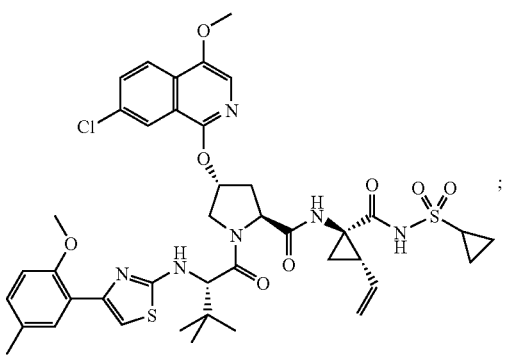

-continued
Compound 55
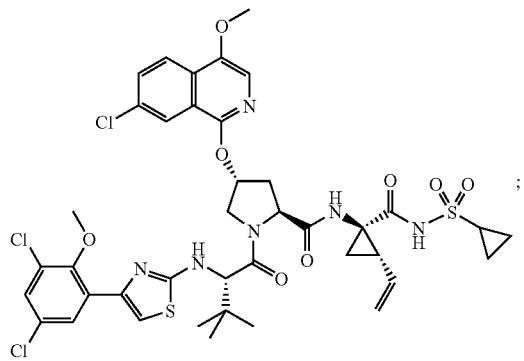
Compound 56
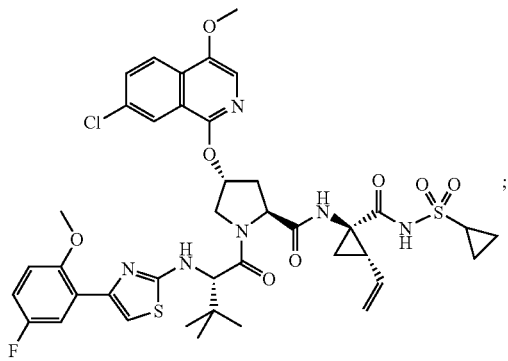
Compound 57
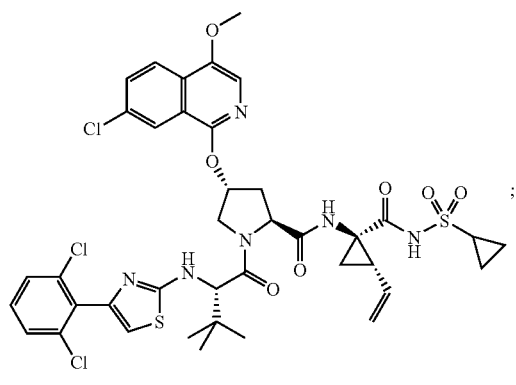
Compound 58
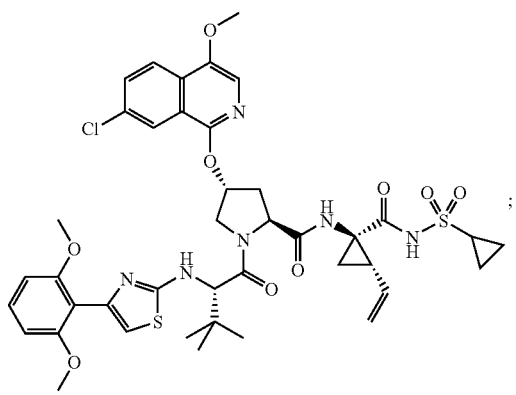
Compound 59
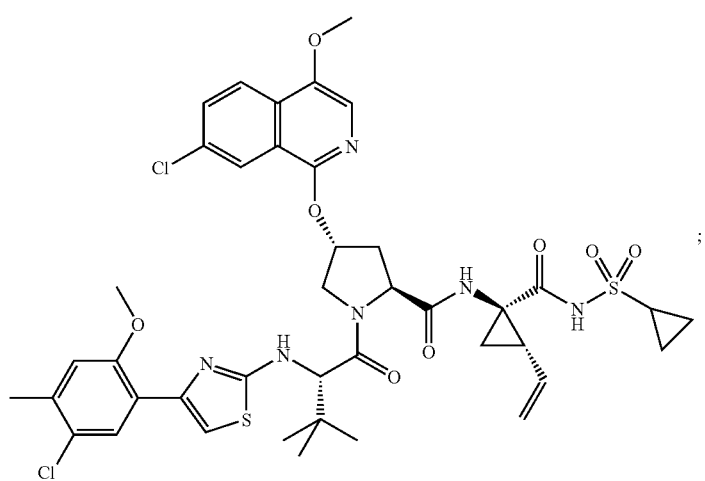

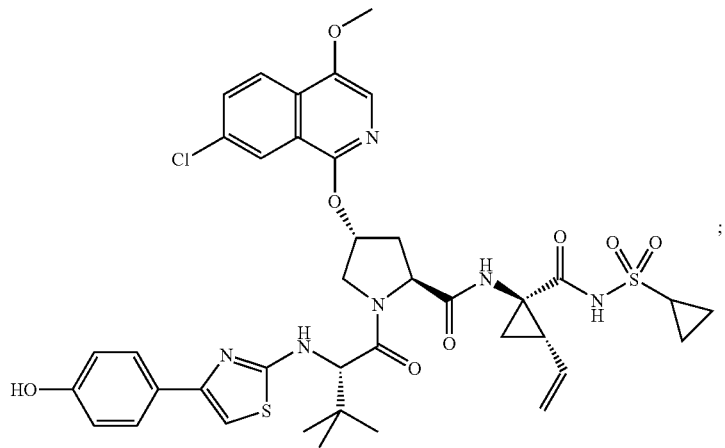
Compound 60
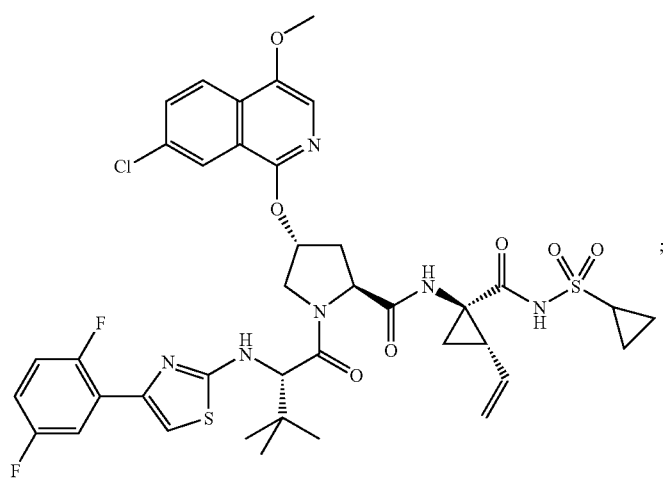
Compound 61
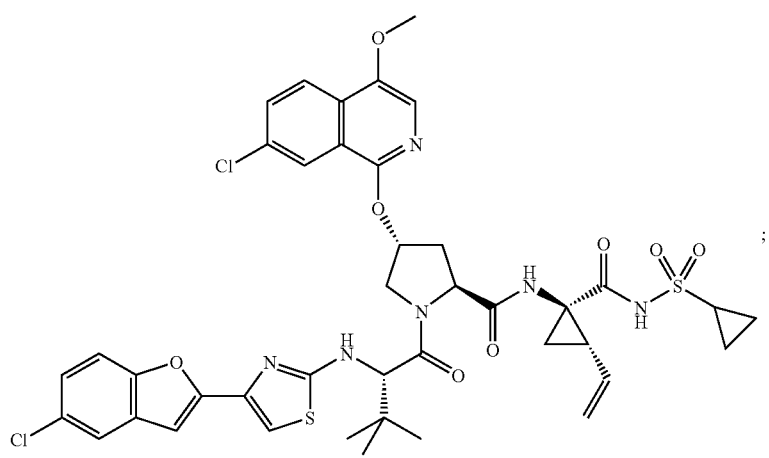
Compound 62

-continued
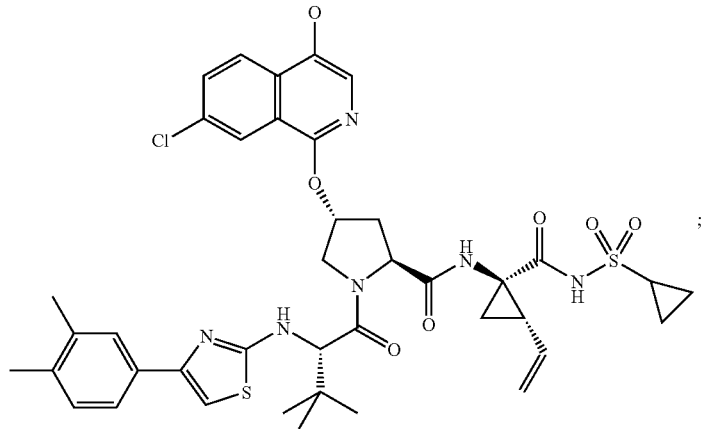
Compound 63
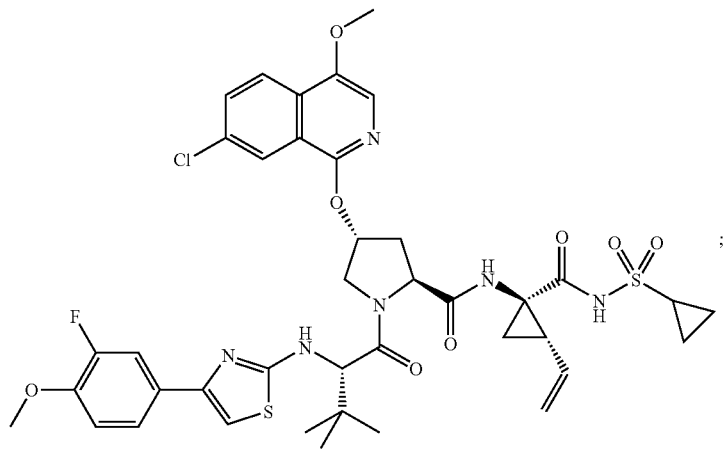
Compound 64
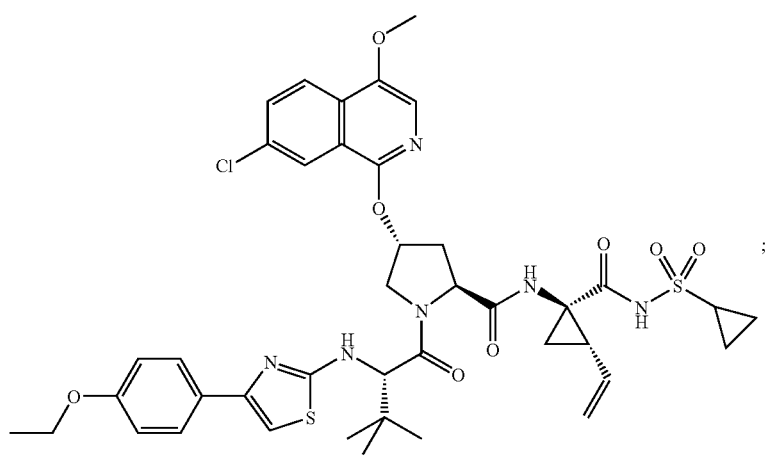
Compound 65

Compound 66
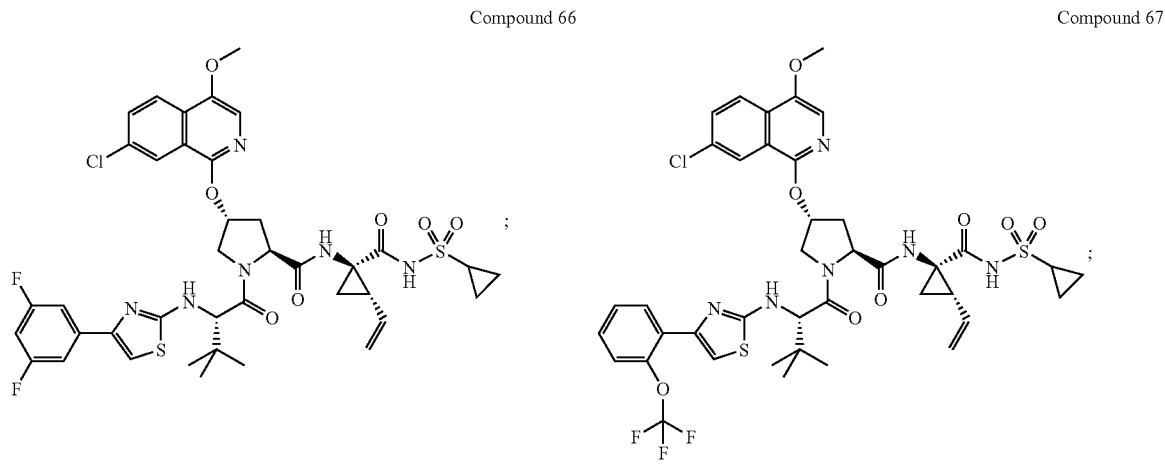
Compound 67
Compound 68
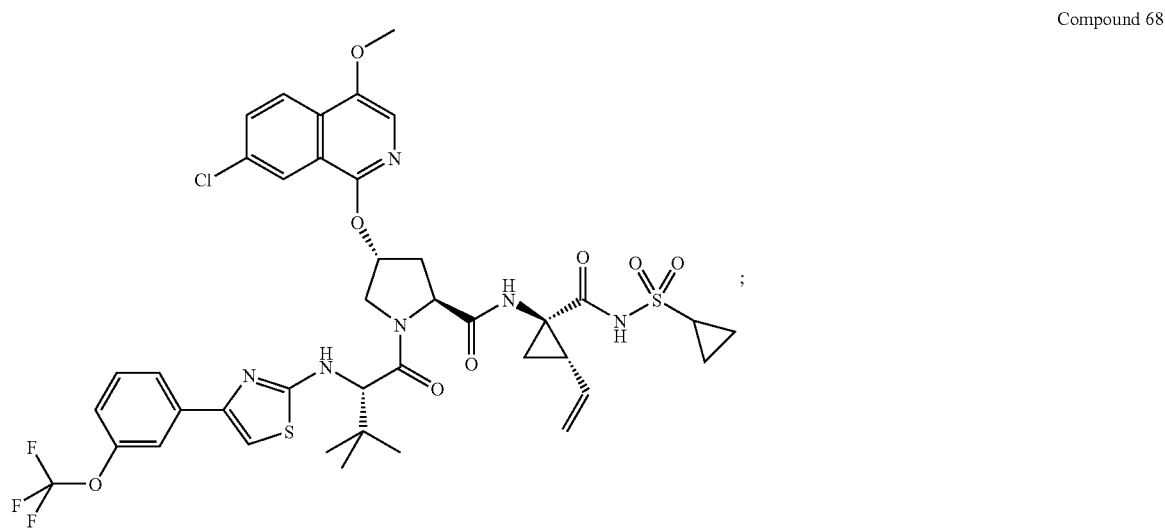
Compound 69
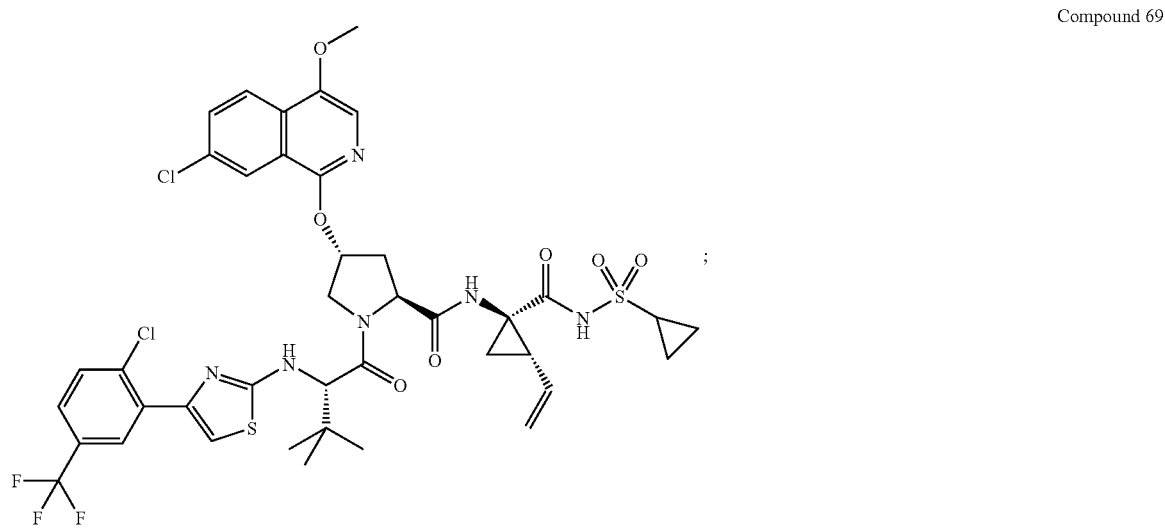

Compound 70
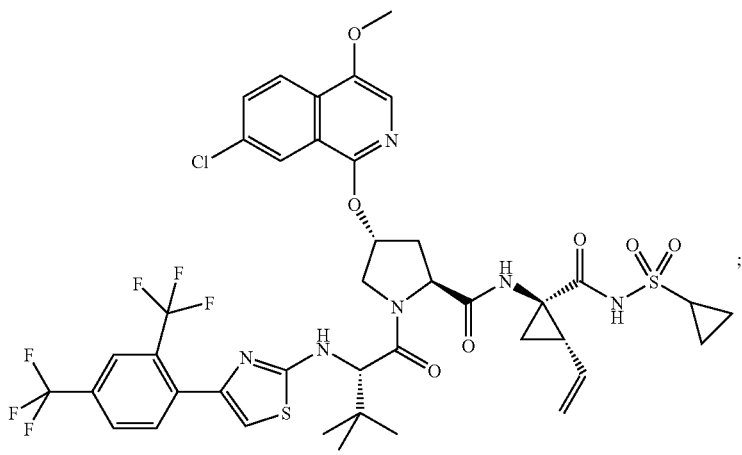
Compound 71
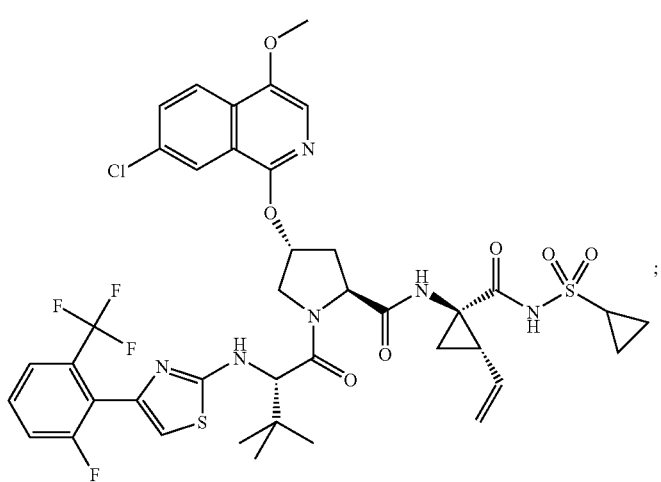
Compound 72
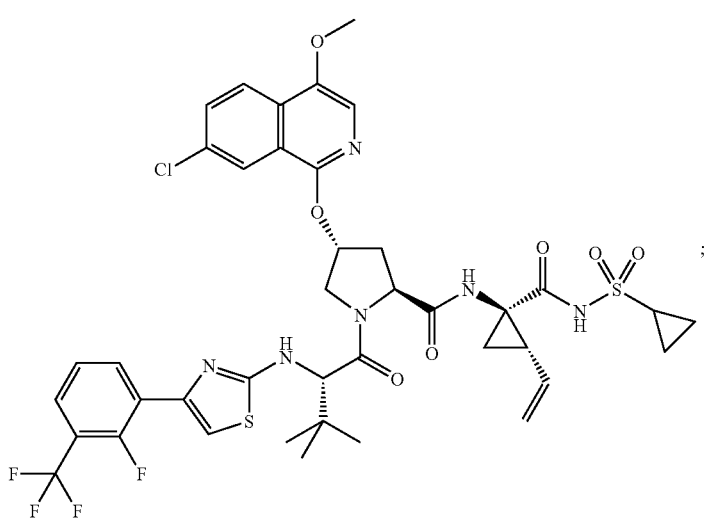

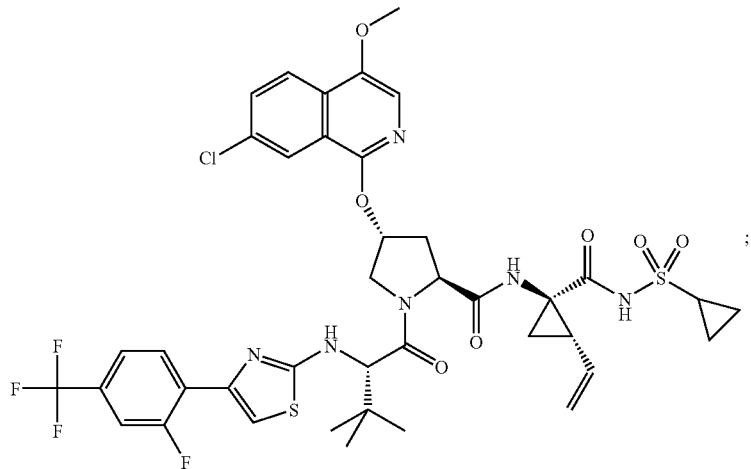
Compound 73
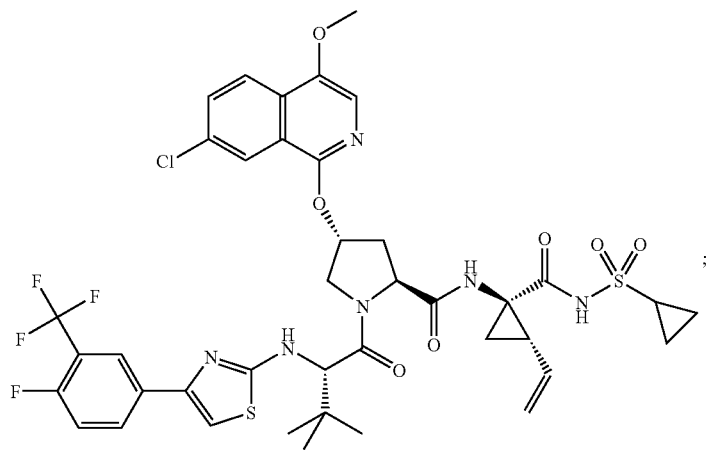
Compound 74
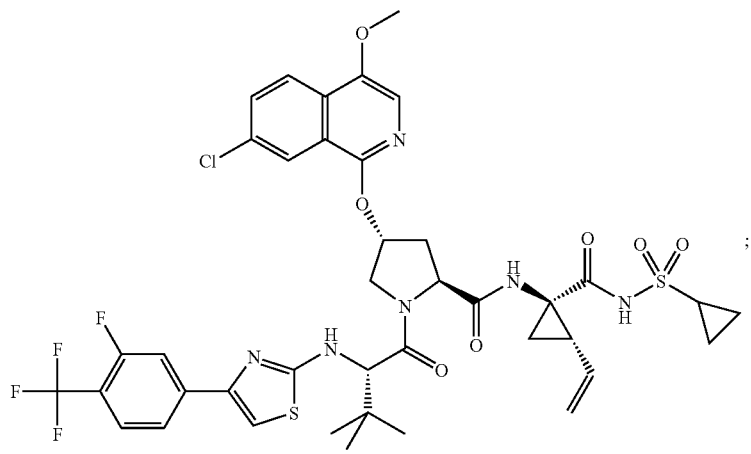
Compound 75

Compound 76
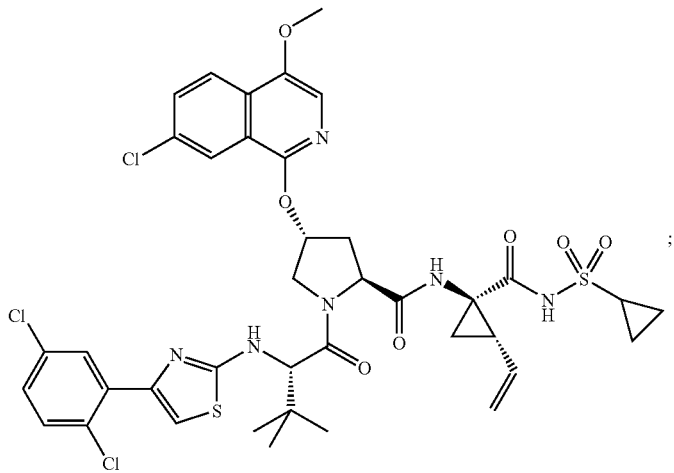
Compound 77
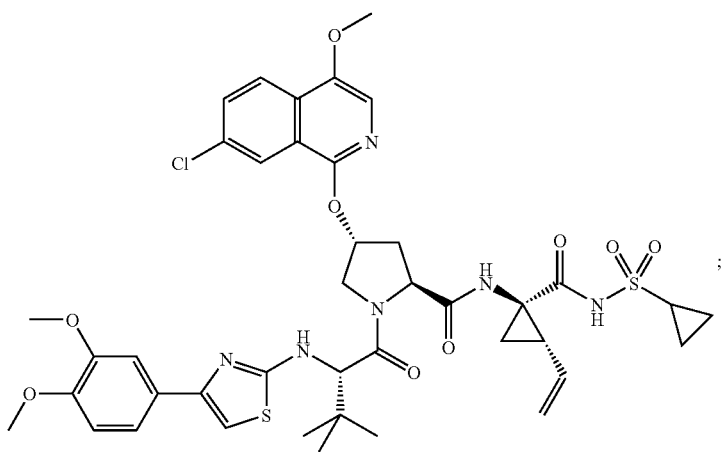
Compound 78
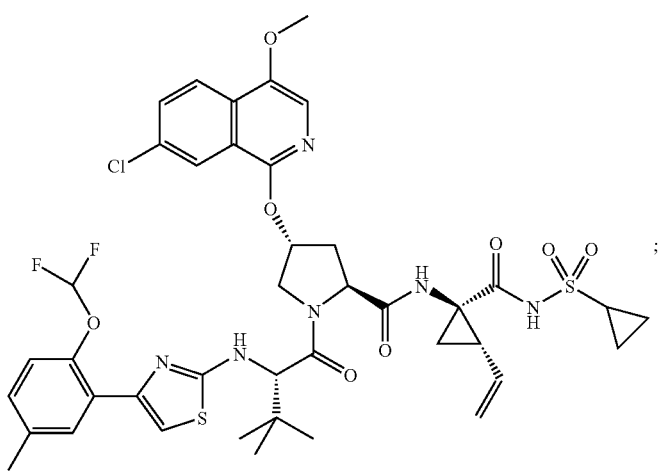

-continued
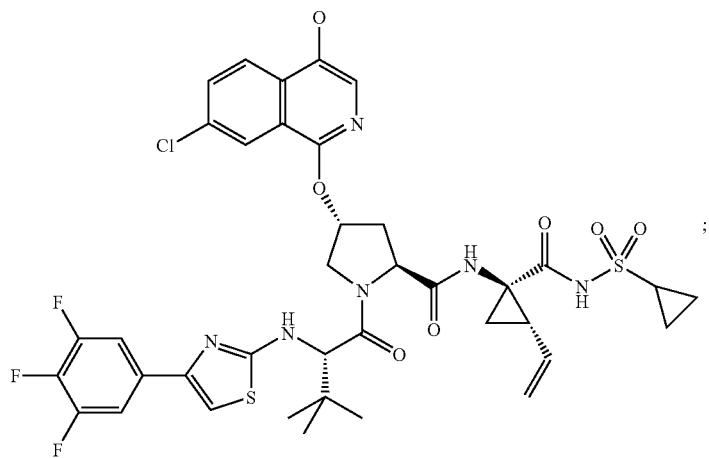
Compound 79
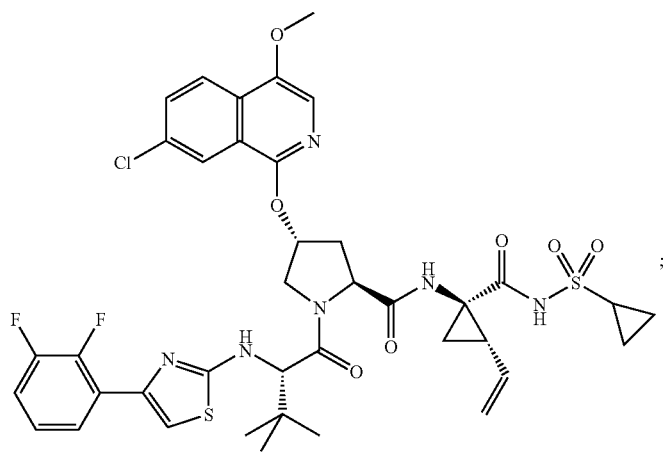
Compound 80
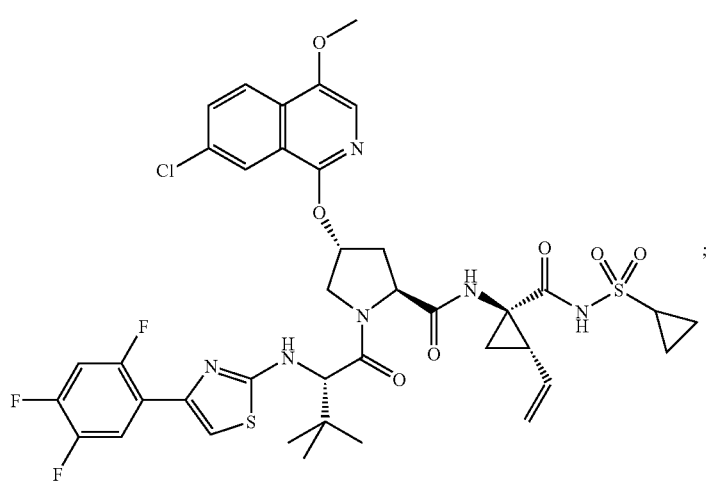
Compound 81

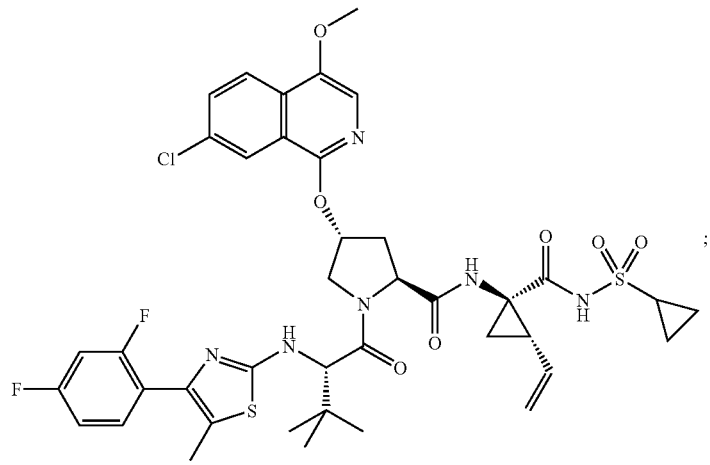
Compound 82
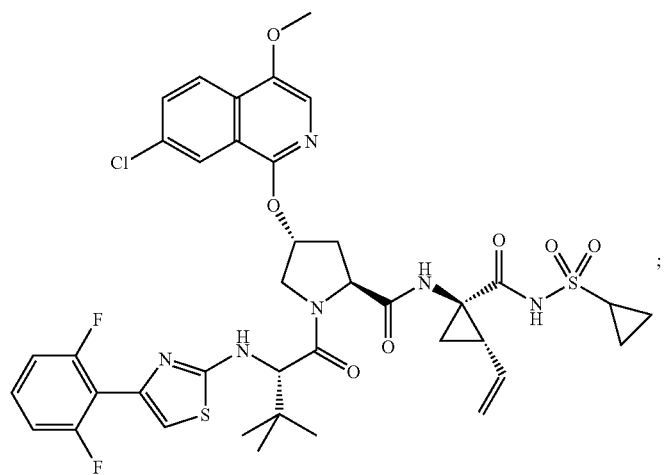
Compound 83
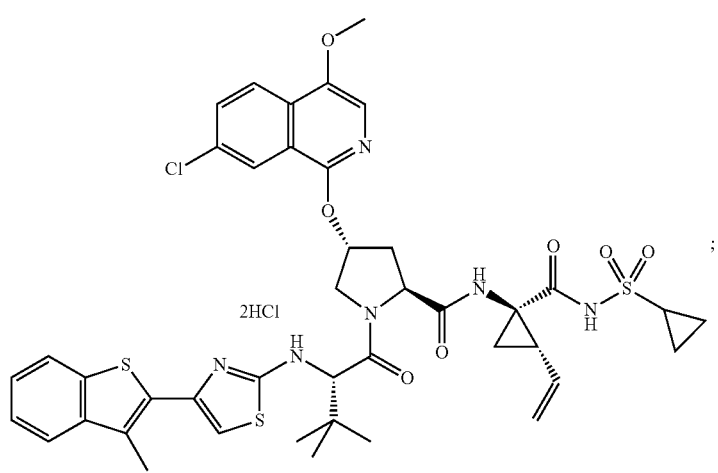
Compound 84

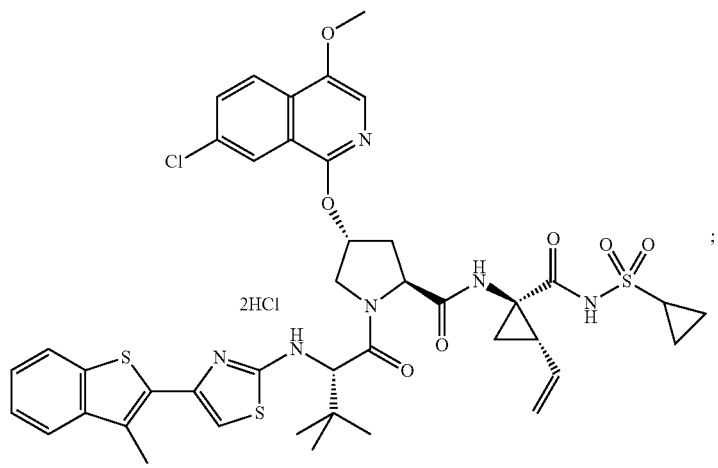
Compound 84
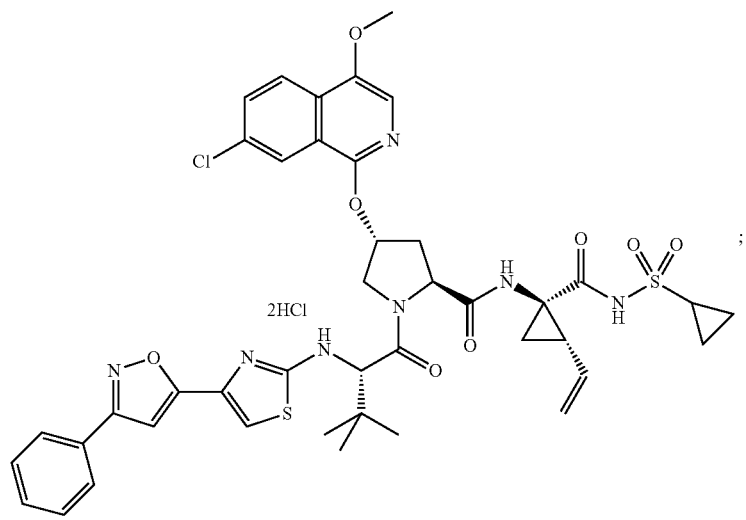
Compound 85
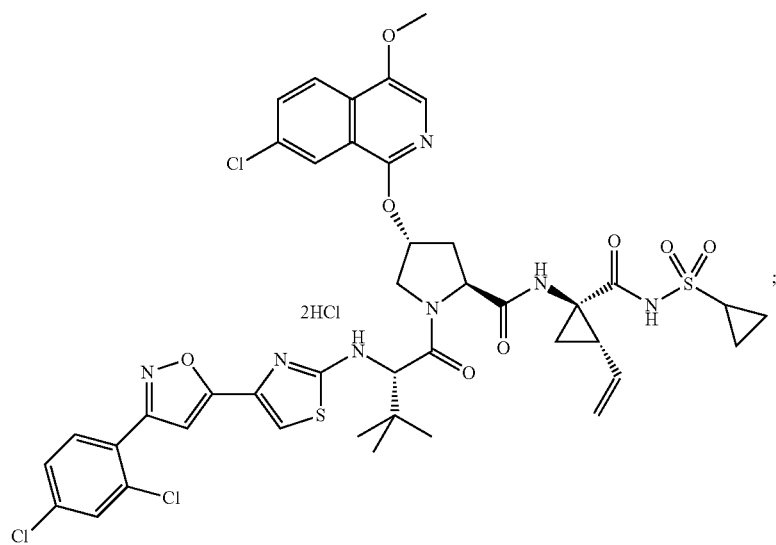
Compound 86

-continued
Compound 87
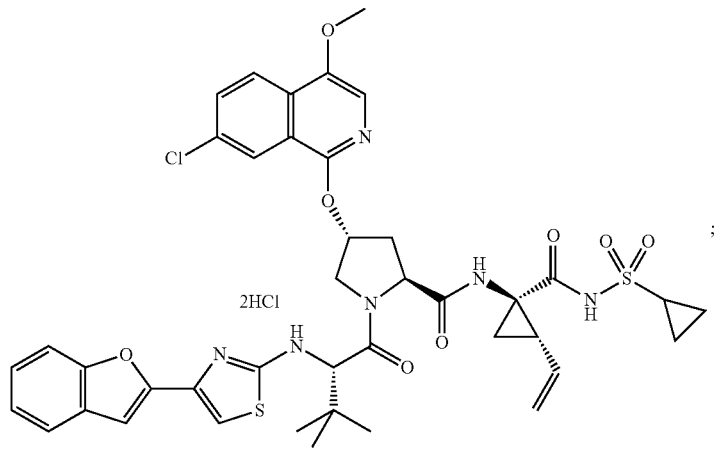
Compound 88
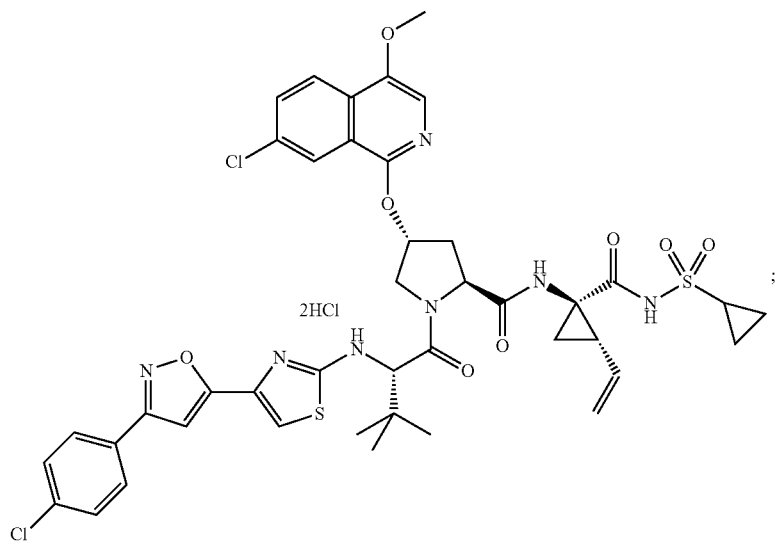
Compound 89
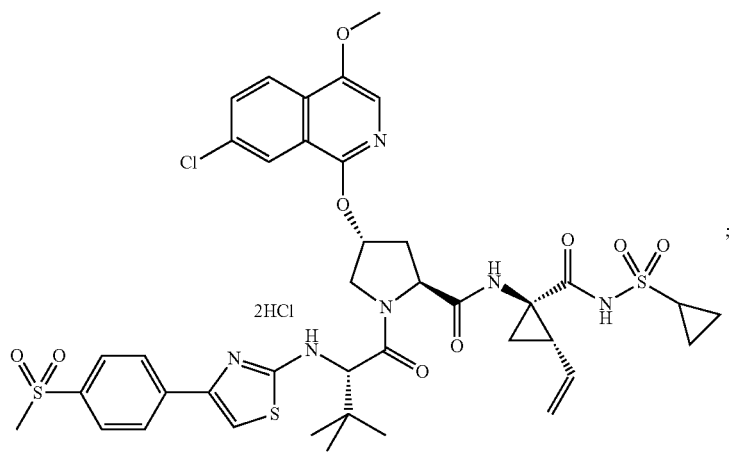

-continued
Compound 90
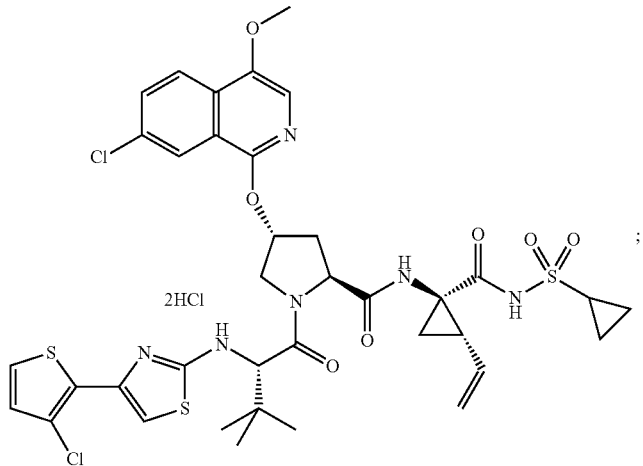
Compound 91
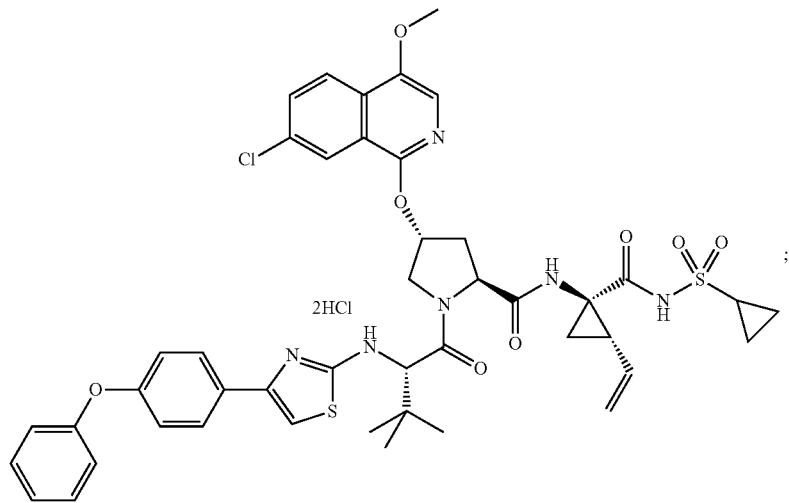
Compound 92
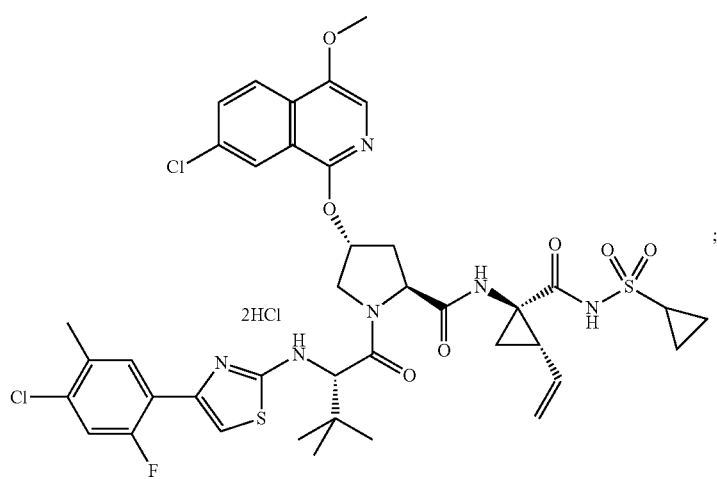

Compound 93
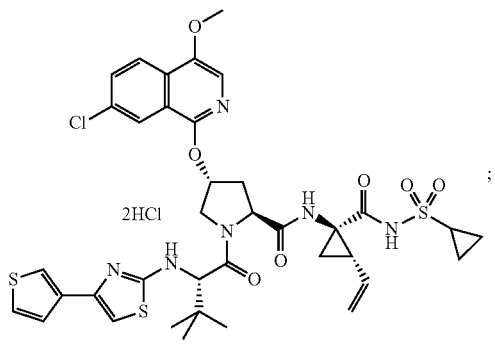
Compound 94
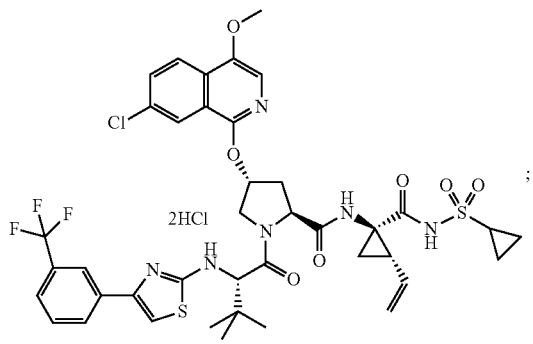
Compound 95
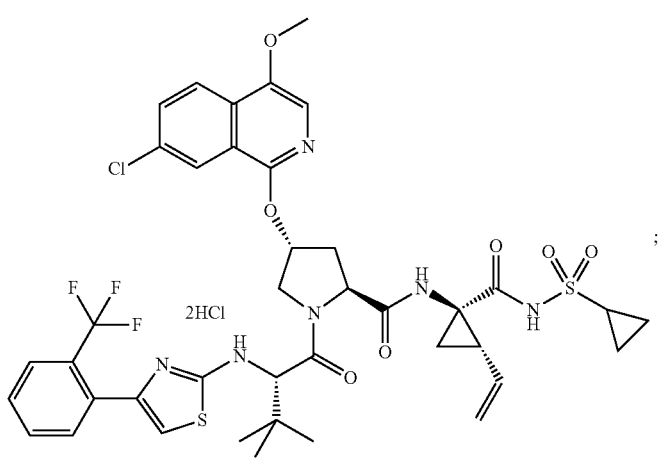
Compound 96
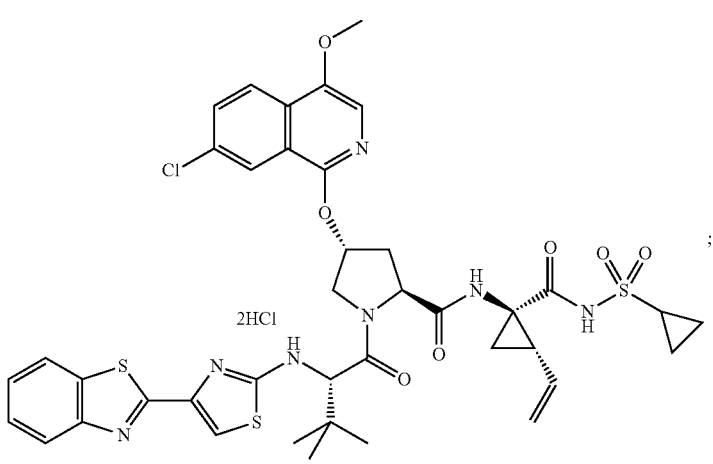

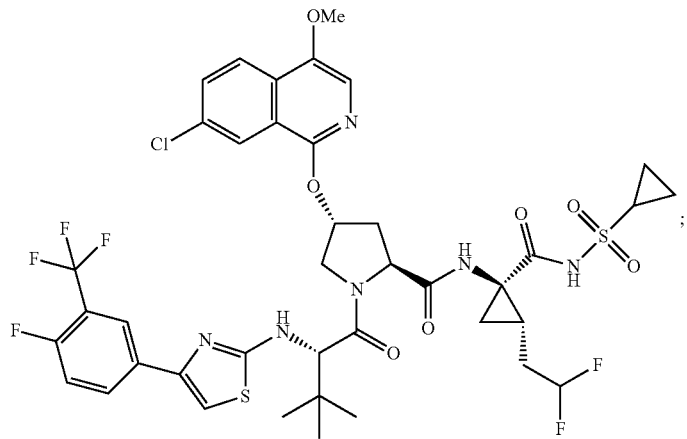
Compound 97
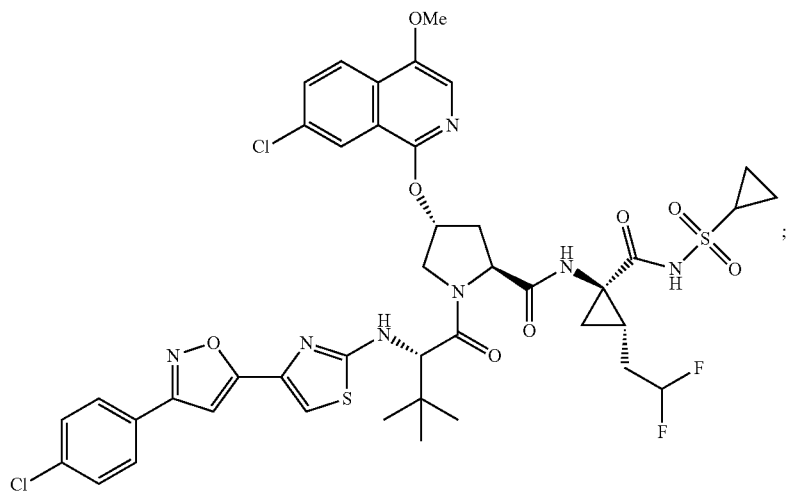
Compound 98
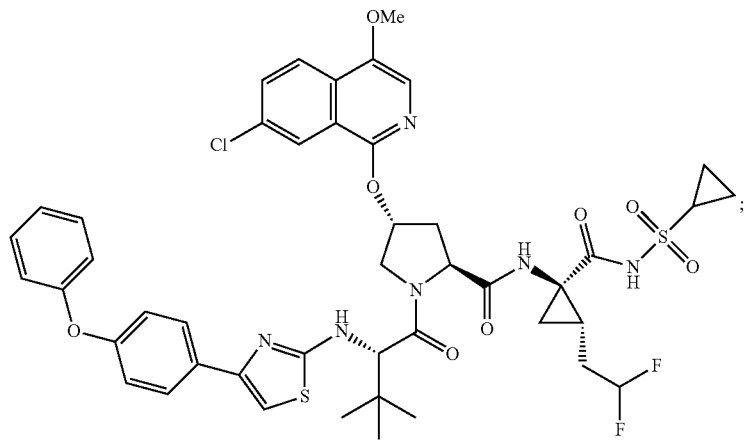
Compound 99

-continued

Compounds 100A

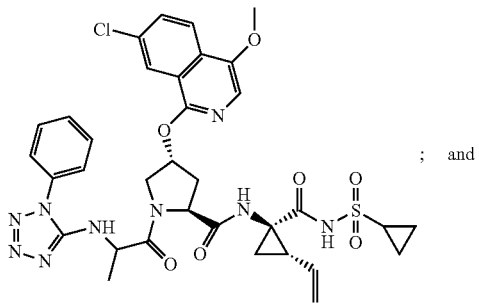

; and

Compounds 100B

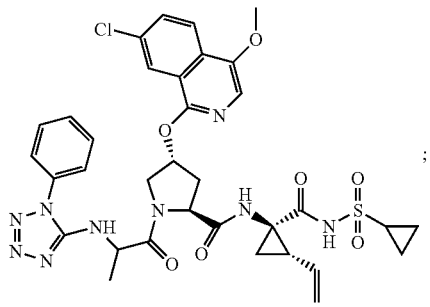

;

or a pharmaceutically acceptable salt thereof.

5. A composition comprising the compound of claim 1, or a pharmaceutically acceptable salt thereof, and a pharmaceutically acceptable carrier.

6. The composition of claim 5 further comprising at least one additional compound having anti-HCV activity.

7. The composition of claim 6 wherein at least one of the additional compounds is an interferon or a ribavirin.

8. The composition of claim 7 wherein the interferon is selected from interferon alpha 2B, pegylated interferon alpha, consensus interferon, interferon alpha 2A, and lymphoblastiod interferon tau.

9. The composition of claim 6 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

10. The composition of claim 6 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

11. A method of treating an HCV infection in a patient, comprising administering to the patient a therapeutically effective amount of a compound of claim 1, or a pharmaceutically acceptable salt thereof.

12. The method of claim 11 further comprising administering at least one additional compounds having anti-HCV activity prior to, after, or simultaneously with the compound of claim 1, or a pharmaceutically acceptable salt thereof.

13. The method of claim 12 wherein at least one of the additional compounds is an interferon or a ribavirin.

14. The method of claim 13 wherein the interferon is selected from interferon alpha 2B, pegylated interferon alpha, consensus interferon, interferon alpha 2A, and lymphoblastiod interferon tau.

15. The method of claim 12 wherein at least one of the additional compounds is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

16. The method of claim 12 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 8,163,921 B2  
APPLICATION NO. : 12/418677  
DATED : April 24, 2012  
INVENTOR(S) : Paul Scola et al.

Page 1 of 3

It is certified that error appears in the above-identified patent and that said Letters Patent is hereby corrected as shown below:

In the Claims:

In Claim 4, col. 165, delete " 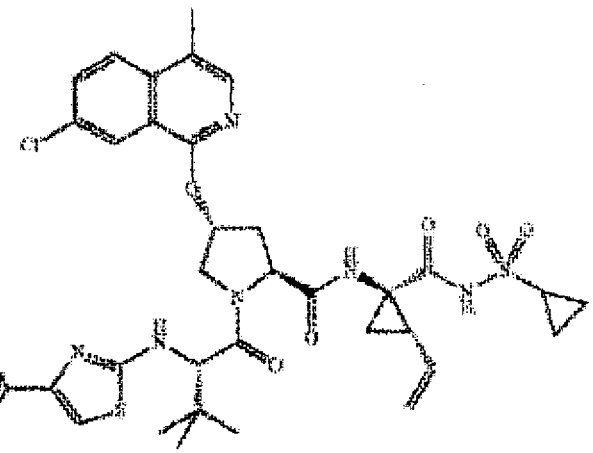 " and insert -- 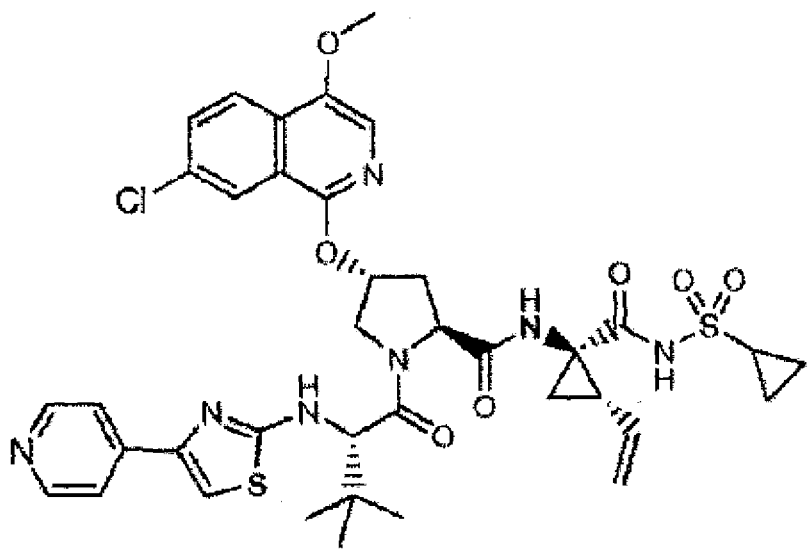 --, therefor.

Signed and Sealed this  
Eighth Day of April, 2014

Michelle K. Lee  
*Deputy Director of the United States Patent and Trademark Office*

CERTIFICATE OF CORRECTION (continued) Page 2 of 3
U.S. Pat. No. 8,163,921 B2

In the Claims:

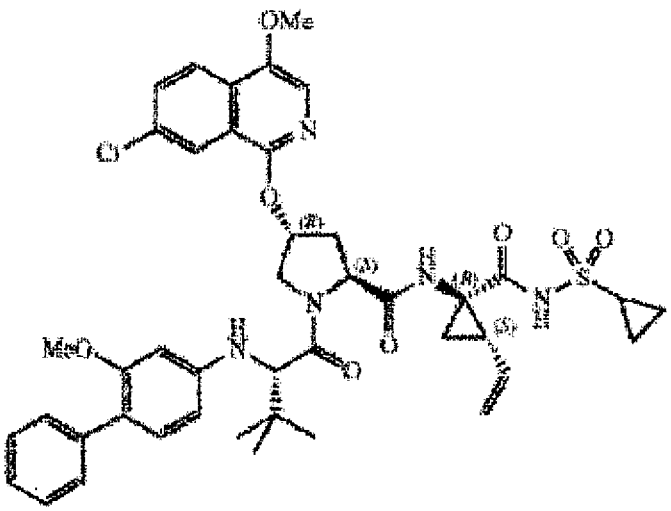

In Claim 4, col. 165, delete " " and

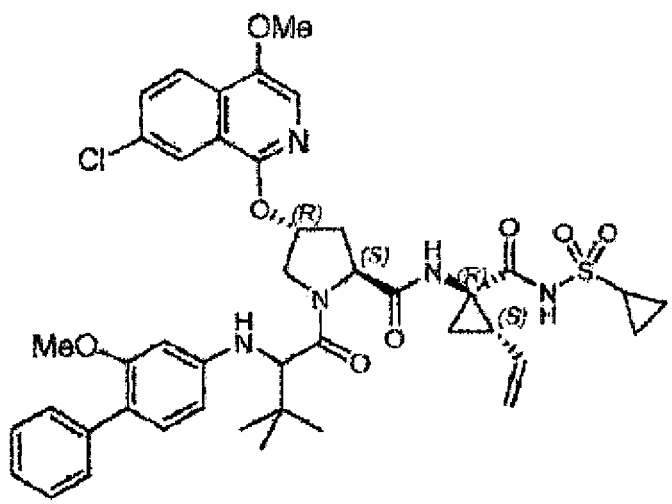

insert -- --, therefor.

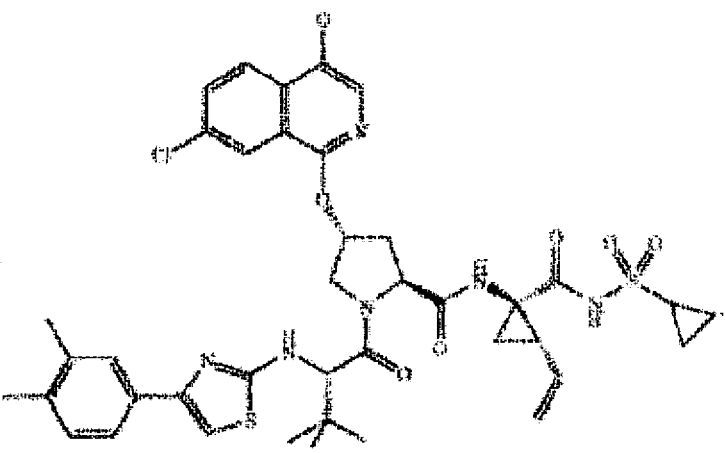

In Claim 4, col. 193, delete " "

CERTIFICATE OF CORRECTION (continued)
U.S. Pat. No. 8,163,921 B2

In the Claims:

and insert -- 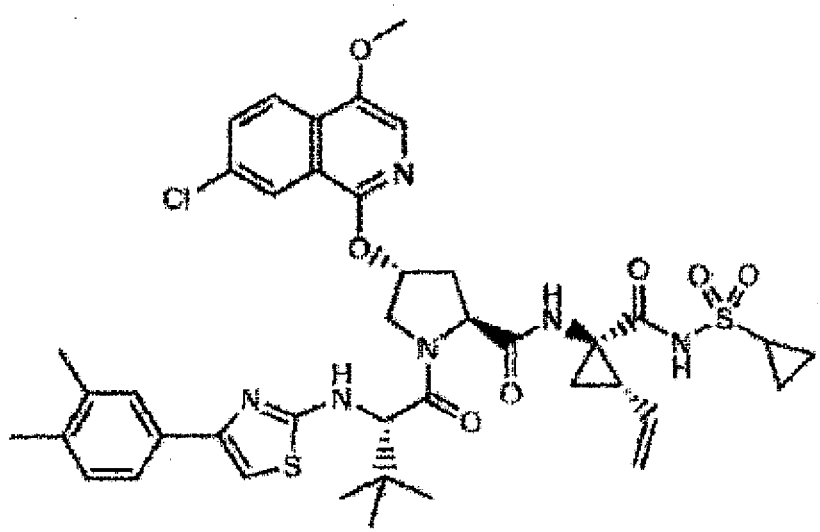 --, therefor.

In Claim 8, col. 217, lines 26-27, delete "lymphoblastiod" and insert -- lymphoblastoid --, therefor.

In Claim 9, col. 217, line 31, delete "Imiqimod," and insert -- Imiquimod, --, therefor.

In Claim 9, col. 217, line 32, delete "5'-monophospate" and insert -- 5'-monophosphate --, therefor.

In Claim 14, col. 218, lines 26-27, delete "lymphoblastiod" and insert -- lymphoblastoid --, therefor.

In Claim 15, col. 218, line 31, delete "Imiqimod," and insert -- Imiquimod, --, therefor.

In Claim 15, col. 218, line 32, delete "5'-monophospate" and insert -- 5'-monophosphate --, therefor.